United States Patent
Shock et al.

(10) Patent No.: US 12,312,617 B2
(45) Date of Patent: May 27, 2025

(54) CELL WALL HYDROLASES TARGETING C. ACNES

(71) Applicant: Topaz Biosciences, Inc., Emeryville, CA (US)

(72) Inventors: Jennifer Shock, San Francisco, CA (US); Maritza Miller, Oakland, CA (US); Oliver Liu, San Francisco, CA (US); Teresa Shock, San Francisco, CA (US)

(73) Assignee: Topaz Biosciences, Inc., Emeryville, CA (US)

( * ) Notice: Subject to any disclaimer, the term of this patent is extended or adjusted under 35 U.S.C. 154(b) by 0 days.

(21) Appl. No.: 18/882,341

(22) Filed: Sep. 11, 2024

(65) Prior Publication Data

US 2025/0034537 A1    Jan. 30, 2025

Related U.S. Application Data

(63) Continuation of application No. PCT/US2024/039933, filed on Jul. 26, 2024.

(60) Provisional application No. 63/529,224, filed on Jul. 27, 2023.

(51) Int. Cl.
| | |
|---|---|
| *C12N 9/00* | (2006.01) |
| *A61K 9/00* | (2006.01) |
| *A61K 38/47* | (2006.01) |
| *A61P 17/10* | (2006.01) |
| *C12N 9/24* | (2006.01) |

(52) U.S. Cl.
CPC .......... *C12N 9/2402* (2013.01); *A61K 9/0014* (2013.01); *A61K 38/47* (2013.01); *A61P 17/10* (2018.01); *C12Y 302/01017* (2013.01)

(58) Field of Classification Search
CPC ............ A61P 31/04; C12Y 304/24075; C12Y 403/01024; C12Y 302/01017; C12N 9/88
USPC .......................................................... 435/195
See application file for complete search history.

(56) References Cited

U.S. PATENT DOCUMENTS

2022/0315908 A1    10/2022    Corsini

FOREIGN PATENT DOCUMENTS

| WO | WO-2021175606 A1 | 9/2021 |
| WO | WO-2025024827 A1 | 1/2025 |

OTHER PUBLICATIONS

Kisselev L., (Structure, 2002, vol. 10: 8-9.*
Witkowski et al., (Biochemistry 38:11643-11650, 1999.*
Whisstock et al., (Quarterly Reviews of Biophysics 2003, vol. 36 (3): 307-340.*
Devos et al., (Proteins: Structure, Function and Genetics, 2000, vol. 41: 98-107.*
Murray et al., "Global burden of bacterial antimicrobial resistance in 2019: a systematic analysis" Lancet. Feb. 12, 2022; 399(10325):629-655.
Bailey et al., "The MEME Suite" Nucleic Acids Res. Jul. 1, 2015; 43(W1):W39-W49.
Bickers et al., "The burden of skin diseases: 2004: A joint project of the American Academy of Dermatology Association and the Society for Investigative Dermatology" J Am Acad Dermatol. Sep. 2006; 55(3):490-500.
Briers et al., "A standardized approach for accurate quantification of murein hydrolase activity in high-throughput assays" J Biochem Biophys Methods. Apr. 10, 2007; 70(3):531-533.
Bruggemann et al., "A Janus-Faced Bacterium: Host-Beneficial and-Detrimental Roles of Cutibacterium acnes" Front Microbiol. May 31, 2021; 12:673845. 22 pages.
Bustamante et al., "Deciphering how Cpl-7 cell wall-binding repeats recognize the bacterial peptidoglycan" Sci Rep. Nov. 28, 2017; 7(1):16494. 17 pages.
Chien et al., "Association of Systemic Antibiotic Treatment of Acne With Skin Microbiota Characteristics" JAMA Dermatol. Apr. 1, 2019; 155(4):425-434.
Dams et al., "Enzybiotics: Enzyme-Based Antibacterials as Therapeutics" Adv Exp Med Biol. (2019) 1148:233-253.
Fitz-Gibbon et al., "Propionibacterium acnes strain populations in the human skin microbiome associated with acne" J Invest Dermatol. Sep. 2013; 133(9):2152-2160.
Gallitano et al., "How Acne Bumps Cause the Blues: The Influence of Acne Vulgaris on Self-Esteem" Int J Womens Dermatol. (2017) Dec. 6, 2017; 4(1):12-17.
Gerstmans et al., "Synthetic biology of modular endolysins" Biotechnol Adv. May-Jun. 2018; 36(3):624-640.
Gutierrez et al., "Are Phage Lytic Proteins the Secret Weapon To Kill Staphylococcus aureus?" mBio. Jan. 2018; 9(1):e01923-17. 17 pages.
Invitation to pay additional fees for International Application No. PCT/US2024/039933, mailed Oct. 7, 2024, 3 pages.
Jin et al., "Roles of bacteriophage GVE2 endolysin in host lysis at high temperatures" Microbiology (Reading). Aug. 2013; 159(Pt 8):1597-1605.
Liu et al., "The diversity and host interactions of Propionibacterium acnes bacteriophages on human skin" ISME J. Sep. 2015; 9(9):2078-2093.

(Continued)

*Primary Examiner* — Robert B Mondesi
*Assistant Examiner* — Mohammad Y Meah
(74) *Attorney, Agent, or Firm* — Cooley LLP

(57) ABSTRACT

The present disclosure relates to novel cell wall binding domains, enzymatically active domains, and chimeric cell wall hydrolases with anti-*Cutibacterium acnes* activity. The disclosure also relates to compositions comprising these, and uses thereof in the treatment of conditions associated with *Cutibacterium acnes*.

25 Claims, 55 Drawing Sheets

Specification includes a Sequence Listing.

(56) References Cited

OTHER PUBLICATIONS

Lomholt et al., "A comparative study of Cutibacterium (Propionibacterium) acnes clones from acne patients and healthy controls" Anaerobe. Oct. 2017; 47:57-63.

Madeira et al., "The EMBL-EBI Job Dispatcher sequence analysis tools framework in 2024" Nucleic Acids Res. Jul. 5, 2024; 52(W1):W521-W525.

Marinelli et al., "Propionibacterium acnes bacteriophages display limited genetic diversity and broad killing activity against bacterial skin isolates" mBio. Sep. 25, 2012; 3(5):e00279-12. 13 pages.

Matsuzaki et al., "Bacteriophage therapy: a revitalized therapy against bacterial infectious diseases" Journal of Infection and Chemotherapy. (2005) 11:211-219.

Mayer et al., "Molecular characterization of a Clostridium difficile bacteriophage and its cloned biologically active endolysin" J Bacteriol. Oct. 2008; 190(20):6734-6740.

Mias et al., "Recent advances in understanding inflammatory acne: Deciphering the relationship between Cutibacterium acnes and Th17 inflammatory pathway" J Eur Acad Dermatol Venereol. Mar. 2023: 37 (Suppl 2):3-11.

Natarelli et al., "Bacteriophages and the Microbiome in Dermatology: The Role of the Phageome and a Potential Therapeutic Strategy" Int J Mol Sci. Jan. 31, 2023; 24(3):2695. 11 pages.

NCBI Accession ID: YP_006907103.1, Jan. 8, 2023, 2 pages.

Oliveira et al., "Staphylococci phages display vast genomic diversity and evolutionary relationships" BMC Genomics. May 9, 2019; 20(1):357. 14 pages.

Patangia et al., "Impact of antibiotics on the human microbiome and consequences for host health" Microbiologyopen. Feb. 2022; 11(1):e1260. 23 pages.

Varotsou et al., "Characterization and Engineering Studies of a New Endolysin from the Propionibacterium acnes Bacteriophage PAC1 for the Development of a Broad-Spectrum Artilysin with Altered Specificity" Int J Mol Sci. May 10, 2023; 24(10):8523. 19 pages.

Vermassen et al., "Cell wall hydrolases in bacteria: insight on the diversity of cell wall amidases, glycosidases and peptidases toward peptidoglycan" Frontiers in Microbiology. (2019) 10:331. 27 pages.

Wang et al., "Protein domain identification methods and online resources," Comput Struct Biotechnol J (2021)19:1145-1153.

Zaenglein et al., "Guidelines of care for the management of acne vulgaris" J Am Acad Dermatol. (2016) May 74(5):945-973.e33.

Zhang et al., "Antimicrobial Susceptibility, Biotypes and Phylotypes of Clinical Cutibacterium (Formerly Propionibacterium) acnes Strains Isolated from Acne Patients: An Observational Study" Dermatol Ther (Heidelb). Dec. 2019; 9(4):735-746.

International Search Report and Written Opinion for PCT Application No. PCT/US2024/039933 mailed Dec. 11, 2024, 17 pages.

UniProtKB Accession No. A0A2W5K6W6, N-acetylmuramoyl-L-alanine amidase. Sep. 12, 2018 [online]. [Retrieved on Nov. 27, 2024]. Retrieved from the internet: URL: [https://www.uniprot.org/uniprotkb/A0A2W5K6W6/entry], 6 pages.

UniProtKB Accession No. A0A3E2DMAO, N-acetylmuramoyl-L-alanine amidase. Jan. 16, 2019 [online]. [Retrieved on Nov. 27, 2024]. Retrieved from the internet: URL: [https://www.uniprot.org/uniprotkb/A0A3E2DMA0/entry], 4 pages.

\* cited by examiner

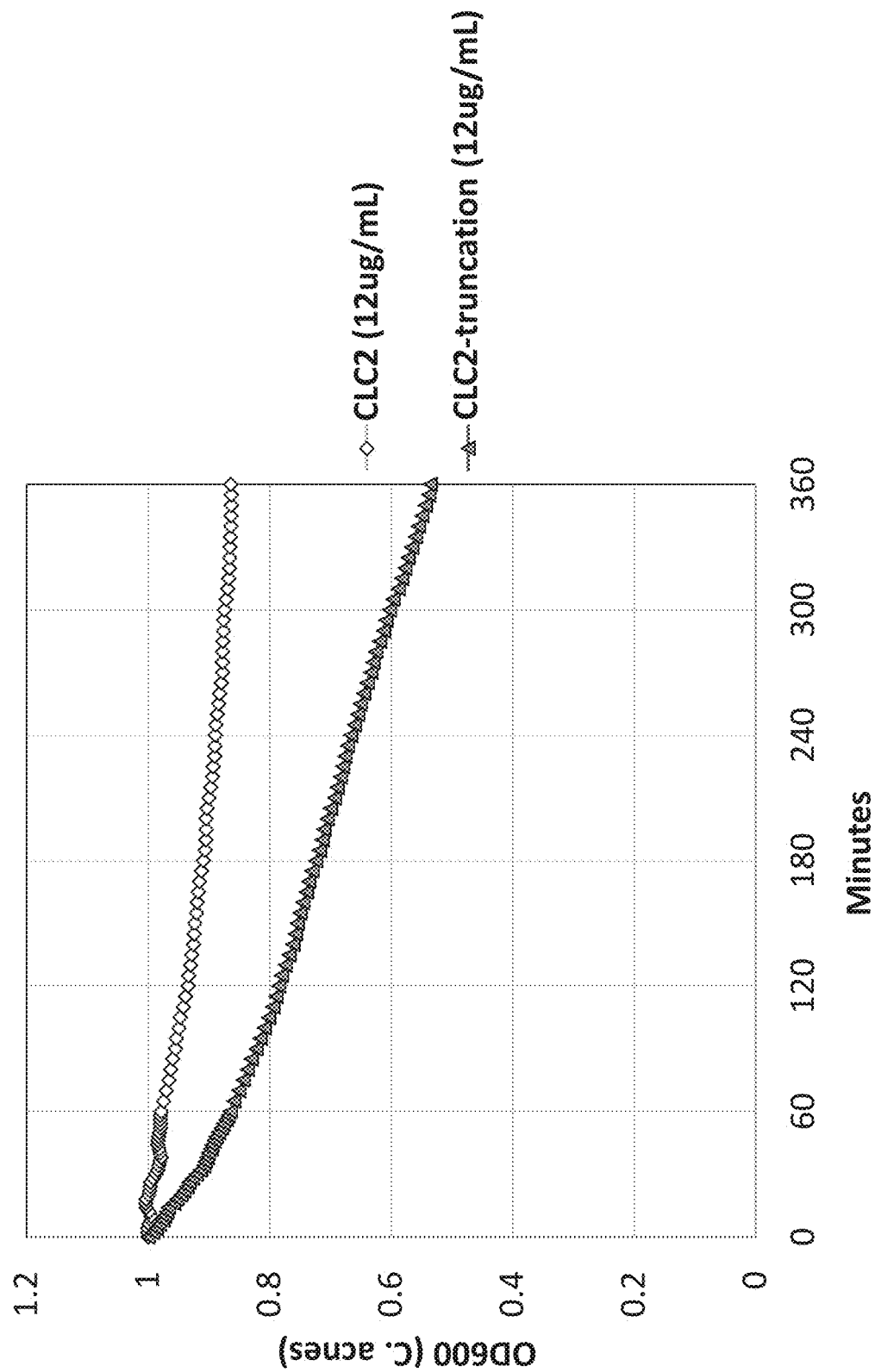

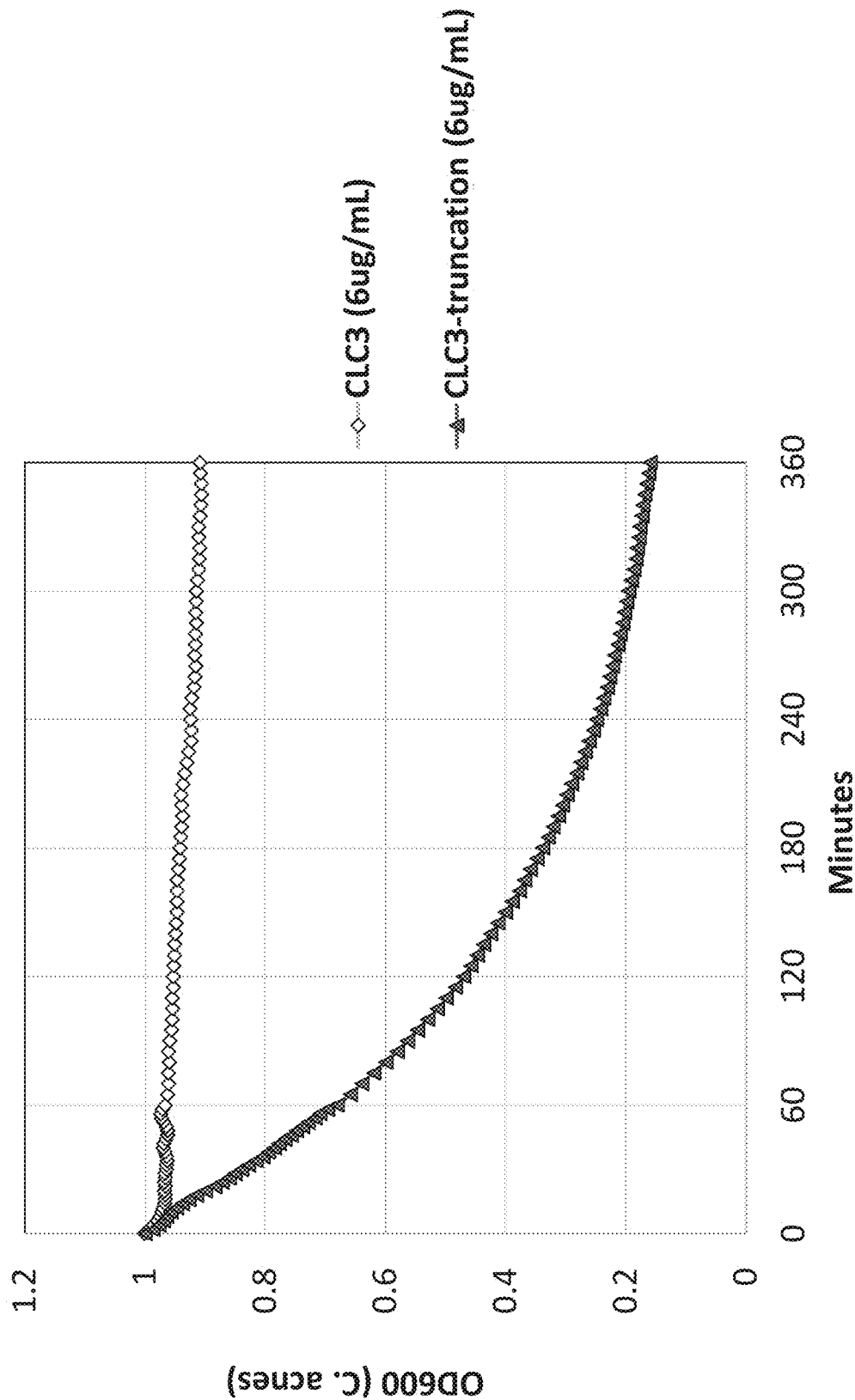

FIG. 8A

Source of EAD: CD27L
Native target: *Clostridium difficile*

- CD27L-EAD + CLB1-CBD (12ug/mL)
- CD27L-EAD + CLB2-CBD (12ug/mL)
- Native CD27L (48ug/mL)

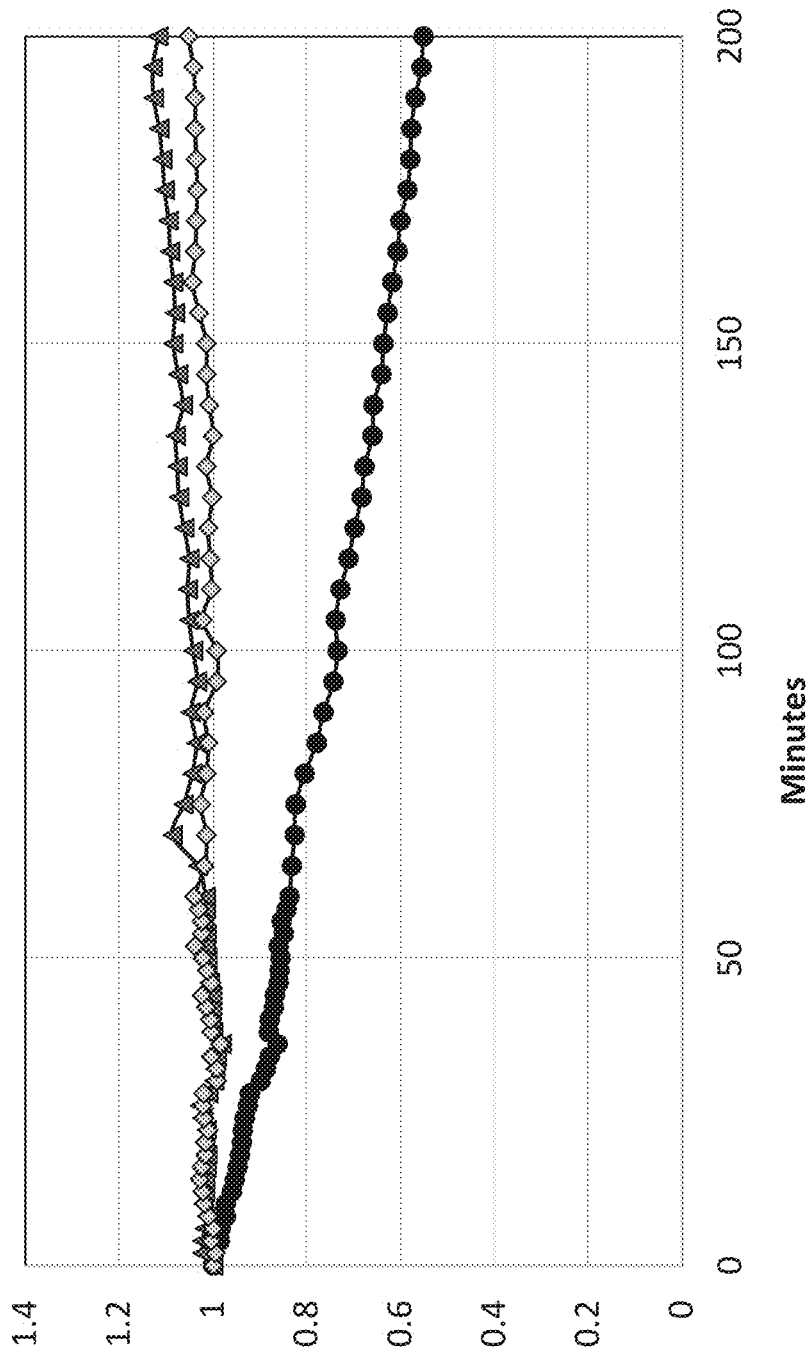

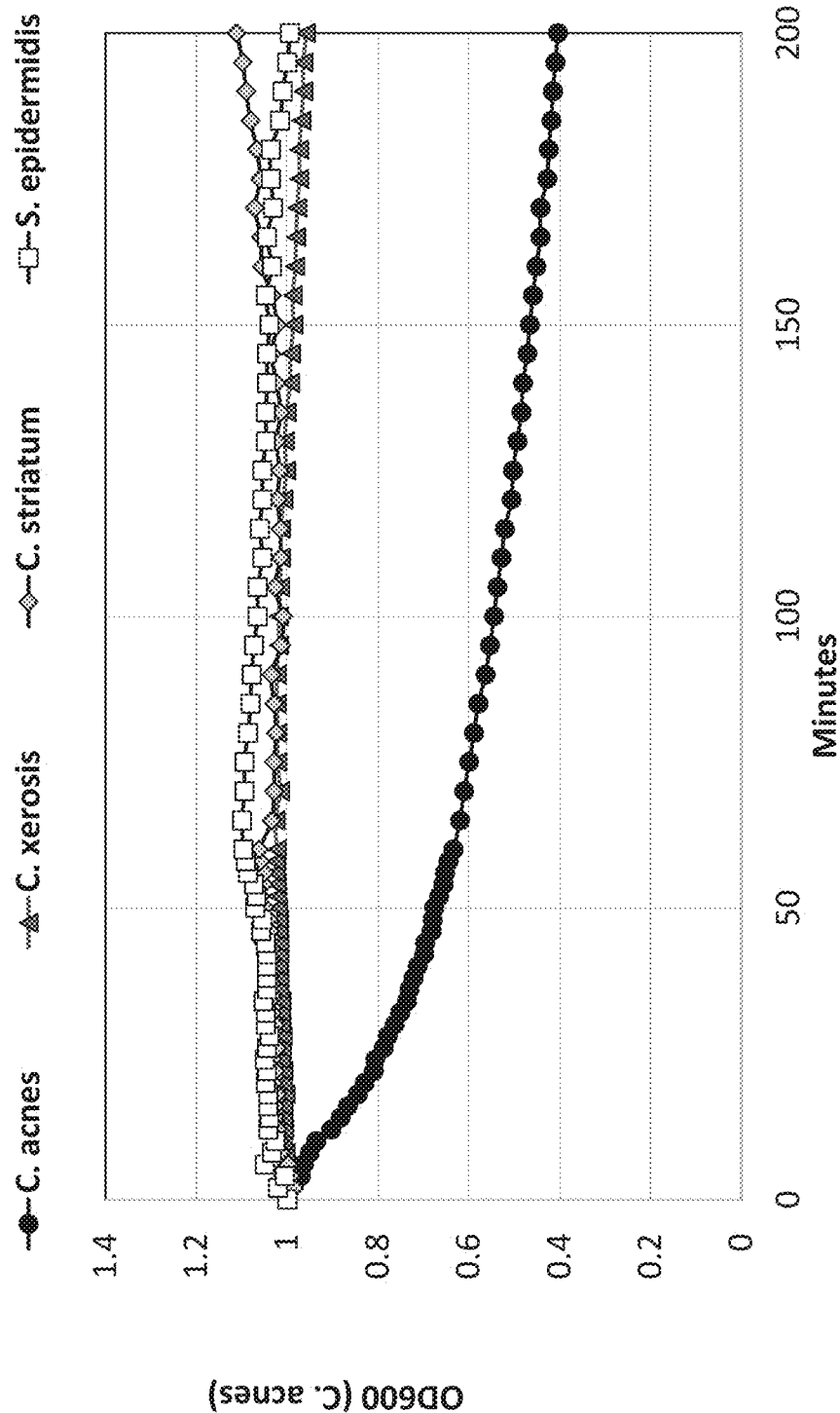

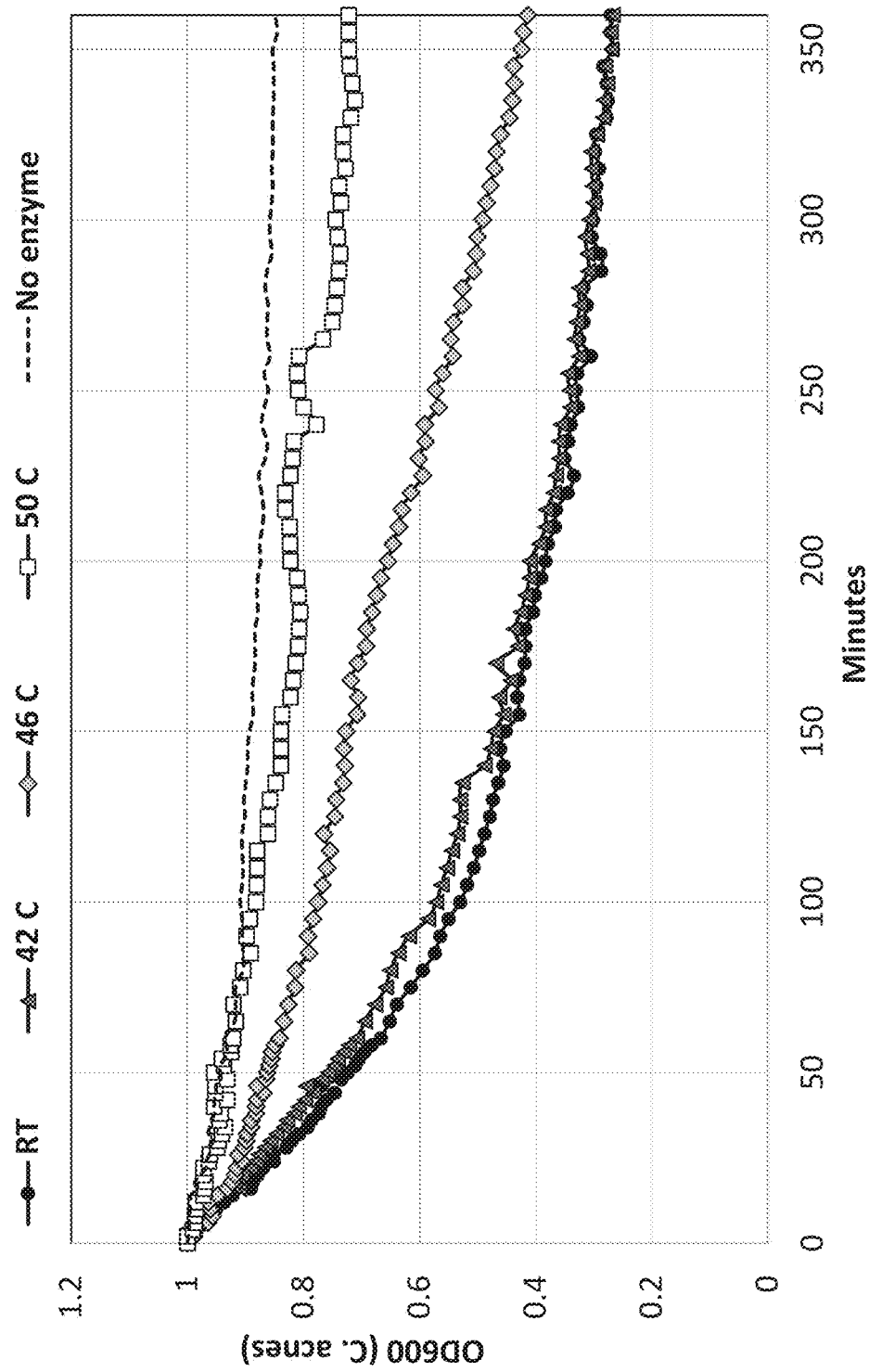

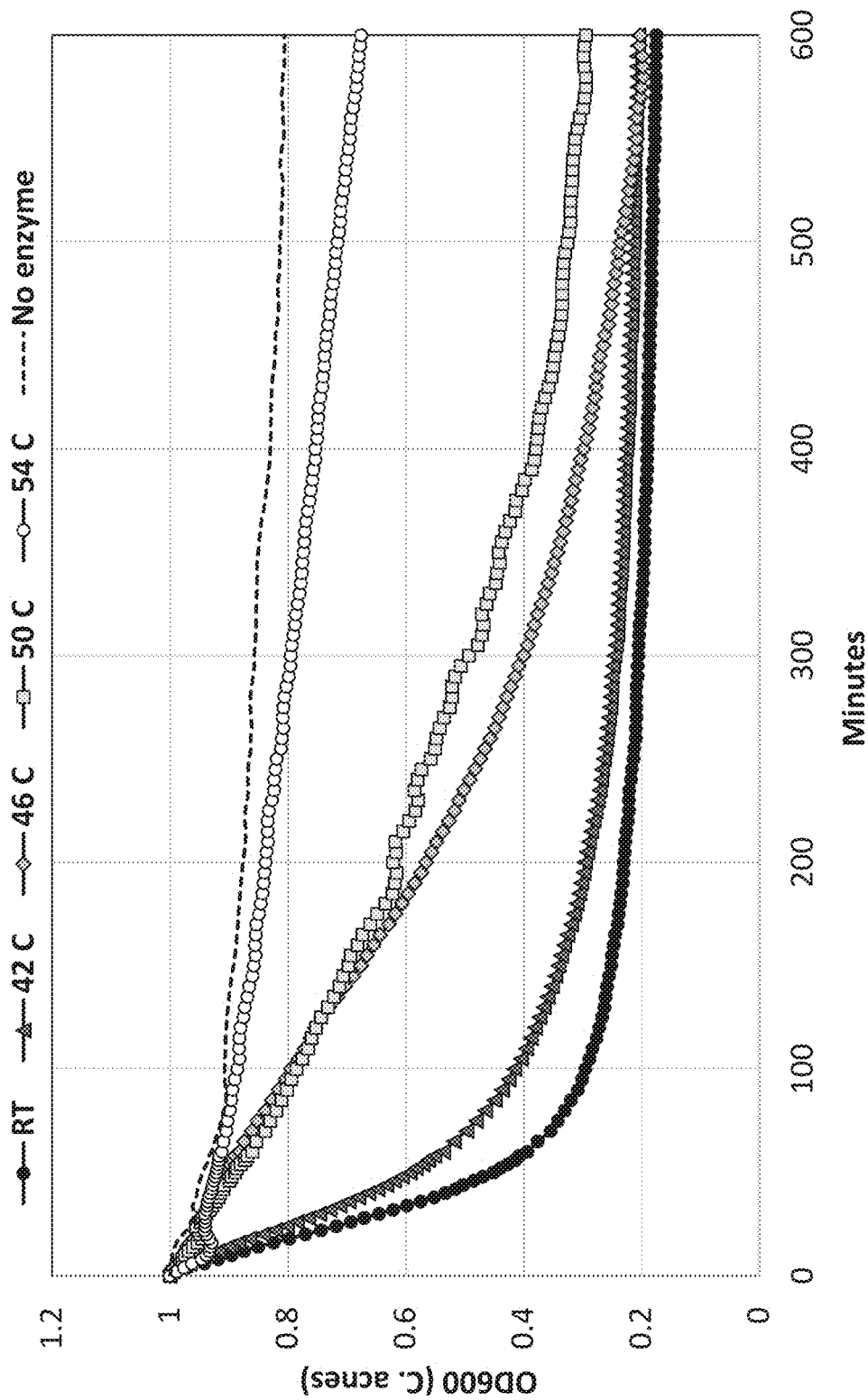

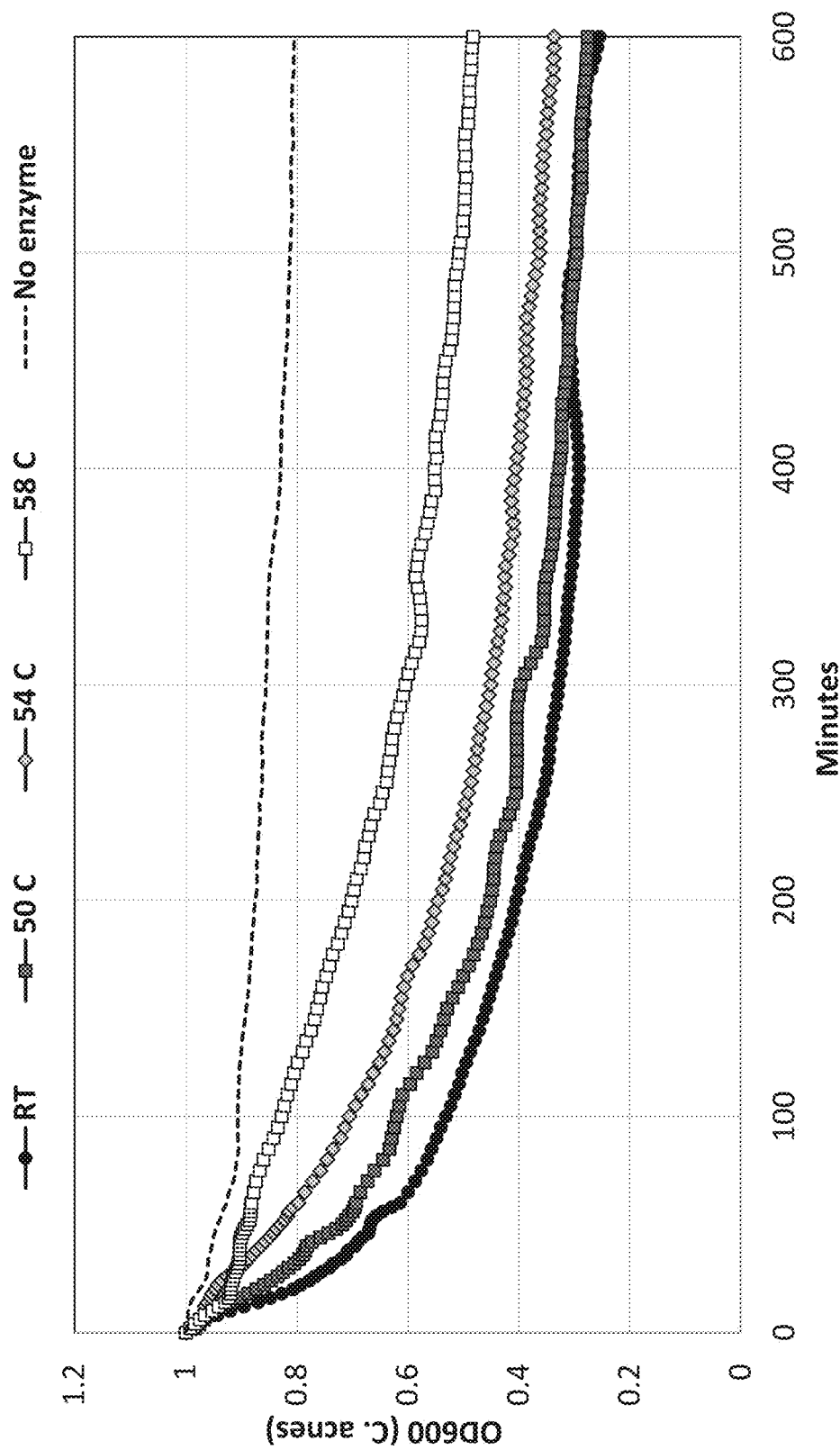

FIG. 17

| | CLC1-EAD | CLC5-EAD | CLC4-EAD | CLC8-EAD | CLC3-EAD | CLC10-EAD | CLC2-EAD | CLC14-EAD | CLC16-EAD |
|---|---|---|---|---|---|---|---|---|---|
| CLC1-EAD | 100 | 96.27 | 95.65 | 90.68 | 88.2 | 88.2 | 88.82 | 80.12 | 78.26 |
| CLC5-EAD | 96.27 | 100 | 94.41 | 88.82 | 86.96 | 88.2 | 86.34 | 79.5 | 79.5 |
| CLC4-EAD | 95.65 | 94.41 | 100 | 90.68 | 89.44 | 85.71 | 86.96 | 78.26 | 77.02 |
| CLC8-EAD | 90.68 | 88.82 | 90.68 | 100 | 92.55 | 85.71 | 84.47 | 80.12 | 78.26 |
| CLC3-EAD | 88.2 | 86.96 | 89.44 | 92.55 | 100 | 81.99 | 84.47 | 81.37 | 79.5 |
| CLC10-EAD | 88.2 | 88.2 | 85.71 | 85.71 | 81.99 | 100 | 81.99 | 79.5 | 77.64 |
| CLC2-EAD | 88.82 | 86.34 | 86.96 | 84.47 | 84.47 | 81.99 | 100 | 83.85 | 78.26 |
| CLC14-EAD | 80.12 | 79.5 | 78.26 | 80.12 | 81.37 | 79.5 | 83.85 | 100 | 79.5 |
| CLC16-EAD | 78.26 | 79.5 | 77.02 | 78.26 | 79.5 | 77.64 | 78.26 | 79.5 | 100 |

CLC14-EAD + CLB2-CBD

CLC16-EAD + CLB2-CBD

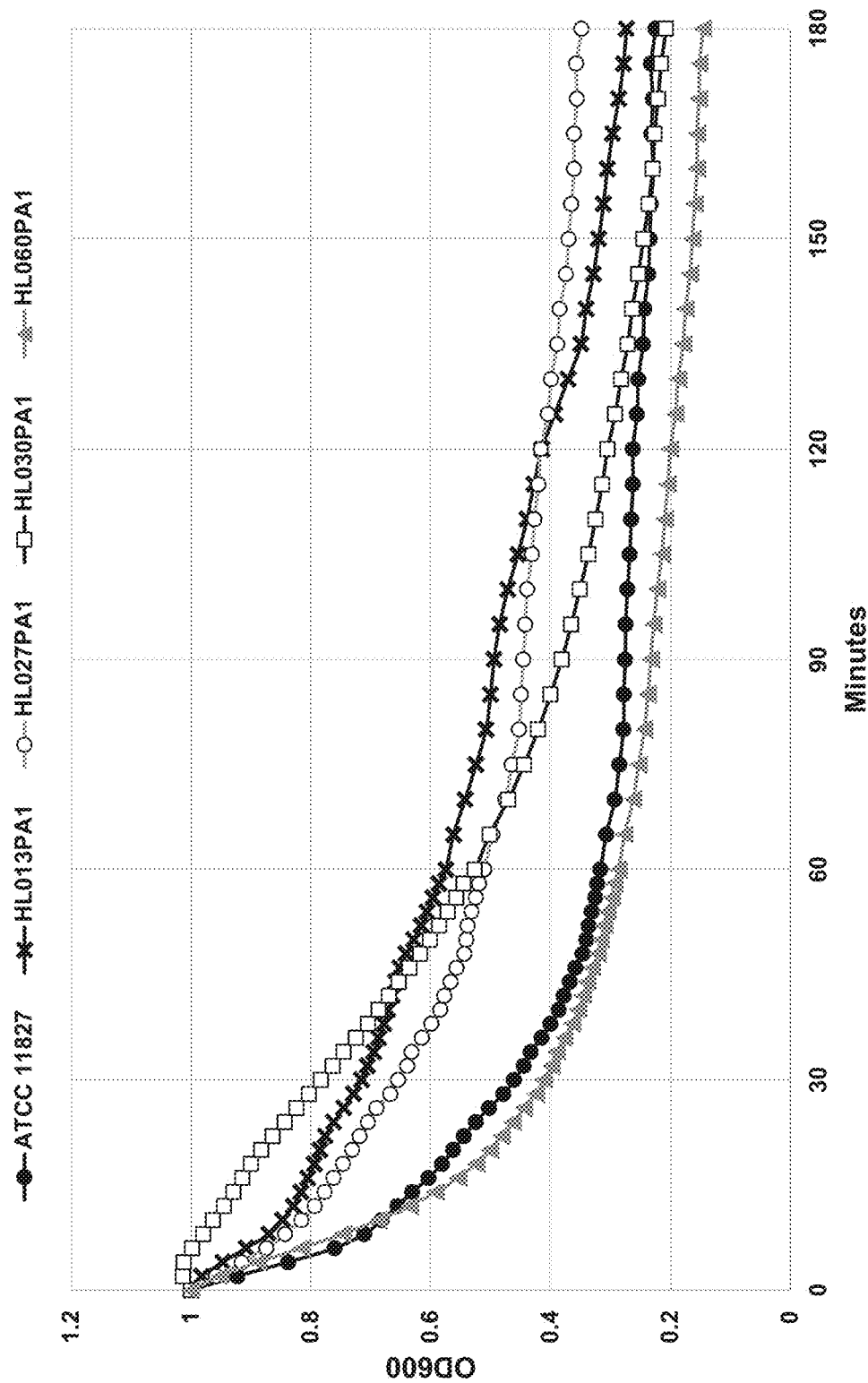

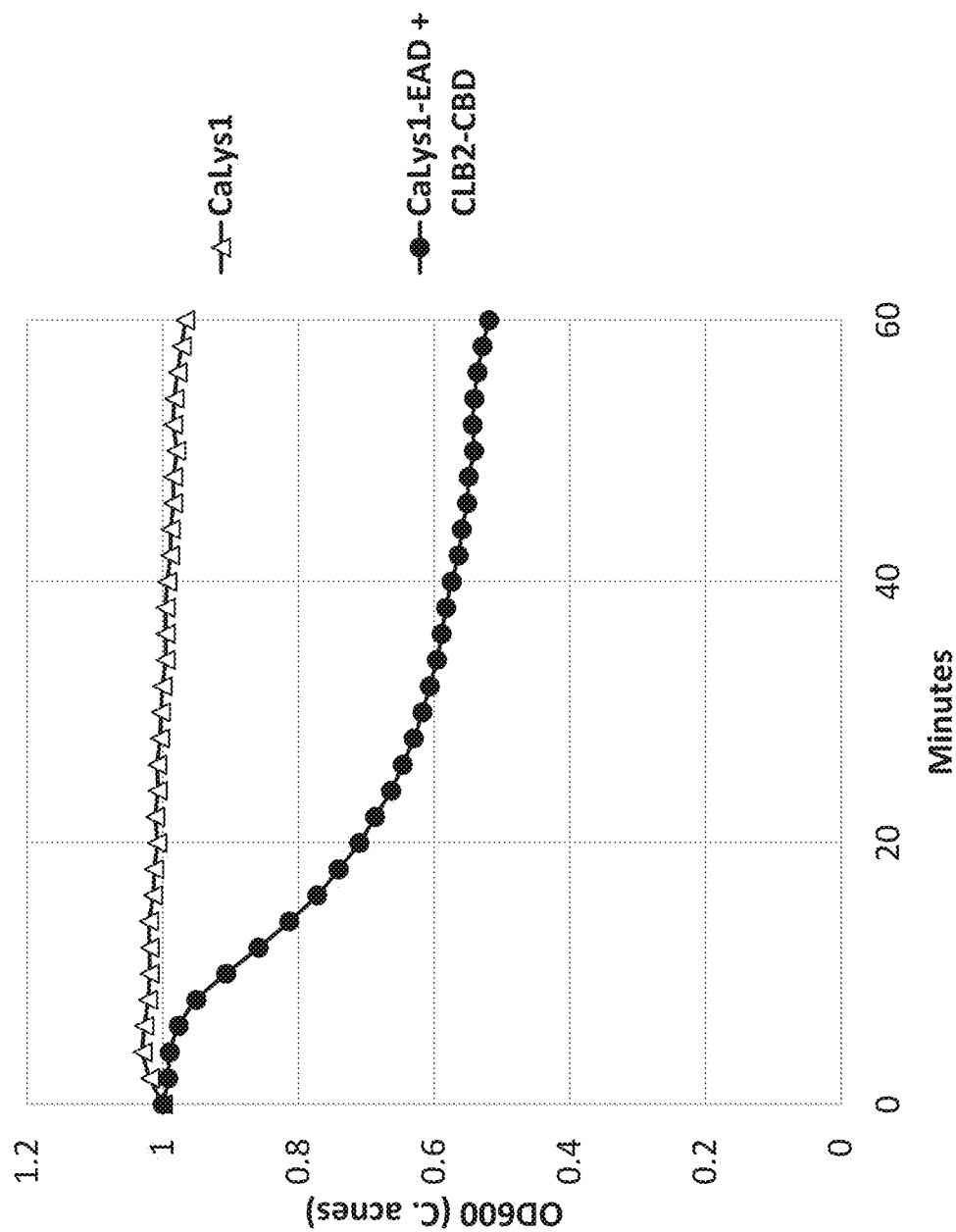

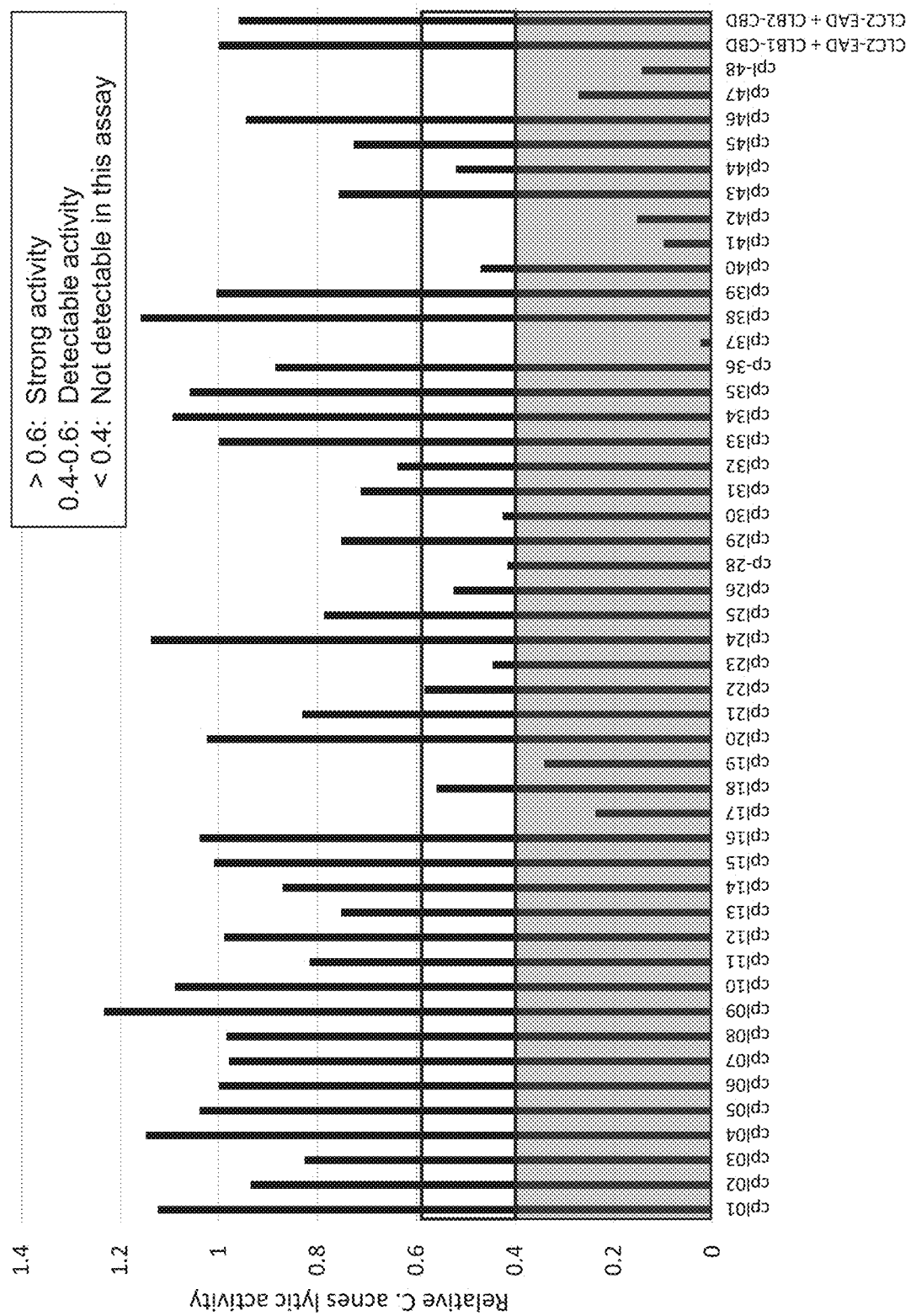

Motif 1:
YXXXQWLSXXVWX
PAVERAAXLARXXC
ICXRXXIPXRXL
XXXXXVXGXGI
XG

Motif 2:
RXXSAHYXXDXXXG
XTXQCLXEXXGI
XHAPPNXXSIGXS
EICXXGGSXXF

Motif 3:
RXVIHXTCPDXG
XPXASXAGRAXS
TAXYF

Motif 4:
VSXAFXXSDHDD
PG

Motif 5:
NXPV/IT/S

CELL WALL HYDROLASES TARGETING C. ACNES

CROSS-REFERENCE TO RELATED APPLICATIONS

This application is a continuation of International Application PCT/US2024/039933, filed Jul. 26, 2024, which claims the benefit of and priority to U.S. Provisional Patent Application No. 63/529,224, filed on Jul. 27, 2023, the contents of which are herein incorporated by reference in their entirety.

STATEMENT REGARDING FEDERALLY SPONSORED RESEARCH

This invention was made with government support under R43 AR082722 awarded by the National Institutes of Health. The government has certain rights in the invention.

REFERENCE TO AN ELECTRONIC SEQUENCE LISTING

The contents of the electronic sequence listing (TOPB_003_01WO_SeqList_ST26.xml; Size: 3,993,956 bytes; and Date of Creation: Jul. 26, 2024) are herein incorporated by reference in their entirety.

FIELD OF THE DISCLOSURE

The present disclosure relates to novel enzymatically active domains, cell wall binding domains, and cell wall hydrolases with activity against *Cutibacterium acnes*. The disclosure also relates to compositions comprising these recombinant domains and proteins, and methods of treating conditions associated with *Cutibacterium acnes*.

BACKGROUND

Acne vulgaris (acne) is a chronic inflammatory disease of the pilosebaceous unit, affecting up to 50 million people in the U.S. annually. Acne can have significant negative effects on psychosocial functioning including higher rates of anxiety, low self-esteem, depression, failure to thrive at school, and suicidal ideation. *Cutibacterium acnes* (previously known as *Propionibacterium acnes*), an anaerobic, gram-positive bacterium, plays a prominent role in acne pathogenesis. *C. acnes* is the most common species in the pilosebaceous unit, and contrary to previous models that linked acne with *C. acnes* proliferation, metagenomic analyses now indicate that the relative abundance of *C. acnes* is similar between healthy and acneic skin. Instead, acne development is now understood to be associated with a loss of *C. acnes* phylotype diversity. *C. acnes* strains are classified into six main phylotypes: $IA_1$, $IA_2$, IB, IC, II and III based on their genomic sequences. Numerous studies have linked acne to higher relative abundances of phylotype $IA_1$. It is believed that it is specifically decreases in non-phylotype $IA_1$ strains that triggers innate immune stimulation and acne pathogenesis. Antibiotics continue to play a central role in the treatment of acne. First-line combination treatments include topical antibiotics for mild to moderate acne and systemic oral antibiotics for moderate to severe acne. While effective, high levels of antibiotic use, particularly systemic oral antibiotics, pose challenges. First, there may be unintended negative effects on the gut and skin microbiomes, including changes in microbial composition, reduced microbial diversity, and changes in functional attributes. Second, overuse of antibiotics promotes antimicrobial resistance, a pressing public health threat. As such, there is a strong need for novel antimicrobial agents that can target *C. acnes* and provide a microbiome-friendly alternative to standard antibiotics.

Endolysins are phage-encoded bacterial cell wall-degrading enzymes that catalyze rapid and selective killing of bacteria in the skin microbiome. Endolysins are normally expressed late in the phage lytic cycle. The endolysin binds and rapidly degrades the host bacterium cell wall, causing the cell to burst, freeing the mature viral particles. Endolysins can lyse their cognate bacteria, even within biofilms, and bacteria are difficult to evolve resistance to endolysins due to the difficulty of changing their peptidoglycan without deleterious effects. However, all prior attempts to develop endolysins targeting *C. acnes* have faced significant challenges.

First, the diversity of known *C. acnes* phages/endolysins is extremely low. Comprehensive efforts to isolate and sequence *C. acnes* phage diversity have found that all isolated *C. acnes* phages thus far are highly similar to each other, with little variation in gene content from genome to genome. The nucleotide sequence identity between any pair of *C. acnes* phage genomes ranges from 85-100% (Liu et al., ISME J. 2015 September; 9(9): 2078-2093; Marinelli et al., mBio. 2012 September-October; 3(5): e00279-12). These genomes contain only a single highly-conserved endolysin (as exemplified by the protein sequence with NCBI accession ID: YP_006907103.1, which is referred to as "CaLys1" hereinafter) greatly limiting the amount of natural diversity that can be leveraged for endolysin development. In contrast, endolysins that target *Staphylococcus* sp. can be divided into at least 27 sub-groups (Oliveira et al., BMC Genomics. 2019 May 9; 20(1):357).

The second challenge is that attempts to characterize CaLys1 and close homologs from *C. acnes* phages have encountered issues with low solubility and low activity. Multiple groups have attempted to recombinantly express CaLys1 and close homologs and found the protein to be insoluble. Labor-intensive methods such as the use of urea gradients are needed to resolubilize the protein, an approach that is not commercially viable. In addition, this endolysin has exhibited low activity with activity assays utilizing high concentrations of protein (e.g. 100 mg/mL) (see, e.g., WO 2021/175606; Varotsou et al., Int J Mol Sci. 2023 May 10; 24(10):8523).

Thus, there is a strong unmet need for new endolysins (and bacterial cell wall hydrolases more generally) that can selectively target *C. acnes* with improved characteristics compared to the currently known CaLys1 family.

BRIEF SUMMARY

The present disclosure teaches chimeric cell wall hydrolases (CWH) with desirable properties. In some embodiments, the CWHs of the present disclosure are capable of selectively treating conditions associated with *Cutibacterium acnes*.

In one aspect, the present disclosure provides a chimeric cell wall hydrolase (CWH) comprising: a CW_7 cell wall binding domain (CBD), and a CLC1-family enzymatically active domain (EAD).

In another aspect, the present disclosure provides a chimeric cell wall hydrolase (CWH) comprising:
a. a cell wall binding domain (CBD) comprising a CW_7 amino acid sequence having at least 40, 45, 50, 55, 60, 65, 70, 75, 80, 85, 90, 95, 96, 97, 98, or 99% sequence identity to, or having the sequence of:
  i. SEQ ID NO: 47;
  ii. an amino acid sequence selected from the group consisting of SEQ ID NO: 45, 46, 48, 49, 50, and 51;
  iii. a CW_7 sequence comprised by an amino acid sequence selected from the group consisting of SEQ ID NO: 166-223;
  iv. a CW_7 sequence comprised by an amino acid sequence selected from the group consisting of SEQ ID NO: 282-2938; or
  v. a CW_7 sequence comprised by an amino acid sequence selected from Table 7; and
b. an enzymatically active domain (EAD) comprising an amino acid sequence having at least 40, 45, 50, 55, 60, 65, 70, 75, 80, 85, 90, 95, 96, 97, 98, or 99% sequence identity to, or having the sequence of:
  i. SEQ ID NO: 35;
  ii. SEQ ID NO: 21;
  iii SEQ ID NO: 73;
  iv. an amino acid sequence selected from the group consisting of SEQ ID NO: 20-36;
  v. an EAD derived from SEQ ID NO: 1-19;
  vi. an EAD derived from CLC16, CLC2, CLC1, CLC3, CLC4, CLC5, CLC6, CLC7, CLC8, CLC9, CLC10, CLC11, CLC12, CLC13, CLC14, CLC15, CLC17, CLC18, or CLC19;
  vii. SEQ ID NO: 64; or
  viii. SEQ ID NO: 63.

In another aspect, the present disclosure provides a recombinant protein comprising a CLC1-family enzymatically active domain (EAD).

In another aspect, the present disclosure provides a recombinant protein comprising a CW_7 cell wall binding domain (CBD).

In another aspect, the present disclosure provides an enzymatically active, C-terminally truncated recombinant CLC1-family protein or CaLys1 protein.

In another aspect, the present disclosure provides a formulation comprising a chimeric CWH, recombinant protein, or truncated protein of any one of the foregoing embodiments, optionally wherein the formulation is a topical formulation.

In another aspect, the present disclosure provides a method of treating a condition associated with *Cutibacterium acnes* (*C. acnes*), the method comprising: administering a composition comprising a recombinant protein, chimeric CWH, or truncated protein of any one of the foregoing embodiments or a formulation of any one of the foregoing embodiments.

In another aspect, the present disclosure provides a method of restoring the phylotype diversity of *Cutibacterium acnes*, the method comprising: administering a composition comprising a recombinant protein, chimeric CWH, or truncated protein of any one of the foregoing embodiments or a formulation of any one of the foregoing embodiments.

In another aspect, the present disclosure also provides a method of identifying a novel CW_7 cell wall binding domain for use in binding, targeting and/or lysing *Cutibacterium acnes*, the method comprising the steps of:
  a. Searching a genetic database with a known CW_7 query sequence;
  b. Identifying sequences exceeding an amino acid sequence identity cutoff to the query sequence;
  c. Cloning the CW_7 sequence, or the CW_7-comprising CBD sequence, into a chimeric cell wall hydrolase in combination with an enzymatically active domain (EAD) to form a CW_7 chimera; and
  d. Assaying the CW_7 chimera for binding, targeting, and/or lytic activity against *Cutibacterium acnes*.

BRIEF DESCRIPTION OF THE SEVERAL VIEWS OF THE DRAWINGS

The accompanying figures, which are incorporated herein and form a part of the specification, illustrate some, but not the only or exclusive, example embodiments and/or features. It is intended that the embodiments and figures disclosed herein are to be considered illustrative rather than limiting.

FIG. 5A-5D show the results of turbidity reduction assays against *C. acnes* comparing C-terminal truncations to full-length native CLC1-family proteins and CaLys1. Results correspond to CLC2 (FIG. 5A), CLC3 (FIG. 5B), CLC16 (FIG. 5C) and CaLys1 (FIG. 5D)

FIG. 8A-8B show lytic activity assay results demonstrating that CLB1-CBD and CLB2-CBD can be used to create chimeric endolysins that target *C. acnes*. Results are shown for CLB1-CBD and CLB2-CBD in combination with an EAD from a protein that targets *Clostridium dificile* (CD27L) (FIG. 8A) and in combination with an EAD from a protein that targets *Geobacillus* sp. (PlyGVE2) (FIG. 8B).

FIG. 13A-13D show results of turbidity reduction assays, demonstrating selectivity for *C. acnes* over commensal skin bacteria from other genera for four chimeric proteins of the disclosure: CLC1-EAD+CLB1-CBD (FIG. 13A); CLC1-EAD+CLB2-CBD (FIG. 13B); CLC3-EAD+CLB1-CBD (FIG. 13C); and CLC3-EAD+CLB2-CBD (FIG. 13D).

FIG. 14A-14D show results of thermostability assays on four chimeric proteins of the disclosure: CLC1-EAD+CLB1-CBD (FIG. 14A); CLC1-EAD+CLB2-CBD (FIG. 14B); CLC3-EAD+CLB1-CBD (FIG. 14C); and CLC3-EAD+CLB2-CBD (FIG. 14D).

FIG. 17 shows the percent amino acid sequence identity among the EADs from CLC1, CLC5, CLC4, CLC8, CLC3, CLC10, CLC2, CLC14, and CLC16.

FIG. 20A-20D show the results of turbidity reduction assays against different strains and phyla of *C. acnes* for two chimeras of the disclosure. FIG. 20A shows results for the CLC1-EAD+CLB2-CBD chimera against strains ATCC 11827, HL013PA1, HL027PA1, HL030PA1, and HL060PA1. FIG. 20B shows results for the CLC1-EAD+CLB2-CBD chimera against strains ATCC 11827, HL001PA1, and HL056PA1. FIG. 20C shows results for the CLC16-EAD+CLB2-CBD chimera against strains ATCC 11827, HL013PA1, HL027PA1, HL030PA1, and HL060PA1. FIG. 20D shows results for the CLC16-EAD+CLB2-CBD chimera against strains ATCC 11827, HL001PA1, and HL056PA1.

FIG. 21A-21C show the results of turbidity reduction assays for full-length CaLys1 and the CaLys1-EAD+CLB2-CBD chimeric protein against *C. acnes* (FIG. 21A), *C. striatum* (FIG. 21B), and *S. aureus* (FIG. 21C).

FIG. 23A shows the result of whole cell lysate screening of diverse CW_7 CBD comprising chimeras in a turbidity reduction assay.

DETAILED DESCRIPTION

Figure 1A:
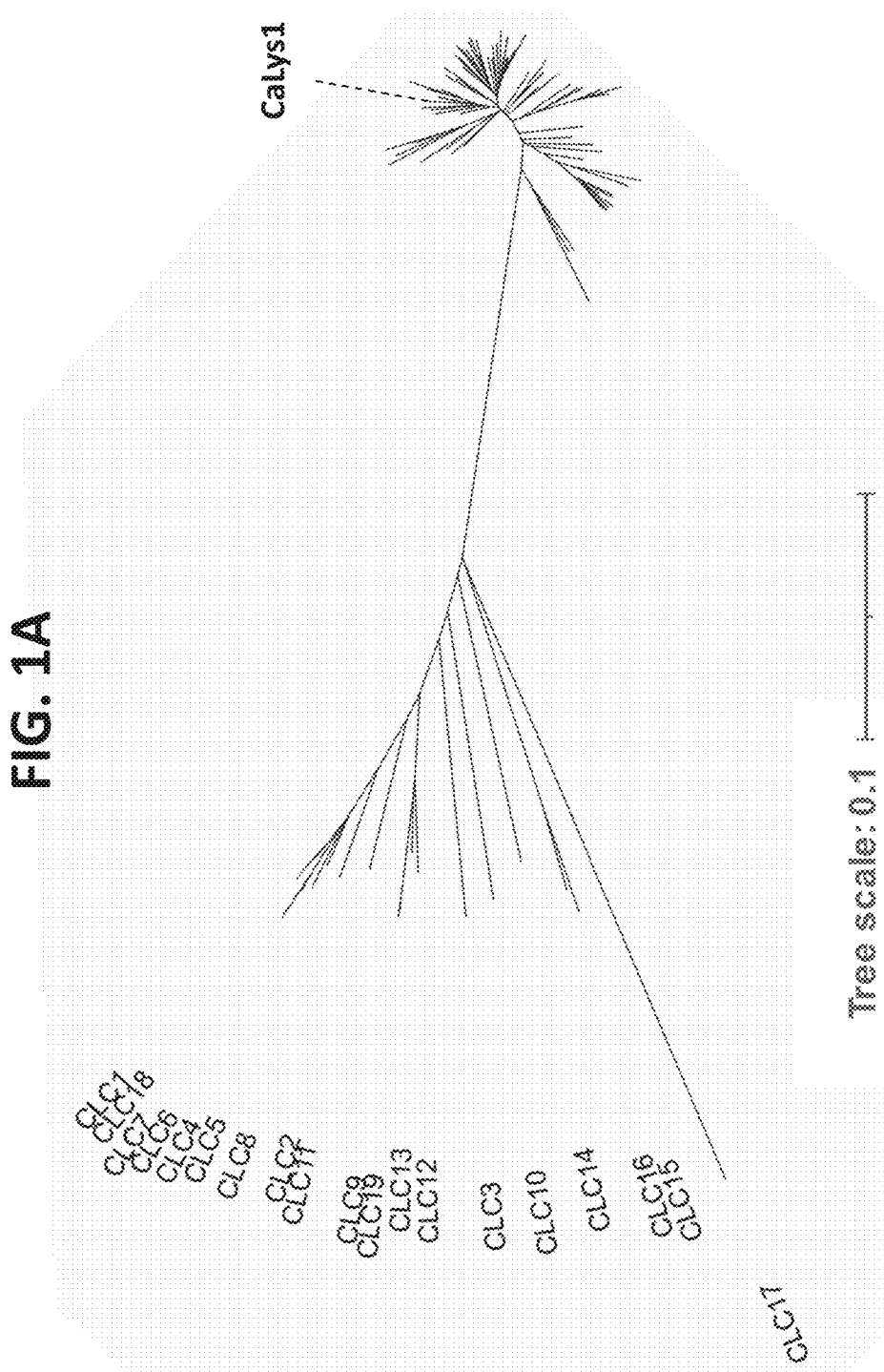
FIG. 1A shows a phylogenetic tree containing CLC1-CLC19 as well as endolysins found in the genomes of *C. acnes* strains/phages including CaLys1. The CLC1 family of proteins form a distinct grouping separate from the CaLys1 family of endolysins.

All publications, patents and patent applications, including any drawings and appendices, are herein incorporated by reference to the same extent as if each individual publication or patent application was specifically and individually indicated to be incorporated by reference.

The following description includes information that may be useful in understanding the present disclosure. It is not an admission that any of the information provided herein is prior art, or that any publication specifically or implicitly referenced is prior art.

Definitions

The term "a" or "an" refers to one or more of that entity, i.e. can refer to plural referents. As such, the terms "a," "an," "one or more," and "at least one" are used interchangeably herein. In addition, reference to "an element" by the indefinite article "a" or "an" does not exclude the possibility that more than one of the elements is present, unless the context clearly requires that there is one and only one of the elements.

Throughout this application, the term "about" is used to indicate that a value includes the inherent variation of error for the device or the method being employed to determine the value, or the variation that exists among the samples being measured. Unless otherwise stated or otherwise evident from the context, the term "about" means within 10% above or below the reported numerical value (except where such number would exceed 100% of a possible value or go below 0%). When used in conjunction with a range or series of values, the term "about" applies to the endpoints of the range or each of the values enumerated in the series, unless otherwise indicated. As used in this application, the terms "about" and "approximately" are used as equivalents.

Unless otherwise indicated, it is to be understood that all numbers expressing quantities, ratios, and numerical properties of ingredients, reaction conditions, and so forth, used in the specification and claims are contemplated to be able to be modified in all instances by the term "about".

As used herein, the term "cell wall hydrolase" or "CWH" refers to bacterial cell wall hydrolases, which are enzymes that degrade peptidoglycan in bacterial cell walls by cleaving bonds in the peptidoglycan chain and side-chain branches. Cell wall hydrolases may have different domain architectures. CWHs comprise an "enzymatically active domain" or "EAD," which is a domain responsible for degrading peptidoglycan. In some embodiments, the EAD has glycosidase, amidase, and/or peptidase enzymatic activity. In some embodiments, CWHs comprise a "cell wall binding domain" or "CBD", which is a domain that binds to a bacterial cell wall.

A "native" protein is used to indicate a protein that occurs in nature and has not been artificially modified or recombined.

The term "recombinant" is used herein to describe nucleic acids, proteins, vectors, and host cells which do not occur in nature or, in the context of nucleic acids, are in an arrangement not found in nature. A "recombinant protein" therefore refers to a protein which does not occur in nature. In some embodiments, recombinant protein, as used herein, refers to a chimeric protein. In some embodiments, recombinant protein refers to the expression product of any of the presently disclosed EAD or CBD sequences alone, or within a protein that does not occur in nature. For example, the present disclosure envisions recombinant EAD or CBD sequences of the disclosure fused to any protein tags, such as 6×His.

As used herein, "heterologous" refers to any genetic material that is artificially introduced into a non-native context. E.g., a heterologous domain refers to a domain, such as an EAD or CBD, that is artificially introduced into a recombinant protein sequence, wherein the resulting recombinant protein sequence is non-native. Two polypeptide sequences or domains are heterologous to one another if they are derived from different native polypeptide sequences or proteins. For example, in some embodiments, a CBD and an EAD are heterologous to each other if they are derived from different native proteins.

As used herein, a "chimeric protein" is any recombinant protein comprising two or more heterologous domains, e.g., EADs and/or CBDs.

As used herein, a "domain" of a protein is a functional and/or structural subunit in a protein. In some embodiments, they are responsible for a particular function or interaction, contributing to the overall role of a protein. Protein domains are fundamental units of protein structure, folding, function, evolution and design. See, e.g., Wang et al., "Protein domain identification methods and online resources," *Comput Struct Biotechnol J* 2021; 19:1145-1153, incorporated by reference herein.

As used herein, a "chimeric cell wall hydrolase" or "chimeric CWH" is a chimeric protein that acts as a cell wall hydrolase and comprises at least one heterologous domain, e.g., a heterologous EAD or CBD, compared to a native CWH sequence. In some embodiments, a chimeric CWH refers herein to a recombinant protein comprising two heterologous CWH domains, e.g., an EAD and a CBD.

As used herein, "activity" refers to the ability of a chimeric protein to inhibit the growth of and/or lyse a cell from a *Cutibacterium acnes* species. The term "active against", as used herein with reference to a target species of *Cutibacterium acnes*, refers to a chimeric protein, e.g., a CWH, of the disclosure that is able to inhibit the growth of and/or lyse cells belonging to that target species of *Cutibacterium acnes*. Activity can be calculated in different ways, depending on the assay performed. In some embodiments, level of activity is indicated based on minimum inhibitory concentration ("MIC"), e.g., the minimum concentration of the protein required to prevent growth of the target *Cutibacterium acnes* species in an MIC assay. In some embodiments, level of activity is indicated based on turbidity reduction, e.g., with activity calculated as $-\Delta OD_{600}/min/(mg$ of enzyme). In some embodiments, activity is indicated based on the decrease in viable bacterial cells in a culture after a period of incubation (e.g., 2 hours) with a protein.

In the context of anti-*Cutibacterium acnes* activity, the terms "selective" and "selectivity" as used herein refer to the property of showing higher activity toward one target species of *Cutibacterium acnes* in comparison to a second species of *Cutibacterium acnes*. Selectivity can be calculated by comparing the inverse of the MIC of a chimeric protein toward a first species to the MIC of the protein toward a second species. In some embodiments, selectivity is determined based on relative activity in a turbidity reduction assay.

As used herein the term "sequence identity" refers to the extent to which two optimally aligned polynucleotides or polypeptide sequences are invariant throughout a window of alignment of residues, e.g. nucleotides or amino acids. An "identity fraction" for aligned segments of a test sequence and a reference sequence is the number of identical residues which are shared by the two aligned sequences divided by the total number of residues in the reference sequence segment, i.e. the entire reference sequence or a smaller defined part of the reference sequence. "Percent identity" is the identity fraction times 100. Comparison of sequences to determine percent identity can be accomplished by a number of well-known methods, including for example by using mathematical algorithms, such as, for example, those in the BLAST suite of sequence analysis programs. Unless noted otherwise, the term "sequence identity" in the claims refers to sequence identity as calculated by MUSCLE (www.ebi.ac.uk/Tools/msa/muscle/) using default parameters.

As used herein, the term "CW_7 cell wall binding domain" or "CW_7 CBD" refers to a cell wall binding domain containing one or more CW_7 sequences. In some embodiments, a CW_7 CBD comprises, consists essentially of, or consists of a CW_7 sequence.

The term "including all ranges and subranges therebetween" or equivalents, are used herein to denote the intention that disclosure of any range or series of possible values, inherently also discloses all ranges and subranges encompassed by the highest and lowest values disclosed. This term includes the entire range from highest to lowest disclosed values, as well as subranges from any two or more disclosed points. This term is also intended to disclose any subranges encompassed anywhere within the highest and lowest disclosed values, including between two points that are explicitly recited in the document, up to one decimal point. Thus, disclosure of values 0, 5, 10, 15, 20, including all ranges and subranges therebetween, should be interpreted as also encompassing a range from 0-20, a range from 0-5 or 5-15, as well as a range from 2-16, or 3.1 to 19.8, etc.

Unless otherwise indicated, it is to be understood that all numbers expressing quantities, ratios, and numerical properties of ingredients, reaction conditions, and so forth, used in the specification are contemplated to be able to be modified in all instances by the term "including all ranges and subranges therebetween".

Overview

The present disclosure provides novel enzymatically active domains (EADs), truncated enzymes, cell wall binding domains (CBDs), and chimeric cell wall hydrolases (CWHs) that exhibit binding and/or enzymatic activity against *Cutibacterium acnes*. Also provided herein are compositions comprising the EADs, truncated enzymes, CBDs, and chimeric CWHs, as well as uses thereof in targeting *Cutibacterium acnes* and treating conditions associated with *Cutibacterium acnes*.

CWHs are enzymes that degrade bacterial peptidoglycan by cleaving bonds in the peptidoglycan chain and side-chain branches. Degradation of peptidoglycan cell walls by CWHs can result in rapid lysis of a bacterial cell due to an inability to resist internal turgor pressure. The advantages of using CWHs to treat *Cutibacterium acnes* associated conditions include their high specificity. CWHs, e.g., gram-positive endolysins, have one or more cell wall-binding domains that bind specific epitopes within the target cell wall. Because the composition and organization of the peptidoglycan cell wall can vary greatly between bacterial species, CWHs often have lytic specificity down to a genus, species, or even subspecies. In active acne, the diversity of *C. acnes* phylotypes has decreased such that broad removal of resident *C. acnes* may help re-establish phylotype diversity. CWHs also provide a more direct and stable mechanism of action than phage therapy, another proposed antibiotic alternative.

As demonstrated in the Examples herein, the present disclosure provides novel and highly effective EADs, truncated enzymes, CBDs, and chimeric CWHs, exhibiting high lytic activity and/or *Cutibacterium acnes* species-specificity. In some embodiments, the chimeric CWH is composed of domains from parent proteins and has properties that are superior to any of the parent proteins. In some embodiments, CWHs herein bind very specific epitopes in target cell walls. In some embodiments, CWHs herein have lytic activity down to a single species or group of related species. Because of these properties, in some embodiments, the CWHs herein act as high-specificity skin microbiome modulators. For example, in some embodiments, CWHs herein are able to specifically kill or modulate the diversity of *Cutibacterium acnes*, while exhibiting significantly less activity against healthy, commensal bacteria.

Enzymatically Active Domains (EADs) and Truncated Enzymes

In some embodiments, a recombinant protein of the disclosure comprises an EAD, enzyme, or truncated enzyme disclosed herein. In some embodiments, a recombinant protein of the disclosure comprises an EAD disclosed herein. In some embodiments, a recombinant protein of the disclosure consists essentially of or consists of an EAD disclosed herein. In some embodiments, the recombinant protein is a chimeric protein or a chimeric CWH comprising an EAD. In some embodiments, a recombinant protein of the disclosure comprises an EAD disclosed herein in combination with a CBD disclosed herein.

The present disclosure provides novel enzymes and enzymatically active domains (EADs). The inventors of the present disclosure discovered a novel class of enzymes with activity against *C. acnes*, termed herein the CLC1-family enzymes. See FIGS. 1A-1B and Tables 1-2. As shown in the Examples herein, these novel enzymes, and the EADs they comprise, exhibit significant activity against *C. acnes*, even in the absence of a CBD.

TABLE 1

CLC1-family enzymes.

| ID | Organism | Genbank Acc. # | SEQ ID NO |
|---|---|---|---|
| CLC1 | Cutibacterium avidum TM16 | ERF59075.1 | 1 |
| CLC2 | Cutibacterium granulosum DSM 20700 | ERF55529.1 | 2 |
| CLC3 | Cutibacterium avidum | WP_065673254.1 | 3 |
| CLC4 | *Caudoviricetes* sp. | DAI62752.1 | 4 |
| CLC5 | Cutibacterium avidum | BCQ03178.1 | 5 |
| CLC6 | Cutibacterium avidum | MCO6633004.1 | 6 |
| CLC7 | Cutibacterium avidum | WP_279187040.1 | 7 |
| CLC8 | Cutibacterium avidum | WP_202725644.1 | 8 |
| CLC9 | Cutibacterium avidum | MCO6684721.1 | 9 |
| CLC10 | Cutibacterium porci | WP_154562382.1 | 10 |
| CLC11 | Cutibacterium granulosum DSM 20700 | KAG9059780.1 | 11 |
| CLC12 | Cutibacterium avidum | WP_252923283.1 | 12 |
| CLC13 | *Propionibacterium* sp. KPL2005 | ERS24858.1 | 13 |
| CLC14 | Cutibacterium avidum | WP_117188621.1 | 14 |
| CLC15 | *Caudoviricetes* sp. | DAX95823.1 | 15 |
| CLC16 | *Caudoviricetes* sp. | DAK10468.1 | 16 |
| CLC17 | Cutibacterium avidum | WP_202711633.1 | 17 |
| CLC18 | Cutibacterium avidum | MCO6632604.1 | 18 |
| CLC19 | Cutibacterium avidum | MCO6688344.1 | 19 |

TABLE 2

CLC1-family EADs.

| EAD | SEQ ID # | Amino Acid Sequence |
|---|---|---|
| CLC1-EAD | 20 | SNTPITRLVIHATCPDVGYPSASKAGRAVS TAEYFASTSRSASAHYVCDVSATVQCLSEE TIGYHAPPNSHSIGIEICADGGSRASFEKA SHAYTREQWLSPQVWPAVERAAILARGICH RHHIPVRKLTTAQVKSGMSGICGHDNVSDA FHQSDHDDPGP |
| CLC2-EAD | 21 | SNTPITRLVIHATCPDVGFPSASRAGRAVS TAEYFASTSRSASAHYVCDISTTVQCLSEA TIGYHAPPNAHSIGIEICADGGSRASFEKA SHAYTREQWLSPQVWPAVERAAILARDICH RHHIPIRRLSVAQVRAGERGICGHNEVSEA FHQSDHDDPGP |
| CLC3-EAD | 22 | SNAPITRLVIHATCPDVGYPSASKAGRAVS TANYFATTDRPASAHYVCDIATTVQCLSEE TIGYHAPPNSHSIGIEICADGGSHASFEKA SHAYTRDQWLSDDVWPAVERAAILARDICQ RHRIPVRKLSTAQVKAGLSGICGHDNVSGA FHQSDHDDPGP |
| CLC4-EAD | 23 | SNAPITRLVIHATCPDVGYPSASKAGRAVS TAEYFASTSRSASAHYVCDIAATVQCLSEE AIGFHAPPNSHSIGIEICADGGSRASFEKA SHAYTREQWLSPQVWPAVERAAILARDICR RHHIPVRKLTTAQVKSGMSGICGHDNVSDA FHQSDHDDPGP |
| CLC5-EAD | 24 | SNTPVTRLVIHATCPDVGYPSASKAGRAVS TAEYFASTSRSASAHYVCDVSATVQCLSEE |

TABLE 2-continued

CLC1-family EADs.

| EAD | SEQ ID # | Amino Acid Sequence |
|---|---|---|
|  |  | AIGYHAPPNSHSIGIEICADGGSHASFETA SHAYTREQWLSPQVWPAVERAAILARDICH RHHIPVRKLTTAQVKSGMSGICGHDNVSDA FRQSDHDDPGP |
| CLC6-EAD | 25 | SNNPVTRLVIHATCPDVGYPSASKAGRAVS TAQYFASTSRPASAHYVCDVSATVQCLSEE TIGYHAPPNAHSIGIEICSDGGSRASFEKA SHAYSREQWLSPQVWPAVERAAILARDICH RHRIPVRKLTAAQVKSGMSGICGHDNVSDA FRQSDHDDPGP |
| CLC7-EAD | 26 | SNAPITRLVIHATCPDVGYPSASKAGRAVS TAHYFAEATRPASAHYVCDVSATVQCLSEE TIGYHAPPNAHSIGIEICSDGGSRASFEKA SHAYSREQWLSPQVWPAVERAAILARDICH RHRIPVRKLTAAQVKSGMSGICGHDNVSDA FRQSDHDDPGP |
| CLC8-EAD | 27 | SNTPITRLVIHATCPDVGYPSASRAGRAAS TANYFATTDRPASAHYVCDIATTVQCLSEE VIGFHAPPNSHSIGIEICADGGSHASFEKA SHAYTREQWLSDDVWPAVERAAILARGICH RHHIPVRKLSTAQVKSGMSGICGHDNVSDA FHQSDHDDPGP |
| CLC9-EAD | 28 | TNAPVTRLVIHSTCPDVGFPSASRAGRAVS TAGYFASTSRPASAHYVVDVTTTVQCLPEN TIGYHAPPNSHSIGIEICSDGGSRASFENP SHAYTREQWLSPQVWPAVERAAILARGICH RHHIPVRKLTTAQVKNGMSGICGHDNVSDA FHQSDHDDPGP |
| CLC10-EAD | 29 | NTPVTRLVIHATCPDTGYPSASRAGRAAST ARYFQSTSRPTSAHYVCDVTATVQCLSEET IGYHAPPNAHSIGIEICADGGSKSSFDNPS HSYTREQWLSPQVWPAVERAAILARDICHR HHIPVRKLSTAQVKSGMSGICGHDNVSDAF HQSDHDDPGP |
| CLC11-EAD | 30 | SNTPITRLVIHATCPDVGFPSASRAGRAVS TAEYFASTSRSASAHYVCDISTTVQCLSEA TIGYHAPPNAHSIGIEICAAGGSRASFEKA SHAYTREQWLSPQVWPAVERAAILARDICH RHHIPIRRLSVAQVRAGERGICGHNEVSEA FHQSDHDDPGP |
| CLC12-EAD | 31 | TNAPVSRLVIHSTCPDVGFPSASRAGRAVS TAEYFASTSRPASAHYVVDIATTVQCLPEN TIGYHAPPNSHSIGIEICSDGGSRASFEKA SHAYTREQWLSPQVWPAVERAAILARDICH RHRIPVRKLSTAQVKNGMSGICGHDNVSDA FHQSDHDDPG |
| CLC13-EAD | 32 | TNAPVTRLVIHSTCPDVGFPSASRAGRAVS TAGYFASTSRPASAHYVVDVTTTVQCLPEN TIGYHAPPNSHSIGIEICSDGGSRASFENP SHAYTREQWLSPQVWPAVERAAILARDICH RHRIPVRKLSTAQVKNGMSGICGHDNVSDA FHQSDHDDPGP |
| CLC14-EAD | 33 | NNPPVTRLVIHATCPDVGYPSASRAGRAVS TAHYFQETTRPASAHYICDISTTVQCLSEE TVGYHAPPNSHSIGIEICADGGSHASFSNP AHAYTREQWLSPQVWPAVERAAMLARGICQ RHNIPIRRLSIADVKAGKRGICGHNEVSEA FHQSDHDDPGP |
| CLC15-EAD | 34 | SNKPVTRLVIHSTCPDVGFPSASRAGRAES TANYFADSSRPASAHYVCDVSTTIQCLHED VVGYHAPPNSHSIGIEICSDGGSRASFRNP NHAYTREQWLSPQVWPAVERAAVLARDICK RNGIPIRKLSTSEVKAGRSGICGHNNVSDA FHQSDHDDPGP |
| CLC16-EAD | 35 | SNKPVTRLVIHSTCPDVGFPSASRAGRAES TANYFADSSRPASAHYVCDVSTTIQCLHED IVGYHAPPNSHSIGIEICSDGGSHASFNNP KHAYTRDQWLSPQVWPAVERAAVLARDICK RNGIPIRKLSTSEVKAGRSGICGHNNVSDA FHQSDHDDPGP |
| CLC17-EAD | 36 | TNAPVSRIVIHSTCPDVGFPAASKAGRAVS TANYFASTSRPASAHYVVDIATTVQCLPEN TVGYHAPPNSGSIGIEICSDGGSKGSFENP AHAYTTTQWLSPEVWPAVERAAILAREICH RHHIPIRRLSVAQVRAGERGICGHNEVSEA FHRSDHDDPGP |

In some embodiments, a recombinant protein of the disclosure comprises a CLC1-family EAD. In some embodiments, a recombinant protein of the disclosure comprises an EAD having at least 40, 45, 50, 55, 60, 65, 70, 75, 80, 85, 90, 95, 96, 97, 98, 99, or 100% sequence identity to a CLC1-family EAD. In some embodiments, a recombinant protein of the disclosure comprises an EAD having at least 80, 81, 82, 83, 84, 85, 86, 87, 88, 89, 90, 91, 92, 93, 94, 95, 96, 97, 98, 99, or 100% sequence identity to a CLC1-family EAD. In some embodiments, a recombinant protein of the disclosure comprises an EAD differing by 1, 2, 3, 4, 5, 6, 7, 8, 9, 10, 11, 12, 13, 14, or 15 amino acids from a CLC1-family EAD.

In some embodiments, a recombinant protein of the disclosure comprises a CLC1-family EAD disclosed in Table 2. In some embodiments, a recombinant protein of the disclosure comprises an EAD having at least 40, 45, 50, 55, 60, 65, 70, 75, 80, 85, 90, 95, 96, 97, 98, 99, or 100% sequence identity to a CLC1-family EAD disclosed in Table 2. In some embodiments, a recombinant protein of the disclosure comprises an EAD having at least 80, 81, 82, 83, 84, 85, 86, 87, 88, 89, 90, 91, 92, 93, 94, 95, 96, 97, 98, 99, or 100% sequence identity to a CLC1-family EAD disclosed in Table 2. In some embodiments, a recombinant protein of the disclosure comprises an EAD differing by 1, 2, 3, 4, 5, 6, 7, 8, 9, 10, 11, 12, 13, 14, or 15 amino acids from a CLC1-family EAD disclosed in Table 2.

In some embodiments, a recombinant protein of the disclosure comprises the CLC16 EAD (SEQ ID NO: 35). In some embodiments, a recombinant protein of the disclosure comprises an EAD having at least 40, 45, 50, 55, 60, 65, 70, 75, 80, 85, 90, 95, 96, 97, 98, 99, or 100% sequence identity to the CLC16 EAD (SEQ ID NO: 35). In some embodiments, a recombinant protein of the disclosure comprises an EAD having at least 80, 81, 82, 83, 84, 85, 86, 87, 88, 89, 90, 91, 92, 93, 94, 95, 96, 97, 98, 99, or 100% sequence identity to the CLC16 EAD (SEQ ID NO: 35). In some embodiments, a recombinant protein of the disclosure comprises an EAD differing by 1, 2, 3, 4, 5, 6, 7, 8, 9, 10, 11, 12, 13, 14, or 15 amino acids from the CLC16 EAD (SEQ ID NO: 35).

In some embodiments, a recombinant protein of the disclosure comprises the CLC2 EAD (SEQ ID NO: 21). In some embodiments, a recombinant protein of the disclosure comprises an EAD having at least 40, 45, 50, 55, 60, 65, 70, 75, 80, 85, 90, 95, 96, 97, 98, 99, or 100% sequence identity to the CLC2 EAD (SEQ ID NO: 21). In some embodiments, a recombinant protein of the disclosure comprises an EAD having at least 80, 81, 82, 83, 84, 85, 86, 87, 88, 89, 90, 91, 92, 93, 94, 95, 96, 97, 98, 99, or 100% sequence identity to the CLC2 EAD (SEQ ID NO: 21). In some embodiments, a recombinant protein of the disclosure comprises an EAD differing by 1, 2, 3, 4, 5, 6, 7, 8, 9, 10, 11, 12, 13, 14, or 15 amino acids from the CLC2 EAD (SEQ ID NO: 21).

The newly discovered CLC1-family EADs share a conserved sequence motif, the "CLC1-family EAD motif," having the following sequence, where X represents any amino acid:

```
                                        (SEQ ID NO: 2939)
XNXPXXXRXVIHXTCPDXGXPXASXAGRAXSTAXYFXXXXRXXSAH

YXXDXXXTXQCLXEXXXGXHAPPNXXSIGIEICXXGGSXXSFXXX

XHXYXXXQWLSXXVWPAVERAAXLARXICXRXXIPXRXLXXXXVX

XGXXGICGHXXVSXAFXXSDHDDPGX.
```

In some embodiments, a recombinant protein of the disclosure comprises an EAD comprising the CLC1-family EAD motif (SEQ ID NO: 2939). In some embodiments, a recombinant protein of the disclosure comprises an EAD comprising the CLC1-family EAD motif (SEQ ID NO: 2939) and having at least 40, 45, 50, 55, 60, 65, 70, 75, 80, 85, 90, 95, 96, 97, 98, 99, or 100% sequence identity to a CLC1-family EAD disclosed in Table 2. In some embodiments, a recombinant protein of the disclosure comprises an EAD comprising the CLC1-family EAD motif (SEQ ID NO: 2939) and having at least 80, 81, 82, 83, 84, 85, 86, 87, 88, 89, 90, 91, 92, 93, 94, 95, 96, 97, 98, 99, or 100% sequence identity to a CLC1-family EAD disclosed in Table 2. In some embodiments, a recombinant protein of the disclosure comprises an EAD comprising the CLC1-family EAD motif (SEQ ID NO: 2939) and differing by 1, 2, 3, 4, 5, 6, 7, 8, 9, 10, 11, 12, 13, 14, or 15 amino acids from a CLC1-family EAD disclosed in Table 2.

In some embodiments, a recombinant protein of the disclosure comprises an EAD consisting of a sequence according to any one of SEQ ID NO: 20-36 or the EAD region of any one of SEQ ID NO: 1-19. In some embodiments, a recombinant protein of the disclosure comprises an EAD comprising a sequence according to any one of SEQ ID NO: 20-36 or the EAD region of any one of SEQ ID NO: 1-19. In some embodiments, a recombinant protein of the disclosure comprises an EAD having at least 80, 81, 82, 83, 84, 85, 86, 87, 88, 89, 90, 91, 92, 93, 94, 95, 96, 97, 98, or 99 identity with a sequence according to any one of SEQ ID NO: 20-36 or the EAD region of any one of SEQ ID NO: 1-19. In some embodiments, a recombinant protein of the disclosure comprises an EAD differing by 1, 2, 3, 4, 5, 6, 7, 8, 9, 10, 11, 12, 13, 14, or 15 amino acids from a sequence according to any one of SEQ ID NO: 20-36 or the EAD region of any one of SEQ ID NO: 1-19.

TABLE 3

Additional enzymes of the disclosure.

| Description Taxonomy GenBank Acc. No. | Sequence |
| --- | --- |
| CD27L Clostridioides difficile WP_009898411.1 SEQ ID NO: 60 | MKICITVGHSILKSGACTSADGVVNEYQYNKSLAPVLADTFRK EGHKVDVIICPEKQFKTKNEEKSYKIPRVNSGGYDLLIELHLN ASNGQGKGSEVLYYSNKGLEYATRICDKLGTVFKNRGAKLDKR LYILNSSKPTAVLIESFFCDNKEDYDKAKKLGHEGIAKLIVEG VLNKNINNEGVKQMYKHTIVYDGEVDKISATVVGWGYNDGKIL ICDIKDYVPGQTQNLYVVGGGACEKISSITKEKFIMIKGNDRF DTLYKALDFINR |
| PlyGVE2 Geobacillus virus E2 YP_001285830.1 SEQ ID NO: 61 | MKKIFWDKGHGGSDPGAVANGLQEKNLTHKIVEYATDYLAAH YEGFTQRVSREGDQSLTLDQRADMANKWGADVFVSVHINAGK GTGFEIYVHPNASPQSIALQNVLHGEILSAMRQFGNITDRGK KRANYAVLRETKMPAVLTENLFIDSNDAKHLKNEAFLKAVGE AHARGVAKFLGLKEKQKAQPEAKPQQKPSDKKLYRVQVGAFA DRENAERLAEELKRKGYPVYITD |
| PlyD6E Deep-sea thermophilic phage D6E YP_007010941.1 SEQ ID NO: 62 | MVRIVLDAGHGGKDSGAVGNGLREKDLTLNIVKKIGNLLAEYE GVEVHYTRTDDRFLELSERAEIANRLKADYFISVHINAGGGTG FESYIYNGNVSSATIAYQNVIHSEIMKAIGNVTDRGKKRANYA VLRETHMPALLTENLFIDNKNDAAKLDSEQFLLQVAHGHVQGI VKAFGLKKKATPQPQQKVSDKKLYRVQVGAFADRKNAERLADE LKKKGYPVYITD |
| CaLys1 Propionibacterium phage ATCC29399B_T YP_006906916.1 SEQ ID NO: 72 | MRYIPAAHHSAGSNHPVNRVVIHATCPDVGFPSASRKGRAVST ANYFASPSSGGSAHYVCDIGETVQCLSEGTIGWHAPPNPHSLG IEICADGGSHASFRVPGHAYTREQWLDPRVWPAVEKAAILCRR LCDKYNVPKRKLSAADLKAGRRGVCGHVDVTDAWHQSDHDDPG PWFPWDRFMAVVNGHNESGELTVADVKALHDQIKQLSAQLAGS VNKLHHDVGVVQVQNGDLGKRVDALSWVKNPVTGKLWRTKDAL WSVWYYVLECRSRIDRLESAVNGLKK |

TABLE 4

Additional EADs of the disclosure.

| Description & SEQ ID NO | Sequence |
| --- | --- |
| CD27L-EAD SEQ ID NO: 63 | MKICITVGHSILKSGACTSADGVVNEYQYNK SLAPVLADTFRKEGHKVDVIICPEKQFKTKN EEKSYKIPRVNSGGYDLLIELHLNASNGQGK GSEVLYYSNKGLEYATRICDKLGTVFKNRGA |

TABLE 4-continued

Additional EADs of the disclosure.

| Description & SEQ ID NO | Sequence |
|---|---|
| | KLDKRLYILNSSKPTAVLIESFFCDNKEDYD |
| | KAKKLGHEGIAKLIVEGVLNKNINNEGVKQM |
| | YKHTIVYDGEVDK |
| PlyGVE2-EAD SEQ ID NO: 64 | MKKIFWDKGHGGSDPGAVANGLQEKNLTHKI VEYATDYLAAHYEGFTQRVSREGDQSLTLDQ RADMANKWGADVFVSVHINAGKGTGFEIYVH PNASPQSIALQNVLHGEILSAMRQFGNITDR GKKRANYAVLRETKMPAVLTENLFIDSNDAK HLKNEAFLKAVGEAHARGVAKFLGLK |
| PlyD6E-EAD SEQ ID NO: 65 | MVRIVLDAGHGGKDSGAVGNGLREKDLTLNIV KKIGNLLAEYEGVEVHYTRTDDRFLELSERAE IANRLKADYFISVHINAGGGTGFESYIYNGNV SSATIAYQNVIHSEIMKAIGNVTDRGKKRANY AVLRETHMPALLTENLFIDNKNDAAKLDSEQF LLQVAHGHVQGIVKAFGLKKKAT |
| CaLys1-EAD SEQ ID NO: 66 | SNHPVNRVVIHATCPDVGFPSASRK-GRAVSTANY FASPSSGGSAHYVCDI-GETVQCLSEGTIGWHAPP NPHSLGIEICADGGSHASFRVPGHAY-TREQWLDP RVWPAVEKAAILCRRLCDKYNVPKRKL-SAADLKA GRRGVCGHVDVTDAWHQSDHDDPGP |

In some embodiments, a recombinant protein of the disclosure comprises an EAD consisting of a sequence in Table 4 or the EAD region of a sequence in Table 3. In some embodiments, a recombinant protein of the disclosure comprises an EAD comprising a sequence in Table 4 or the EAD region of a sequence in Table 3. In some embodiments, a recombinant protein of the disclosure comprises an EAD having at least 80, 81, 82, 83, 84, 85, 86, 87, 88, 89, 90, 91, 92, 93, 94, 95, 96, 97, 98, or 99% identity with a sequence in Table 4 or the EAD region of a sequence in Table 3. In some embodiments, a recombinant protein of the disclosure comprises an EAD differing by 1, 2, 3, 4, 5, 6, 7, 8, 9, 10, 11, 12, 13, 14, or 15 amino acids from a sequence in Table 4 or the EAD region of a sequence in Table 3.

In some embodiments, a recombinant protein of the disclosure comprises an EAD from CD27L or PlyGVE2. In some embodiments, a recombinant protein of the disclosure comprises an EAD consisting of a sequence according to any one of SEQ ID NO: 63-64 or the EAD region of any one of SEQ ID NO: 60-61. In some embodiments, a recombinant protein of the disclosure comprises an EAD comprising a sequence according to any one of SEQ ID NO: 63-64 or the EAD region of any one of SEQ ID NO: 60-61. In some embodiments, a recombinant protein of the disclosure comprises an EAD having at least 80, 81, 82, 83, 84, 85, 86, 87, 88, 89, 90, 91, 92, 93, 94, 95, 96, 97, 98, or 99% identity with a sequence according to any one of SEQ ID NO: 63-64 or the EAD region of any one of SEQ ID NO: 60-61. In some embodiments, a recombinant protein of the disclosure comprises an EAD differing by 1, 2, 3, 4, 5, 6, 7, 8, 9, 10, 11, 12, 13, 14, or 15 amino acids from a sequence according to any one of SEQ ID NO: 63-64 or the EAD region of any one of SEQ ID NO: 60-61.

In some embodiments, a recombinant protein of the disclosure comprises the EAD of CaLys1. In some embodiments, a recombinant protein of the disclosure comprises an EAD consisting of a sequence according to SEQ ID NO: 73 or the EAD region of SEQ ID NO: 72. In some embodiments, a recombinant protein of the disclosure comprises an EAD comprising a sequence according to SEQ ID NO: 73 or the EAD region of SEQ ID NO: 72. In some embodiments, a recombinant protein of the disclosure comprises an EAD having at least 80, 81, 82, 83, 84, 85, 86, 87, 88, 89, 90, 91, 92, 93, 94, 95, 96, 97, 98, or 99% identity with a sequence according to SEQ ID NO: 73 or the EAD region of SEQ ID NO: 72. In some embodiments, a recombinant protein of the disclosure comprises an EAD differing by 1, 2, 3, 4, 5, 6, 7, 8, 9, 10, 11, 12, 13, 14, or 15 amino acids from a sequence according to SEQ ID NO: 73 or the EAD region of SEQ ID NO: 72.

In some embodiments, a recombinant protein of the disclosure comprises an EAD derived from a lysin. In some embodiments, the lysin is an endolysin, a tail lysin, an exolysin, a bacteriocin, or an autolysin. In some embodiments, the EAD is derived from any one of the endolysins listed herein. In some embodiments, the EAD is a glycosidase. In some embodiments, the EAD is an amidase. In some embodiments, the EAD is a peptidase.

In some embodiments, a recombinant protein herein comprises an EAD according to any one of the foregoing embodiments. In some embodiments, a recombinant protein herein comprises 1 EAD. In some embodiments, the recombinant protein comprises more than one EAD. In some embodiments, the recombinant protein comprises 2 EADs. In some embodiments, the recombinant protein comprises 3, 4, 5, 6, 7, 8, 9, or 10 EADs.

Truncated Enzymes

In one aspect, the present disclosure provides truncated enzymes with lytic activity against *C. acnes*. As demonstrated in the Examples herein, the inventors surprisingly discovered that truncation of a conserved C-terminal region of CLC1-family enzymes and CaLys1 led to truncated enzymes with higher lytic activity than the corresponding full-length native protein. Table 5 provides illustrative truncated enzymes of the disclosure.

TABLE 5

CaLys1 and CLC1-family truncations.

| Description & SEQ ID | Amino Acid Sequence |
|---|---|
| CaLys1-truncation, SEQ ID | MVRYIPAAHHSAGSNHPVNRVVIHATCPDVGFPSASRKGRAVSTANYF ASPSSGGSAHYVCDIGETVQCLSEGTIGWHAPPNPHSLGIEICADGGS HASFRVPGHAYTREQWLDPRVWPAVEKAAILCRRLCDKYNVPKRKLSA |

TABLE 5-continued

CaLys1 and CLC1-family truncations.

| Description & SEQ ID | Amino Acid Sequence |
|---|---|
| NO: 74 | ADLKAGRRGVCGHVDVTDAWHQSDHDDPGPWFPWDRFMAVVNGHNE<br>SGELTVADVK |
| CLC1-<br>truncation,<br>SEQ ID<br>NO: 75 | MTFIQARHHGGNSNTPITRLVIHATCPDVGYPSASKAGRAVSTAEYFAS<br>TSRSASAHYVCDVSATVQCLSEETIGYHAPPNSHSIGIEICADGGSRAS<br>FEKASHAYTREQWLSPQVWPAVERAAILARGICHRHHIPVRKLTTAQVK<br>SGMSGICGHDNVSDAFHQSDHDDPGPYFPWNEFIAAIQGKNTNKGELSM<br>SDV |
| CLC2-<br>truncation,<br>SEQ ID<br>NO: 76 | MTFIQAAHRGGTSNTPITRLVIHATCPDVGFPSASRAGRAVSTAEYFAST<br>SRSASAHYVCDISTTVQCLSEATIGYHAPPNAHSIGIEICADGGSRASFE<br>KASHAYTREQWLSPQVWPAVERAAILARDICHRHHIPIRRLSVAQVRAGE<br>RGICGHNEVSEAFHQSDHDDPGPYFPWNEFIAAVQGKTTTPEGELSMSD |
| CLC3-<br>truncation,<br>SEQ ID<br>NO: 77 | MTFIQARHHGGNSNAPITRLVIHATCPDVGYPSASKAGRAVSTANYFATT<br>DRPASAHYVCDIATTVQCLSEETIGYHAPPNSHSIGIEICADGGSHASFE<br>KASHAYTRDQWLSDDVWPAVERAAILARDICQRHRIPVRKLSTAQVKA<br>GLSGICGHDNVSGAFHQSDHDDPGPYFPWDQFMALVQGKPATPGDLT<br>MADI |
| CLC4-<br>truncation,<br>SEQ ID<br>NO: 78 | MTFIQARHHGGNSNAPITRLVIHATCPDVGYPSASKAGRAVSTAEYFAS<br>TSRSASAHYVCDIAATVQCLSEEAIGFHAPPNSHSIGIEICADGGSRAS<br>FEKASHAYTREQWLSPQVWPAVERAAILARDICRRHHIPVRKLTTAQVK<br>SGMSGICGHDNVSDAFHQSDHDDPGPYFPWNEFIAAVQGKNTNKGELS<br>MSDV |
| CLC5-<br>truncation,<br>SEQ ID<br>NO: 79 | MTFIQARHHGGNSNTPVTRLVIHATCPDVGYPSASKAGRAVSTAEYFAS<br>TSRSASAHYVCDVSATVQCLSEEAIGYHAPPNSHSIGIEICADGGSHASF<br>ETASHAYTREQWLSPQVWPAVERAAILARDICHRHHIPVRKLTTAQVKS<br>GMSGICGHDNVSDAFRQSDHDDPGPYFPWNEFIAAVQGKTTNKGELSM<br>SDV |
| CLC6-<br>truncation,<br>SEQ ID<br>NO: 80 | MTFIQARHHGGNSNNPVTRLVIHATCPDVGYPSASKAGRAVSTAQYFA<br>STSRPASAHYVCDVSATVQCLSEETIGYHAPPNAHSIGIEICSDGGSRASF<br>EKASHAYSREQWLSPQVWPAVERAAILARDICHRHRIPVRKLTAAQVK<br>SGMSGICGHDNVSDAFRQSDHDDPGPYFPWNEFIAAVQGKNTNKGELS<br>MSDV |
| CLC7-<br>truncation,<br>SEQ ID<br>NO: 81 | MTFIQARHHGGNSNAPITRLVIHATCPDVGYPSASKAGRAVSTAHYFAE<br>ATRPASAHYVCDVSATVQCLSEETIGYHAPPNAHSIGIEICSDGGSRASF<br>EKASHAYSREQWLSPQVWPAVERAAILARDICHRHRIPVRKLTAAQVK<br>SGMSGICGHDNVSDAFRQSDHDDPGPYFPWNEFIAAVQGKTTNKGELS<br>MSDV |
| CLC8-<br>truncation,<br>SEQ ID<br>NO: 82 | MTFIQARHHGGNSNTPITRLVIHATCPDVGYPSASRAGRAASTANYFAT<br>TDRPASAHYVCDIATTVQCLSEEVIGFHAPPNSHSIGIEICADGGSHASFE<br>KASHAYTREQWLSDDVWPAVERAAILARGICHRHHIPVRKLSTAQVKS<br>GMSGICGHDNVSDAFHQSDHDDPGPHFPWNEFIAAVQGKTTNKGELSM<br>SDV |
| CLC9-<br>truncation,<br>SEQ ID<br>NO: 83 | MTFIQARHHGGNTNAPVTRLVIHSTCPDVGFPSASRAGRAVSTAGYFAS<br>TSRPASAHYVVDVTTTVQCLPENTIGYHAPPNSHSIGIEICSDGGSRASFE<br>NPSHAYTREQWLSPQVWPAVERAAILARGICHRHHIPVRKLTTAQVKN<br>GMSGICGHDNVSDAFHQSDHDDPGPYFPWDKFIAAVQGKNTTSEGELS<br>MSDI |
| CLC10-<br>truncation,<br>SEQ ID<br>NO: 84 | MQFIQAKHHGGNENTPVTRLVIHATCPDTGYPSASRAGRAASTARYFQS<br>TSRPTSAHYVCDVTATVQCLSEETIGYHAPPNAHSIGIEICADGGSKSSFD<br>NPSHSYTREQWLSPQVWPAVERAAILARDICHRHHIPVRKLSTAQVKSG<br>MSGICGHDNVSDAFHQSDHDDPGPYFPWDRFMAAITNTHPEELTMADV |
| CLC11-<br>truncation,<br>SEQ ID<br>NO: 85 | MTFIQAAHRGGTSNTPITRLVIHATCPDVGFPSASRAGRAVSTAEYFAST<br>SRSASAHYVCDISTTVQCLSEATIGYHAPPNAHSIGIEICAAGGSRASFEK<br>ASHAYTREQWLSPQVWPAVERAAILARDICHRHHIPIRRLSVAQVRAGE<br>RGICGHNEVSEAFHQSDHDDPGPYFPWNEFIAAVQGKTTTPEGELSMSD<br>V |
| CLC12-<br>truncation,<br>SEQ ID<br>NO: 86 | MTFIQARHHGGNTNAPVSRLVIHSTCPDVGFPSASRAGRAVSTAEYFAS<br>TSRPASAHYVVDIATTVQCLPENTIGYHAPPNSHSIGIEICSDGGSRASFE<br>KASHAYTREQWLSPQVWPAVERAAILARDICHRHRIPVRKLSTAQVKN<br>GMSGICGHDNVSDAFHQSDHDDPGLYFPWDRFIAAIQGKNTTTKGELS<br>MSDV |
| CLC13-<br>truncation,<br>SEQ ID | MTFIQARHHGGNTNAPVTRLVIHSTCPDVGFPSASRAGRAVSTAGYFAS<br>TSRPASAHYVVDVTTTVQCLPENTIGYHAPPNSHSIGIEICSDGGSRASFE<br>NPSHAYTREQWLSPQVWPAVERAAILARDICHRHRIPVRKLSTAQVKN |

TABLE 5-continued

CaLys1 and CLC1-family truncations.

| Description & SEQ ID | Amino Acid Sequence |
|---|---|
| NO: 87 | GMSGICGHDNVSDAFHQSDHDDPGPYFPWDKFIAAVQGKNTTSEGELSMSDI |
| CLC14-truncation, SEQ ID NO: 88 | MTFIQAKHHGGHNNPPVTRLVIHATCPDVGYPSASRAGRAVSTAHYFQETTRPASAHYICDISTTVQCLSEETVGYHAPPNSHSIGIEICADGGSHASFSNPAHAYTREQWLSPQVWPAVERAAMLARGICQRHNIPIRRLSIADVKAGKRGICGHNEVSEAFHQSDHDDPGPYFPWDGFIALVNGHSAPSRQEELTVSDVH |
| CLC15-truncation, SEQ ID NO: 89 | MRYIQAKHHGGASNKPVTRLVIHSTCPDVGFPSASRAGRAESTANYFADSSRPASAHYVCDVSTTIQCLHEDVVGYHAPPNSHSIGIEICSDGGSRASFRNPNHAYTREQWLSPQVWPAVERAAVLARDICKRNGIPIRKLSTSEVKAGRSGICGHNNVSDAFHQSDHDDPGPYFPWDKFIAAVNGAKVTSEGALSMSDV |
| CLC16-truncation, SEQ ID NO: 90 | MRYIQAKHHGAASNKPVTRLVIHSTCPDVGFPSASRAGRAESTANYFADSSRPASAHYVCDVSTTIQCLHEDIVGYHAPPNSHSIGIEICSDGGSHASFNNPKHAYTRDQWLSPQVWPAVERAAVLARDICKRNGIPIRKLSTSEVKAGRSGICGHNNVSDAFHQSDHDDPGPYFPWDKFIAAVNGAKVTSEGALSMSDV |
| CLC17-truncation, SEQ ID NO: 91 | MTYIPAAHHGPTTNAPVSRIVIHSTCPDVGFPAASKAGRAVSTANYFASTSRPASAHYVVDIATTVQCLPENTVGYHAPPNSGSIGIEICSDGGSKGSFENPAHAYTTTQWLSPEVWPAVERAAILAREICHRHHIPIRRLSVAQVRAGERGICGHNEVSEAFHRSDHDDPGPWFPWDRFILEVKGIPTEGMSMSDI |
| CLC18-truncation, SEQ ID NO: 92 | MTFIQARHHGGNSNTPITRLVIHATCPDVGYPSASKAGRAVSTAEYFASTSRSASAHYVCDVSATVQCLSEETIGYHAPPNSHSIGIEICADGGSRASFEKASHAYTREQWLSPQVWPAVERAAILARGICHRHHIPVRKLTTAQVKSGMSGICGHDNVSDAFHQSDHDDPGPYFPWNEFIAAIQGKNTNKGELSMSDV |
| CLC19-truncation, SEQ ID NO: 93 | MTFIQARHHGGNTNAPVTRLVIHSTCPDVGFPSASRAGRAVSTAGYFASTSRPASAHYVVDVTTTVQCLPENTIGYHAPPNSHSIGIEICSDGGSRASFENPSHAYTREQWLSPQVWPAVERAAILARDICHRHRIPVRKLSTAQVKNGMSGICGHDNVSDAFHQSDHDDPGPYFPWDKFIAAVQGKNTTSEGELSMSDI |

In some embodiments, a recombinant protein of the disclosure comprises a truncated enzyme sequence disclosed herein. In some embodiments, a recombinant protein of the disclosure consists of a truncated enzyme sequence disclosed herein. In some embodiments, a recombinant protein of the disclosure comprises a truncated enzyme having at least 80, 81, 82, 83, 84, 85, 86, 87, 88, 89, 90, 91, 92, 93, 94, 95, 96, 97, 98, or 99% identity with a truncated enzyme sequence disclosed herein. In some embodiments, a recombinant protein of the disclosure comprises a truncated enzyme that differs by 1, 2, 3, 4, 5, 6, 7, 8, 9, 10, 11, 12, 13, 14, or 15 amino acids from a sequence disclosed herein.

In some embodiments, a recombinant protein of the disclosure comprises a truncated enzyme sequence disclosed in Table 5. In some embodiments, a recombinant protein of the disclosure consists of a truncated enzyme sequence disclosed in Table 5. In some embodiments, a recombinant protein of the disclosure comprises a truncated enzyme having at least 80, 81, 82, 83, 84, 85, 86, 87, 88, 89, 90, 91, 92, 93, 94, 95, 96, 97, 98, or 99% identity with a truncated enzyme sequence disclosed in Table 5. In some embodiments, a recombinant protein of the disclosure comprises a truncated enzyme that differs by 1, 2, 3, 4, 5, 6, 7, 8, 9, 10, 11, 12, 13, 14, or 15 amino acids from a sequence disclosed in Table 5.

In some embodiments, a recombinant protein of the disclosure comprises a C-terminal truncation of an enzyme sequence disclosed in Table 1 or Table 3. In some embodiments, a recombinant protein of the disclosure consists of a C-terminal truncation of an enzyme sequence disclosed in Table 1 or Table 3. In some embodiments, a recombinant protein of the disclosure comprises a truncated enzyme having at least 80, 81, 82, 83, 84, 85, 86, 87, 88, 89, 90, 91, 92, 93, 94, 95, 96, 97, 98, or 99% identity with a C-terminal truncation of an enzyme sequence disclosed in Table 1 or Table 3. In some embodiments, a recombinant protein of the disclosure comprises a truncated enzyme that differs by 1, 2, 3, 4, 5, 6, 7, 8, 9, 10, 11, 12, 13, 14, or 15 amino acids from a C-terminal truncation of an enzyme sequence disclosed in Table 1 or Table 3.

In some embodiments, the C-terminal truncation is a truncation of the entire C-terminal region following the EAD. In some embodiments, the C-terminal truncation is a truncation of the conserved C-terminal tail. In some embodiments, the C-terminal truncation is a truncation of the C-terminal region of the enzyme that does not have any protein domain annotation. In some embodiments, the C-terminal truncation is a truncation of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 amino acids from the C terminus. In some embodiments, the C-terminal truncation is a truncation of about 10, 15, 20, 25, 30, 35, 40, 45, 50, 55, 60, 65, 70, 75, 80, 85, 90, 95, 100, 105, 110, 115, 120, 125, 130, 135, 140, 145, or 150 amino acids from the C-terminus. In some embodiments, the C-terminal truncation is a truncation of about 60-90 amino acids from the C-terminus.

In some embodiments, the truncated enzyme is truncated CLC1 and the truncation is a truncation of about 60-90 amino acids from the full-length CLC1 enzyme. In some embodiments, the truncated enzyme is truncated CLC1 and the truncation is a truncation of about 60-90 amino acids from the full-length CLC1 enzyme. In some embodiments, the truncated enzyme is truncated CLC1 and the truncation is a truncation of about 60-90 amino acids from the full-length CLC1 enzyme.

In some embodiments, the truncated enzyme is truncated CaLys1, CLC1, CLC2, CLC3, CLC4, CLC5, CLC6, CLC7, CLC8, CLC9, CLC10, CLC11, CLC12, CLC13, CLC14, CLC16, CLC18, or CLC19 and the truncation is a truncation of about 50-90 amino acids from the C-terminus of the full-length, native enzyme. In some embodiments, the truncated enzyme is truncated CaLys1, CLC1, CLC2, CLC3, CLC4, CLC5, CLC6, CLC7, CLC8, CLC9, CLC10, CLC11, CLC12, CLC13, CLC14, CLC16, CLC18, or CLC19 and the truncation is a truncation of about 80-85 amino acids from the C-terminus of the full-length, native enzyme.

In some embodiments, the truncated enzyme is truncated CLC15 and the truncation is a truncation of about 90-130 amino acids from the full-length CLC15 enzyme. In some embodiments, the truncated enzyme is truncated CLC15 and the truncation is a truncation of about 120-125 amino acids from the full-length CLC15 enzyme.

In some embodiments, the truncated enzyme is truncated CLC17 and the truncation is a truncation of about 30-70 amino acids from the full-length CLC17 enzyme. In some embodiments, the truncated enzyme is truncated CLC17 and the truncation is a truncation of about 60-70 amino acids from the full-length CLC17 enzyme.

Cell Wall Binding Domains (CBDs)

In some embodiments, a recombinant protein of the disclosure comprises a cell wall binding domain (CBD).

The inventors discovered a novel class of *C. acnes* binding CBDs comprising CW_7 sequences. As shown in the Examples of the disclosure, a wide variety of these CW_7 CBDs were able to increase lytic activity against *C. acnes* in combination with a CLC1-family EAD compared to the corresponding full-length CLC1-family enzyme. Information for CLB1-4 is provided in Table 6.

TABLE 6

CLB1-4 Taxonomy, GenBank Acc. No. and Sequences.

| Protein | Taxonomy | GenBank Acc. No. | Full length SEQ ID | CBD SEQ ID | CW_7 SEQ IDs |
|---------|----------|------------------|--------------------|-----------|--------------|
| CLB1 | Cutibacterium avidum | WP_015583338.1 | 37 | 41 | 45, 46 |
| CLB2 | Cutibacterium acnes | WP_002535464.1 | 38 | 42 | 47 |
| CLB3 | Propionimicrobium lymphoophilum | WP_016455084.1 | 39 | 43 | 48, 49 |
| CLB4 | Propionimicrobium lymphoophilum | WP_016456264.1 | 40 | 44 | 50, 51 |

In some embodiments, a recombinant protein of the disclosure comprises a CBD comprising a CW_7 sequence. In some embodiments, a recombinant protein of the disclosure comprises a CBD comprising a CW_7 sequence disclosed herein. In some embodiments, a recombinant protein of the disclosure comprises a CBD comprising a CW_7 sequence assigned to Interpro domain entry IPR013168. In some embodiments, the CBD consists of a CW_7 sequence.

In some embodiments, a recombinant protein of the disclosure comprises the CBD of any one of CLB1-4. In some embodiments, the CBD consists of a sequence according to any one of SEQ ID NO: 41-44 or the CBD region of any one of SEQ ID NO: 37-40. In some embodiments, the CBD comprises a sequence according to any one of SEQ ID NO: 41-44 or the CBD region of any one of SEQ ID NO: 37-40. In some embodiments, the CBD has at least 80, 81, 82, 83, 84, 85, 86, 87, 88, 89, 90, 91, 92, 93, 94, 95, 96, 97, 98, or 99% identity with a sequence according to any one of SEQ ID NO: 41-44 or the CBD region of any one of SEQ ID NO: 37-40. In some embodiments, the CBD differs by 1, 2, 3, 4, 5, 6, 7, 8, 9, 10, 11, 12, 13, 14, or 15 amino acids from a sequence according to any one of SEQ ID NO: 41-44 or the CBD region of any one of SEQ ID NO: 37-40.

In some embodiments, a recombinant protein of the disclosure comprises the CBD of CLB2. In some embodiments, the CBD consists of a sequence according to SEQ ID NO: 42 or the CBD region of SEQ ID NO: 38. In some embodiments, the CBD comprises a sequence according to SEQ ID NO: 42 or the CBD region of SEQ ID NO: 38. In some embodiments, the CBD has at least 80, 81, 82, 83, 84, 85, 86, 87, 88, 89, 90, 91, 92, 93, 94, 95, 96, 97, 98, or 99% identity with a sequence according to SEQ ID NO: 42 or the CBD region of SEQ ID NO: 38. In some embodiments, the CBD differs by 1, 2, 3, 4, 5, 6, 7, 8, 9, 10, 11, 12, 13, 14, or 15 amino acids from a sequence according to SEQ ID NO: 42 or the CBD region of SEQ ID NO: 38.

In some embodiments, a recombinant protein of the disclosure comprises a CBD comprising a CW_7 sequence from CLB1-4. In some embodiments, the CW_7 sequence consists of a sequence according to any one of SEQ ID NO: 45-51. In some embodiments, the CW_7 sequence comprises a sequence according to any one of SEQ ID NO: 45-51. In some embodiments, the CW_7 sequence has at least 40, 45, 50, 55, 60, 65, 70, 75, 80, 85, 90, or 95% identity with a sequence according to any one of SEQ ID NO: 45-51. In some embodiments, the CW_7 sequence comprises a sequence according to any one of SEQ ID NO: 45-51. In some embodiments, the CW_7 sequence has at least 80, 81, 82, 83, 84, 85, 86, 87, 88, 89, 90, 91, 92, 93, 94, 95, 96, 97, 98, or 99% identity with a sequence according to any one of SEQ ID NO: 45-51. In some embodiments, the CW_7 sequence differs by 1, 2, 3, 4, 5, 6, 7, 8, 9, 10, 11, 12, 13, 14, or 15 amino acids from a sequence according to any one of SEQ ID NO: 45-51.

In some embodiments, a recombinant protein of the disclosure comprises a CBD comprising the CW_7 sequence of CLB2. In some embodiments, the CW_7 sequence consists of a sequence according to SEQ ID NO: 47. In some embodiments, the CW_7 sequence comprises a sequence according to SEQ ID NO: 47. In some embodiments, the CW_7 sequence has at least 40, 45, 50, 55, 60, 65, 70, 75, 80, 85, 90, or 95% identity with a sequence according to SEQ ID NO: 47. In some embodiments, the CW_7 sequence comprises a sequence according to SEQ ID NO: 47. In some embodiments, the CW_7 sequence has at least 80, 81, 82, 83, 84, 85, 86, 87, 88, 89, 90, 91, 92, 93, 94, 95, 96, 97, 98, or 99% identity with a sequence according to SEQ ID NO: 47. In some embodiments, the CW_7 sequence differs by 1, 2, 3, 4, 5, 6, 7, 8, 9, 10, 11, 12, 13, 14, or 15 amino acids from a sequence according to SEQ ID NO: 47.

In some embodiments, a recombinant protein of the disclosure comprises the CBD of any one of the CPL-designated proteins exemplified in the Examples herein. In some embodiments, the CBD consists of a sequence according to any one of SEQ ID NO: 166-223 or the CBD region of any one of SEQ ID NO: 108-165. In some embodiments, the CBD comprises a sequence according to any one of SEQ ID NO: 166-223 or the CBD region of any one of SEQ ID NO: 108-165. In some embodiments, the CBD has at least 80, 81, 82, 83, 84, 85, 86, 87, 88, 89, 90, 91, 92, 93, 94, 95, 96, 97, 98, or 99% identity with a sequence according to any one of SEQ ID NO: 166-223 or the CBD region of any one of SEQ ID NO: 108-165. In some embodiments, the CBD differs by 1, 2, 3, 4, 5, 6, 7, 8, 9, 10, 11, 12, 13, 14, or 15 amino acids from a sequence according to any one of SEQ ID NO: 166-223 or the CBD region of any one of SEQ ID NO: 108-165.

In some embodiments, a recombinant protein of the disclosure comprises a CW_7 sequence from any one of the CPL-designated proteins exemplified in the Examples herein. In some embodiments, the recombinant protein comprises a CW_7 sequence comprised by any one of SEQ ID NO: 166-223 or the CBD region of any one of SEQ ID NO: 108-165. In some embodiments, the recombinant protein comprises a CW_7 sequence contained in any one of any one of SEQ ID NO: 166-223 or the CBD region of any one of SEQ ID NO: 108-165. In some embodiments, the recombinant protein comprises a CW_7 sequence having at least 40, 45, 50, 55, 60, 65, 70, 75, 80, 85, 90, or 95% identity with a CW_7 sequence comprised by any one of SEQ ID NO: 166-223 or the CBD region of any one of SEQ ID NO: 108-165. In some embodiments, the recombinant protein comprises a CW_7 sequence having at least 80, 81, 82, 83, 84, 85, 86, 87, 88, 89, 90, 91, 92, 93, 94, 95, 96, 97, 98, or 99% identity with a CW_7 sequence comprised by any one of SEQ ID NO: 166-223 or the CBD region of any one of SEQ ID NO: 108-165. In some embodiments, the CW_7 sequence differs by 1, 2, 3, 4, 5, 6, 7, 8, 9, 10, 11, 12, 13, 14, or 15 amino acids from a CW_7 sequence comprised by any one of SEQ ID NO: 166-223 or the CBD region of any one of SEQ ID NO: 108-165.

In some embodiments, a recombinant protein of the disclosure comprises a CW_7 CBD from the family of proteins comprising CW_7 CBDs disclosed herein. In some embodiments, the recombinant protein comprises a CW_7 CBD comprised by a sequence according to any one of SEQ ID NO: 282-2938. In some embodiments, the recombinant protein comprises the CBD contained in any one of SEQ ID NO: 282-2938. In some embodiments, the recombinant protein comprises a CBD having at least 40, 45, 50, 55, 60, 65, 70, 75, 80, 85, 90, or 95% identity with the CBD comprised by a sequence according to any one of SEQ ID NO: 282-2938. In some embodiments, the recombinant protein comprises a CBD having at least 80, 81, 82, 83, 84, 85, 86, 87, 88, 89, 90, 91, 92, 93, 94, 95, 96, 97, 98, or 99% identity with the CBD comprised by a sequence according to any one of SEQ ID NO: 282-2938. In some embodiments, the CBD sequence differs by 1, 2, 3, 4, 5, 6, 7, 8, 9, 10, 11, 12, 13, 14, or 15 amino acids from the CBD sequence comprised by a sequence according to any one of SEQ ID NO: 282-2938.

In some embodiments, a recombinant protein of the disclosure comprises a CW_7 sequence from the family of proteins comprising CW_7 sequences disclosed herein. In some embodiments, the recombinant protein comprises a CW_7 sequence comprised by a sequence according to any one of SEQ ID NO: 282-2938. In some embodiments, the recombinant protein comprises a CW_7 sequence contained in any one of SEQ ID NO: 282-2938. In some embodiments, the recombinant protein comprises a CW_7 sequence having at least 40, 45, 50, 55, 60, 65, 70, 75, 80, 85, 90, or 95% identity with a CW_7 sequence comprised by a sequence according to any one of SEQ ID NO: 282-2938. In some embodiments, the recombinant protein comprises a CW_7 sequence having at least 80, 81, 82, 83, 84, 85, 86, 87, 88, 89, 90, 91, 92, 93, 94, 95, 96, 97, 98, or 99% identity with a CW_7 sequence comprised by a sequence according to any one of SEQ ID NO: 282-2938. In some embodiments, the CW_7 sequence differs by 1, 2, 3, 4, 5, 6, 7, 8, 9, 10, 11, 12, 13, 14, or 15 amino acids from a CW_7 sequence comprised by a sequence according to any one of SEQ ID NO: 282-2938.

In some embodiments, a recombinant protein of the disclosure comprises a CW_7 CBD from the family of proteins comprising CW_7 CBDs disclosed herein. In some embodiments, the recombinant protein comprises a CW_7 CBD comprised by a sequence in Table 7. In some embodiments, the recombinant protein comprises the CBD contained in any one of the sequences in Table 7. In some embodiments, the recombinant protein comprises a CBD having at least 40, 45, 50, 55, 60, 65, 70, 75, 80, 85, 90, or 95% identity with the CBD comprised by a sequence in Table 7. In some embodiments, the recombinant protein comprises a CBD having at least 80, 81, 82, 83, 84, 85, 86, 87, 88, 89, 90, 91, 92, 93, 94, 95, 96, 97, 98, or 99% identity with the CBD comprised by a sequence in Table 7. In some embodiments, the CBD sequence differs by 1, 2, 3, 4, 5, 6, 7, 8, 9, 10, 11, 12, 13, 14, or 15 amino acids from the CBD sequence comprised by a sequence in Table 7.

In some embodiments, a recombinant protein of the disclosure comprises a CW_7 sequence from the family of proteins comprising CW_7 sequences disclosed herein. In some embodiments, the recombinant protein comprises a CW_7 sequence comprised by a sequence in Table 7. In some embodiments, the recombinant protein comprises a CW_7 sequence contained by a sequence in Table 7. In some embodiments, the recombinant protein comprises a CW_7 sequence having at least 40, 45, 50, 55, 60, 65, 70, 75, 80, 85, 90, or 95% identity with a CW_7 sequence comprised by a sequence in Table 7. In some embodiments, the recombinant protein comprises a CW_7 sequence having at least 80, 81, 82, 83, 84, 85, 86, 87, 88, 89, 90, 91, 92, 93, 94, 95, 96, 97, 98, or 99% identity with a CW_7 sequence comprised by a sequence in Table 7. In some embodiments, the CW_7 sequence differs by 1, 2, 3, 4, 5, 6, 7, 8, 9, 10, 11, 12, 13, 14, or 15 amino acids from a CW_7 sequence comprised by a sequence in Table 7.

In some embodiments, a recombinant protein of the disclosure comprises 1 CBD. In some embodiments, a recombinant protein of the disclosure comprises more than one CBD. In some embodiments, a recombinant protein of the disclosure comprises 2 CBDs. In some embodiments, a recombinant protein of the disclosure comprises 3, 4, 5, 6, 7, 8, 9, or 10 CBDs.

In some embodiments, a recombinant protein of the disclosure comprises 1 CW_7 sequence. In some embodiments, a recombinant protein of the disclosure comprises more than one CW_7 sequence. In some embodiments, a recombinant protein of the disclosure comprises 2 CW_7 sequences. In some embodiments, a recombinant protein of the disclosure comprises 3, 4, 5, 6, 7, 8, 9, or 10 CW_7 sequences.

In some embodiments, a recombinant protein of the disclosure comprises a CBD comprising a CW_7 sequence having the CW_7-21 motif (SEQ ID NO: 2940). In some embodiments, a recombinant protein of the disclosure comprises a CW_7 sequence having the CW_7-21 motif (SEQ ID NO: 2940). In some embodiments, the CW_7 sequence has the CW_7-21 motif (SEQ ID NO: 2940) and has at least 40, 45, 50, 55, 60, 65, 70, 75, 80, 85, 90, 95, 96, 97, 98, or 99% identity to the CLB2 CW_7 repeat. In some embodiments, the CW_7 sequence has the CW_7-21 motif (SEQ ID NO: 2940) and has at least 43% or at least 58% identity to the CLB2 CW_7 repeat. In some embodiments, the CW_7 sequence has the CW_7-21 motif (SEQ ID NO: 2940) and differs from the CLB2 CW_7 repeat by 1, 2, 3, 4, 5, 6, 7, 8, 9, 10, 11, 12, 13, 14, 15, 16, 17, 18, 19, 20, or 21 amino acids.

In some embodiments, a recombinant protein of the disclosure comprises a CBD comprising a CW_7 sequence having the CW_7-19 motif (SEQ ID NO: 2941). In some embodiments, a recombinant protein of the disclosure comprises a CW_7 sequence having the CW_7-19 motif (SEQ ID NO: 2941). In some embodiments, the CW_7 sequence has the CW_7-19 motif (SEQ ID NO 2941) and has at least 40, 45, 50, 55, 60, 65, 70, 75, 80, 85, 90, 95, 96, 97, 98, or 991 identity to the CLB2 CW_7 repeat. In some embodiments, the CW_7 sequence has the CW_7-19 motif (SEQ ID NO: 2941) and has at least 43% or at least 58% identity to the CLB32 CW_7 repeat. In some embodiments, the CW_7 sequence has the CW_7-19 motif (SEQ ID NO: 2941) and differs from the CLB32 CW_7 repeat by 1, 2, 3, 4, 5, 6, 7, 8, 9, 10, 11, 12, 13, 14, 15, 16, 17, 18, 19, 20, or 21 amino acids.

TABLE 7

CW_7 repeat-containing protein sequences and sequence identity to CLB2 CW_7.

| GenBank | SEQ | ID % |
|---|---|---|
| ALT38678.1 | 282 | 100 |
| MCD1109535.1 | 283 | 100 |
| MES6262332.1 | 284 | 100 |
| MES6899268.1 | 285 | 100 |
| MES7343073.1 | 286 | 100 |
| MES7636639.1 | 287 | 100 |
| MES8928379.1 | 288 | 100 |
| TLG05051.1 | 289 | 100 |
| WP_002519882.1 | 290 | 100 |
| WP_002535464.1 | 291 | 100 |
| WP_008598644.1 | 292 | 100 |
| WP_235694824.1 | 293 | 100 |
| WP_236891855.1 | 294 | 100 |
| WP_254926916.1 | 295 | 100 |
| WP_255024679.1 | 296 | 100 |
| WP_304161512.1 | 297 | 100 |
| HAT6583124.1 | 298 | 89.5 |
| WP_239663653.1 | 299 | 89.5 |
| WP_240927088.1 | 300 | 89.5 |
| CAB0517890.1 | 301 | 89.5 |
| HAT1491020.1 | 302 | 89.5 |
| HAT6436788.1 | 303 | 89.5 |
| HCG2965566.1 | 304 | 89.5 |
| KDS92380.1 | 305 | 89.5 |
| MCI6532281.1 | 306 | 89.5 |
| MDK7181277.1 | 307 | 89.5 |
| MDO5722416.1 | 308 | 89.5 |
| RKX02296.1 | 309 | 89.5 |
| WP_013888915.1 | 310 | 89.5 |
| WP_015583338.1 | 311 | 89.5 |

TABLE 7-continued

CW_7 repeat-containing protein sequences and sequence identity to CLB2 CW_7.

| GenBank | SEQ | ID % |
|---|---|---|
| WP_016455226.1 | 312 | 89.5 |
| WP_025296038.1 | 313 | 89.5 |
| WP_028821773.1 | 314 | 89.5 |
| WP_049157417.1 | 315 | 89.5 |
| WP_060797830.1 | 316 | 89.5 |
| WP_065415355.1 | 317 | 89.5 |
| WP_070491102.1 | 318 | 89.5 |
| WP_071345796.1 | 319 | 89.5 |
| WP_092101380.1 | 320 | 89.5 |
| WP_101630683.1 | 321 | 89.5 |
| WP_158382059.1 | 322 | 89.5 |
| WP_169762692.1 | 323 | 89.5 |
| WP_197551992.1 | 324 | 89.5 |
| WP_201771333.1 | 325 | 89.5 |
| WP_204398955.1 | 326 | 89.5 |
| WP_240628810.1 | 327 | 89.5 |
| WP_253254962.1 | 328 | 89.5 |
| WP_256881555.1 | 329 | 89.5 |
| WP_278972212.1 | 330 | 89.5 |
| WP_291499654.1 | 331 | 89.5 |
| WP_306496136.1 | 332 | 89.5 |
| WP_307014028.1 | 333 | 89.5 |
| WP_311519246.1 | 334 | 89.5 |
| WP_317586632.1 | 335 | 89.5 |
| WP_332106481.1 | 336 | 89.5 |
| WP_334353377.1 | 337 | 89.5 |
| WZJ88807.1 | 338 | 89.5 |
| WP_234457481.1 | 339 | 89.2 |
| WP_234458146.1 | 340 | 89.2 |
| WP_238996146.1 | 341 | 89.2 |
| MCT1709611.1 | 342 | 86.8 |
| MDK8532691.1 | 343 | 86.8 |
| WP_244268667.1 | 344 | 86.8 |
| CAB0561870.1 | 345 | 86.8 |
| CAB0573975.1 | 346 | 86.8 |
| CAB0853767.1 | 347 | 86.8 |
| CAB1016170.1 | 348 | 86.8 |
| CRH60380.1 | 349 | 86.8 |
| EFU82458.1 | 350 | 86.8 |
| HAT1145999.1 | 351 | 86.8 |
| HAT1171169.1 | 352 | 86.8 |
| HAT1197533.1 | 353 | 86.8 |
| HAT1428302.1 | 354 | 86.8 |
| HAT6437209.1 | 355 | 86.8 |
| MCI6574417.1 | 356 | 86.8 |
| MCQ9371168.1 | 357 | 86.8 |
| MDD7384156.1 | 358 | 86.8 |
| MDK8663827.1 | 359 | 86.8 |
| MDR6938515.1 | 360 | 86.8 |
| MDU1353073.1 | 361 | 86.8 |
| MDU1522419.1 | 362 | 86.8 |
| MDU7484863.1 | 363 | 86.8 |
| MDY5273730.1 | 364 | 86.8 |
| SPT54212.1 | 365 | 86.8 |
| WP_004007218.1 | 366 | 86.8 |
| WP_007000824.1 | 367 | 86.8 |
| WP_013888240.1 | 368 | 86.8 |
| WP_024330609.1 | 369 | 86.8 |
| WP_028822236.1 | 370 | 86.8 |
| WP_034652719.1 | 371 | 86.8 |
| WP_038604127.1 | 372 | 86.8 |
| WP_049619209.1 | 373 | 86.8 |
| WP_070448229.1 | 374 | 86.8 |
| WP_070544612.1 | 375 | 86.8 |
| WP_070816420.1 | 376 | 86.8 |
| WP_071128892.1 | 377 | 86.8 |
| WP_073717436.1 | 378 | 86.8 |
| WP_087453585.1 | 379 | 86.8 |
| WP_099720846.1 | 380 | 86.8 |
| WP_101634554.1 | 381 | 86.8 |
| WP_102217290.1 | 382 | 86.8 |
| WP_126416900.1 | 383 | 86.8 |
| WP_129864718.1 | 384 | 86.8 |
| WP_134316353.1 | 385 | 86.8 |
| WP_154545415.1 | 386 | 86.8 |
| WP_196974892.1 | 387 | 86.8 |
| WP_196982820.1 | 388 | 86.8 |
| WP_197553691.1 | 389 | 86.8 |
| WP_201517949.1 | 390 | 86.8 |
| WP_201613418.1 | 391 | 86.8 |
| WP_201806563.1 | 392 | 86.8 |
| WP_221187359.1 | 393 | 86.8 |
| WP_232751616.1 | 394 | 86.8 |
| WP_272707364.1 | 395 | 86.8 |
| WP_278012690.1 | 396 | 86.8 |
| WP_278611638.1 | 397 | 86.8 |
| WP_284827109.1 | 398 | 86.8 |
| WP_285112029.1 | 399 | 86.8 |
| WP_306496060.1 | 400 | 86.8 |
| WP_309956151.1 | 401 | 86.8 |
| WP_313274597.1 | 402 | 86.8 |
| WP_332107270.1 | 403 | 86.8 |
| WP_342675009.1 | 404 | 86.8 |
| WP_353061657.1 | 405 | 86.8 |
| WP_353065943.1 | 406 | 86.8 |
| WP_367249073.1 | 407 | 86.8 |
| WP_367263310.1 | 408 | 86.8 |
| WP_367266795.1 | 409 | 86.8 |
| WP_87453585.1 | 410 | 86.8 |
| WP_144744155.1 | 411 | 86.7 |
| MDK6900427.1 | 412 | 84.2 |
| MDK7340938.1 | 413 | 84.2 |
| MDK8804557.1 | 414 | 84.2 |
| PMC93990.1 | 415 | 84.2 |
| CAB0855742.1 | 416 | 84.2 |
| GAA0209635.1 | 417 | 84.2 |
| HAT1275965.1 | 418 | 84.2 |
| HAT1320501.1 | 419 | 84.2 |
| HAT1420995.1 | 420 | 84.2 |
| HJG29905.1 | 421 | 84.2 |
| MBS6101077.1 | 422 | 84.2 |
| MBS6620458.1 | 423 | 84.2 |
| MCI6205518.1 | 424 | 84.2 |
| MCI7552202.1 | 425 | 84.2 |
| MDD7505539.1 | 426 | 84.2 |
| MDE1643196.1 | 427 | 84.2 |
| MEN8963084.1 | 428 | 84.2 |
| OFQ56130.1 | 429 | 84.2 |
| PXY12082.1 | 430 | 84.2 |
| WP_005295621.1 | 431 | 84.2 |
| WP_014320292.1 | 432 | 84.2 |
| WP_024110547.1 | 433 | 84.2 |
| WP_025252126.1 | 434 | 84.2 |
| WP_034370666.1 | 435 | 84.2 |
| WP_034652730.1 | 436 | 84.2 |
| WP_038606893.1 | 437 | 84.2 |
| WP_048707924.1 | 438 | 84.2 |
| WP_070464947.1 | 439 | 84.2 |
| WP_100622299.1 | 440 | 84.2 |
| WP_101628633.1 | 441 | 84.2 |
| WP_101679291.1 | 442 | 84.2 |
| WP_102216815.1 | 443 | 84.2 |
| WP_122821163.1 | 444 | 84.2 |
| WP_193326978.1 | 445 | 84.2 |
| WP_197550925.1 | 446 | 84.2 |
| WP_219585294.1 | 447 | 84.2 |
| WP_239541478.1 | 448 | 84.2 |
| WP_246816308.1 | 449 | 84.2 |
| WP_246818655.1 | 450 | 84.2 |
| WP_253254959.1 | 451 | 84.2 |
| WP_253255071.1 | 452 | 84.2 |
| WP_256885595.1 | 453 | 84.2 |
| WP_263466925.1 | 454 | 84.2 |
| WP_263478195.1 | 455 | 84.2 |
| WP_274734577.1 | 456 | 84.2 |
| WP_274735440.1 | 457 | 84.2 |
| WP_277035150.1 | 458 | 84.2 |
| WP_284896939.1 | 459 | 84.2 |
| WP_284925209.1 | 460 | 84.2 |
| WP_285347112.1 | 461 | 84.2 |

TABLE 7-continued

CW_7 repeat-containing protein sequences
and sequence identity to CLB2 CW_7.

| GenBank | SEQ | ID % |
|---|---|---|
| WP_285371671.1 | 462 | 84.2 |
| WP_289827642.1 | 463 | 84.2 |
| WP_291461635.1 | 464 | 84.2 |
| WP_307738025.1 | 465 | 84.2 |
| WP_311497467.1 | 466 | 84.2 |
| WP_311586796.1 | 467 | 84.2 |
| WP_316280109.1 | 468 | 84.2 |
| WP_320764396.1 | 469 | 84.2 |
| WP_342683263.1 | 470 | 84.2 |
| WP_346674736.1 | 471 | 84.2 |
| WP_366965808.1 | 472 | 84.2 |
| WP_367266299.1 | 473 | 84.2 |
| ERH14802.1 | 474 | 81.6 |
| HIY51284.1 | 475 | 81.6 |
| KTF03634.1 | 476 | 81.6 |
| MBS4941952.1 | 477 | 81.6 |
| MBS6276004.1 | 478 | 81.6 |
| MBS6365653.1 | 479 | 81.6 |
| MBS6934773.1 | 480 | 81.6 |
| MDD5800782.1 | 481 | 81.6 |
| MDD6565536.1 | 482 | 81.6 |
| MDK8300961.1 | 483 | 81.6 |
| MDU1351097.1 | 484 | 81.6 |
| MDU2312762.1 | 485 | 81.6 |
| MDU5247738.1 | 486 | 81.6 |
| MED9961294.1 | 487 | 81.6 |
| WIK88022.1 | 488 | 81.6 |
| WP_004007598.1 | 489 | 81.6 |
| WP_004009149.1 | 490 | 81.6 |
| WP_006680348.1 | 491 | 81.6 |
| WP_007000727.1 | 492 | 81.6 |
| WP_022865293.1 | 493 | 81.6 |
| WP_024058359.1 | 494 | 81.6 |
| WP_070726928.1 | 495 | 81.6 |
| WP_071128441.1 | 496 | 81.6 |
| WP_071129517.1 | 497 | 81.6 |
| WP_072510112.1 | 498 | 81.6 |
| WP_086414274.1 | 499 | 81.6 |
| WP_087186594.1 | 500 | 81.6 |
| WP_087201200.1 | 501 | 81.6 |
| WP_087315485.1 | 502 | 81.6 |
| WP_102184077.1 | 503 | 81.6 |
| WP_165315851.1 | 504 | 81.6 |
| WP_166683304.1 | 505 | 81.6 |
| WP_193326349.1 | 506 | 81.6 |
| WP_204212539.1 | 507 | 81.6 |
| WP_204559735.1 | 508 | 81.6 |
| WP_204880317.1 | 509 | 81.6 |
| WP_218957875.1 | 510 | 81.6 |
| WP_227909790.1 | 511 | 81.6 |
| WP_239181537.1 | 512 | 81.6 |
| WP_252673749.1 | 513 | 81.6 |
| WP_264371188.1 | 514 | 81.6 |
| WP_270772239.1 | 515 | 81.6 |
| WP_276869678.1 | 516 | 81.6 |
| WP_285084311.1 | 517 | 81.6 |
| WP_285444565.1 | 518 | 81.6 |
| WP_285470750.1 | 519 | 81.6 |
| WP_287058228.1 | 520 | 81.6 |
| WP_288335642.1 | 521 | 81.6 |
| WP_288336691.1 | 522 | 81.6 |
| WP_288738045.1 | 523 | 81.6 |
| WP_289826693.1 | 524 | 81.6 |
| WP_301586619.1 | 525 | 81.6 |
| WP_308516211.1 | 526 | 81.6 |
| WP_311588034.1 | 527 | 81.6 |
| WP_316077010.1 | 528 | 81.6 |
| WP_320755504.1 | 529 | 81.6 |
| WP_323456950.1 | 530 | 81.6 |
| WP_324249269.1 | 531 | 81.6 |
| WP_330029979.1 | 532 | 81.6 |
| WP_367263175.1 | 533 | 81.6 |
| MDM8289123.1 | 534 | 81.6 |
| MDM8289214.1 | 535 | 81.6 |
| SCH06965.1 | 536 | 81.6 |
| WP_253254875.1 | 537 | 81.6 |
| WP_275052423.1 | 538 | 81.6 |
| WP_316083719.1 | 539 | 80.0 |
| MBM7824673.1 | 540 | 79.3 |
| AOZ72034.1 | 541 | 79.0 |
| DAE38969.1 | 542 | 79.0 |
| DAF83770.1 | 543 | 79.0 |
| DAH27442.1 | 544 | 79.0 |
| DAM21410.1 | 545 | 79.0 |
| DAM24911.1 | 546 | 79.0 |
| DAQ44887.1 | 547 | 79.0 |
| DAR31986.1 | 548 | 79.0 |
| DAU07580.1 | 549 | 79.0 |
| DAX08694.1 | 550 | 79.0 |
| HJA28948.1 | 551 | 79.0 |
| HJA29771.1 | 552 | 79.0 |
| HJH43109.1 | 553 | 79.0 |
| MBM6953313.1 | 554 | 79.0 |
| MCH4084529.1 | 555 | 79.0 |
| MCI1933832.1 | 556 | 79.0 |
| MDD6693199.1 | 557 | 79.0 |
| MDR3777680.1 | 558 | 79.0 |
| MDU6662690.1 | 559 | 79.0 |
| MEE0310276.1 | 560 | 79.0 |
| QFG04694.1 | 561 | 79.0 |
| QNL30979.1 | 562 | 79.0 |
| RHD35880.1 | 563 | 79.0 |
| RRF89371.1 | 564 | 79.0 |
| UVG34591.1 | 565 | 79.0 |
| UVM90174.1 | 566 | 79.0 |
| UVY04019.1 | 567 | 79.0 |
| UWG22304.1 | 568 | 79.0 |
| UWI11321.1 | 569 | 79.0 |
| WP_003841933.1 | 570 | 79.0 |
| WP_060919922.1 | 571 | 79.0 |
| WP_073708844.1 | 572 | 79.0 |
| WP_087220826.1 | 573 | 79.0 |
| WP_087353727.1 | 574 | 79.0 |
| WP_158567694.1 | 575 | 79.0 |
| WP_204204740.1 | 576 | 79.0 |
| WP_204672929.1 | 577 | 79.0 |
| WP_206108987.1 | 578 | 79.0 |
| WP_214364869.1 | 579 | 79.0 |
| WP_235422776.1 | 580 | 79.0 |
| WP_235810848.1 | 581 | 79.0 |
| WP_236842337.1 | 582 | 79.0 |
| WP_274959455.1 | 583 | 79.0 |
| WP_288738164.1 | 584 | 79.0 |
| WP_296762242.1 | 585 | 79.0 |
| WP_296773940.1 | 586 | 79.0 |
| WP_303251645.1 | 587 | 79.0 |
| WP_311776999.1 | 588 | 79.0 |
| WP_346697391.1 | 589 | 79.0 |
| WP_349075738.1 | 590 | 79.0 |
| WP_367191929.1 | 591 | 79.0 |
| MBM6687374.1 | 592 | 78.9 |
| WP_278620445.1 | 593 | 78.9 |
| MDU0864496.1 | 594 | 78.1 |
| WP_012577862.1 | 595 | 77.8 |
| WP_025221589.1 | 596 | 77.8 |
| WP_052789112.1 | 597 | 77.8 |
| WP_234988952.1 | 598 | 77.8 |
| WP_236716372.1 | 599 | 77.8 |
| WP_274982763.1 | 600 | 77.8 |
| WP_283713660.1 | 601 | 77.8 |
| WP_340509866.1 | 602 | 77.8 |
| WP_258499797.1 | 603 | 77.1 |
| WP_262360601.1 | 604 | 77.1 |
| WP_367245872.1 | 605 | 77.1 |
| CVH78623.1 | 606 | 76.3 |
| DAE90129.1 | 607 | 76.3 |
| DAJ02646.1 | 608 | 76.3 |
| DAL62644.1 | 609 | 76.3 |
| DAO39398.1 | 610 | 76.3 |
| DAQ08365.1 | 611 | 76.3 |

TABLE 7-continued

CW_7 repeat-containing protein sequences and sequence identity to CLB2 CW_7.

| GenBank | SEQ | ID % |
|---|---|---|
| DAT85648.1 | 612 | 76.3 |
| DAU71552.1 | 613 | 76.3 |
| ETJ02050.1 | 614 | 76.3 |
| HOU67165.1 | 615 | 76.3 |
| MBP3885850.1 | 616 | 76.3 |
| MBQ3283982.1 | 617 | 76.3 |
| MBR3160977.1 | 618 | 76.3 |
| MBS5339596.1 | 619 | 76.3 |
| MCI6273107.1 | 620 | 76.3 |
| MDO4797292.1 | 621 | 76.3 |
| MED9896471.1 | 622 | 76.3 |
| MEE0150117.1 | 623 | 76.3 |
| MEE1202220.1 | 624 | 76.3 |
| MEE8722548.1 | 625 | 76.3 |
| MEE8722860.1 | 626 | 76.3 |
| OUO64324.1 | 627 | 76.3 |
| SPJ41463.1 | 628 | 76.3 |
| UVY20648.1 | 629 | 76.3 |
| UVY22418.1 | 630 | 76.3 |
| UVY41455.1 | 631 | 76.3 |
| UVY42807.1 | 632 | 76.3 |
| UVY62299.1 | 633 | 76.3 |
| WP_013189212.1 | 634 | 76.3 |
| WP_018340121.1 | 635 | 76.3 |
| WP_039171927.1 | 636 | 76.3 |
| WP_051417651.1 | 637 | 76.3 |
| WP_053793915.1 | 638 | 76.3 |
| WP_072374346.1 | 639 | 76.3 |
| WP_073712978.1 | 640 | 76.3 |
| WP_101454355.1 | 641 | 76.3 |
| WP_118239140.1 | 642 | 76.3 |
| WP_120358882.1 | 643 | 76.3 |
| WP_129868423.1 | 644 | 76.3 |
| WP_129887274.1 | 645 | 76.3 |
| WP_129905530.1 | 646 | 76.3 |
| WP_129913053.1 | 647 | 76.3 |
| WP_157005339.1 | 648 | 76.3 |
| WP_196326954.1 | 649 | 76.3 |
| WP_197695792.1 | 650 | 76.3 |
| WP_204877685.1 | 651 | 76.3 |
| WP_231234722.1 | 652 | 76.3 |
| WP_235001784.1 | 653 | 76.3 |
| WP_240833659.1 | 654 | 76.3 |
| WP_240834043.1 | 655 | 76.3 |
| WP_255463933.1 | 656 | 76.3 |
| WP_258340775.1 | 657 | 76.3 |
| WP_277035292.1 | 658 | 76.3 |
| WP_278787610.1 | 659 | 76.3 |
| WP_281511047.1 | 660 | 76.3 |
| WP_288734903.1 | 661 | 76.3 |
| WP_289606002.1 | 662 | 76.3 |
| WP_294379484.1 | 663 | 76.3 |
| WP_302011171.1 | 664 | 76.3 |
| WP_306718268.1 | 665 | 76.3 |
| WP_308652068.1 | 666 | 76.3 |
| WP_309957417.1 | 667 | 76.3 |
| WP_311167331.1 | 668 | 76.3 |
| WP_320756401.1 | 669 | 76.3 |
| WP_321050744.1 | 670 | 76.3 |
| WP_330045465.1 | 671 | 76.3 |
| WP_343006893.1 | 672 | 76.3 |
| WP_343283724.1 | 673 | 76.3 |
| WP_349091822.1 | 674 | 76.3 |
| MBS4998786.1 | 675 | 76.3 |
| MCW1069382.1 | 676 | 76.3 |
| VTX63007.1 | 677 | 76.3 |
| WP_256363451.1 | 678 | 76.3 |
| WP_297993492.1 | 679 | 76.3 |
| WP_330959005.1 | 680 | 76.0 |
| MDE6078888.1 | 681 | 75.0 |
| WP_071477988.1 | 682 | 75.0 |
| MBQ9954849.1 | 683 | 74.3 |
| QFP95395.1 | 684 | 74.3 |
| QPX62467.1 | 685 | 74.3 |
| WP_225841104.1 | 686 | 74.3 |
| WP_241157056.1 | 687 | 74.3 |
| WP_320678874.1 | 688 | 74.3 |
| YP_009603465.1 | 689 | 74.3 |
| MBM6776861.1 | 690 | 73.7 |
| DAG79896.1 | 691 | 73.7 |
| DAH93651.1 | 692 | 73.7 |
| DAH96130.1 | 693 | 73.7 |
| DAM79893.1 | 694 | 73.7 |
| MBP3884765.1 | 695 | 73.7 |
| MBR2684294.1 | 696 | 73.7 |
| MBR3313910.1 | 697 | 73.7 |
| MBR3383747.1 | 698 | 73.7 |
| MBU3995549.1 | 699 | 73.7 |
| MCI1963232.1 | 700 | 73.7 |
| MCI6772718.1 | 701 | 73.7 |
| MDY5585074.1 | 702 | 73.7 |
| OUO89971.1 | 703 | 73.7 |
| RGK64659.1 | 704 | 73.7 |
| WP_021725214.1 | 705 | 73.7 |
| WP_071164539.1 | 706 | 73.7 |
| WP_077597407.1 | 707 | 73.7 |
| WP_083443693.1 | 708 | 73.7 |
| WP_095507846.1 | 709 | 73.7 |
| WP_108726243.1 | 710 | 73.7 |
| WP_129914362.1 | 711 | 73.7 |
| WP_140396461.1 | 712 | 73.7 |
| WP_158551533.1 | 713 | 73.7 |
| WP_166078452.1 | 714 | 73.7 |
| WP_169769106.1 | 715 | 73.7 |
| WP_169770235.1 | 716 | 73.7 |
| WP_172119268.1 | 717 | 73.7 |
| WP_197695294.1 | 718 | 73.7 |
| WP_231204509.1 | 719 | 73.7 |
| WP_288766823.1 | 720 | 73.7 |
| WP_302799763.1 | 721 | 73.7 |
| WP_307389411.1 | 722 | 73.7 |
| WP_311553230.1 | 723 | 73.7 |
| WP_316076978.1 | 724 | 73.7 |
| WP_316114142.1 | 725 | 73.7 |
| WP_320756186.1 | 726 | 73.7 |
| WP_367258047.1 | 727 | 73.7 |
| MBR3159555.1 | 728 | 72.0 |
| MCC6107950.1 | 729 | 71.4 |
| WP_232335355.1 | 730 | 71.4 |
| WP_288517741.1 | 731 | 71.4 |
| WP_314841170.1 | 732 | 71.4 |
| WP_288439705.1 | 733 | 71.1 |
| BCQ03072.1 | 734 | 71.1 |
| DAF74911.1 | 735 | 71.1 |
| DAK03040.1 | 736 | 71.1 |
| GAA0830428.1 | 737 | 71.1 |
| HJF65141.1 | 738 | 71.1 |
| KAB1937510.1 | 739 | 71.1 |
| MBF0930954.1 | 740 | 71.1 |
| MBQ6650832.1 | 741 | 71.1 |
| MBR3160912.1 | 742 | 71.1 |
| MBR3226812.1 | 743 | 71.1 |
| MBR3314005.1 | 744 | 71.1 |
| MBR3315877.1 | 745 | 71.1 |
| MCH3926258.1 | 746 | 71.1 |
| MCH3943076.1 | 747 | 71.1 |
| MCH3967202.1 | 748 | 71.1 |
| MCH4179945.1 | 749 | 71.1 |
| MCI6574112.1 | 750 | 71.1 |
| MDD3485675.1 | 751 | 71.1 |
| MDD5894634.1 | 752 | 71.1 |
| MDY5854438.1 | 753 | 71.1 |
| OCA93596.1 | 754 | 71.1 |
| OUN44218.1 | 755 | 71.1 |
| QQM68406.1 | 756 | 71.1 |
| RDB69432.1 | 757 | 71.1 |
| RXZ54872.1 | 758 | 71.1 |
| WP_026645545.1 | 759 | 71.1 |
| WP_081929442.1 | 760 | 71.1 |
| WP_083078413.1 | 761 | 71.1 |

TABLE 7-continued

CW_7 repeat-containing protein sequences and sequence identity to CLB2 CW_7.

| GenBank | SEQ | ID % |
|---|---|---|
| WP_085382352.1 | 762 | 71.1 |
| WP_087431060.1 | 763 | 71.1 |
| WP_095615304.1 | 764 | 71.1 |
| WP_099333256.1 | 765 | 71.1 |
| WP_099721457.1 | 766 | 71.1 |
| WP_101930602.1 | 767 | 71.1 |
| WP_102166064.1 | 768 | 71.1 |
| WP_114950125.1 | 769 | 71.1 |
| WP_161566699.1 | 770 | 71.1 |
| WP_197691245.1 | 771 | 71.1 |
| WP_204206713.1 | 772 | 71.1 |
| WP_206214603.1 | 773 | 71.1 |
| WP_211309516.1 | 774 | 71.1 |
| WP_221269321.1 | 775 | 71.1 |
| WP_231205335.1 | 776 | 71.1 |
| WP_234737297.1 | 777 | 71.1 |
| WP_257060362.1 | 778 | 71.1 |
| WP_257098767.1 | 779 | 71.1 |
| WP_270573768.1 | 780 | 71.1 |
| WP_273396550.1 | 781 | 71.1 |
| WP_273398208.1 | 782 | 71.1 |
| WP_276766181.1 | 783 | 71.1 |
| WP_285371490.1 | 784 | 71.1 |
| WP_294641980.1 | 785 | 71.1 |
| WP_329740163.1 | 786 | 71.1 |
| WP_347018137.1 | 787 | 71.1 |
| WP_353065929.1 | 788 | 71.1 |
| WP_353936116.1 | 789 | 71.1 |
| WP_367247011.1 | 790 | 71.1 |
| WP_021626552.1 | 791 | 71.0 |
| WP_291237374.1 | 792 | 71.0 |
| ERI05436.1 | 793 | 71.0 |
| ASR83301.1 | 794 | 70.3 |
| MEE8759108.1 | 795 | 70.3 |
| WP_131203990.1 | 796 | 70.3 |
| WP_195403441.1 | 797 | 70.3 |
| WP_150380808.1 | 798 | 69.4 |
| WZJ61236.1 | 799 | 69.4 |
| MDY5370263.1 | 800 | 69.2 |
| WP_094391330.1 | 801 | 69.2 |
| MDU4970728.1 | 802 | 69.2 |
| WP_002563352.1 | 803 | 69.2 |
| WP_275052505.1 | 804 | 68.6 |
| WP_081111191.1 | 805 | 68.6 |
| MBM6868472.1 | 806 | 68.4 |
| MCG4618262.1 | 807 | 68.4 |
| CAG9066035.1 | 808 | 68.4 |
| DAO21151.1 | 809 | 68.4 |
| DAZ27822.1 | 810 | 68.4 |
| DAZ80103.1 | 811 | 68.4 |
| KAB5616903.1 | 812 | 68.4 |
| MBH8616716.1 | 813 | 68.4 |
| MBQ9005563.1 | 814 | 68.4 |
| MDU4244491.1 | 815 | 68.4 |
| MDU5247007.1 | 816 | 68.4 |
| MDU5311827.1 | 817 | 68.4 |
| MDU5317220.1 | 818 | 68.4 |
| QFG09299.1 | 819 | 68.4 |
| QFG09714.1 | 820 | 68.4 |
| QFG14375.1 | 821 | 68.4 |
| QRI58918.1 | 822 | 68.4 |
| WP_003839536.1 | 823 | 68.4 |
| WP_014760674.1 | 824 | 68.4 |
| WP_024058694.1 | 825 | 68.4 |
| WP_033520074.1 | 826 | 68.4 |
| WP_052814115.1 | 827 | 68.4 |
| WP_065457245.1 | 828 | 68.4 |
| WP_084620827.1 | 829 | 68.4 |
| WP_101397356.1 | 830 | 68.4 |
| WP_101673666.1 | 831 | 68.4 |
| WP_118238945.1 | 832 | 68.4 |
| WP_129869804.1 | 833 | 68.4 |
| WP_129901458.1 | 834 | 68.4 |
| WP_129966908.1 | 835 | 68.4 |
| WP_131223742.1 | 836 | 68.4 |
| WP_131294595.1 | 837 | 68.4 |
| WP_167801519.1 | 838 | 68.4 |
| WP_196321401.1 | 839 | 68.4 |
| WP_204562218.1 | 840 | 68.4 |
| WP_206215061.1 | 841 | 68.4 |
| WP_228369686.1 | 842 | 68.4 |
| WP_231235716.1 | 843 | 68.4 |
| WP_238128205.1 | 844 | 68.4 |
| WP_239512813.1 | 845 | 68.4 |
| WP_242358332.1 | 846 | 68.4 |
| WP_278611176.1 | 847 | 68.4 |
| WP_288336440.1 | 848 | 68.4 |
| WP_288704103.1 | 849 | 68.4 |
| WP_290368091.1 | 850 | 68.4 |
| WP_298579913.1 | 851 | 68.4 |
| WP_302476469.1 | 852 | 68.4 |
| WP_320754788.1 | 853 | 68.4 |
| WP_320759177.1 | 854 | 68.4 |
| WP_347889375.1 | 855 | 68.4 |
| WP_367200856.1 | 856 | 68.4 |
| XCB30969.1 | 857 | 68.4 |
| MDE5808296.1 | 858 | 67.9 |
| MDE6027283.1 | 859 | 67.9 |
| MDO4973172.1 | 860 | 67.7 |
| MBD5311228.1 | 861 | 67.7 |
| MDE5643225.1 | 862 | 67.7 |
| MDE6670541.1 | 863 | 67.7 |
| MDY5956946.1 | 864 | 67.7 |
| MDY5957234.1 | 865 | 67.7 |
| WP_300108134.1 | 866 | 67.7 |
| WP_320875837.1 | 867 | 67.7 |
| WP_320881686.1 | 868 | 67.7 |
| DAU53159.1 | 869 | 67.7 |
| DAL75307.1 | 870 | 67.6 |
| MDU3738515.1 | 871 | 67.6 |
| WP_101628961.1 | 872 | 67.6 |
| WP_131305949.1 | 873 | 67.6 |
| WP_195549566.1 | 874 | 67.6 |
| MBR2558341.1 | 875 | 66.7 |
| WP_004835137.1 | 876 | 66.7 |
| WP_148466389.1 | 877 | 66.7 |
| WP_295149054.1 | 878 | 66.7 |
| WP_316131312.1 | 879 | 66.7 |
| WP_350446096.1 | 880 | 66.7 |
| WP_353746390.1 | 881 | 66.7 |
| WP_071415326.1 | 882 | 65.9 |
| DAL98440.1 | 883 | 65.8 |
| DAQ17303.1 | 884 | 65.8 |
| KAB5611598.1 | 885 | 65.8 |
| MBQ0159319.1 | 886 | 65.8 |
| MBR1689370.1 | 887 | 65.8 |
| MBS6345050.1 | 888 | 65.8 |
| MBS6401169.1 | 889 | 65.8 |
| MCH3961119.1 | 890 | 65.8 |
| MCI1344319.1 | 891 | 65.8 |
| MCI8753725.1 | 892 | 65.8 |
| MDO4391700.1 | 893 | 65.8 |
| MDU4287412.1 | 894 | 65.8 |
| MDY4471581.1 | 895 | 65.8 |
| MDY4719988.1 | 896 | 65.8 |
| MDY4947425.1 | 897 | 65.8 |
| MDY5002985.1 | 898 | 65.8 |
| MDY5809713.1 | 899 | 65.8 |
| MEO2302128.1 | 900 | 65.8 |
| MVN48724.1 | 901 | 65.8 |
| MVN54540.1 | 902 | 65.8 |
| OFR30555.1 | 903 | 65.8 |
| UWF80397.1 | 904 | 65.8 |
| WP_016455084.1 | 905 | 65.8 |
| WP_017767652.1 | 906 | 65.8 |
| WP_022865527.1 | 907 | 65.8 |
| WP_029691326.1 | 908 | 65.8 |
| WP_048349524.1 | 909 | 65.8 |
| WP_064468301.1 | 910 | 65.8 |
| WP_070664409.1 | 911 | 65.8 |

TABLE 7-continued

CW_7 repeat-containing protein sequences and sequence identity to CLB2 CW_7.

| GenBank | SEQ | ID % |
|---|---|---|
| WP_094689643.1 | 912 | 65.8 |
| WP_105302716.1 | 913 | 65.8 |
| WP_111835664.1 | 914 | 65.8 |
| WP_129853666.1 | 915 | 65.8 |
| WP_187323888.1 | 916 | 65.8 |
| WP_196322039.1 | 917 | 65.8 |
| WP_196716870.1 | 918 | 65.8 |
| WP_212927898.1 | 919 | 65.8 |
| WP_214373396.1 | 920 | 65.8 |
| WP_217952654.1 | 921 | 65.8 |
| WP_226814206.1 | 922 | 65.8 |
| WP_233187685.1 | 923 | 65.8 |
| WP_269801654.1 | 924 | 65.8 |
| WP_270416430.1 | 925 | 65.8 |
| WP_297152199.1 | 926 | 65.8 |
| WP_308806891.1 | 927 | 65.8 |
| WP_332309264.1 | 928 | 65.8 |
| WP_332309275.1 | 929 | 65.8 |
| WP_367246455.1 | 930 | 65.8 |
| DAS09555.1 | 931 | 65.7 |
| DAU44944.1 | 932 | 65.7 |
| MBO6229297.1 | 933 | 65.7 |
| MBS6611818.1 | 934 | 65.7 |
| UQS94678.1 | 935 | 65.7 |
| UVK58666.1 | 936 | 65.7 |
| UVK62826.1 | 937 | 65.7 |
| WNN94508.1 | 938 | 65.7 |
| WNT45387.1 | 939 | 65.7 |
| WP_321109965.1 | 940 | 65.7 |
| MDR2064222.1 | 941 | 65.6 |
| NLB86109.1 | 942 | 65.6 |
| MDE6562206.1 | 943 | 65.5 |
| DAV71436.1 | 944 | 64.9 |
| DAX88488.1 | 945 | 64.9 |
| WP_241513445.1 | 946 | 64.9 |
| WP_298648273.1 | 947 | 64.9 |
| WP_347014598.1 | 948 | 64.9 |
| WP_347017587.1 | 949 | 64.9 |
| YP_010749833.1 | 950 | 64.9 |
| YP_010750018.1 | 951 | 64.9 |
| YP_010750454.1 | 952 | 64.9 |
| YP_010750543.1 | 953 | 64.9 |
| MDE5876126.1 | 954 | 64.5 |
| MDE6098411.1 | 955 | 64.5 |
| MDK7734839.1 | 956 | 64.5 |
| CRH88545.1 | 957 | 64.1 |
| DAZ79371.1 | 958 | 64.1 |
| MDD7306634.1 | 959 | 64.1 |
| WP_108831516.1 | 960 | 64.1 |
| WP_316711815.1 | 961 | 64.1 |
| WP_316716122.1 | 962 | 64.1 |
| WP_290163399.1 | 963 | 63.9 |
| WP_321973189.1 | 964 | 63.9 |
| WP_322354807.1 | 965 | 63.9 |
| WP_332058111.1 | 966 | 63.9 |
| MCM1222971.1 | 967 | 63.6 |
| DAX21245.1 | 968 | 63.4 |
| DAG21365.1 | 969 | 63.4 |
| DAG38064.1 | 970 | 63.4 |
| DAQ11137.1 | 971 | 63.4 |
| DAQ74288.1 | 972 | 63.4 |
| DAV69797.1 | 973 | 63.4 |
| MBD8989282.1 | 974 | 63.4 |
| MBR7058092.1 | 975 | 63.4 |
| MBS4949125.1 | 976 | 63.4 |
| MCI5948801.1 | 977 | 63.4 |
| MCQ2455584.1 | 978 | 63.4 |
| MDO4397246.1 | 979 | 63.4 |
| MDU2202814.1 | 980 | 63.4 |
| MDU3153525.1 | 981 | 63.4 |
| WP_004815548.1 | 982 | 63.4 |
| WP_040398502.1 | 983 | 63.4 |
| WP_102198006.1 | 984 | 63.4 |
| WP_236784742.1 | 985 | 63.4 |
| WP_271190939.1 | 986 | 63.4 |
| WP_276876721.1 | 987 | 63.4 |
| WP_316125110.1 | 988 | 63.4 |
| WP_316259699.1 | 989 | 63.4 |
| DAE10185.1 | 990 | 63.2 |
| DAE37447.1 | 991 | 63.2 |
| DAP86395.1 | 992 | 63.2 |
| EFM41449.1 | 993 | 63.2 |
| HAP28934.1 | 994 | 63.2 |
| HEP3485709.1 | 995 | 63.2 |
| HEP3594365.1 | 996 | 63.2 |
| MBQ9001100.1 | 997 | 63.2 |
| MBR3224217.1 | 998 | 63.2 |
| MCH4205199.1 | 999 | 63.2 |
| MDE5633374.1 | 1000 | 63.2 |
| MEE0972498.1 | 1001 | 63.2 |
| QFG09112.1 | 1002 | 63.2 |
| RXE73511.1 | 1003 | 63.2 |
| WP_003843926.1 | 1004 | 63.2 |
| WP_043036829.1 | 1005 | 63.2 |
| WP_069996976.1 | 1006 | 63.2 |
| WP_070021810.1 | 1007 | 63.2 |
| WP_070043600.1 | 1008 | 63.2 |
| WP_077323271.1 | 1009 | 63.2 |
| WP_094726333.1 | 1010 | 63.2 |
| WP_105302986.1 | 1011 | 63.2 |
| WP_119875702.1 | 1012 | 63.2 |
| WP_160213661.1 | 1013 | 63.2 |
| WP_163583485.1 | 1014 | 63.2 |
| WP_166339669.1 | 1015 | 63.2 |
| WP_195920298.1 | 1016 | 63.2 |
| WP_196334987.1 | 1017 | 63.2 |
| WP_223355836.1 | 1018 | 63.2 |
| WP_264340631.1 | 1019 | 63.2 |
| WP_264340658.1 | 1020 | 63.2 |
| WP_285112198.1 | 1021 | 63.2 |
| WP_301356913.1 | 1022 | 63.2 |
| WP_305296540.1 | 1023 | 63.2 |
| YP_010749746.1 | 1024 | 63.2 |
| YP_010749926.1 | 1025 | 63.2 |
| KIS17957.1 | 1026 | 63.2 |
| WP_300954678.1 | 1027 | 63.0 |
| WP_270471910.1 | 1028 | 63.0 |
| DAE91224.1 | 1029 | 62.5 |
| DAM24539.1 | 1030 | 62.5 |
| DAP80735.1 | 1031 | 62.5 |
| DAY46996.1 | 1032 | 62.5 |
| MBD9043651.1 | 1033 | 62.5 |
| MCB0539258.1 | 1034 | 62.5 |
| MCI5982561.1 | 1035 | 62.5 |
| MDR1881842.1 | 1036 | 62.5 |
| MEE1347036.1 | 1037 | 62.5 |
| NLK93115.1 | 1038 | 62.5 |
| RHD34509.1 | 1039 | 62.5 |
| WP_256267913.1 | 1040 | 62.5 |
| WP_288518369.1 | 1041 | 62.5 |
| WP_303014023.1 | 1042 | 62.5 |
| WP_329993587.1 | 1043 | 62.5 |
| DAG78306.1 | 1044 | 62.2 |
| DAR99974.1 | 1045 | 62.2 |
| DAW92160.1 | 1046 | 62.2 |
| DAY92830.1 | 1047 | 62.2 |
| HEM3681644.1 | 1048 | 62.2 |
| UVX57188.1 | 1049 | 62.2 |
| WP_214358849.1 | 1050 | 62.2 |
| WP_226674200.1 | 1051 | 62.2 |
| WP_241513637.1 | 1052 | 62.2 |
| WP_293817352.1 | 1053 | 62.2 |
| MBR1792531.1 | 1054 | 62.1 |
| MDR0573062.1 | 1055 | 62.1 |
| KWZ98309.1 | 1056 | 61.5 |
| MDU2025612.1 | 1057 | 61.5 |
| MDU2710058.1 | 1058 | 61.5 |
| MDU6032175.1 | 1059 | 61.5 |
| MDY3119231.1 | 1060 | 61.5 |
| WP_002834858.1 | 1061 | 61.5 |

TABLE 7-continued

CW_7 repeat-containing protein sequences and sequence identity to CLB2 CW_7.

| GenBank | SEQ | ID % |
|---|---|---|
| WP_066130500.1 | 1062 | 61.5 |
| WP_071125805.1 | 1063 | 61.5 |
| WP_075659837.1 | 1064 | 61.5 |
| WP_094206257.1 | 1065 | 61.5 |
| WP_094208061.1 | 1066 | 61.5 |
| WP_131749276.1 | 1067 | 61.5 |
| WP_148466397.1 | 1068 | 61.5 |
| WP_273497912.1 | 1069 | 61.5 |
| WP_277219390.1 | 1070 | 61.5 |
| WP_285083715.1 | 1071 | 61.5 |
| WP_316258004.1 | 1072 | 61.5 |
| WP_316277261.1 | 1073 | 61.5 |
| WP_316536349.1 | 1074 | 61.5 |
| WP_349169999.1 | 1075 | 61.5 |
| WZE63394.1 | 1076 | 61.5 |
| MDE5655895.1 | 1077 | 61.3 |
| DAD93583.1 | 1078 | 61.1 |
| DAI70013.1 | 1079 | 61.1 |
| MBD5171685.1 | 1080 | 61.1 |
| MBD5323526.1 | 1081 | 61.1 |
| MBR4886392.1 | 1082 | 61.1 |
| MBS6101062.1 | 1083 | 61.1 |
| MCC8176492.1 | 1084 | 61.1 |
| WP_102218431.1 | 1085 | 61.1 |
| WP_135040546.1 | 1086 | 61.1 |
| WP_204458078.1 | 1087 | 61.1 |
| WP_211810791.1 | 1088 | 61.1 |
| WP_211820463.1 | 1089 | 61.1 |
| WP_297572425.1 | 1090 | 61.1 |
| WP_314699748.1 | 1091 | 61.1 |
| WP_315363016.1 | 1092 | 61.1 |
| WP_315582330.1 | 1093 | 61.1 |
| DAG35656.1 | 1094 | 61.0 |
| DAH42994.1 | 1095 | 61.0 |
| DAN42819.1 | 1096 | 61.0 |
| DAR58693.1 | 1097 | 61.0 |
| DAS75787.1 | 1098 | 61.0 |
| DAS80110.1 | 1099 | 61.0 |
| DAU24415.1 | 1100 | 61.0 |
| DAV78720.1 | 1101 | 61.0 |
| DAY24267.1 | 1102 | 61.0 |
| DAY92418.1 | 1103 | 61.0 |
| HEN0920928.1 | 1104 | 61.0 |
| HES5977255.1 | 1105 | 61.0 |
| KGF33253.1 | 1106 | 61.0 |
| KWZ97970.1 | 1107 | 61.0 |
| MCC9971120.1 | 1108 | 61.0 |
| MCX4357018.1 | 1109 | 61.0 |
| MDE6733460.1 | 1110 | 61.0 |
| MDU0946473.1 | 1111 | 61.0 |
| MDU6064502.1 | 1112 | 61.0 |
| MDY6062382.1 | 1113 | 61.0 |
| QBX15581.1 | 1114 | 61.0 |
| QQO40300.1 | 1115 | 61.0 |
| RGJ72596.1 | 1116 | 61.0 |
| WP_004817817.1 | 1117 | 61.0 |
| WP_020758810.1 | 1118 | 61.0 |
| WP_020760684.1 | 1119 | 61.0 |
| WP_028505417.1 | 1120 | 61.0 |
| WP_048782353.1 | 1121 | 61.0 |
| WP_049690569.1 | 1122 | 61.0 |
| WP_053942762.1 | 1123 | 61.0 |
| WP_058890964.1 | 1124 | 61.0 |
| WP_063633074.1 | 1125 | 61.0 |
| WP_065957164.1 | 1126 | 61.0 |
| WP_070584868.1 | 1127 | 61.0 |
| WP_076002731.1 | 1128 | 61.0 |
| WP_085875841.1 | 1129 | 61.0 |
| WP_116691955.1 | 1130 | 61.0 |
| WP_117625149.1 | 1131 | 61.0 |
| WP_150412426.1 | 1132 | 61.0 |
| WP_150891248.1 | 1133 | 61.0 |
| WP_156667719.1 | 1134 | 61.0 |
| WP_163104227.1 | 1135 | 61.0 |
| WP_206151972.1 | 1136 | 61.0 |
| WP_264347151.1 | 1137 | 61.0 |
| WP_271528891.1 | 1138 | 61.0 |
| WP_276771163.1 | 1139 | 61.0 |
| WP_278578613.1 | 1140 | 61.0 |
| WP_284346615.1 | 1141 | 61.0 |
| WP_303825152.1 | 1142 | 61.0 |
| WP_303886853.1 | 1143 | 61.0 |
| WP_306487063.1 | 1144 | 61.0 |
| WP_311370301.1 | 1145 | 61.0 |
| WP_311436783.1 | 1146 | 61.0 |
| WP_315027119.1 | 1147 | 61.0 |
| WP_316081316.1 | 1148 | 61.0 |
| WP_316083149.1 | 1149 | 61.0 |
| WP_349820259.1 | 1150 | 61.0 |
| DAO69701.1 | 1151 | 61.0 |
| MED5763440.1 | 1152 | 61.0 |
| WP_118750982.1 | 1153 | 61.0 |
| WP_150861031.1 | 1154 | 61.0 |
| QFG13613.1 | 1155 | 60.7 |
| DAZ27128.1 | 1156 | 60.6 |
| MBQ9658343.1 | 1157 | 60.6 |
| CDE95606.1 | 1158 | 60.5 |
| DAE07393.1 | 1159 | 60.5 |
| DAH51102.1 | 1160 | 60.5 |
| DAJ01481.1 | 1161 | 60.5 |
| DAN98945.1 | 1162 | 60.5 |
| DAO39897.1 | 1163 | 60.5 |
| DAQ97161.1 | 1164 | 60.5 |
| DAU96762.1 | 1165 | 60.5 |
| DAV93860.1 | 1166 | 60.5 |
| DAW58986.1 | 1167 | 60.5 |
| DAW64646.1 | 1168 | 60.5 |
| DAZ06134.1 | 1169 | 60.5 |
| HEL0787365.1 | 1170 | 60.5 |
| HEL1580504.1 | 1171 | 60.5 |
| HEL1588637.1 | 1172 | 60.5 |
| HEL1785799.1 | 1173 | 60.5 |
| HEL2261299.1 | 1174 | 60.5 |
| HEM3680527.1 | 1175 | 60.5 |
| HEM3695368.1 | 1176 | 60.5 |
| HEP4476158.1 | 1177 | 60.5 |
| HEP5759258.1 | 1178 | 60.5 |
| HEQ9431484.1 | 1179 | 60.5 |
| HEQ9463603.1 | 1180 | 60.5 |
| HIS39969.1 | 1181 | 60.5 |
| KAA6140981.1 | 1182 | 60.5 |
| KAB5910941.1 | 1183 | 60.5 |
| MBG9981762.1 | 1184 | 60.5 |
| MBM6747214.1 | 1185 | 60.5 |
| MBP3771575.1 | 1186 | 60.5 |
| MBR2258270.1 | 1187 | 60.5 |
| MBR3314243.1 | 1188 | 60.5 |
| MBT9645934.1 | 1189 | 60.5 |
| MCC9684219.1 | 1190 | 60.5 |
| MCC9697169.1 | 1191 | 60.5 |
| MCI5976192.1 | 1192 | 60.5 |
| MCI6713172.1 | 1193 | 60.5 |
| MCX4355861.1 | 1194 | 60.5 |
| MDE6928620.1 | 1195 | 60.5 |
| MDW8721211.1 | 1196 | 60.5 |
| MDY3797592.1 | 1197 | 60.5 |
| QBX23791.1 | 1198 | 60.5 |
| QFG08678.1 | 1199 | 60.5 |
| RGV16217.1 | 1200 | 60.5 |
| RHJ17266.1 | 1201 | 60.5 |
| RHP71026.1 | 1202 | 60.5 |
| RHU32963.1 | 1203 | 60.5 |
| UVY58840.1 | 1204 | 60.5 |
| UWD73207.1 | 1205 | 60.5 |
| UWF84366.1 | 1206 | 60.5 |
| UWH97680.1 | 1207 | 60.5 |
| WGH21693.1 | 1208 | 60.5 |
| WP_033499054.1 | 1209 | 60.5 |
| WP_043026720.1 | 1210 | 60.5 |
| WP_044760627.1 | 1211 | 60.5 |

TABLE 7-continued

CW_7 repeat-containing protein sequences and sequence identity to CLB2 CW_7.

| GenBank | SEQ | ID % |
|---|---|---|
| WP_075105316.1 | 1212 | 60.5 |
| WP_093649504.1 | 1213 | 60.5 |
| WP_099721625.1 | 1214 | 60.5 |
| WP_101541573.1 | 1215 | 60.5 |
| WP_115283083.1 | 1216 | 60.5 |
| WP_154052834.1 | 1217 | 60.5 |
| WP_164406171.1 | 1218 | 60.5 |
| WP_165737659.1 | 1219 | 60.5 |
| WP_174850419.1 | 1220 | 60.5 |
| WP_182438950.1 | 1221 | 60.5 |
| WP_190278465.1 | 1222 | 60.5 |
| WP_212973039.1 | 1223 | 60.5 |
| WP_215678720.1 | 1224 | 60.5 |
| WP_231148010.1 | 1225 | 60.5 |
| WP_231367239.1 | 1226 | 60.5 |
| WP_239459142.1 | 1227 | 60.5 |
| WP_242698100.1 | 1228 | 60.5 |
| WP_257384659.1 | 1229 | 60.5 |
| WP_259302491.1 | 1230 | 60.5 |
| WP_259328150.1 | 1231 | 60.5 |
| WP_259328953.1 | 1232 | 60.5 |
| WP_270202457.1 | 1233 | 60.5 |
| WP_270625927.1 | 1234 | 60.5 |
| WP_271718045.1 | 1235 | 60.5 |
| WP_282209729.1 | 1236 | 60.5 |
| WP_284790345.1 | 1237 | 60.5 |
| WP_301587153.1 | 1238 | 60.5 |
| WP_332058383.1 | 1239 | 60.5 |
| WP_336261417.1 | 1240 | 60.5 |
| WP_367256048.1 | 1241 | 60.5 |
| MBQ2316265.1 | 1242 | 60.5 |
| WP_078390735.1 | 1243 | 60.5 |
| WP_182426743.1 | 1244 | 60.5 |
| AYD87216.1 | 1245 | 60.0 |
| DAE60825.1 | 1246 | 60.0 |
| DAF33844.1 | 1247 | 60.0 |
| DAH53468.1 | 1248 | 60.0 |
| DAI57608.1 | 1249 | 60.0 |
| DAI85954.1 | 1250 | 60.0 |
| DAJ72724.1 | 1251 | 60.0 |
| DAJ84296.1 | 1252 | 60.0 |
| DAL31530.1 | 1253 | 60.0 |
| DAN17868.1 | 1254 | 60.0 |
| DAP36906.1 | 1255 | 60.0 |
| DAT94504.1 | 1256 | 60.0 |
| DAV66269.1 | 1257 | 60.0 |
| DAX28918.1 | 1258 | 60.0 |
| DAZ39095.1 | 1259 | 60.0 |
| DAZ43436.1 | 1260 | 60.0 |
| EDN82835.1 | 1261 | 60.0 |
| EPT97855.1 | 1262 | 60.0 |
| GDY96701.1 | 1263 | 60.0 |
| GDZ14048.1 | 1264 | 60.0 |
| HJI53419.1 | 1265 | 60.0 |
| KAB5913358.1 | 1266 | 60.0 |
| MBQ1440049.1 | 1267 | 60.0 |
| MBQ1440213.1 | 1268 | 60.0 |
| MBS5344990.1 | 1269 | 60.0 |
| MCX4364628.1 | 1270 | 60.0 |
| MDB0584235.1 | 1271 | 60.0 |
| MDB0584332.1 | 1272 | 60.0 |
| MDB1402780.1 | 1273 | 60.0 |
| MDG3146345.1 | 1274 | 60.0 |
| MDO4394948.1 | 1275 | 60.0 |
| MDO4873232.1 | 1276 | 60.0 |
| MDR3744106.1 | 1277 | 60.0 |
| MEO5392119.1 | 1278 | 60.0 |
| MEO5545186.1 | 1279 | 60.0 |
| OZG68262.1 | 1280 | 60.0 |
| PKY88156.1 | 1281 | 60.0 |
| RGY75950.1 | 1282 | 60.0 |
| RHL94559.1 | 1283 | 60.0 |
| WP_094636851.1 | 1284 | 60.0 |
| WP_106621505.1 | 1285 | 60.0 |
| WP_135156249.1 | 1286 | 60.0 |
| WP_138296803.1 | 1287 | 60.0 |
| WP_152026998.1 | 1288 | 60.0 |
| WP_155972593.1 | 1289 | 60.0 |
| WP_158087765.1 | 1290 | 60.0 |
| WP_162008473.1 | 1291 | 60.0 |
| WP_179141965.1 | 1292 | 60.0 |
| WP_182432327.1 | 1293 | 60.0 |
| WP_195247765.1 | 1294 | 60.0 |
| WP_198051789.1 | 1295 | 60.0 |
| WP_217063305.1 | 1296 | 60.0 |
| WP_223895965.1 | 1297 | 60.0 |
| WP_226562967.1 | 1298 | 60.0 |
| WP_226676390.1 | 1299 | 60.0 |
| WP_227990307.1 | 1300 | 60.0 |
| WP_229027019.1 | 1301 | 60.0 |
| WP_230456860.1 | 1302 | 60.0 |
| WP_240836407.1 | 1303 | 60.0 |
| WP_241157620.1 | 1304 | 60.0 |
| WP_257964118.1 | 1305 | 60.0 |
| WP_270301365.1 | 1306 | 60.0 |
| WP_270557813.1 | 1307 | 60.0 |
| WP_271718013.1 | 1308 | 60.0 |
| WP_271735398.1 | 1309 | 60.0 |
| WP_276610523.1 | 1310 | 60.0 |
| WP_300955093.1 | 1311 | 60.0 |
| WP_302691238.1 | 1312 | 60.0 |
| WP_346971473.1 | 1313 | 60.0 |
| WP_346974628.1 | 1314 | 60.0 |
| WP_347029834.1 | 1315 | 60.0 |
| WP_347309308.1 | 1316 | 60.0 |
| YP_009603377.1 | 1317 | 60.0 |
| DAE68824.1 | 1318 | 59.5 |
| DAE83464.1 | 1319 | 59.5 |
| DAL50846.1 | 1320 | 59.5 |
| DAL69393.1 | 1321 | 59.5 |
| DAM40440.1 | 1322 | 59.5 |
| DAO47211.1 | 1323 | 59.5 |
| DAV24095.1 | 1324 | 59.5 |
| DAW47376.1 | 1325 | 59.5 |
| MBT9823866.1 | 1326 | 59.5 |
| MBU9067560.1 | 1327 | 59.5 |
| MCZ4448492.1 | 1328 | 59.5 |
| MDN4192218.1 | 1329 | 59.5 |
| MDU4035230.1 | 1330 | 59.5 |
| PXY87351.1 | 1331 | 59.5 |
| QHJ78355.1 | 1332 | 59.5 |
| UAU37679.1 | 1333 | 59.5 |
| UVY26228.1 | 1334 | 59.5 |
| UWG12920.1 | 1335 | 59.5 |
| UWG28836.1 | 1336 | 59.5 |
| WP_025301165.1 | 1337 | 59.5 |
| WP_058101879.1 | 1338 | 59.5 |
| WP_058102379.1 | 1339 | 59.5 |
| WP_117656824.1 | 1340 | 59.5 |
| WP_171842699.1 | 1341 | 59.5 |
| WP_181415636.1 | 1342 | 59.5 |
| WP_223616784.1 | 1343 | 59.5 |
| WP_226598371.1 | 1344 | 59.5 |
| WP_227248116.1 | 1345 | 59.5 |
| WP_237973881.1 | 1346 | 59.5 |
| WP_269374407.1 | 1347 | 59.5 |
| WP_270198036.1 | 1348 | 59.5 |
| WP_288923530.1 | 1349 | 59.5 |
| WP_306172973.1 | 1350 | 59.5 |
| WP_347011742.1 | 1351 | 59.5 |
| WP_367304467.1 | 1352 | 59.5 |
| WP_252195685.1 | 1353 | 59.5 |
| DAN65483.1 | 1354 | 59.4 |
| MBS5527381.1 | 1355 | 59.4 |
| MDB0925878.1 | 1356 | 59.4 |
| MDD7150974.1 | 1357 | 59.4 |
| MEE1371684.1 | 1358 | 59.4 |
| WP_005651920.1 | 1359 | 59.4 |
| WP_016662242.1 | 1360 | 59.4 |
| WP_032944750.1 | 1361 | 59.4 |

TABLE 7-continued

CW_7 repeat-containing protein sequences and sequence identity to CLB2 CW_7.

| GenBank | SEQ | ID % |
|---|---|---|
| WP_055167641.1 | 1362 | 59.4 |
| WP_117907320.1 | 1363 | 59.4 |
| WP_117983990.1 | 1364 | 59.4 |
| WP_221734782.1 | 1365 | 59.4 |
| WP_234250675.1 | 1366 | 59.4 |
| WP_237464145.1 | 1367 | 59.4 |
| WP_308006913.1 | 1368 | 59.4 |
| WP_347502903.1 | 1369 | 59.4 |
| WP_349167250.1 | 1370 | 59.4 |
| UVX48964.1 | 1371 | 59.4 |
| WP_278698178.1 | 1372 | 59.4 |
| WP_304330030.1 | 1373 | 59.4 |
| MCI7239121.1 | 1374 | 59.0 |
| MDO4662903.1 | 1375 | 59.0 |
| MDU3805833.1 | 1376 | 59.0 |
| MDU5807467.1 | 1377 | 59.0 |
| MDU6792092.1 | 1378 | 59.0 |
| MDU7502579.1 | 1379 | 59.0 |
| MEE3451439.1 | 1380 | 59.0 |
| MEE3495404.1 | 1381 | 59.0 |
| WP_019117835.1 | 1382 | 59.0 |
| WP_019131806.1 | 1383 | 59.0 |
| WP_044565592.1 | 1384 | 59.0 |
| WP_049690785.1 | 1385 | 59.0 |
| WP_068370136.1 | 1386 | 59.0 |
| WP_070699874.1 | 1387 | 59.0 |
| WP_072469687.1 | 1388 | 59.0 |
| WP_085875992.1 | 1389 | 59.0 |
| WP_176269698.1 | 1390 | 59.0 |
| WP_176270218.1 | 1391 | 59.0 |
| WP_195445719.1 | 1392 | 59.0 |
| WP_242846544.1 | 1393 | 59.0 |
| WP_265214713.1 | 1394 | 59.0 |
| WP_273497992.1 | 1395 | 59.0 |
| WP_278726342.1 | 1396 | 59.0 |
| WP_285072970.1 | 1397 | 59.0 |
| WP_285091446.1 | 1398 | 59.0 |
| WP_297789646.1 | 1399 | 59.0 |
| WP_304065734.1 | 1400 | 59.0 |
| WP_316082558.1 | 1401 | 59.0 |
| WP_316263983.1 | 1402 | 59.0 |
| WP_316271836.1 | 1403 | 59.0 |
| WP_316531565.1 | 1404 | 59.0 |
| WP_316713042.1 | 1405 | 59.0 |
| WP_320595860.1 | 1406 | 59.0 |
| WP_339351660.1 | 1407 | 59.0 |
| MBM3454677.1 | 1408 | 58.8 |
| WP_137658154.1 | 1409 | 58.8 |
| MBP3823215.1 | 1410 | 58.6 |
| DAD72903.1 | 1411 | 58.5 |
| DAE36560.1 | 1412 | 58.5 |
| DAE79616.1 | 1413 | 58.5 |
| DAG71853.1 | 1414 | 58.5 |
| DAH37335.1 | 1415 | 58.5 |
| DAH73610.1 | 1416 | 58.5 |
| DAJ49710.1 | 1417 | 58.5 |
| DAK79329.1 | 1418 | 58.5 |
| DAL72843.1 | 1419 | 58.5 |
| DAN00457.1 | 1420 | 58.5 |
| DAN97814.1 | 1421 | 58.5 |
| DAO78994.1 | 1422 | 58.5 |
| DAQ88132.1 | 1423 | 58.5 |
| DAR90074.1 | 1424 | 58.5 |
| DAT70674.1 | 1425 | 58.5 |
| DAU07598.1 | 1426 | 58.5 |
| DAX83517.1 | 1427 | 58.5 |
| DAY55160.1 | 1428 | 58.5 |
| DAY63153.1 | 1429 | 58.5 |
| DAY70274.1 | 1430 | 58.5 |
| DAZ06055.1 | 1431 | 58.5 |
| EDR98670.1 | 1432 | 58.5 |
| HCB90396.1 | 1433 | 58.5 |
| HEN3196485.1 | 1434 | 58.5 |
| HEO2154627.1 | 1435 | 58.5 |
| HEP7759283.1 | 1436 | 58.5 |
| HES5012758.1 | 1437 | 58.5 |
| MBE5719514.1 | 1438 | 58.5 |
| MBF0935596.1 | 1439 | 58.5 |
| MBF0942281.1 | 1440 | 58.5 |
| MBF0942750.1 | 1441 | 58.5 |
| MBO5554600.1 | 1442 | 58.5 |
| MBP3868423.1 | 1443 | 58.5 |
| MBQ1535426.1 | 1444 | 58.5 |
| MBQ7536269.1 | 1445 | 58.5 |
| MBQ8069001.1 | 1446 | 58.5 |
| MBR2990305.1 | 1447 | 58.5 |
| MBR4455732.1 | 1448 | 58.5 |
| MBS4899850.1 | 1449 | 58.5 |
| MBS5114513.1 | 1450 | 58.5 |
| MCH5195954.1 | 1451 | 58.5 |
| MCH5207535.1 | 1452 | 58.5 |
| MCI8753175.1 | 1453 | 58.5 |
| MCM1497131.1 | 1454 | 58.5 |
| MCR0265655.1 | 1455 | 58.5 |
| MDB7998989.1 | 1456 | 58.5 |
| MDO4872672.1 | 1457 | 58.5 |
| MDO5018820.1 | 1458 | 58.5 |
| MDR0880914.1 | 1459 | 58.5 |
| MDR3136782.1 | 1460 | 58.5 |
| MDU2292470.1 | 1461 | 58.5 |
| MDU3325762.1 | 1462 | 58.5 |
| MDU3532159.1 | 1463 | 58.5 |
| MDU5246805.1 | 1464 | 58.5 |
| MDY2940917.1 | 1465 | 58.5 |
| MED5846031.1 | 1466 | 58.5 |
| QAT50916.1 | 1467 | 58.5 |
| QBZ72893.1 | 1468 | 58.5 |
| QBZ73215.1 | 1469 | 58.5 |
| QDH92752.1 | 1470 | 58.5 |
| QKH47416.1 | 1471 | 58.5 |
| RFT36047.1 | 1472 | 58.5 |
| RIY29961.1 | 1473 | 58.5 |
| RKW14997.1 | 1474 | 58.5 |
| SFE01904.1 | 1475 | 58.5 |
| UVM99539.1 | 1476 | 58.5 |
| WNM67997.1 | 1477 | 58.5 |
| WP_009269295.1 | 1478 | 58.5 |
| WP_019133547.1 | 1479 | 58.5 |
| WP_019190634.1 | 1480 | 58.5 |
| WP_020757759.1 | 1481 | 58.5 |
| WP_022866279.1 | 1482 | 58.5 |
| WP_023391808.1 | 1483 | 58.5 |
| WP_065189629.1 | 1484 | 58.5 |
| WP_070641721.1 | 1485 | 58.5 |
| WP_071132528.1 | 1486 | 58.5 |
| WP_071705048.1 | 1487 | 58.5 |
| WP_073382452.1 | 1488 | 58.5 |
| WP_074667897.1 | 1489 | 58.5 |
| WP_074667968.1 | 1490 | 58.5 |
| WP_075523958.1 | 1491 | 58.5 |
| WP_075712035.1 | 1492 | 58.5 |
| WP_101887622.1 | 1493 | 58.5 |
| WP_103013458.1 | 1494 | 58.5 |
| WP_103014085.1 | 1495 | 58.5 |
| WP_103043209.1 | 1496 | 58.5 |
| WP_116440732.1 | 1497 | 58.5 |
| WP_116712567.1 | 1498 | 58.5 |
| WP_132226174.1 | 1499 | 58.5 |
| WP_172355546.1 | 1500 | 58.5 |
| WP_208075871.1 | 1501 | 58.5 |
| WP_222199098.1 | 1502 | 58.5 |
| WP_230454752.1 | 1503 | 58.5 |
| WP_268445599.1 | 1504 | 58.5 |
| WP_269310727.1 | 1505 | 58.5 |
| WP_284761781.1 | 1506 | 58.5 |
| WP_285068298.1 | 1507 | 58.5 |
| WP_285072900.1 | 1508 | 58.5 |
| WP_285085367.1 | 1509 | 58.5 |
| WP_288686255.1 | 1510 | 58.5 |
| WP_291431937.1 | 1511 | 58.5 |

TABLE 7-continued

CW_7 repeat-containing protein sequences and sequence identity to CLB2 CW_7.

| GenBank | SEQ | ID % |
|---|---|---|
| WP_291432595.1 | 1512 | 58.5 |
| WP_291454566.1 | 1513 | 58.5 |
| WP_294143885.1 | 1514 | 58.5 |
| WP_303766305.1 | 1515 | 58.5 |
| WP_311466807.1 | 1516 | 58.5 |
| WP_311468163.1 | 1517 | 58.5 |
| WP_311537681.1 | 1518 | 58.5 |
| WP_314050720.1 | 1519 | 58.5 |
| WP_314064708.1 | 1520 | 58.5 |
| WP_314181765.1 | 1521 | 58.5 |
| WP_314198117.1 | 1522 | 58.5 |
| WP_314211913.1 | 1523 | 58.5 |
| WP_314250476.1 | 1524 | 58.5 |
| WP_314330401.1 | 1525 | 58.5 |
| WP_314693334.1 | 1526 | 58.5 |
| WP_314943685.1 | 1527 | 58.5 |
| WP_315025765.1 | 1528 | 58.5 |
| WP_315272755.1 | 1529 | 58.5 |
| WP_315600779.1 | 1530 | 58.5 |
| WP_316054981.1 | 1531 | 58.5 |
| WP_316276503.1 | 1532 | 58.5 |
| WP_316278639.1 | 1533 | 58.5 |
| WP_316709084.1 | 1534 | 58.5 |
| WP_320756368.1 | 1535 | 58.5 |
| WP_338153073.1 | 1536 | 58.5 |
| WP_338543391.1 | 1537 | 58.5 |
| YP_009624165.1 | 1538 | 58.5 |
| YP_009624223.1 | 1539 | 58.5 |
| AIA84369.1 | 1540 | 58.5 |
| MCL2545587.1 | 1541 | 58.5 |
| MCR5486349.1 | 1542 | 58.5 |
| WP_308609988.1 | 1543 | 58.5 |
| WP_314181128.1 | 1544 | 58.5 |
| MDE5642763.1 | 1545 | 58.3 |
| WP_153122072.1 | 1546 | 58.3 |
| AUI56361.1 | 1547 | 58.3 |
| DAF70151.1 | 1548 | 58.3 |
| DAG86485.1 | 1549 | 58.3 |
| DAJ59400.1 | 1550 | 58.3 |
| DAR23206.1 | 1551 | 58.3 |
| HIU04681.1 | 1552 | 58.3 |
| MBR3977748.1 | 1553 | 58.3 |
| MCI5543680.1 | 1554 | 58.3 |
| MCI7050931.1 | 1555 | 58.3 |
| MDE5791455.1 | 1556 | 58.3 |
| MDE6409347.1 | 1557 | 58.3 |
| MDY4557163.1 | 1558 | 58.3 |
| MEE0092799.1 | 1559 | 58.3 |
| WP_007365856.1 | 1560 | 58.3 |
| WP_009010225.1 | 1561 | 58.3 |
| WP_024628003.1 | 1562 | 58.3 |
| WP_077140485.1 | 1563 | 58.3 |
| WP_102048277.1 | 1564 | 58.3 |
| WP_131285126.1 | 1565 | 58.3 |
| WP_198208408.1 | 1566 | 58.3 |
| WP_277153947.1 | 1567 | 58.3 |
| WP_293965845.1 | 1568 | 58.3 |
| WP_296929086.1 | 1569 | 58.3 |
| WP_299282351.1 | 1570 | 58.3 |
| WP_305278004.1 | 1571 | 58.3 |
| WP_320643000.1 | 1572 | 58.3 |
| WP_320800265.1 | 1573 | 58.3 |
| WP_346748512.1 | 1574 | 58.3 |
| HER5200536.1 | 1575 | 57.9 |
| HES3276599.1 | 1576 | 57.9 |
| HRJ06874.1 | 1577 | 57.9 |
| MBO5028976.1 | 1578 | 57.9 |
| MCM1399858.1 | 1579 | 57.9 |
| VTZ99185.1 | 1580 | 57.9 |
| WP_012767360.1 | 1581 | 57.9 |
| WP_115253245.1 | 1582 | 57.9 |
| WP_158457394.1 | 1583 | 57.9 |
| WP_242668385.1 | 1584 | 57.9 |
| ACD98581.1 | 1585 | 57.9 |
| AUD83070.1 | 1586 | 57.9 |
| AZR97677.1 | 1587 | 57.9 |
| DAD57082.1 | 1588 | 57.9 |
| DAE09850.1 | 1589 | 57.9 |
| DAF51537.1 | 1590 | 57.9 |
| DAG04105.1 | 1591 | 57.9 |
| DAM40397.1 | 1592 | 57.9 |
| DAM70826.1 | 1593 | 57.9 |
| DAO55094.1 | 1594 | 57.9 |
| DAO79557.1 | 1595 | 57.9 |
| DAO88179.1 | 1596 | 57.9 |
| DAQ54961.1 | 1597 | 57.9 |
| DAT51229.1 | 1598 | 57.9 |
| DAT69343.1 | 1599 | 57.9 |
| DAT78118.1 | 1600 | 57.9 |
| DAT86970.1 | 1601 | 57.9 |
| DAV58332.1 | 1602 | 57.9 |
| DAW17549.1 | 1603 | 57.9 |
| DAW28399.1 | 1604 | 57.9 |
| DAW97714.1 | 1605 | 57.9 |
| DAY73495.1 | 1606 | 57.9 |
| DAZ29637.1 | 1607 | 57.9 |
| GDZ20669.1 | 1608 | 57.9 |
| GDZ39116.1 | 1609 | 57.9 |
| GDZ42888.1 | 1610 | 57.9 |
| HEL1579987.1 | 1611 | 57.9 |
| HEL1588853.1 | 1612 | 57.9 |
| HEL1656628.1 | 1613 | 57.9 |
| HEL1701650.1 | 1614 | 57.9 |
| HEL1771769.1 | 1615 | 57.9 |
| HEL1826226.1 | 1616 | 57.9 |
| HEL2068769.1 | 1617 | 57.9 |
| HEL2246364.1 | 1618 | 57.9 |
| HEL2620179.1 | 1619 | 57.9 |
| HEL2723699.1 | 1620 | 57.9 |
| HEL9635983.1 | 1621 | 57.9 |
| HEM2738596.1 | 1622 | 57.9 |
| HEM3451942.1 | 1623 | 57.9 |
| HEM3544385.1 | 1624 | 57.9 |
| HEM3602480.1 | 1625 | 57.9 |
| HEM3616496.1 | 1626 | 57.9 |
| HEM4003223.1 | 1627 | 57.9 |
| HEM4275232.1 | 1628 | 57.9 |
| HEM5103866.1 | 1629 | 57.9 |
| HEM5107069.1 | 1630 | 57.9 |
| HEM5175194.1 | 1631 | 57.9 |
| HEM6233304.1 | 1632 | 57.9 |
| HEM6253175.1 | 1633 | 57.9 |
| HEN2239575.1 | 1634 | 57.9 |
| HEN2249115.1 | 1635 | 57.9 |
| HEN7671129.1 | 1636 | 57.9 |
| HEO0332119.1 | 1637 | 57.9 |
| HEO5518101.1 | 1638 | 57.9 |
| HEO6871682.1 | 1639 | 57.9 |
| HEO7195634.1 | 1640 | 57.9 |
| HEP2841441.1 | 1641 | 57.9 |
| HEQ2314291.1 | 1642 | 57.9 |
| HES3505100.1 | 1643 | 57.9 |
| KAB5830440.1 | 1644 | 57.9 |
| KAB6879382.1 | 1645 | 57.9 |
| KAB6912924.1 | 1646 | 57.9 |
| KAB7203424.1 | 1647 | 57.9 |
| KAB7247809.1 | 1648 | 57.9 |
| MBD9019592.1 | 1649 | 57.9 |
| MBL6538710.1 | 1650 | 57.9 |
| MBP3705894.1 | 1651 | 57.9 |
| MBP3773205.1 | 1652 | 57.9 |
| MBQ0154945.1 | 1653 | 57.9 |
| MBQ2174130.1 | 1654 | 57.9 |
| MBR0451785.1 | 1655 | 57.9 |
| MBR3244943.1 | 1656 | 57.9 |
| MBR3355398.1 | 1657 | 57.9 |
| MBS4750310.1 | 1658 | 57.9 |
| MBS4751124.1 | 1659 | 57.9 |
| MBS5806401.1 | 1660 | 57.9 |
| MCC9684189.1 | 1661 | 57.9 |

TABLE 7-continued

CW_7 repeat-containing protein sequences and sequence identity to CLB2 CW_7.

| GenBank | SEQ | ID % |
|---|---|---|
| MCT6836136.1 | 1662 | 57.9 |
| MDB6802159.1 | 1663 | 57.9 |
| MDD6314572.1 | 1664 | 57.9 |
| MDE7031932.1 | 1665 | 57.9 |
| MDO5137252.1 | 1666 | 57.9 |
| MDO5763724.1 | 1667 | 57.9 |
| MDR3975362.1 | 1668 | 57.9 |
| MDR4068528.1 | 1669 | 57.9 |
| MDU1103542.1 | 1670 | 57.9 |
| MDU2273731.1 | 1671 | 57.9 |
| MDU2645528.1 | 1672 | 57.9 |
| MDU3739750.1 | 1673 | 57.9 |
| MDU6842693.1 | 1674 | 57.9 |
| MDU7112524.1 | 1675 | 57.9 |
| MZN84138.1 | 1676 | 57.9 |
| NEW62762.1 | 1677 | 57.9 |
| NQI37392.1 | 1678 | 57.9 |
| NQI43944.1 | 1679 | 57.9 |
| NQK17566.1 | 1680 | 57.9 |
| NQL70505.1 | 1681 | 57.9 |
| NQM29350.1 | 1682 | 57.9 |
| NQO28153.1 | 1683 | 57.9 |
| NRG75228.1 | 1684 | 57.9 |
| QBX31095.1 | 1685 | 57.9 |
| QCH29864.1 | 1686 | 57.9 |
| QSJ04948.1 | 1687 | 57.9 |
| RHK25409.1 | 1688 | 57.9 |
| TCE30094.1 | 1689 | 57.9 |
| UVY50696.1 | 1690 | 57.9 |
| VTT22659.1 | 1691 | 57.9 |
| VUX27149.1 | 1692 | 57.9 |
| WP_000405192.1 | 1693 | 57.9 |
| WP_003058531.1 | 1694 | 57.9 |
| WP_003809895.1 | 1695 | 57.9 |
| WP_012577888.1 | 1696 | 57.9 |
| WP_012578122.1 | 1697 | 57.9 |
| WP_015512446.1 | 1698 | 57.9 |
| WP_016456264.1 | 1699 | 57.9 |
| WP_016462192.1 | 1700 | 57.9 |
| WP_017646318.1 | 1701 | 57.9 |
| WP_021975127.1 | 1702 | 57.9 |
| WP_024381117.1 | 1703 | 57.9 |
| WP_024402343.1 | 1704 | 57.9 |
| WP_025221567.1 | 1705 | 57.9 |
| WP_028124894.1 | 1706 | 57.9 |
| WP_029172513.1 | 1707 | 57.9 |
| WP_029174192.1 | 1708 | 57.9 |
| WP_029177039.1 | 1709 | 57.9 |
| WP_029188011.1 | 1710 | 57.9 |
| WP_029944245.1 | 1711 | 57.9 |
| WP_032511597.1 | 1712 | 57.9 |
| WP_033499772.1 | 1713 | 57.9 |
| WP_042989283.1 | 1714 | 57.9 |
| WP_043035813.1 | 1715 | 57.9 |
| WP_043035881.1 | 1716 | 57.9 |
| WP_044475375.1 | 1717 | 57.9 |
| WP_044685867.1 | 1718 | 57.9 |
| WP_044762272.1 | 1719 | 57.9 |
| WP_044768355.1 | 1720 | 57.9 |
| WP_044981197.1 | 1721 | 57.9 |
| WP_044981552.1 | 1722 | 57.9 |
| WP_044981988.1 | 1723 | 57.9 |
| WP_044983651.1 | 1724 | 57.9 |
| WP_046999710.1 | 1725 | 57.9 |
| WP_052789094.1 | 1726 | 57.9 |
| WP_052789180.1 | 1727 | 57.9 |
| WP_052828307.1 | 1728 | 57.9 |
| WP_052828864.1 | 1729 | 57.9 |
| WP_053793983.1 | 1730 | 57.9 |
| WP_060618769.1 | 1731 | 57.9 |
| WP_065359301.1 | 1732 | 57.9 |
| WP_065435955.1 | 1733 | 57.9 |
| WP_065463870.1 | 1734 | 57.9 |
| WP_069483631.1 | 1735 | 57.9 |
| WP_071478650.1 | 1736 | 57.9 |
| WP_074390740.1 | 1737 | 57.9 |
| WP_074410879.1 | 1738 | 57.9 |
| WP_074412339.1 | 1739 | 57.9 |
| WP_077387445.1 | 1740 | 57.9 |
| WP_080788981.1 | 1741 | 57.9 |
| WP_080825764.1 | 1742 | 57.9 |
| WP_085061783.1 | 1743 | 57.9 |
| WP_085462022.1 | 1744 | 57.9 |
| WP_094750245.1 | 1745 | 57.9 |
| WP_094754216.1 | 1746 | 57.9 |
| WP_095346227.1 | 1747 | 57.9 |
| WP_099806553.1 | 1748 | 57.9 |
| WP_099831302.1 | 1749 | 57.9 |
| WP_099872288.1 | 1750 | 57.9 |
| WP_101625614.1 | 1751 | 57.9 |
| WP_103619853.1 | 1752 | 57.9 |
| WP_105105021.1 | 1753 | 57.9 |
| WP_105121160.1 | 1754 | 57.9 |
| WP_105141124.1 | 1755 | 57.9 |
| WP_105146533.1 | 1756 | 57.9 |
| WP_105148944.1 | 1757 | 57.9 |
| WP_105243469.1 | 1758 | 57.9 |
| WP_106621362.1 | 1759 | 57.9 |
| WP_106641205.1 | 1760 | 57.9 |
| WP_106641922.1 | 1761 | 57.9 |
| WP_106642225.1 | 1762 | 57.9 |
| WP_106647769.1 | 1763 | 57.9 |
| WP_117675095.1 | 1764 | 57.9 |
| WP_117760746.1 | 1765 | 57.9 |
| WP_118233682.1 | 1766 | 57.9 |
| WP_118240201.1 | 1767 | 57.9 |
| WP_124879890.1 | 1768 | 57.9 |
| WP_125968961.1 | 1769 | 57.9 |
| WP_130082218.1 | 1770 | 57.9 |
| WP_131202632.1 | 1771 | 57.9 |
| WP_131204644.1 | 1772 | 57.9 |
| WP_131211467.1 | 1773 | 57.9 |
| WP_131213011.1 | 1774 | 57.9 |
| WP_131215343.1 | 1775 | 57.9 |
| WP_131219195.1 | 1776 | 57.9 |
| WP_131222987.1 | 1777 | 57.9 |
| WP_131223344.1 | 1778 | 57.9 |
| WP_131226490.1 | 1779 | 57.9 |
| WP_131227588.1 | 1780 | 57.9 |
| WP_131232821.1 | 1781 | 57.9 |
| WP_131269643.1 | 1782 | 57.9 |
| WP_131272326.1 | 1783 | 57.9 |
| WP_131274815.1 | 1784 | 57.9 |
| WP_131276520.1 | 1785 | 57.9 |
| WP_131308332.1 | 1786 | 57.9 |
| WP_131311849.1 | 1787 | 57.9 |
| WP_131312620.1 | 1788 | 57.9 |
| WP_140489375.1 | 1789 | 57.9 |
| WP_141430348.1 | 1790 | 57.9 |
| WP_141671924.1 | 1791 | 57.9 |
| WP_141674572.1 | 1792 | 57.9 |
| WP_143882195.1 | 1793 | 57.9 |
| WP_143935305.1 | 1794 | 57.9 |
| WP_143935360.1 | 1795 | 57.9 |
| WP_150335069.1 | 1796 | 57.9 |
| WP_154536374.1 | 1797 | 57.9 |
| WP_155778325.1 | 1798 | 57.9 |
| WP_156624917.1 | 1799 | 57.9 |
| WP_166985220.1 | 1800 | 57.9 |
| WP_170078900.1 | 1801 | 57.9 |
| WP_172636267.1 | 1802 | 57.9 |
| WP_174773048.1 | 1803 | 57.9 |
| WP_193641916.1 | 1804 | 57.9 |
| WP_193642109.1 | 1805 | 57.9 |
| WP_195215338.1 | 1806 | 57.9 |
| WP_195242395.1 | 1807 | 57.9 |
| WP_195327706.1 | 1808 | 57.9 |
| WP_195403507.1 | 1809 | 57.9 |
| WP_195546269.1 | 1810 | 57.9 |
| WP_195554420.1 | 1811 | 57.9 |

TABLE 7-continued

CW_7 repeat-containing protein sequences and sequence identity to CLB2 CW_7.

| GenBank | SEQ | ID % |
|---|---|---|
| WP_195950182.1 | 1812 | 57.9 |
| WP_207121999.1 | 1813 | 57.9 |
| WP_212104396.1 | 1814 | 57.9 |
| WP_213291891.1 | 1815 | 57.9 |
| WP_221864722.1 | 1816 | 57.9 |
| WP_222366459.1 | 1817 | 57.9 |
| WP_225030917.1 | 1818 | 57.9 |
| WP_225724420.1 | 1819 | 57.9 |
| WP_226590796.1 | 1820 | 57.9 |
| WP_227112735.1 | 1821 | 57.9 |
| WP_227248064.1 | 1822 | 57.9 |
| WP_227976749.1 | 1823 | 57.9 |
| WP_230334819.1 | 1824 | 57.9 |
| WP_230335156.1 | 1825 | 57.9 |
| WP_232782508.1 | 1826 | 57.9 |
| WP_233889466.1 | 1827 | 57.9 |
| WP_237936378.1 | 1828 | 57.9 |
| WP_238374775.1 | 1829 | 57.9 |
| WP_238708320.1 | 1830 | 57.9 |
| WP_238715806.1 | 1831 | 57.9 |
| WP_238716089.1 | 1832 | 57.9 |
| WP_238718653.1 | 1833 | 57.9 |
| WP_240332476.1 | 1834 | 57.9 |
| WP_243093111.1 | 1835 | 57.9 |
| WP_247214245.1 | 1836 | 57.9 |
| WP_251178057.1 | 1837 | 57.9 |
| WP_254426360.1 | 1838 | 57.9 |
| WP_270266914.1 | 1839 | 57.9 |
| WP_270552974.1 | 1840 | 57.9 |
| WP_270557501.1 | 1841 | 57.9 |
| WP_274982750.1 | 1842 | 57.9 |
| WP_276340766.1 | 1843 | 57.9 |
| WP_277837921.1 | 1844 | 57.9 |
| WP_277846827.1 | 1845 | 57.9 |
| WP_279276159.1 | 1846 | 57.9 |
| WP_281108839.1 | 1847 | 57.9 |
| WP_281109158.1 | 1848 | 57.9 |
| WP_282917198.1 | 1849 | 57.9 |
| WP_283840623.1 | 1850 | 57.9 |
| WP_286112456.1 | 1851 | 57.9 |
| WP_286275937.1 | 1852 | 57.9 |
| WP_302395969.1 | 1853 | 57.9 |
| WP_308748144.1 | 1854 | 57.9 |
| WP_311896896.1 | 1855 | 57.9 |
| WP_313175263.1 | 1856 | 57.9 |
| WP_316113874.1 | 1857 | 57.9 |
| WP_316719505.1 | 1858 | 57.9 |
| WP_319640467.1 | 1859 | 57.9 |
| WP_322116319.1 | 1860 | 57.9 |
| WP_332404635.1 | 1861 | 57.9 |
| WP_332419454.1 | 1862 | 57.9 |
| WP_336375084.1 | 1863 | 57.9 |
| WP_336382926.1 | 1864 | 57.9 |
| WP_336622045.1 | 1865 | 57.9 |
| WP_340506320.1 | 1866 | 57.9 |
| WP_340508667.1 | 1867 | 57.9 |
| WP_346980136.1 | 1868 | 57.9 |
| WP_353061843.1 | 1869 | 57.9 |
| WP_353341891.1 | 1870 | 57.9 |
| WP_367007134.1 | 1871 | 57.9 |
| HCC03445.1 | 1872 | 57.6 |
| DAF78738.1 | 1873 | 57.5 |
| DAG19841.1 | 1874 | 57.5 |
| DAH71804.1 | 1875 | 57.5 |
| MDO4558618.1 | 1876 | 57.5 |
| MEE0108856.1 | 1877 | 57.5 |
| MBR4693974.1 | 1878 | 57.1 |
| QHJ77966.1 | 1879 | 57.1 |
| WP_052046911.1 | 1880 | 57.1 |
| WP_171002150.1 | 1881 | 57.1 |
| WP_275950418.1 | 1882 | 57.1 |
| WP_278755745.1 | 1883 | 57.1 |
| CDC16819.1 | 1884 | 57.1 |
| DAH53788.1 | 1885 | 57.1 |
| DAZ67110.1 | 1886 | 57.1 |
| MBR2553442.1 | 1887 | 57.1 |
| MCI1791735.1 | 1888 | 57.1 |
| MDB1433275.1 | 1889 | 57.1 |
| MDB1522669.1 | 1890 | 57.1 |
| NQP40272.1 | 1891 | 57.1 |
| QGZ17207.1 | 1892 | 57.1 |
| UVX44797.1 | 1893 | 57.1 |
| UWH96150.1 | 1894 | 57.1 |
| WP_078392067.1 | 1895 | 57.1 |
| WP_179395066.1 | 1896 | 57.1 |
| WP_179395723.1 | 1897 | 57.1 |
| WP_270199170.1 | 1898 | 57.1 |
| WP_270435525.1 | 1899 | 57.1 |
| WP_291290432.1 | 1900 | 57.1 |
| WP_304312188.1 | 1901 | 57.1 |
| WP_304313039.1 | 1902 | 57.1 |
| WP_331341121.1 | 1903 | 57.1 |
| DAL77996.1 | 1904 | 56.8 |
| DAO11437.1 | 1905 | 56.8 |
| DAP14690.1 | 1906 | 56.8 |
| DAP15758.1 | 1907 | 56.8 |
| DAQ77759.1 | 1908 | 56.8 |
| DAS01115.1 | 1909 | 56.8 |
| GDZ75061.1 | 1910 | 56.8 |
| KAB5744127.1 | 1911 | 56.8 |
| MBS5345044.1 | 1912 | 56.8 |
| MBV3434105.1 | 1913 | 56.8 |
| MDU6622586.1 | 1914 | 56.8 |
| NEG90614.1 | 1915 | 56.8 |
| PIB81455.1 | 1916 | 56.8 |
| QHJ77918.1 | 1917 | 56.8 |
| RHI43312.1 | 1918 | 56.8 |
| WP_051872044.1 | 1919 | 56.8 |
| WP_055308661.1 | 1920 | 56.8 |
| WP_117632188.1 | 1921 | 56.8 |
| WP_163191062.1 | 1922 | 56.8 |
| WP_180753752.1 | 1923 | 56.8 |
| WP_182300940.1 | 1924 | 56.8 |
| WP_195537610.1 | 1925 | 56.8 |
| WP_215641116.1 | 1926 | 56.8 |
| WP_217374874.1 | 1927 | 56.8 |
| WP_217752127.1 | 1928 | 56.8 |
| WP_236716572.1 | 1929 | 56.8 |
| WP_239512566.1 | 1930 | 56.8 |
| WP_248004584.1 | 1931 | 56.8 |
| WP_254879273.1 | 1932 | 56.8 |
| WP_281097719.1 | 1933 | 56.8 |
| WP_291789214.1 | 1934 | 56.8 |
| WP_333721000.1 | 1935 | 56.8 |
| WP_340504884.1 | 1936 | 56.8 |
| WP_347009974.1 | 1937 | 56.8 |
| WP_347010046.1 | 1938 | 56.8 |
| WP_347012031.1 | 1939 | 56.8 |
| WP_349615380.1 | 1940 | 56.8 |
| MCI1220142.1 | 1941 | 56.8 |
| MCI1831558.1 | 1942 | 56.8 |
| MDB1467710.1 | 1943 | 56.8 |
| MDQ8821206.1 | 1944 | 56.8 |
| WP_155971571.1 | 1945 | 56.8 |
| WP_237373375.1 | 1946 | 56.8 |
| WP_270435228.1 | 1947 | 56.8 |
| WP_278759887.1 | 1948 | 56.8 |
| WP_297571616.1 | 1949 | 56.8 |
| DAZ11612.1 | 1950 | 56.4 |
| KGF10429.1 | 1951 | 56.4 |
| MBG9985043.1 | 1952 | 56.4 |
| MBQ9141165.1 | 1953 | 56.4 |
| MBQ9702954.1 | 1954 | 56.4 |
| MCI7239241.1 | 1955 | 56.4 |
| MCM1164526.1 | 1956 | 56.4 |
| MDD6060844.1 | 1957 | 56.4 |
| MDD7512789.1 | 1958 | 56.4 |
| MDE7229523.1 | 1959 | 56.4 |
| MEE0955794.1 | 1960 | 56.4 |
| MEE3495755.1 | 1961 | 56.4 |

TABLE 7-continued

CW_7 repeat-containing protein sequences and sequence identity to CLB2 CW_7.

| GenBank | SEQ | ID % |
|---|---|---|
| WP_008901321.1 | 1962 | 56.4 |
| WP_018659237.1 | 1963 | 56.4 |
| WP_144398628.1 | 1964 | 56.4 |
| WP_151410295.1 | 1965 | 56.4 |
| WP_151410757.1 | 1966 | 56.4 |
| WP_171332503.1 | 1967 | 56.4 |
| WP_242949812.1 | 1968 | 56.4 |
| WP_270289037.1 | 1969 | 56.4 |
| WP_277261500.1 | 1970 | 56.4 |
| WP_278662706.1 | 1971 | 56.4 |
| WP_278735896.1 | 1972 | 56.4 |
| WP_316085599.1 | 1973 | 56.4 |
| WP_316131176.1 | 1974 | 56.4 |
| WP_332087527.1 | 1975 | 56.4 |
| HJA82050.1 | 1976 | 56.3 |
| MBR3611803.1 | 1977 | 56.3 |
| MCF0103977.1 | 1978 | 56.3 |
| MDD6079003.1 | 1979 | 56.3 |
| MDE7414300.1 | 1980 | 56.3 |
| MDR1723185.1 | 1981 | 56.3 |
| OQC00166.1 | 1982 | 56.3 |
| WP_028906126.1 | 1983 | 56.3 |
| WP_100190139.1 | 1984 | 56.3 |
| WP_278901691.1 | 1985 | 56.3 |
| WP_297036228.1 | 1986 | 56.3 |
| WP_308274766.1 | 1987 | 56.3 |
| AMP42248.1 | 1988 | 56.1 |
| ARP51107.1 | 1989 | 56.1 |
| DAF09946.1 | 1990 | 56.1 |
| DAF26406.1 | 1991 | 56.1 |
| DAG63190.1 | 1992 | 56.1 |
| DAH75037.1 | 1993 | 56.1 |
| DAI26982.1 | 1994 | 56.1 |
| DAJ84232.1 | 1995 | 56.1 |
| DAK28228.1 | 1996 | 56.1 |
| DAL27502.1 | 1997 | 56.1 |
| DAM76220.1 | 1998 | 56.1 |
| DAN07658.1 | 1999 | 56.1 |
| DAO49025.1 | 2000 | 56.1 |
| DAP74572.1 | 2001 | 56.1 |
| DAT44560.1 | 2002 | 56.1 |
| DAT72634.1 | 2003 | 56.1 |
| DAT94336.1 | 2004 | 56.1 |
| DAU31694.1 | 2005 | 56.1 |
| DAU45238.1 | 2006 | 56.1 |
| DAU79771.1 | 2007 | 56.1 |
| DAV68083.1 | 2008 | 56.1 |
| DAW88059.1 | 2009 | 56.1 |
| DAX35828.1 | 2010 | 56.1 |
| DAX71914.1 | 2011 | 56.1 |
| DAX82425.1 | 2012 | 56.1 |
| DAY37231.1 | 2013 | 56.1 |
| DAY91644.1 | 2014 | 56.1 |
| DAZ08544.1 | 2015 | 56.1 |
| DAZ77564.1 | 2016 | 56.1 |
| EHI70229.1 | 2017 | 56.1 |
| EIK77200.1 | 2018 | 56.1 |
| EPI46407.1 | 2019 | 56.1 |
| HAK0935252.1 | 2020 | 56.1 |
| HDI3439610.1 | 2021 | 56.1 |
| HDM9179001.1 | 2022 | 56.1 |
| HEL8297230.1 | 2023 | 56.1 |
| HEL9517570.1 | 2024 | 56.1 |
| HIT89969.1 | 2025 | 56.1 |
| HJD00439.1 | 2026 | 56.1 |
| MBD5112395.1 | 2027 | 56.1 |
| MBE0296378.1 | 2028 | 56.1 |
| MBO5504405.1 | 2029 | 56.1 |
| MBP3793179.1 | 2030 | 56.1 |
| MBQ1368950.1 | 2031 | 56.1 |
| MBQ3052987.1 | 2032 | 56.1 |
| MBQ3195980.1 | 2033 | 56.1 |
| MBQ4247358.1 | 2034 | 56.1 |
| MBQ5522068.1 | 2035 | 56.1 |
| MBR1810973.1 | 2036 | 56.1 |
| MBR2552781.1 | 2037 | 56.1 |
| MBS6321888.1 | 2038 | 56.1 |
| MBY0585225.1 | 2039 | 56.1 |
| MCF1635260.1 | 2040 | 56.1 |
| MCR0459289.1 | 2041 | 56.1 |
| MDB7995994.1 | 2042 | 56.1 |
| MDH6602989.1 | 2043 | 56.1 |
| MDK0907098.1 | 2044 | 56.1 |
| MDU2829572.1 | 2045 | 56.1 |
| MEE3405559.1 | 2046 | 56.1 |
| MEO2812417.1 | 2047 | 56.1 |
| MEQ3114896.1 | 2048 | 56.1 |
| RFT26883.1 | 2049 | 56.1 |
| RGD77276.1 | 2050 | 56.1 |
| RHT19196.1 | 2051 | 56.1 |
| RIY26770.1 | 2052 | 56.1 |
| RYN08726.1 | 2053 | 56.1 |
| WP_002563674.1 | 2054 | 56.1 |
| WP_006268703.1 | 2055 | 56.1 |
| WP_014554482.1 | 2056 | 56.1 |
| WP_015527548.1 | 2057 | 56.1 |
| WP_019190763.1 | 2058 | 56.1 |
| WP_019260892.1 | 2059 | 56.1 |
| WP_022003216.1 | 2060 | 56.1 |
| WP_048730021.1 | 2061 | 56.1 |
| WP_057002046.1 | 2062 | 56.1 |
| WP_064340486.1 | 2063 | 56.1 |
| WP_070210517.1 | 2064 | 56.1 |
| WP_076002856.1 | 2065 | 56.1 |
| WP_084229876.1 | 2066 | 56.1 |
| WP_101890267.1 | 2067 | 56.1 |
| WP_102165511.1 | 2068 | 56.1 |
| WP_112928578.1 | 2069 | 56.1 |
| WP_115716436.1 | 2070 | 56.1 |
| WP_116691926.1 | 2071 | 56.1 |
| WP_150225723.1 | 2072 | 56.1 |
| WP_154574073.1 | 2073 | 56.1 |
| WP_156329537.1 | 2074 | 56.1 |
| WP_163051994.1 | 2075 | 56.1 |
| WP_169755928.1 | 2076 | 56.1 |
| WP_169759672.1 | 2077 | 56.1 |
| WP_174142812.1 | 2078 | 56.1 |
| WP_198609025.1 | 2079 | 56.1 |
| WP_203244668.1 | 2080 | 56.1 |
| WP_212821115.1 | 2081 | 56.1 |
| WP_227205741.1 | 2082 | 56.1 |
| WP_234944194.1 | 2083 | 56.1 |
| WP_235807546.1 | 2084 | 56.1 |
| WP_238609359.1 | 2085 | 56.1 |
| WP_248902513.1 | 2086 | 56.1 |
| WP_250310248.1 | 2087 | 56.1 |
| WP_257479905.1 | 2088 | 56.1 |
| WP_259295317.1 | 2089 | 56.1 |
| WP_262011342.1 | 2090 | 56.1 |
| WP_263477118.1 | 2091 | 56.1 |
| WP_270627091.1 | 2092 | 56.1 |
| WP_273497945.1 | 2093 | 56.1 |
| WP_278631542.1 | 2094 | 56.1 |
| WP_279361440.1 | 2095 | 56.1 |
| WP_284599057.1 | 2096 | 56.1 |
| WP_287714527.1 | 2097 | 56.1 |
| WP_287847047.1 | 2098 | 56.1 |
| WP_290944891.1 | 2099 | 56.1 |
| WP_301969808.1 | 2100 | 56.1 |
| WP_308460332.1 | 2101 | 56.1 |
| WP_314388786.1 | 2102 | 56.1 |
| WP_316263974.1 | 2103 | 56.1 |
| WP_316720043.1 | 2104 | 56.1 |
| WP_318779072.1 | 2105 | 56.1 |
| WP_320759079.1 | 2106 | 56.1 |
| WP_324250384.1 | 2107 | 56.1 |
| WP_346793692.1 | 2108 | 56.1 |
| WP_347561346.1 | 2109 | 56.1 |
| WP_349054446.1 | 2110 | 56.1 |
| WP_349198654.1 | 2111 | 56.1 |

TABLE 7-continued

CW_7 repeat-containing protein sequences and sequence identity to CLB2 CW_7.

| GenBank | SEQ | ID % |
|---|---|---|
| WP_353884781.1 | 2112 | 56.1 |
| WZL78343.1 | 2113 | 56.1 |
| DAJ95793.1 | 2114 | 56.1 |
| DAK 11742.1 | 2115 | 56.1 |
| DAY93561.1 | 2116 | 56.1 |
| EEG51680.1 | 2117 | 56.1 |
| MBF1710231.1 | 2118 | 56.1 |
| MBQ1482671.1 | 2119 | 56.1 |
| MBQ9354911.1 | 2120 | 56.1 |
| MCH4013796.1 | 2121 | 56.1 |
| MCQ2451066.1 | 2122 | 56.1 |
| MDE7398977.1 | 2123 | 56.1 |
| MDR2531453.1 | 2124 | 56.1 |
| WP_040413169.1 | 2125 | 56.1 |
| WP_101695398.1 | 2126 | 56.1 |
| WP_132226251.1 | 2127 | 56.1 |
| WP_166083092.1 | 2128 | 56.1 |
| WP_243036783.1 | 2129 | 56.1 |
| WP_266162965.1 | 2130 | 56.1 |
| WP_268445257.1 | 2131 | 56.1 |
| WP_303041128.1 | 2132 | 56.1 |
| DAF33623.1 | 2133 | 55.6 |
| DAF83562.1 | 2134 | 55.6 |
| DAI93989.1 | 2135 | 55.6 |
| DAN35609.1 | 2136 | 55.6 |
| DAP73465.1 | 2137 | 55.6 |
| DAQ10417.1 | 2138 | 55.6 |
| DAS90063.1 | 2139 | 55.6 |
| DAT59724.1 | 2140 | 55.6 |
| DAV85879.1 | 2141 | 55.6 |
| MBD5239140.1 | 2142 | 55.6 |
| MBD5307471.1 | 2143 | 55.6 |
| MBD5317425.1 | 2144 | 55.6 |
| MBD5329294.1 | 2145 | 55.6 |
| MBD5340291.1 | 2146 | 55.6 |
| MBF1066417.1 | 2147 | 55.6 |
| MBR6774619.1 | 2148 | 55.6 |
| MCI7597306.1 | 2149 | 55.6 |
| MCI7789137.1 | 2150 | 55.6 |
| MDE5949100.1 | 2151 | 55.6 |
| MDE7462233.1 | 2152 | 55.6 |
| MDR1847647.1 | 2153 | 55.6 |
| MEE1303351.1 | 2154 | 55.6 |
| WP_261254574.1 | 2155 | 55.6 |
| MCC8118958.1 | 2156 | 55.6 |
| MCM1139099.1 | 2157 | 55.6 |
| MDE6681836.1 | 2158 | 55.6 |
| MDY4174437.1 | 2159 | 55.6 |
| ROT06162.1 | 2160 | 55.6 |
| WP_298666286.1 | 2161 | 55.6 |
| WP_301425618.1 | 2162 | 55.6 |
| WP_317605757.1 | 2163 | 55.6 |
| DAD92565.1 | 2164 | 55.3 |
| DAP18054.1 | 2165 | 55.3 |
| DAV53526.1 | 2166 | 55.3 |
| ESA48234.1 | 2167 | 55.3 |
| HEL0213567.1 | 2168 | 55.3 |
| HEP1405784.1 | 2169 | 55.3 |
| HEP1471752.1 | 2170 | 55.3 |
| HER5200537.1 | 2171 | 55.3 |
| HES2369659.1 | 2172 | 55.3 |
| MBE6125010.1 | 2173 | 55.3 |
| MBS1338628.1 | 2174 | 55.3 |
| WP_003047591.1 | 2175 | 55.3 |
| WP_008788454.1 | 2176 | 55.3 |
| WP_027970273.1 | 2177 | 55.3 |
| WP_070021432.1 | 2178 | 55.3 |
| WP_072137518.1 | 2179 | 55.3 |
| WP_129735104.1 | 2180 | 55.3 |
| WP_143978738.1 | 2181 | 55.3 |
| WP_172636359.1 | 2182 | 55.3 |
| WP_278753828.1 | 2183 | 55.3 |
| WP_298625755.1 | 2184 | 55.3 |
| WP_332059051.1 | 2185 | 55.3 |
| CYW30588.1 | 2186 | 55.3 |
| DAE63310.1 | 2187 | 55.3 |
| DAE64095.1 | 2188 | 55.3 |
| DAH63468.1 | 2189 | 55.3 |
| DAI67139.1 | 2190 | 55.3 |
| DAL62505.1 | 2191 | 55.3 |
| DAN71249.1 | 2192 | 55.3 |
| DAO18124.1 | 2193 | 55.3 |
| DAO62516.1 | 2194 | 55.3 |
| DAY91163.1 | 2195 | 55.3 |
| HBA62284.1 | 2196 | 55.3 |
| HEL1607036.1 | 2197 | 55.3 |
| HEL1731552.1 | 2198 | 55.3 |
| HEL1827824.1 | 2199 | 55.3 |
| HEL1848996.1 | 2200 | 55.3 |
| HEL1906690.1 | 2201 | 55.3 |
| HEL1946020.1 | 2202 | 55.3 |
| HEL1990045.1 | 2203 | 55.3 |
| HEL2165130.1 | 2204 | 55.3 |
| HEL2204622.1 | 2205 | 55.3 |
| HEL2246585.1 | 2206 | 55.3 |
| HEL2274455.1 | 2207 | 55.3 |
| HEL2309173.1 | 2208 | 55.3 |
| HEL2361048.1 | 2209 | 55.3 |
| HEL2388842.1 | 2210 | 55.3 |
| HEL2532983.1 | 2211 | 55.3 |
| HEL2556427.1 | 2212 | 55.3 |
| HEL2623501.1 | 2213 | 55.3 |
| HEL2706394.1 | 2214 | 55.3 |
| HEL2737527.1 | 2215 | 55.3 |
| HEL9642804.1 | 2216 | 55.3 |
| HEM2578492.1 | 2217 | 55.3 |
| HEM2592442.1 | 2218 | 55.3 |
| HEM2716994.1 | 2219 | 55.3 |
| HEM2739629.1 | 2220 | 55.3 |
| HEM2744577.1 | 2221 | 55.3 |
| HEM2779440.1 | 2222 | 55.3 |
| HEM2965232.1 | 2223 | 55.3 |
| HEM3009479.1 | 2224 | 55.3 |
| HEM3188929.1 | 2225 | 55.3 |
| HEM3538283.1 | 2226 | 55.3 |
| HEM3568839.1 | 2227 | 55.3 |
| HEM3629242.1 | 2228 | 55.3 |
| HEM3634875.1 | 2229 | 55.3 |
| HEM3901436.1 | 2230 | 55.3 |
| HEM4159957.1 | 2231 | 55.3 |
| HEM4165687.1 | 2232 | 55.3 |
| HEM4211656.1 | 2233 | 55.3 |
| HEM4249624.1 | 2234 | 55.3 |
| HEM4275191.1 | 2235 | 55.3 |
| HEM4558431.1 | 2236 | 55.3 |
| HEM4669938.1 | 2237 | 55.3 |
| HEM4758691.1 | 2238 | 55.3 |
| HEM4809978.1 | 2239 | 55.3 |
| HEM5025496.1 | 2240 | 55.3 |
| HEM5155687.1 | 2241 | 55.3 |
| HEM5178871.1 | 2242 | 55.3 |
| HEM5208341.1 | 2243 | 55.3 |
| HEM5273925.1 | 2244 | 55.3 |
| HEM5414756.1 | 2245 | 55.3 |
| HEM5558310.1 | 2246 | 55.3 |
| HEM5914790.1 | 2247 | 55.3 |
| HEM6020058.1 | 2248 | 55.3 |
| HEM6060094.1 | 2249 | 55.3 |
| HEM6260877.1 | 2250 | 55.3 |
| HEM6539922.1 | 2251 | 55.3 |
| HEM6559758.1 | 2252 | 55.3 |
| HEN2620235.1 | 2253 | 55.3 |
| HEN6330911.1 | 2254 | 55.3 |
| HEN6765196.1 | 2255 | 55.3 |
| HEO4075700.1 | 2256 | 55.3 |
| HEP1824881.1 | 2257 | 55.3 |
| HEP1837845.1 | 2258 | 55.3 |
| HJI55575.1 | 2259 | 55.3 |
| KFI70369.1 | 2260 | 55.3 |
| MBD3948437.1 | 2261 | 55.3 |

TABLE 7-continued

CW_7 repeat-containing protein sequences and sequence identity to CLB2 CW_7.

| GenBank | SEQ | ID % |
|---|---|---|
| MBE6045466.1 | 2262 | 55.3 |
| MBM6800422.1 | 2263 | 55.3 |
| MBQ8300278.1 | 2264 | 55.3 |
| MBQ8829692.1 | 2265 | 55.3 |
| MBQ9314973.1 | 2266 | 55.3 |
| MCF0235551.1 | 2267 | 55.3 |
| MCK3958294.1 | 2268 | 55.3 |
| MCK4043381.1 | 2269 | 55.3 |
| MCK 4069752.1 | 2270 | 55.3 |
| MCK 4074199.1 | 2271 | 55.3 |
| MCT6837299.1 | 2272 | 55.3 |
| MCW6664506.1 | 2273 | 55.3 |
| MDB1414146.1 | 2274 | 55.3 |
| MDG3222526.1 | 2275 | 55.3 |
| MDG3327297.1 | 2276 | 55.3 |
| MDG4515229.1 | 2277 | 55.3 |
| MDO5044959.1 | 2278 | 55.3 |
| MDU2257702.1 | 2279 | 55.3 |
| MDU3152876.1 | 2280 | 55.3 |
| MDW8651054.1 | 2281 | 55.3 |
| MDW8691147.1 | 2282 | 55.3 |
| MEO2365327.1 | 2283 | 55.3 |
| MEO5477776.1 | 2284 | 55.3 |
| NCB79970.1 | 2285 | 55.3 |
| NQJ72043.1 | 2286 | 55.3 |
| NQN97692.1 | 2287 | 55.3 |
| NQP51549.1 | 2288 | 55.3 |
| QIG78226.1 | 2289 | 55.3 |
| RGJ86708.1 | 2290 | 55.3 |
| RGL08985.1 | 2291 | 55.3 |
| RGP03643.1 | 2292 | 55.3 |
| UNY50240.1 | 2293 | 55.3 |
| WP_000405191.1 | 2294 | 55.3 |
| WP_000405193.1 | 2295 | 55.3 |
| WP_000405194.1 | 2296 | 55.3 |
| WP_000512610.1 | 2297 | 55.3 |
| WP_000512611.1 | 2298 | 55.3 |
| WP_015984430.1 | 2299 | 55.3 |
| WP_024411103.1 | 2300 | 55.3 |
| WP_027972598.1 | 2301 | 55.3 |
| WP_031873482.1 | 2302 | 55.3 |
| WP_043033233.1 | 2303 | 55.3 |
| WP_044475330.1 | 2304 | 55.3 |
| WP_044673607.1 | 2305 | 55.3 |
| WP_044686576.1 | 2306 | 55.3 |
| WP_044765379.1 | 2307 | 55.3 |
| WP_044768204.1 | 2308 | 55.3 |
| WP_044769727.1 | 2309 | 55.3 |
| WP_044770619.1 | 2310 | 55.3 |
| WP_044777638.1 | 2311 | 55.3 |
| WP_044980624.1 | 2312 | 55.3 |
| WP_047199272.1 | 2313 | 55.3 |
| WP_050139094.1 | 2314 | 55.3 |
| WP_052109203.1 | 2315 | 55.3 |
| WP_053338578.1 | 2316 | 55.3 |
| WP_074390440.1 | 2317 | 55.3 |
| WP_074411214.1 | 2318 | 55.3 |
| WP_074412935.1 | 2319 | 55.3 |
| WP_075105671.1 | 2320 | 55.3 |
| WP_081888422.1 | 2321 | 55.3 |
| WP_086992449.1 | 2322 | 55.3 |
| WP_087013717.1 | 2323 | 55.3 |
| WP_093650205.1 | 2324 | 55.3 |
| WP_093651367.1 | 2325 | 55.3 |
| WP_105249449.1 | 2326 | 55.3 |
| WP_112477644.1 | 2327 | 55.3 |
| WP_115268807.1 | 2328 | 55.3 |
| WP_117649242.1 | 2329 | 55.3 |
| WP_121835595.1 | 2330 | 55.3 |
| WP_125064509.1 | 2331 | 55.3 |
| WP_141453391.1 | 2332 | 55.3 |
| WP_154312470.1 | 2333 | 55.3 |
| WP_170238636.1 | 2334 | 55.3 |
| WP_171842697.1 | 2335 | 55.3 |
| WP_172008793.1 | 2336 | 55.3 |
| WP_172049131.1 | 2337 | 55.3 |
| WP_172146131.1 | 2338 | 55.3 |
| WP_181974363.1 | 2339 | 55.3 |
| WP_181974846.1 | 2340 | 55.3 |
| WP_181978001.1 | 2341 | 55.3 |
| WP_184493500.1 | 2342 | 55.3 |
| WP_187324399.1 | 2343 | 55.3 |
| WP_187643793.1 | 2344 | 55.3 |
| WP_192584820.1 | 2345 | 55.3 |
| WP_201326711.1 | 2346 | 55.3 |
| WP_201344752.1 | 2347 | 55.3 |
| WP_208952971.1 | 2348 | 55.3 |
| WP_209107509.1 | 2349 | 55.3 |
| WP_226556948.1 | 2350 | 55.3 |
| WP_229026203.1 | 2351 | 55.3 |
| WP_229038133.1 | 2352 | 55.3 |
| WP_230233589.1 | 2353 | 55.3 |
| WP_238709205.1 | 2354 | 55.3 |
| WP_238712652.1 | 2355 | 55.3 |
| WP_240213898.1 | 2356 | 55.3 |
| WP_249547221.1 | 2357 | 55.3 |
| WP_250241380.1 | 2358 | 55.3 |
| WP_250243719.1 | 2359 | 55.3 |
| WP_253214900.1 | 2360 | 55.3 |
| WP_267399516.1 | 2361 | 55.3 |
| WP_270198124.1 | 2362 | 55.3 |
| WP_270545005.1 | 2363 | 55.3 |
| WP_271739249.1 | 2364 | 55.3 |
| WP_276861367.1 | 2365 | 55.3 |
| WP_277839434.1 | 2366 | 55.3 |
| WP_287847975.1 | 2367 | 55.3 |
| WP_288805159.1 | 2368 | 55.3 |
| WP_289875544.1 | 2369 | 55.3 |
| WP_307121200.1 | 2370 | 55.3 |
| WP_309465310.1 | 2371 | 55.3 |
| WP_312248546.1 | 2372 | 55.3 |
| WP_312249646.1 | 2373 | 55.3 |
| WP_313166747.1 | 2374 | 55.3 |
| WP_320891825.1 | 2375 | 55.3 |
| WP_322116448.1 | 2376 | 55.3 |
| WP_334116176.1 | 2377 | 55.3 |
| WP_336316985.1 | 2378 | 55.3 |
| WP_345754366.1 | 2379 | 55.3 |
| DAQ64515.1 | 2380 | 55.0 |
| MBR2793855.1 | 2381 | 55.0 |
| MCR4580955.1 | 2382 | 55.0 |
| WP_150888728.1 | 2383 | 55.0 |
| WP_236159998.1 | 2384 | 55.0 |
| WP_242225508.1 | 2385 | 55.0 |
| WP_314451601.1 | 2386 | 55.0 |
| DAH03703.1 | 2387 | 54.6 |
| BDR53684.1 | 2388 | 54.3 |
| DAK11539.1 | 2389 | 54.3 |
| DAV00982.1 | 2390 | 54.3 |
| HEM4972121.1 | 2391 | 54.3 |
| MCX4255226.1 | 2392 | 54.3 |
| MDR1544361.1 | 2393 | 54.3 |
| UYL88198.1 | 2394 | 54.3 |
| WP_231474071.1 | 2395 | 54.3 |
| WP_294158152.1 | 2396 | 54.3 |
| WP_337666808.1 | 2397 | 54.3 |
| WP_054278781.1 | 2398 | 54.3 |
| WP_179394738.1 | 2399 | 54.3 |
| DAQ00190.1 | 2400 | 54.1 |
| DAQ28118.1 | 2401 | 54.1 |
| WP_267444247.1 | 2402 | 54.1 |
| WP_277177605.1 | 2403 | 54.1 |
| DAJ50320.1 | 2404 | 54.1 |
| DAV30475.1 | 2405 | 54.1 |
| MBW3095564.1 | 2406 | 54.1 |
| WP_051616628.1 | 2407 | 54.1 |
| WP_236028236.1 | 2408 | 54.1 |
| DAQ21213.1 | 2409 | 53.9 |
| DAR46995.1 | 2410 | 53.9 |
| DAZ40338.1 | 2411 | 53.9 |

TABLE 7-continued

CW_7 repeat-containing protein sequences and sequence identity to CLB2 CW_7.

| GenBank | SEQ | ID % |
|---|---|---|
| HAF26374.1 | 2412 | 53.9 |
| MCI2061742.1 | 2413 | 53.9 |
| MDE5582231.1 | 2414 | 53.9 |
| MDE5763399.1 | 2415 | 53.9 |
| MDR0566243.1 | 2416 | 53.9 |
| WP_180501095.1 | 2417 | 53.9 |
| WP_294575553.1 | 2418 | 53.9 |
| WP_294575736.1 | 2419 | 53.9 |
| DAH16669.1 | 2420 | 53.8 |
| DAM77358.1 | 2421 | 53.8 |
| MBE6683485.1 | 2422 | 53.8 |
| MCR4996488.1 | 2423 | 53.8 |
| WP_242838930.1 | 2424 | 53.8 |
| WP_246441556.1 | 2425 | 53.8 |
| WP_282193015.1 | 2426 | 53.8 |
| WP_301425180.1 | 2427 | 53.8 |
| AMP54172.1 | 2428 | 53.7 |
| DAE09281.1 | 2429 | 53.7 |
| DAG15149.1 | 2430 | 53.7 |
| DAG39953.1 | 2431 | 53.7 |
| DAG53708.1 | 2432 | 53.7 |
| DAG63911.1 | 2433 | 53.7 |
| DAG74337.1 | 2434 | 53.7 |
| DAH39424.1 | 2435 | 53.7 |
| DAI53402.1 | 2436 | 53.7 |
| DAJ57149.1 | 2437 | 53.7 |
| DAO60284.1 | 2438 | 53.7 |
| DAQ84859.1 | 2439 | 53.7 |
| DAR42995.1 | 2440 | 53.7 |
| DAS34344.1 | 2441 | 53.7 |
| DAU05993.1 | 2442 | 53.7 |
| DAW50327.1 | 2443 | 53.7 |
| DAW54980.1 | 2444 | 53.7 |
| DAZ27623.1 | 2445 | 53.7 |
| EAC3599428.1 | 2446 | 53.7 |
| EAE8703439.1 | 2447 | 53.7 |
| EAF5068626.1 | 2448 | 53.7 |
| EEU7573063.1 | 2449 | 53.7 |
| EMG1576682.1 | 2450 | 53.7 |
| EOS70995.1 | 2451 | 53.7 |
| HBM3641119.1 | 2452 | 53.7 |
| HCJ4368719.1 | 2453 | 53.7 |
| MBQ8132902.1 | 2454 | 53.7 |
| MBQ9977163.1 | 2455 | 53.7 |
| MBR2677669.1 | 2456 | 53.7 |
| MBR2825753.1 | 2457 | 53.7 |
| MCD1906081.1 | 2458 | 53.7 |
| MCD3416480.1 | 2459 | 53.7 |
| MCI6652173.1 | 2460 | 53.7 |
| MCI6653629.1 | 2461 | 53.7 |
| MCM1333781.1 | 2462 | 53.7 |
| MCR0203747.1 | 2463 | 53.7 |
| MCR0248983.1 | 2464 | 53.7 |
| MDB6823545.1 | 2465 | 53.7 |
| MDD2490300.1 | 2466 | 53.7 |
| MDD6645959.1 | 2467 | 53.7 |
| MDD6708531.1 | 2468 | 53.7 |
| MDE8061506.1 | 2469 | 53.7 |
| MDK6295905.1 | 2470 | 53.7 |
| MEE0173444.1 | 2471 | 53.7 |
| MEQ2775527.1 | 2472 | 53.7 |
| RGS41704.1 | 2473 | 53.7 |
| UVN03315.1 | 2474 | 53.7 |
| UVY23390.1 | 2475 | 53.7 |
| WP_003762664.1 | 2476 | 53.7 |
| WP_004853830.1 | 2477 | 53.7 |
| WP_018659529.1 | 2478 | 53.7 |
| WP_065189413.1 | 2479 | 53.7 |
| WP_067632669.1 | 2480 | 53.7 |
| WP_127722940.1 | 2481 | 53.7 |
| WP_138190522.1 | 2482 | 53.7 |
| WP_170089747.1 | 2483 | 53.7 |
| WP_195522634.1 | 2484 | 53.7 |
| WP_204652652.1 | 2485 | 53.7 |
| WP_214814049.1 | 2486 | 53.7 |
| WP_235315432.1 | 2487 | 53.7 |
| WP_256192134.1 | 2488 | 53.7 |
| WP_269207105.1 | 2489 | 53.7 |
| WP_270275186.1 | 2490 | 53.7 |
| WP_280378258.1 | 2491 | 53.7 |
| WP_285060750.1 | 2492 | 53.7 |
| WP_288970341.1 | 2493 | 53.7 |
| WP_294674478.1 | 2494 | 53.7 |
| WP_295219398.1 | 2495 | 53.7 |
| WP_298482140.1 | 2496 | 53.7 |
| WP_303671887.1 | 2497 | 53.7 |
| WP_304000784.1 | 2498 | 53.7 |
| WP_330222616.1 | 2499 | 53.7 |
| WP_341436196.1 | 2500 | 53.7 |
| WP_347012186.1 | 2501 | 53.7 |
| WP_347016822.1 | 2502 | 53.7 |
| WP_349202855.1 | 2503 | 53.7 |
| CCY18180.1 | 2504 | 53.7 |
| DAT44003.1 | 2505 | 53.7 |
| DAW29180.1 | 2506 | 53.7 |
| DAZ07179.1 | 2507 | 53.7 |
| HIQ93672.1 | 2508 | 53.7 |
| MBQ8133981.1 | 2509 | 53.7 |
| MBU0279366.1 | 2510 | 53.7 |
| MCH4062957.1 | 2511 | 53.7 |
| MCK9331277.1 | 2512 | 53.7 |
| MCM1168194.1 | 2513 | 53.7 |
| MCM1272176.1 | 2514 | 53.7 |
| MCR5418230.1 | 2515 | 53.7 |
| MCX4337403.1 | 2516 | 53.7 |
| NBI63475.1 | 2517 | 53.7 |
| QIW55085.1 | 2518 | 53.7 |
| WP_118524427.1 | 2519 | 53.7 |
| WP_163545681.1 | 2520 | 53.7 |
| WP_216279804.1 | 2521 | 53.7 |
| WP_295196707.1 | 2522 | 53.7 |
| WP_314073335.1 | 2523 | 53.7 |
| DAJ01384.1 | 2524 | 53.3 |
| DAS81663.1 | 2525 | 53.1 |
| HAH19201.1 | 2526 | 52.9 |
| UVN08622.1 | 2527 | 52.9 |
| WP_097025346.1 | 2528 | 52.9 |
| WP_244040559.1 | 2529 | 52.9 |
| MBR1904850.1 | 2530 | 52.8 |
| MDR3118441.1 | 2531 | 52.8 |
| WP_130806529.1 | 2532 | 52.8 |
| WP_160198836.1 | 2533 | 52.8 |
| WP_160198838.1 | 2534 | 52.8 |
| WP_221646160.1 | 2535 | 52.8 |
| WP_277142867.1 | 2536 | 52.8 |
| HBC22357.1 | 2537 | 52.8 |
| MBS7345301.1 | 2538 | 52.8 |
| MCD8297175.1 | 2539 | 52.8 |
| MCH5224281.1 | 2540 | 52.8 |
| MCM1141253.1 | 2541 | 52.8 |
| MDR2511989.1 | 2542 | 52.8 |
| MEE1113079.1 | 2543 | 52.8 |
| MEE1226274.1 | 2544 | 52.8 |
| PXY80406.1 | 2545 | 52.8 |
| WP_022400792.1 | 2546 | 52.8 |
| WP_025078191.1 | 2547 | 52.8 |
| WP_156730610.1 | 2548 | 52.8 |
| WP_195950852.1 | 2549 | 52.8 |
| DAZ34092.1 | 2550 | 52.6 |
| HEP1456418.1 | 2551 | 52.6 |
| HEP1471724.1 | 2552 | 52.6 |
| HER1886433.1 | 2553 | 52.6 |
| HER2582471.1 | 2554 | 52.6 |
| HES0462566.1 | 2555 | 52.6 |
| MBQ2659786.1 | 2556 | 52.6 |
| MBQ3271428.1 | 2557 | 52.6 |
| MBQ8429076.1 | 2558 | 52.6 |
| MBR3246619.1 | 2559 | 52.6 |
| MCI5777383.1 | 2560 | 52.6 |
| MCI9524472.1 | 2561 | 52.6 |

TABLE 7-continued

CW_7 repeat-containing protein sequences and sequence identity to CLB2 CW_7.

| GenBank | SEQ | ID % |
|---|---|---|
| MDY2598391.1 | 2562 | 52.6 |
| WP_051917032.1 | 2563 | 52.6 |
| WP_052122821.1 | 2564 | 52.6 |
| WP_111679224.1 | 2565 | 52.6 |
| WP_118584594.1 | 2566 | 52.6 |
| WP_125703673.1 | 2567 | 52.6 |
| WP_136073651.1 | 2568 | 52.6 |
| WP_136116607.1 | 2569 | 52.6 |
| WP_243091776.1 | 2570 | 52.6 |
| WP_274726326.1 | 2571 | 52.6 |
| WP_298048783.1 | 2572 | 52.6 |
| WP_304321143.1 | 2573 | 52.6 |
| AGM99860.1 | 2574 | 52.6 |
| CDD50240.1 | 2575 | 52.6 |
| DAE44343.1 | 2576 | 52.6 |
| DAI23626.1 | 2577 | 52.6 |
| DAW88811.1 | 2578 | 52.6 |
| HEL1929654.1 | 2579 | 52.6 |
| HEL1952478.1 | 2580 | 52.6 |
| HEL1991626.1 | 2581 | 52.6 |
| HEL2343545.1 | 2582 | 52.6 |
| HEM2577081.1 | 2583 | 52.6 |
| HEM2761199.1 | 2584 | 52.6 |
| HEM3013643.1 | 2585 | 52.6 |
| HEM3474618.1 | 2586 | 52.6 |
| HEM3538581.1 | 2587 | 52.6 |
| HEM3553770.1 | 2588 | 52.6 |
| HEM3657365.1 | 2589 | 52.6 |
| HEM3710124.1 | 2590 | 52.6 |
| HEM3893460.1 | 2591 | 52.6 |
| HEM4192226.1 | 2592 | 52.6 |
| HEM4699491.1 | 2593 | 52.6 |
| HEM4718477.1 | 2594 | 52.6 |
| HEM4776316.1 | 2595 | 52.6 |
| HEM4911015.1 | 2596 | 52.6 |
| HEM4919345.1 | 2597 | 52.6 |
| HEM5004686.1 | 2598 | 52.6 |
| HEM5090714.1 | 2599 | 52.6 |
| HEM5109720.1 | 2600 | 52.6 |
| HEM5119153.1 | 2601 | 52.6 |
| HEM5121716.1 | 2602 | 52.6 |
| HEM5132744.1 | 2603 | 52.6 |
| HEM5942296.1 | 2604 | 52.6 |
| HEM5978676.1 | 2605 | 52.6 |
| HEM6067931.1 | 2606 | 52.6 |
| HEM6145106.1 | 2607 | 52.6 |
| HEM6189466.1 | 2608 | 52.6 |
| HEM6250848.1 | 2609 | 52.6 |
| HEM6413220.1 | 2610 | 52.6 |
| HEM6505100.1 | 2611 | 52.6 |
| HEM6558438.1 | 2612 | 52.6 |
| KAB5638136.1 | 2613 | 52.6 |
| KAB5706536.1 | 2614 | 52.6 |
| KAB5710959.1 | 2615 | 52.6 |
| MBQ1292045.1 | 2616 | 52.6 |
| MBQ8994235.1 | 2617 | 52.6 |
| MCK3895826.1 | 2618 | 52.6 |
| MDD7566620.1 | 2619 | 52.6 |
| MDO5363071.1 | 2620 | 52.6 |
| MDW8705952.1 | 2621 | 52.6 |
| MEE0418147.1 | 2622 | 52.6 |
| NQJ93880.1 | 2623 | 52.6 |
| NQK27632.1 | 2624 | 52.6 |
| NQL21799.1 | 2625 | 52.6 |
| NQL79699.1 | 2626 | 52.6 |
| NQM31408.1 | 2627 | 52.6 |
| NQN69251.1 | 2628 | 52.6 |
| NQO20695.1 | 2629 | 52.6 |
| NQP05400.1 | 2630 | 52.6 |
| NQP14213.1 | 2631 | 52.6 |
| NQQ83748.1 | 2632 | 52.6 |
| RGV16643.1 | 2633 | 52.6 |
| WP_000290198.1 | 2634 | 52.6 |
| WP_013976664.1 | 2635 | 52.6 |
| WP_024390533.1 | 2636 | 52.6 |
| WP_024412345.1 | 2637 | 52.6 |
| WP_024414926.1 | 2638 | 52.6 |
| WP_029171101.1 | 2639 | 52.6 |
| WP_029943833.1 | 2640 | 52.6 |
| WP_029997156.1 | 2641 | 52.6 |
| WP_044675234.1 | 2642 | 52.6 |
| WP_044682843.1 | 2643 | 52.6 |
| WP_044764139.1 | 2644 | 52.6 |
| WP_044980382.1 | 2645 | 52.6 |
| WP_071126739.1 | 2646 | 52.6 |
| WP_074392165.1 | 2647 | 52.6 |
| WP_074392304.1 | 2648 | 52.6 |
| WP_099776207.1 | 2649 | 52.6 |
| WP_105095266.1 | 2650 | 52.6 |
| WP_105125678.1 | 2651 | 52.6 |
| WP_105142100.1 | 2652 | 52.6 |
| WP_105152938.1 | 2653 | 52.6 |
| WP_105159137.1 | 2654 | 52.6 |
| WP_105206431.1 | 2655 | 52.6 |
| WP_105208073.1 | 2656 | 52.6 |
| WP_105248968.1 | 2657 | 52.6 |
| WP_105257074.1 | 2658 | 52.6 |
| WP_106464647.1 | 2659 | 52.6 |
| WP_125177550.1 | 2660 | 52.6 |
| WP_141600219.1 | 2661 | 52.6 |
| WP_184493990.1 | 2662 | 52.6 |
| WP_205025891.1 | 2663 | 52.6 |
| WP_216395541.1 | 2664 | 52.6 |
| WP_226314444.1 | 2665 | 52.6 |
| WP_226943967.1 | 2666 | 52.6 |
| WP_229037239.1 | 2667 | 52.6 |
| WP_230333804.1 | 2668 | 52.6 |
| WP_240020027.1 | 2669 | 52.6 |
| WP_249549528.1 | 2670 | 52.6 |
| WP_258783994.1 | 2671 | 52.6 |
| WP_259302481.1 | 2672 | 52.6 |
| WP_270320041.1 | 2673 | 52.6 |
| WP_270544248.1 | 2674 | 52.6 |
| WP_271717875.1 | 2675 | 52.6 |
| WP_301221300.1 | 2676 | 52.6 |
| WP_301843585.1 | 2677 | 52.6 |
| WP_304068585.1 | 2678 | 52.6 |
| WP_305265450.1 | 2679 | 52.6 |
| WP_310990536.1 | 2680 | 52.6 |
| WP_311047931.1 | 2681 | 52.6 |
| WP_321058515.1 | 2682 | 52.6 |
| WP_336382927.1 | 2683 | 52.6 |
| WP_336383592.1 | 2684 | 52.6 |
| WP_336383648.1 | 2685 | 52.6 |
| WP_336384539.1 | 2686 | 52.6 |
| WP_336385566.1 | 2687 | 52.6 |
| WP_346980751.1 | 2688 | 52.6 |
| DAF84806.1 | 2689 | 52.5 |
| DAH63542.1 | 2690 | 52.5 |
| DAP70393.1 | 2691 | 52.5 |
| HCA29252.1 | 2692 | 52.5 |
| MDY2660134.1 | 2693 | 52.5 |
| WP_244034257.1 | 2694 | 52.5 |
| MBQ8042887.1 | 2695 | 51.4 |
| WP_337418624.1 | 2696 | 51.4 |
| MBN2866661.1 | 2697 | 51.4 |
| WP_276991927.1 | 2698 | 51.4 |
| WP_000215268.1 | 2699 | 51.4 |
| UGL63232.1 | 2700 | 51.4 |
| WP_044474161.1 | 2701 | 51.4 |
| MBP3855013.1 | 2702 | 51.3 |
| MBQ8042669.1 | 2703 | 51.3 |
| MCI7725402.1 | 2704 | 51.3 |
| MCW6653641.1 | 2705 | 51.3 |
| MEA4888530.1 | 2706 | 51.3 |
| WP_205422867.1 | 2707 | 51.3 |
| WP_228099272.1 | 2708 | 51.3 |
| WP_246441386.1 | 2709 | 51.3 |
| WP_278462642.1 | 2710 | 51.3 |
| DAE90652.1 | 2711 | 51.3 |

TABLE 7-continued

CW_7 repeat-containing protein sequences and sequence identity to CLB2 CW_7.

| GenBank | SEQ | ID % |
|---|---|---|
| DAH40856.1 | 2712 | 51.3 |
| DAQ98353.1 | 2713 | 51.3 |
| DAY85555.1 | 2714 | 51.3 |
| MBQ8767093.1 | 2715 | 51.3 |
| MCI7423138.1 | 2716 | 51.3 |
| MCM1277193.1 | 2717 | 51.3 |
| MDY3655021.1 | 2718 | 51.3 |
| MEE1397517.1 | 2719 | 51.3 |
| WP_276712846.1 | 2720 | 51.3 |
| WP_302194501.1 | 2721 | 51.3 |
| WP_302492296.1 | 2722 | 51.3 |
| WP_303130204.1 | 2723 | 51.3 |
| WP_336595095.1 | 2724 | 51.3 |
| AMP55868.1 | 2725 | 51.2 |
| CDA72279.1 | 2726 | 51.2 |
| DAL68036.1 | 2727 | 51.2 |
| DAP75085.1 | 2728 | 51.2 |
| DAQ78532.1 | 2729 | 51.2 |
| DAV91738.1 | 2730 | 51.2 |
| DAW02803.1 | 2731 | 51.2 |
| EKD8202267.1 | 2732 | 51.2 |
| HBA02338.1 | 2733 | 51.2 |
| HIS11692.1 | 2734 | 51.2 |
| KAI4449133.1 | 2735 | 51.2 |
| MBD5111060.1 | 2736 | 51.2 |
| MBD5112703.1 | 2737 | 51.2 |
| MBP3891536.1 | 2738 | 51.2 |
| MBP5596521.1 | 2739 | 51.2 |
| MBQ0088390.1 | 2740 | 51.2 |
| MBQ1287777.1 | 2741 | 51.2 |
| MBQ1674891.1 | 2742 | 51.2 |
| MBQ1900870.1 | 2743 | 51.2 |
| MBQ2079735.1 | 2744 | 51.2 |
| MBQ2584970.1 | 2745 | 51.2 |
| MBQ4019433.1 | 2746 | 51.2 |
| MBQ5554531.1 | 2747 | 51.2 |
| MBR6232899.1 | 2748 | 51.2 |
| MBS6584689.1 | 2749 | 51.2 |
| MCR4633162.1 | 2750 | 51.2 |
| MDB2012643.1 | 2751 | 51.2 |
| MDD6644622.1 | 2752 | 51.2 |
| MDD6708609.1 | 2753 | 51.2 |
| MDD6963734.1 | 2754 | 51.2 |
| MDO4187588.1 | 2755 | 51.2 |
| MDY2959829.1 | 2756 | 51.2 |
| MEE0186129.1 | 2757 | 51.2 |
| MEE0559652.1 | 2758 | 51.2 |
| MEE8886263.1 | 2759 | 51.2 |
| NBH27251.1 | 2760 | 51.2 |
| OCN03654.1 | 2761 | 51.2 |
| OKZ66166.1 | 2762 | 51.2 |
| OLA05444.1 | 2763 | 51.2 |
| UWI13691.1 | 2764 | 51.2 |
| WP_002593395.1 | 2765 | 51.2 |
| WP_009244112.1 | 2766 | 51.2 |
| WP_013485728.1 | 2767 | 51.2 |
| WP_114526792.1 | 2768 | 51.2 |
| WP_117704983.1 | 2769 | 51.2 |
| WP_117846743.1 | 2770 | 51.2 |
| WP_118401314.1 | 2771 | 51.2 |
| WP_122789676.1 | 2772 | 51.2 |
| WP_180703455.1 | 2773 | 51.2 |
| WP_202029995.1 | 2774 | 51.2 |
| WP_227220159.1 | 2775 | 51.2 |
| WP_249297460.1 | 2776 | 51.2 |
| WP_256305981.1 | 2777 | 51.2 |
| WP_276703428.1 | 2778 | 51.2 |
| WP_286316643.1 | 2779 | 51.2 |
| WP_286317512.1 | 2780 | 51.2 |
| WP_287937916.1 | 2781 | 51.2 |
| WP_295026378.1 | 2782 | 51.2 |
| WP_303767572.1 | 2783 | 51.2 |
| WP_303995039.1 | 2784 | 51.2 |
| WP_304428199.1 | 2785 | 51.2 |
| WP_305182534.1 | 2786 | 51.2 |
| WP_317413750.1 | 2787 | 51.2 |
| WP_330602045.1 | 2788 | 51.2 |
| WP_337781637.1 | 2789 | 51.2 |
| DAF66658.1 | 2790 | 50.0 |
| DAV12354.1 | 2791 | 50.0 |
| DAV84657.1 | 2792 | 50.0 |
| HEL1150974.1 | 2793 | 50.0 |
| HEM3538720.1 | 2794 | 50.0 |
| MBD5189010.1 | 2795 | 50.0 |
| MBD5386855.1 | 2796 | 50.0 |
| MBO5720881.1 | 2797 | 50.0 |
| MBO5799345.1 | 2798 | 50.0 |
| MBO6237701.1 | 2799 | 50.0 |
| MBO7404159.1 | 2800 | 50.0 |
| MBO7713376.1 | 2801 | 50.0 |
| MBR5533013.1 | 2802 | 50.0 |
| MCD8386023.1 | 2803 | 50.0 |
| MDE6560386.1 | 2804 | 50.0 |
| MDE6742153.1 | 2805 | 50.0 |
| NQR64229.1 | 2806 | 50.0 |
| QYA47864.1 | 2807 | 50.0 |
| RHK26519.1 | 2808 | 50.0 |
| WP_024853126.1 | 2809 | 50.0 |
| WP_025076850.1 | 2810 | 50.0 |
| WP_052327315.1 | 2811 | 50.0 |
| WP_061747786.1 | 2812 | 50.0 |
| WP_105104943.1 | 2813 | 50.0 |
| WP_105242580.1 | 2814 | 50.0 |
| WP_114866868.1 | 2815 | 50.0 |
| WP_117801139.1 | 2816 | 50.0 |
| WP_121796544.1 | 2817 | 50.0 |
| WP_135988502.1 | 2818 | 50.0 |
| WP_147525328.1 | 2819 | 50.0 |
| WP_195569855.1 | 2820 | 50.0 |
| WP_216417053.1 | 2821 | 50.0 |
| WP_219522559.1 | 2822 | 50.0 |
| WP_257713925.1 | 2823 | 50.0 |
| WP_287643461.1 | 2824 | 50.0 |
| WP_308397947.1 | 2825 | 50.0 |
| WP_332415804.1 | 2826 | 50.0 |
| DAG84186.1 | 2827 | 48.8 |
| DAL20377.1 | 2828 | 48.8 |
| DAP32509.1 | 2829 | 48.8 |
| DAQ61516.1 | 2830 | 48.8 |
| HAW06834.1 | 2831 | 48.8 |
| HBL6180668.1 | 2832 | 48.8 |
| HJI60732.1 | 2833 | 48.8 |
| MBD5113123.1 | 2834 | 48.8 |
| MBE6118020.1 | 2835 | 48.8 |
| MBO7505126.1 | 2836 | 48.8 |
| MBP5424287.1 | 2837 | 48.8 |
| MBQ1320366.1 | 2838 | 48.8 |
| MBQ3394210.1 | 2839 | 48.8 |
| MBQ9249886.1 | 2840 | 48.8 |
| MBQ9326958.1 | 2841 | 48.8 |
| MBR0373220.1 | 2842 | 48.8 |
| MBR2788889.1 | 2843 | 48.8 |
| MBR6572198.1 | 2844 | 48.8 |
| MBS5490223.1 | 2845 | 48.8 |
| MCM1166695.1 | 2846 | 48.8 |
| MCM1276394.1 | 2847 | 48.8 |
| MEE1438065.1 | 2848 | 48.8 |
| WP_118745023.1 | 2849 | 48.8 |
| WP_289262844.1 | 2850 | 48.8 |
| WP_289782850.1 | 2851 | 48.8 |
| WP_295272115.1 | 2852 | 48.8 |
| WP_295272150.1 | 2853 | 48.8 |
| DAG19090.1 | 2854 | 48.7 |
| MCI7322026.1 | 2855 | 48.7 |
| NSE26948.1 | 2856 | 48.7 |
| RHU17927.1 | 2857 | 48.7 |
| RHV75689.1 | 2858 | 48.7 |
| WP_117760751.1 | 2859 | 48.7 |
| WP_118667285.1 | 2860 | 48.7 |
| WP_173815311.1 | 2861 | 48.7 |

TABLE 7-continued

CW_7 repeat-containing protein sequences
and sequence identity to CLB2 CW_7.

| GenBank | SEQ | ID % |
|---|---|---|
| WP_270422576.1 | 2862 | 48.7 |
| WP_276692354.1 | 2863 | 48.7 |
| WP_277295283.1 | 2864 | 48.7 |
| WP_330418075.1 | 2865 | 48.7 |
| WP_330427154.1 | 2866 | 48.7 |
| DAQ15831.1 | 2867 | 48.7 |
| MBQ1319894.1 | 2868 | 48.7 |
| MBQ1320175.1 | 2869 | 48.7 |
| MBQ5561787.1 | 2870 | 48.7 |
| MCX4290136.1 | 2871 | 48.7 |
| WP_243036657.1 | 2872 | 48.7 |
| WP_243109257.1 | 2873 | 48.7 |
| WP_317413904.1 | 2874 | 48.7 |
| MBW3077678.1 | 2875 | 48.7 |
| WP_236036727.1 | 2876 | 48.7 |
| WP_332482543.1 | 2877 | 48.7 |
| WP_222759955.1 | 2878 | 48.6 |
| WP_336384256.1 | 2879 | 48.6 |
| MBQ8607098.1 | 2880 | 48.6 |
| WP_147326735.1 | 2881 | 48.6 |
| WP_260805612.1 | 2882 | 48.6 |
| WP_330006255.1 | 2883 | 48.6 |
| WP_319637130.1 | 2884 | 48.5 |
| DAG27820.1 | 2885 | 47.5 |
| DAZ53892.1 | 2886 | 47.5 |
| MBR2159883.1 | 2887 | 47.5 |
| MDD6689222.1 | 2888 | 47.5 |
| WP_150310411.1 | 2889 | 47.5 |
| HEM3698670.1 | 2890 | 47.4 |
| WP_208573214.1 | 2891 | 47.4 |
| WP_270546585.1 | 2892 | 47.4 |
| MBE6720628.1 | 2893 | 47.4 |
| WP_043025021.1 | 2894 | 47.4 |
| WP_044669030.1 | 2895 | 47.4 |
| WP_051444825.1 | 2896 | 47.4 |
| WP_183672697.1 | 2897 | 47.4 |
| DAE02510.1 | 2898 | 46.3 |
| DAL21371.1 | 2899 | 46.3 |
| DAT71827.1 | 2900 | 46.3 |
| MBN2911198.1 | 2901 | 46.3 |
| MBS4969902.1 | 2902 | 46.3 |
| MBS6597037.1 | 2903 | 46.3 |
| MCR5777246.1 | 2904 | 46.3 |
| MDD7452647.1 | 2905 | 46.3 |
| NSE04448.1 | 2906 | 46.3 |
| WP_026507130.1 | 2907 | 46.3 |
| WP_117733863.1 | 2908 | 46.3 |
| WP_171030220.1 | 2909 | 46.3 |
| WP_262122378.1 | 2910 | 46.3 |
| WP_291542845.1 | 2911 | 46.3 |
| WP_294669873.1 | 2912 | 46.3 |
| WP_320856526.1 | 2913 | 46.3 |
| DAO22718.1 | 2914 | 46.3 |
| DAQ09628.1 | 2915 | 46.3 |
| DAY85974.1 | 2916 | 46.3 |
| EFT84078.1 | 2917 | 46.3 |
| HBB46032.1 | 2918 | 46.3 |
| MBR2160169.1 | 2919 | 46.3 |
| WP_132379909.1 | 2920 | 46.3 |
| WP_223293616.1 | 2921 | 46.3 |
| WP_248623490.1 | 2922 | 46.3 |
| WP_302194304.1 | 2923 | 46.3 |
| MBF9702455.1 | 2924 | 45.9 |
| NBK97358.1 | 2925 | 45.9 |
| DAP71737.1 | 2926 | 45.7 |
| MBR5433271.1 | 2927 | 45.7 |
| WP_226557257.1 | 2928 | 45.7 |
| WP_270542317.1 | 2929 | 45.7 |
| DAP18680.1 | 2930 | 45.0 |
| DAY64203.1 | 2931 | 45.0 |
| WP_152787267.1 | 2932 | 45.0 |
| WP_286102280.1 | 2933 | 45.0 |
| WP_298535983.1 | 2934 | 44.4 |
| MBQ1325639.1 | 2935 | 43.9 |
| WP_167958494.1 | 2936 | 43.9 |
| WP_262350103.1 | 2937 | 43.9 |
| MBE7091751.1 | 2938 | 43.6 |

"GenBank": GenBank Accession No.
"SEQ": SEQ ID NO.
"ID %": Top amino acid percent identity to CLB2 CW_7 repeat among CW_7 repeats comprised by the sequence.

Chimeric Cell Wall Hydrolases of the Disclosure

In some embodiments, a recombinant protein of the disclosure is a chimeric protein. In some embodiments, a recombinant protein of the disclosure is a chimeric CWH. The present disclosure is based in part on the inventors' development of novel and highly active chimeric CWHs. As disclosed in the Examples herein, illustrative CWHs of the disclosure are surprising in that they have highly effective anti-*Cutibacterium acnes* properties that arise from the unique properties of the novel CBD and/or EAD comprised by the CWH.

In some embodiments, the present disclosure provides a recombinant protein comprising the sequence of an EAD and/or CBD according to any one of the embodiments disclosed herein. In some embodiments, the recombinant protein is a chimeric protein. In some embodiments, the chimeric protein is a chimeric cell wall hydrolase (CWH). A chimeric CWH herein comprises at least one heterologous domain, e.g., a heterologous EAD or CBD, compared to a native CWH sequence.

In some embodiments, a chimeric CWH herein is a chimeric protein comprising an EAD and a CBD from different native proteins. In some embodiments, a chimeric CWH of the disclosure comprises an EAD disclosed herein and a CBD disclosed herein. In some embodiments, a chimeric CWH of the disclosure comprises an EAD having at least 70, 75, 80, 85, 90, 95, 96, 97, 98, or 99% sequence identity with an EAD disclosed herein and a CBD having at least 70, 75, 80, 85, 90, 95, 96, 97, 98, or 99% sequence identity with a CBD disclosed herein.

In some embodiments, a chimeric CWH of the disclosure comprises a CLC1-family EAD. In some embodiments, a chimeric CWH of the disclosure comprises an EAD having at least 70, 75, 80, 85, 90, 95, 96, 97, 98, or 99% sequence identity with a CLC1-family EAD disclosed herein.

In some embodiments, a chimeric CWH of the disclosure comprises a CW_7 CBD. In some embodiments, a chimeric CWH of the disclosure comprises a CBD having at least 70, 75, 80, 85, 90, 95, 96, 97, 98, or 99% sequence identity with a CW_7 CBD disclosed herein.

In some embodiments, a chimeric CWH of the disclosure comprises a CLC1-family EAD and a CW_7 CBD. In some embodiments, a chimeric CWH of the disclosure comprises an EAD having at least 70, 75, 80, 85, 90, 95, 96, 97, 98, or 99% sequence identity with a CLC1-family EAD disclosed herein and a CBD having at least 70, 75, 80, 85, 90, 95, 96, 97, 98, or 99% sequence identity with a CW_7 CBD disclosed herein.

In some embodiments, a chimeric CWH of the disclosure comprises the EAD from CLC16 (SEQ ID NO: 35). In some embodiments, a chimeric CWH of the disclosure comprises an EAD having at least 70, 75, 80, 85, 90, 95, 96, 97, 98, or 99% sequence identity with the EAD from CLC16 (SEQ ID NO: 35).

In some embodiments, a chimeric CWH of the disclosure comprises the EAD from CLC2 (SEQ ID NO: 21). In some embodiments, a chimeric CWH of the disclosure comprises an EAD having at least 70, 75, 80, 85, 90, 95, 96, 97, 98, or 99% sequence identity with the EAD from CLC2 (SEQ ID NO: 21).

In some embodiments, a chimeric CWH of the disclosure comprises the EAD from CaLys1. In some embodiments, a chimeric CWH of the disclosure comprises an EAD having at least 70, 75, 80, 85, 90, 95, 96, 97, 98, or 99% sequence identity with the EAD from CaLys1.

In some embodiments, a chimeric CWH of the disclosure comprises the CBD from CLB2. In some embodiments, a chimeric CWH of the disclosure comprises a CBD having at least 70, 75, 80, 85, 90, 95, 96, 97, 98, or 99% sequence identity with the CBD from CLB2.

In some embodiments, a chimeric CWH of the disclosure comprises a sequence from Table 8. In some embodiments, a chimeric CWH of the disclosure consists of a sequence from Table 8. In some embodiments, a chimeric CWH of the disclosure has at least 40, 45, 50, 55, 60, 65, 70, 75, 80, 85, 90, or 95% identity with a sequence in Table 8. In some embodiments, a chimeric CWH of the disclosure has at least 80, 81, 82, 83, 84, 85, 86, 87, 88, 89, 90, 91, 92, 93, 94, 95, 96, 97, 98, or 99% identity with a sequence in Table 8. In some embodiments, the sequence of the chimeric CWH differs by 1, 2, 3, 4, 5, 6, 7, 8, 9, 10, 11, 12, 13, 14, or 15 amino acids from a sequence in Table 8.

TABLE 8

Chimeric CWHs.

| Description, SEQ ID NO | Amino Acid Sequence |
|---|---|
| CLC1-EAD + CLB1-CBD, SEQ ID NO: 52 | MTFIQARHHGGNSNTPITRLVIHATCPDVGYPSASKAGRAVSTAEYFASTSRS ASAHYVCDVSATVQCLSEETIGYHAPPNSHSIGIEICADGGSRASFEKASHAY TREQWLSPQVWPAVERAAILARGICHRHHIPVRKLTTAQVKSGMSGICGHD NVSDAFHQSDHDDPGPYFPWNEFIAAIQGKNTNKGELSMSDVTSMTGNTPA PKPAPAPAPAPNIDALADAVIRGEYGNGEERRRRLGANYAAVQKRVNEKLT GHAPAPTPNIDALADAVIRGDYGNGEERRRRLGNLYDQVQARVNQKLGY |
| CLC1-EAD + CLB2-CBD, SEQ ID NO: 53 | MTFIQARHHGGNSNTPITRLVIHATCPDVGYPSASKAGRAVSTAEYFASTSRS ASAHYVCDVSATVQCLSEETIGYHAPPNSHSIGIEICADGGSRASFEKASHAY TREQWLSPQVWPAVERAAILARGICHRHHIPVRKLTTAQVKSGMSGICGHD NVSDAFHQSDHDDPGPYFPWNEFIAAIQGKNTNKGELSMSDVTSHMTGNTP APAPAPAPKPAPTPKPAPNIDALADAVIRGEYGNGNERRRRLGSNYDAVQRRV NEKLRH |
| CLC1-EAD + CLB3-CBD, SEQ ID NO: 54 | MTFIQARHHGGNSNTPITRLVIHATCPDVGYPSASKAGRAVSTAEYFASTSRS ASAHYVCDVSATVQCLSEETIGYHAPPNSHSIGIEICADGGSRASFEKASHAY TREQWLSPQVWPAVERAAILARGICHRHHIPVRKLTTAQVKSGMSGICGHD NVSDAFHQSDHDDPGPYFPWNEFIAAIQGKNTNKGELSMSDVTSLARLDGK PSAKPAPKASAANIERLAHDVINGKFGNGDERRRRLGASYDAVQARVNQML GADAGPNIEQLANDVIAGKYGNGEARRVALGASYDAVQARVNQMLGV |
| CLC1-EAD + CLB4-CBD, SEQ ID NO: 55 | MTFIQARHHGGNSNTPITRLVIHATCPDVGYPSASKAGRAVSTAEYFASTSRS ASAHYVCDVSATVQCLSEETIGYHAPPNSHSIGIEICADGGSRASFEKASHAY TREQWLSPQVWPAVERAAILARGICHRHHIPVRKLTTAQVKSGMSGICGHD NVSDAFHQSDHDDPGPYFPWNEFIAAIQGKNTNKGELSMSDVTSAHLAGKA APAAKPATTSSPNIEQLARDVIAGGYGNGETRRAALGASYDVVQARVNQIL KAGSLAPNIEQLARDVIAGKYGNGETRRAALGASYDVVQARVNQMLGV |
| CLC2-EAD + CLB1-CBD, SEQ ID NO: 56 | MTFIQAAHRGGTSNTPITRLVIHATCPDVGFPSASRAGRAVSTAEYFASTSRS ASAHYVCDISTTVQCLSEATIGYHAPPNAHSIGIEICADGGSRASFEKASHAY TREQWLSPQVWPAVERAAILARDICHRHHIPIRRLSVAQVRAGERGICGHNE VSEAFHQSDHDDPGPYFPWNEFIAAVQGKTTTPEGELSMSDTSMTGNTPAPK PAPAPAPAPNIDALADAVIRGEYGNGEERRRRLGANYAAVQKRVNEKLTGH APAPTPNIDALADAVIRGDYGNGEERRRRLGNLYDQVQARVNQKLGY |
| CLC2-EAD + CLB2-CBD, SEQ ID NO: 57 | MTFIQAAHRGGTSNTPITRLVIHATCPDVGFPSASRAGRAVSTAEYFASTSRS ASAHYVCDISTTVQCLSEATIGYHAPPNAHSIGIEICADGGSRASFEKASHAY TREQWLSPQVWPAVERAAILARDICHRHHIPIRRLSVAQVRAGERGICGHNE VSEAFHQSDHDDPGPYFPWNEFIAAVQGKTTTPEGELSMSDTSHMTGNTPAP APAPKPAPTPKPAPNIDALADAVIRGEYGNGNERRRRLGSNYDAVQRRVNE KLRH |
| CLC3-EAD + CLB1-CBD, SEQ ID NO: 58 | MTFIQARHHGGNSNAPITRLVIHATCPDVGYPSASKAGRAVSTANYFATTDR PASAHYVCDIATTVQCLSEETIGYHAPPNSHSIGIEICADGGSHASFEKASHAY TRDQWLSDDVWPAVERAAILARDICQRHRIPVRKLSTAQVKAGLSGICGHD NVSGAFHQSDHDDPGPYFPWDQFMALVQGKPATPGDLTMADITSMTGNTP APKPAPAPAPAPNIDALADAVIRGEYGNGEERRRRLGANYAAVQKRVNEKL TGHAPAPTPNIDALADAVIRGDYGNGEERRRRLGNLYDQVQARVNQKLGY |
| CLC3-EAD + CLB2-CBD, SEQ ID NO: 59 | MTFIQARHHGGNSNAPITRLVIHATCPDVGYPSASKAGRAVSTANYFATTDR PASAHYVCDIATTVQCLSEETIGYHAPPNSHSIGIEICADGGSHASFEKASHAY TRDQWLSDDVWPAVERAAILARDICQRHRIPVRKLSTAQVKAGLSGICGHD NVSGAFHQSDHDDPGPYFPWDQFMALVQGKPATPGDLTMADITSHMTGNT PAPAPAPKPAPTPKPAPNIDALADAVIRGEYGNGNERRRRLGSNYDAVQRRV NEKLRH |

TABLE 8-continued

Chimeric CWHs.

| Description, SEQ ID NO | Amino Acid Sequence |
|---|---|
| CD27L-EAD + CLB1-CBD, SEQ ID NO: 66 | MKICITVGHSILKSGACTSADGVVNEYQYNKSLAPVLADTFRKEGHKVDVII CPEKQFKTKNEEKSYKIPRVNSGGYDLLIELHLNASNGQGKGSEVLYYSNKG LEYATRICDKLGTVFKNRGAKLDKRLYILNSSKPTAVLIESFFCDNKEDYDK AKKLGHEGIAKLIVEGVLNKNINNEGVKQMYKHTIVYDGEVDKTSMTGNTP APKPAPAPAPAPNIDALADAVIRGEYGNGEERRRLGANYAAVQKRVNEKL TGHAPAPTPNIDALADAVIRGDYGNGEERRRLGNLYDQVQARVNQKLGY |
| CD27L-EAD + CLB2-CBD, SEQ ID NO: 67 | MKICITVGHSILKSGACTSADGVVNEYQYNKSLAPVLADTFRKEGHKVDVII CPEKQFKTKNEEKSYKIPRVNSGGYDLLIELHLNASNGQGKGSEVLYYSNKG LEYATRICDKLGTVFKNRGAKLDKRLYILNSSKPTAVLIESFFCDNKEDYDK AKKLGHEGIAKLIVEGVLNKNINNEGVKQMYKHTIVYDGEVDKTSHMTGN TPAPAPAPKPAPTPKPAPNIDALADAVIRGEYGNGNERRRLGSNYDAVQRR VNEKLRH |
| PlyGVE2-EAD + CLB1-CBD, SEQ ID NO: 68 | MKKIFWDKGHGGSDPGAVANGLQEKNLTHKIVEYATDYLAAHYEGFTQRV SREGDQSLTLDQRADMANKWGADVFVSVHINAGKGTGFEIYVHPNASPQSI ALQNVLHGEILSAMRQFGNITDRGKKRANYAVLRETKMPAVLTENLFIDSN DAKHLKNEAFLKAVGEAHARGVAKFLGLKTSMTGNTPAPKPAPAPAPNI DALADAVIRGEYGNGEERRRLGANYAAVQKRVNEKLTGHAPAPTPNIDAL ADAVIRGDYGNGEERRRLGNLYDQVQARVNQKLGY |
| PlyGVE2-EAD + CLB2-CBD, SEQ ID NO: 69 | MKKIFWDKGHGGSDPGAVANGLQEKNLTHKIVEYATDYLAAHYEGFTQRV SREGDQSLTLDQRADMANKWGADVFVSVHINAGKGTGFEIYVHPNASPQSI ALQNVLHGEILSAMRQFGNITDRGKKRANYAVLRETKMPAVLTENLFIDSN DAKHLKNEAFLKAVGEAHARGVAKFLGLKTSHMTGNTPAPAPAPKPAPTPK PAPNIDALADAVIRGEYGNGNERRRLGSNYDAVQRRVNEKLRH |
| CLC4-EAD + CLB2-CBD, SEQ ID NO: 94 | MTFIQARHHGGNSNAPITRLVIHATCPDVGYPSASKAGRAVSTAEYFASTSR SASAHYVCDIAATVQCLSEEAIGFHAPPNSHSIGIEICADGGSRASFEKASHAY TREQWLSPQVWPAVERAAILARDICRRHHIPVRKLTTAQVKSGMSGICGHD NVSDAFHQSDHDDPGPYFPWNEFIAAVQGKNTNKGELSMSDVTSHMTGNT PAPAPAPKPAPTPKPAPNIDALADAVIRGEYGNGNERRRLGSNYDAVQRRV NEKLRH |
| CLC5-EAD + CLB2-CBD, SEQ ID NO: 95 | MTFIQARHHGGNSNTPVTRLVIHATCPDVGYPSASKAGRAVSTAEYFASTSR SASAHYVCDVSATVQCLSEEEAIGYHAPPNSHSIGIEICADGGSHASFETASHA YTREQWLSPQVWPAVERAAILARDICHRHHIPVRKLTTAQVKSGMSGICGH DNVSDAFRQSDHDDPGPYFPWNEFIAAVQGKTTNKGELSMSDVTSHMTGN TPAPAPAPKPAPTPKPAPNIDALADAVIRGEYGNGNERRRLGSNYDAVQRR VNEKLRH |
| CLC6-EAD + CLB2-CBD, SEQ ID NO: 96 | MTFIQARHHGGNSNNPVTRLVIHATCPDVGYPSASKAGRAVSTAQYFASTSR PASAHYVCDVSATVQCLSEETIGYHAPPNAHSIGIEICSDGGSRASFEKASHA YSREQWLSPQVWPAVERAAILARDICHRHRIPVRKLTAAQVKSGMSGICGH DNVSDAFRQSDHDDPGPYFPWNEFIAAVQGKNTNKGELSMSDVTSHMTGN TPAPAPAPKPAPTPKPAPNIDALADAVIRGEYGNGNERRRLGSNYDAVQRR VNEKLRH |
| CLC7-EAD + CLB2-CBD, SEQ ID NO: 97 | MTFIQARHHGGNSNAPITRLVIHATCPDVGYPSASKAGRAVSTAHYFAEATR PASAHYVCDVSATVQCLSEETIGYHAPPNAHSIGIEICSDGGSRASFEKASHA YSREQWLSPQVWPAVERAAILARDICHRHRIPVRKLTAAQVKSGMSGICGH DNVSDAFRQSDHDDPGPYFPWNEFIAAVQGKTTNKGELSMSDVTSHMTGN TPAPAPAPKPAPTPKPAPNIDALADAVIRGEYGNGNERRRLGSNYDAVQRR VNEKLRH |
| CLC8-EAD + CLB2-CBD, SEQ ID NO: 98 | MTFIQARHHGGNSNTPITRLVIHATCPDVGYPSASRAGRAASTANYFATTDR PASAHYVCDIATTVQCLSEEVIGFHAPPNSHSIGIEICADGGSHASFEKASHAY TREQWLSDDVWPAVERAAILARGICHRHHIPVRKLSTAQVKSGMSGICGHD NVSDAFHQSDHDDPGPHFPWNEFIAAVQGKTTNKGELSMSDVTSHMTGNTP APAPAPKPAPTPKPAPNIDALADAVIRGEYGNGNERRRLGSNYDAVQRRV NEKLRH |
| CLC9-EAD + CLB2-CBD, SEQ ID NO: 99 | MTFIQARHHGGNTNAPVTRLVIHSTCPDVGFPSASRAGRAVSTAGYFASTSR PASAHYVVDVTTTVQCLPENTIGYHAPPNSHSIGIEICSDGGSRASFENPSHA YTREQWLSPQVWPAVERAAILARGICHRHHIPVRKLTTAQVKNGMSGICGH DNVSDAFHQSDHDDPGPYFPWDKFIAAVQGKNTTSEGELSMSDITSHMTGN TPAPAPAPKPAPTPKPAPNIDALADAVIRGEYGNGNERRRLGSNYDAVQRR VNEKLRH |
| CLC10-EAD + CLB2-CBD, SEQ ID NO: | MQFIQAKHHGGNENTPVTRLVIHATCPDTGYPSASRAGRAASTARYFQSTSR PTSAHYVCDVTATVQCLSEETIGYHAPPNAHSIGIEICADGGSKSSFDNPSHS YTREQWLSPQVWPAVERAAILARDICHRHHIPVRKLSTAQVKSGMSGICGH |

TABLE 8-continued

Chimeric CWHs.

| Description, SEQ ID NO | Amino Acid Sequence |
|---|---|
| 100 | DNVSDAFHQSDHDDPGPYFPWDRFMAAITNTHPEELTMADVTSHMTGNTP APAPAPKPAPTPKPAPNIDALADAVIRGEYGNGNERRRRLGSNYDAVQRRV NEKLRH |
| CLC11-EAD + CLB2-CBD, SEQ ID NO: 101 | MTFIQAAHRGGTSNTPITRLVIHATCPDVGFPSASRAGRAVSTAEYFASTSRS ASAHYVCDISTTVQCLSEATIGYHAPPNAHSIGIEICAAGGSRASFEKASHAY TREQWLSPQVWPAVERAAILARDICHRHHIPIRRLSVAQVRAGERGICGHNE VSEAFHQSDHDDPGPYFPWNEFIAAVQGKTTTPEGELSMSDVTSHMTGNTP APAPAPKPAPTPKPAPNIDALADAVIRGEYGNGNERRRRLGSNYDAVQRRV NEKLRH |
| CLC12-EAD + CLB2-CBD, SEQ ID NO: 102 | MTFIQARHHGGNTNAPVSRLVIHSTCPDVGFPSASRAGRAVSTAEYFASTSR PASAHYVVDIATTVQCLPENTIGYHAPPNSHSIGIEICSDGGSRASFEKASHAY TREQWLSPQVWPAVERAAILARDICHRHRIPVRKLSTAQVKNGMSGICGHD NVSDAFHQSDHDDPGLYFPWDRFIAAIQGKNTTTKGELSMSDVTSHMTGNT PAPAPAPKPAPTPKPAPNIDALADAVIRGEYGNGNERRRRLGSNYDAVQRRV NEKLRH |
| CLC13-EAD + CLB2-CBD, SEQ ID NO: 103 | MTFIQARHHGGNTNAPVTRLVIHSTCPDVGFPSASRAGRAVSTAGYFASTSR PASAHYVVDVTTTVQCLPENTIGYHAPPNSHSIGIEICSDGGSRASFENPSHA YTREQWLSPQVWPAVERAAILARDICHRHRIPVRKLSTAQVKNGMSGICGH DNVSDAFHQSDHDDPGPYFPWDKFIAAVQGKNTTSEGELSMSDITSHMTGN TPAPAPAPKPAPTPKPAPNIDALADAVIRGEYGNGNERRRRLGSNYDAVQRR VNEKLRH |
| CLC14-EAD + CLB2-CBD, SEQ ID NO: 104 | MTFIQAKHHGGHNNPPVTRLVIHATCPDVGYPSASRAGRAVSTAHYFQETT RPASAHYICDISTTVQCLSEETVGYHAPPNSHSIGIEICADGGSHASFSNPAHA YTREQWLSPQVWPAVERAAMLARGICQRHNIPIRRLSIADVKAGKRGICGH NEVSEAFHQSDHDDPGPYFPWDGFIALVNGHSAPSRQEELTVSDVTSHMTG NTPAPAPAPKPAPTPKPAPNIDALADAVIRGEYGNGNERRRRLGSNYDAVQR RVNEKLRH |
| CLC15-EAD + CLB2-CBD, SEQ ID NO: 105 | MRYIQAKHHGGASNKPVTRLVIHSTCPDVGFPSASRAGRAESTANYFADSSR PASAHYVCDVSTTIQCLHEDVVGYHAPPNSHSIGIEICSDGGSRASFRNPNHA YTREQWLSPQVWPAVERAAVLARDICKRNGIPIRKLSTSEVKAGRSGICGHN NVSDAFHQSDHDDPGPYFPWDKFIAAVNGAKVTSEGALSMSDVTSHMTGN TPAPAPAPKPAPTPKPAPNIDALADAVIRGEYGNGNERRRRLGSNYDAVQRR VNEKLRH |
| CLC16-EAD + CLB2-CBD, SEQ ID NO: 106 | MRYIQAKHHGAASNKPVTRLVIHSTCPDVGFPSASRAGRAESTANYFADSSR PASAHYVCDVSTTIQCLHEDIVGYHAPPNSHSIGIEICSDGGSHASFNNPKHA YTRDQWLSPQVWPAVERAAVLARDICKRNGIPIRKLSTSEVKAGRSGICGHN NVSDAFHQSDHDDPGPYFPWDKFIAAVNGAKVTSEGALSMSDVTSHMTGN TPAPAPAPKPAPTPKPAPNIDALADAVIRGEYGNGNERRRRLGSNYDAVQRR VNEKLRH |
| CLC17-EAD + CLB2-CBD, SEQ ID NO: 107 | MTYIPAAHHGPTTNAPVSRIVIHSTCPDVGFPAASKAGRAVSTANYFASTSRP ASAHYVVDIATTVQCLPENTVGYHAPPNSGSIGIEICSDGGSKGSFENPAHAY TTTQWLSPEVWPAVERAAILAREICHRHHIPIRRLSVAQVRAGERGICGHNE VSEAFHRSDHDDPGPWFPWDRFILEVKGIPTEGMSMSDITSHMTGNTPAPAP APKPAPTPKPAPNIDALADAVIRGEYGNGNERRRRLGSNYDAVQRRVNEKL RH |
| CLC2-EAD + CPL1-CBD, SEQ ID NO: 224 | MTFIQAAHRGGTSNTPITRLVIHATCPDVGFPSASRAGRAVSTAEYFASTSRS ASAHYVCDISTTVQCLSEATIGYHAPPNAHSIGIEICADGGSRASFEKASHAY TREQWLSPQVWPAVERAAILARDICHRHHIPIRRLSVAQVRAGERGICGHNE VSEAFHQSDHDDPGPYFPWNEFIAAVQGKTTTPEGELSMSDTSAPTPPAKPT PPAPKPSVNIDALADAVIRGEYGNGDERKRRLGSNYAAVQKRVNEKLAGRS PAKPSVNIDALADAVIRGDYGNGEERKHRLGGNYAAVQKRVNEKLGIG |
| CLC2-EAD + CPL2-CBD, SEQ ID NO: 225 | MTFIQAAHRGGTSNTPITRLVIHATCPDVGFPSASRAGRAVSTAEYFASTSRS ASAHYVCDISTTVQCLSEATIGYHAPPNAHSIGIEICADGGSRASFEKASHAY TREQWLSPQVWPAVERAAILARDICHRHHIPIRRLSVAQVRAGERGICGHNE VSEAFHQSDHDDPGPYFPWNEFIAAVQGKTTTPEGELSMSDTSAPTPPAKPT PPAPKPSANIDALADAVIRGEYGNGDERKRRLGSNYAAVQKRVNEKLAGGS PAKPSVNIDALTDAVIRGEYGNGEERKRRLGGNYAAVQKRVNEQLGIS |
| CLC2-EAD + CPL3-CBD, SEQ ID NO: 226 | MTFIQAAHRGGTSNTPITRLVIHATCPDVGFPSASRAGRAVSTAEYFASTSRS ASAHYVCDISTTVQCLSEATIGYHAPPNAHSIGIEICADGGSRASFEKASHAY TREQWLSPQVWPAVERAAILARDICHRHHIPIRRLSVAQVRAGERGICGHNE VSEAFHQSDHDDPGPYFPWNEFIAAVQGKTTTPEGELSMSDTSAPTPPAKPT PPTPKPSANIDALADAVIRGEYGNGDERKRRLGSNYAAVQKRVNEKLAGGS PAKPSVNIDALADAVIRGDYGNVEERKRRLGANYAAVQKRVNEKLGIG |

TABLE 8-continued

Chimeric CWHs.

| Description, SEQ ID NO | Amino Acid Sequence |
|---|---|
| CLC2-EAD + CPL4-CBD, SEQ ID NO: 227 | MTFIQAAHRGGTSNTPITRLVIHATCPDVGFPSASRAGRAVSTAEYFASTSRS ASAHYVCDISTTVQCLSEATIGYHAPPNAHSIGIEICADGGSRASFEKASHAY TREQWLSPQVWPAVERAAILARDICHRHHIPIRRLSVAQVRAGERGICGHNE VSEAFHQSDHDDPGPYFPWNEFIAAVQGKTTTPEGELSMSDTSPVPKQPAKS APTPAPSVNIDALADAVIRGEYGNGNERKRRLGANYAVQKRVNEKLAGN TSKPSVNIDALADAVIRGEYGNGEERKRRLGANYAVVQARVNQKLGY |
| CLC2-EAD + CPL5-CBD, SEQ ID NO: 228 | MTFIQAAHRGGTSNTPITRLVIHATCPDVGFPSASRAGRAVSTAEYFASTSRS ASAHYVCDISTTVQCLSEATIGYHAPPNAHSIGIEICADGGSRASFEKASHAY TREQWLSPQVWPAVERAAILARDICHRHHIPIRRLSVAQVRAGERGICGHNE VSEAFHQSDHDDPGPYFPWNEFIAAVQGKTTTPEGELSMSDTSQKPAEPAPA PAPAPARKDIDTVAREVIAGQWGNNPQRAEKLRAAGYDANAVQARVNQM LGAPAPKPAANIDALADAVIRGDYGNGDERRRLGANYDAVQRRVNQKLG L |
| CLC2-EAD + CPL6-CBD, SEQ ID NO: 229 | MTFIQAAHRGGTSNTPITRLVIHATCPDVGFPSASRAGRAVSTAEYFASTSRS ASAHYVCDISTTVQCLSEATIGYHAPPNAHSIGIEICADGGSRASFEKASHAY TREQWLSPQVWPAVERAAILARDICHRHHIPIRRLSVAQVRAGERGICGHNE VSEAFHQSDHDDPGPYFPWNEFIAAVQGKTTTPEGELSMSDTSTPAKPTPTP KPAPSVPPNIDALADAVIRGEYGNGEERKRRLGANYTAVQRRVNEKLAGKK PAAKPSGPNIDALADAVIRGEYGNGEERKRRLGNLYDQVQKRVNQKLGY |
| CLC2-EAD + CPL7-CBD, SEQ ID NO: 230 | MTFIQAAHRGGTSNTPITRLVIHATCPDVGFPSASRAGRAVSTAEYFASTSRS ASAHYVCDISTTVQCLSEATIGYHAPPNAHSIGIEICADGGSRASFEKASHAY TREQWLSPQVWPAVERAAILARDICHRHHIPIRRLSVAQVRAGERGICGHNE VSEAFHQSDHDDPGPYFPWNEFIAAVQGKTTTPEGELSMSDTSTGTTPTPKP QPTPTPAANIDALADAVIRGDYGNGNERKRRLGANYAAVQKRVNEKLAGG SPSKPSANIDALADSVIRGDYGNGDERRRLGENYVAVQARVNQKLGY |
| CLC2-EAD + CPL8-CBD, SEQ ID NO: 231 | MTFIQAAHRGGTSNTPITRLVIHATCPDVGFPSASRAGRAVSTAEYFASTSRS ASAHYVCDISTTVQCLSEATIGYHAPPNAHSIGIEICADGGSRASFEKASHAY TREQWLSPQVWPAVERAAILARDICHRHHIPIRRLSVAQVRAGERGICGHNE VSEAFHQSDHDDPGPYFPWNEFIAAVQGKTTTPEGELSMSDTSAPTPPAKPT PPAPKPSANIDALADAVIRGEYGNGEERKRRLGANYTAVQKRVNEKLTGGS PAKPSANIDALADAVIRGEYGNGEERKRRLGGNYAAVQKRVNEKLGIG |
| CLC2-EAD + CPL9-CBD, SEQ ID NO: 232 | MTFIQAAHRGGTSNTPITRLVIHATCPDVGFPSASRAGRAVSTAEYFASTSRS ASAHYVCDISTTVQCLSEATIGYHAPPNAHSIGIEICADGGSRASFEKASHAY TREQWLSPQVWPAVERAAILARDICHRHHIPIRRLSVAQVRAGERGICGHNE VSEAFHQSDHDDPGPYFPWNEFIAAVQGKTTTPEGELSMSDTSTGTTPTPKP QPAPAPAPNIDALADAVIRGDYGNGNERKRHLGANYAAVQKRVNEKLAGN TSKPSVNIDALADAVIRGEYGNGEERKRRLGANYDAVQARVNQKLGY |
| CLC2-EAD + CPL10-CBD, SEQ ID NO: 233 | MTFIQAAHRGGTSNTPITRLVIHATCPDVGFPSASRAGRAVSTAEYFASTSRS ASAHYVCDISTTVQCLSEATIGYHAPPNAHSIGIEICADGGSRASFEKASHAY TREQWLSPQVWPAVERAAILARDICHRHHIPIRRLSVAQVRAGERGICGHNE VSEAFHQSDHDDPGPYFPWNEFIAAVQGKTTTPEGELSMSDTSSGKTPAPTA KSASTPSTDIDALADAVIRGEYGNGGERKQRLGANYTAVQKRVNEKLSGAA PAKPDGPNIDALADAVIRGEYGNGDERKQRLGNLYSAVQARVNQKLG |
| CLC2-EAD + CPL11-CBD, SEQ ID NO: 234 | MTFIQAAHRGGTSNTPITRLVIHATCPDVGFPSASRAGRAVSTAEYFASTSRS ASAHYVCDISTTVQCLSEATIGYHAPPNAHSIGIEICADGGSRASFEKASHAY TREQWLSPQVWPAVERAAILARDICHRHHIPIRRLSVAQVRAGERGICGHNE VSEAFHQSDHDDPGPYFPWNEFIAAVQGKTTTPEGELSMSDTSMTGNTPAPA PAPAPAAPNIDALADAVIRGEYGNGDERKRRLGANYAAVQQRVNEKLLGN APATKPAGPNIDALADAVIRGEYGNGEERKRRLGNLYGAVQARVNVKLGY |
| CLC2-EAD + CPL12-CBD, SEQ ID NO: 235 | MTFIQAAHRGGTSNTPITRLVIHATCPDVGFPSASRAGRAVSTAEYFASTSRS ASAHYVCDISTTVQCLSEATIGYHAPPNAHSIGIEICADGGSRASFEKASHAY TREQWLSPQVWPAVERAAILARDICHRHHIPIRRLSVAQVRAGERGICGHNE VSEAFHQSDHDDPGPYFPWNEFIAAVQGKTTTPEGELSMSDTSSGTKPAPAP KPTPAPTPNIDALADAVIRGEYGNGDERRRLGNLYDQVQRRVNEKLAGKK PAPKPAPNIDALADAVIRGEYGNGDERRRLGSLYDQVQRRVNQKLGY |
| CLC2-EAD + CPL13-CBD, SEQ ID NO: 236 | MTFIQAAHRGGTSNTPITRLVIHATCPDVGFPSASRAGRAVSTAEYFASTSRS ASAHYVCDISTTVQCLSEATIGYHAPPNAHSIGIEICADGGSRASFEKASHAY TREQWLSPQVWPAVERAAILARDICHRHHIPIRRLSVAQVRAGERGICGHNE VSEAFHQSDHDDPGPYFPWNEFIAAVQGKTTTPEGELSMSDTSAPTPPAKPT PPAPKPSVNIDALADAVIRGEYGNGEERKRRLGSNYAAVQKRVNEKLTG GNPNKPSVNIDALADAVIRGDYGNGEERKRRLGGNYAAVQKRVNEKLGIS |
| CLC2-EAD + CPL14-CBD, SEQ ID NO: | MTFIQAAHRGGTSNTPITRLVIHATCPDVGFPSASRAGRAVSTAEYFASTSRS ASAHYVCDISTTVQCLSEATIGYHAPPNAHSIGIEICADGGSRASFEKASHAY TREQWLSPQVWPAVERAAILARDICHRHHIPIRRLSVAQVRAGERGICGHNE |

TABLE 8-continued

Chimeric CWHs.

| Description, SEQ ID NO | Amino Acid Sequence |
|---|---|
| 237 | VSEAFHQSDHDDPGPYFPWNEFIAAVQGKTTTPEGELSMSDTSDQMTGTKP<br>APAPAAPSVNIDTFADAVIRGEYGNGDERKRRLGANYAAVQARVNEKLAG<br>KAKPAGKSIETLAREVIRGDWGNGQERYNRLTNAGYNYQQVQNRVNQILN |
| CLC2-EAD + CPL15-CBD, SEQ ID NO: 238 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGPYFPWNEFIAAVQGKTTTPEGELSMSDTSYDQISGNKP<br>QAASASKPDIEALANAVIRGEYGNGDQRRARLGGLYDAVQRRVNEKLAAG<br>SAPAAPNIDALADAVIRGDYGNGATRRARLGNLYNQVQARVNQKLGC |
| CLC2-EAD + CPL16-CBD, SEQ ID NO: 239 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGPYFPWNEFIAAVQGKTTTPEGELSMSDTSKTAAAASVS<br>KPAASKGPNYEALADAVIRGEYGSGEERMRRLGNAYARVQAIVNARLLGG<br>QPTPTPLPAKPAGANIDALAKAVIRGEYGTGDARRQKLGNLYDQVQARVNQ<br>ILGAGATAHRAGANIDALADAVIRGEYGNGDERRVRLGANFAAVQARVNQ<br>KLAA |
| CLC2-EAD + CPL18-CBD, SEQ ID NO: 240 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGPYFPWNEFIAAVQGKTTTPEGELSMSDTSPAPAKPSPA<br>KPAPSTPPNIDALADAVIHGDYGNGEERKRRLGSNHAAVQKRVNEKLAGKK<br>PAVKPAGPNIDALADAVIRGGYGNGDERKRRLGGLYAQVQKRVNQKLGY |
| CLC2-EAD + CPL20-CBD, SEQ ID NO: 241 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGPYFPWNEFIAAVQGKTTTPEGELSMSDTSGAGGAASA<br>SPAPTVPSPDIDALAREVIAGKYGNGDDRRRALGANYGRVQARVNEILGAG<br>ARPHSQVVDVDALARAVIRGEFGNGEERKRRLGANYAAVQRRVNELLS |
| CLC2-EAD + CPL21-CBD, SEQ ID NO: 242 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGPYFPWNEFIAAVQGKTTTPEGELSMSDTSGGGGNGRS<br>ASGVDSPSGDLNALADAVLRGDYGNGDERKRRLGSKYSAVQAIVNQRLGY<br>GSTPVSSGPDLNALADAVIRGEYGNGDERRRLGANYKAVQALVNKKLGY |
| CLC2-EAD + CPL22-CBD, SEQ ID NO: 243 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGPYFPWNEFIAAVQGKTTTPEGELSMSDTSERVETGVAA<br>ENCPDGSTANLAAAVMRGEYGNGDERRKRLGSRYDEVQALINRVSSSSVDD<br>LAKDVLNGVFGNGDTRRAVLGSRYDEVQARVNARSSSVDIDALARAVIRGE<br>YGDGNERRTKLGANFDAVQKRVNELLK |
| CLC2-EAD + CPL23-CBD, SEQ ID NO: 244 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGPYFPWNEFIAAVQGKTTTPEGELSMSDTSTGGGSSGGT<br>TSAAPGGTVAELARRVIAGEFGNGDARRAALGSRYDEVQAEVNRILAGGSG<br>GGAAQAPAADDVDDLARRVIAGEFGNGAARKAALGSRYAEVQARVNEML<br>GAGGSGGPSGGADVDALAHAVIRGDYGNGAERKRRLGSLYDAVQARVNEI<br>LS |
| CLC2-EAD + CPL24-CBD, SEQ ID NO: 245 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGPYFPWNEFIAAVQGKTTTPEGELSMSDTSRVDGKPAPA<br>IKPSSSSSNLDQLADDVLTGKYGNGDERRRRLGASYDAVQARVNQMLSVKS<br>SAPNIDQLADDVINGKYGNGDERRRLGASYDAVQARVNQKLGVR |
| CLC2-EAD + CPL25-CBD, SEQ ID NO: 246 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGPYFPWNEFIAAVQGKTTTPEGELSMSDTSGGSSSSAPS<br>GGSAPSGSATDLAKRVIAGEFGNGDARKAALGSRYDEVQAEVNRILNGGSS<br>SSPSVDIDQMARDVIAGKYGNGDARKAALGSNYDAVQARVNELLGAGGSA<br>TGGADIDALARAVIRGEYGNGEERKRRLGSMYEAVQARVNELL |
| CLC2-EAD + CPL26-CBD, | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY |

TABLE 8-continued

Chimeric CWHs.

| Description, SEQ ID NO | Amino Acid Sequence |
|---|---|
| SEQ ID NO: 247 | TREQWLSPQVWPAVERAAILARDICHRHHIPIRRLSVAQVRAGERGICGHNE<br>VSEAFHQSDHDDPGPYFPWNEFIAAVQGKTTTPEGELSMSDTSFGAAAGGG<br>NGGSAPSGSVAELAQAVIRGDYGNGDARRGALGSRYDEVQAEVNRILGGGS<br>ASGGSSSGGSGADIEALAQAVIRGDYGNGDARRAALGSAYDAVQARVNEIL<br>GAGGSSSGGSGGADIEALAQAVIRGEYGNGDERRHRLGSLYDAVQARVNEI<br>LL |
| CLC2-EAD + CPL28-CBD, SEQ ID NO: 248 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGPYFPWNEFIAAVQGKTTTPEGELSMSDTSDVGGAPGG<br>SGSGAPSGDVSELAERVIAGEFGNGDARRAALGSRYDEVQAEVNRILGGGS<br>GIDVDAMARRVIAGEFGNGDERKRRLGSNYDAVQRRVNEILLGAGSSSTSM<br>DIDAMARAVIRGDYGNGEERRRRLGSYYSIVQSRVNEMLS |
| CLC2-EAD + CPL29-CBD, SEQ ID NO: 249 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGPYFPWNEFIAAVQGKTTTPEGELSMSDTSGGSGSGGS<br>GGPAPSGDVSELARRVINGEFGNGDVRKAALGSSYSAVQTRVNEMLGCGSS<br>GGGSGSAGVDIDALARAVINGDYGNGEERRQRLGANYAAVQRRVNEMLS |
| CLC2-EAD + CPL30-CBD, SEQ ID NO: 250 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGPYFPWNEFIAAVQGKTTTPEGELSMSDTSRVNEILGCG<br>PSASGAASNVDALAHAVINGDYGNGEARRERLGADYEAVQRRVNELLA |
| CLC2-EAD + CPL31-CBD, SEQ ID NO: 251 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGPYFPWNEFIAAVQGKTTTPEGELSMSDTSEPYISGANA<br>VIDTIDDLSIDKLADAVISGKYGSGAERRTRLGQRYDAVQQRVNEKLAKAK<br>LSSSAENPERKAPPKPVPAENSGKDSVVGTSPTGDLEELAAAVIQGKYGNGA<br>ERRARLGDRYQEVQNLVNRKLSS |
| CLC2-EAD + CPL32-CBD, SEQ ID NO: 252 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGPYFPWNEFIAAVQGKTTTPEGELSMSDTSDVGSASTPT<br>GSGAPSGDVSELAARVIAGDFGNGDARRAALGSRYDEVQAEVNRILSGGSSS<br>GSYDVDALARRVIAGEFGNGDDRKRRLGDRYSTVQKRVNEILGASGASSTS<br>MDVDAMARAVIRGDYGNGEERRRRLGSYYSIVQRRVNEMLS |
| CLC2-EAD + CPL33-CBD, SEQ ID NO: 253 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGPYFPWNEFIAAVQGKTTTPEGELSMSDTSAPARPASQP<br>AANSSGSSNLEALADAVIAGKYGNGEARRKALGANYAAVQAIVNRKLGAG<br>GSTSVDLNALADAVIRGDYGNGQERKRRLGANYAAVQALVNKKLGY |
| CLC2-EAD + CPL34-CBD, SEQ ID NO: 254 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGPYFPWNEFIAAVQGKTTTPEGELSMSDTSGGAVASQP<br>APVPSTGGVDINALADAVLRGEYGNGAERRARLGGLYDAVQAVVNQKLGA<br>TGATRGAGVDINALADGVLKGLYGNGAERRQRLGVHYDAVQAEVNRRLG<br>Y |
| CLC2-EAD + CPL35-CBD, SEQ ID NO: 255 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGPYFPWNEFIAAVQGKTTTPEGELSMSDTSAGVPSAHKP<br>PAASAPGGSVDELARAVLAGRYGNGEERKRRLGARYGEVQRRVNELIAGK<br>APAPSAPNLDALANAVLRGEYGNGEERRRRLGSLYQPVQDLVNRKLGIR |
| CLC2-EAD + CPL36-CBD, SEQ ID NO: 256 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGPYFPWNEFIAAVQGKTTTPEGELSMSDTSYITGGSPA<br>APAPSVGGDIEALAQAVICGEYGNGEDRKARLGHLYDAVQARVNAKLSGS<br>APAPAPGPNLDALADAVIRGDYGNGAERRNRLGHLYDAVQAIVNRKLS |
| CLC2-EAD + CPL38-CBD, | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY |

TABLE 8-continued

Chimeric CWHs.

| Description, SEQ ID NO | Amino Acid Sequence |
|---|---|
| SEQ ID NO: 257 | TREQWLSPQVWPAVERAAILARDICHRHHIPIRRLSVAQVRAGERGICGHNE<br>VSEAFHQSDHDDPGYFPWNEFIAAVQGKTTTPEGELSMSDTSGGASAPAA<br>KPQQSTPAVNIDDLARRAIAGEFGNGDERKAKLGGNYAAVQQRVNEMLGQ<br>GGGSSAPSVDLNALADAVIRGDYGNGEERKRRLGGNYAAVQQLVNRKLGY |
| CLC2-EAD + CPL39-CBD, SEQ ID NO: 258 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGYFPWNEFIAAVQGKTTTPEGELSMSDTSGGVPAAVK<br>PPAPTAAGGSVDELARAVIAGKYGNGDERRRLGNRYGEVQARVNELISGK<br>KPAPKPANLDAIANAVLRGEYGNGDERRRLGNLYQPVQDLVNRKLGIR |
| CLC2-EAD + CPL40-CBD, SEQ ID NO: 259 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGYFPWNEFIAAVQGKTTTPEGELSMSDTSSATKQPVDA<br>VSSTTTATDIEEKAKSVIRGEFGNGQERKKRLGSDYSEVQKKVNEIYSKGKS<br>KSK |
| CLC2-EAD + CPL43-CBD, SEQ ID NO: 260 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGYFPWNEFIAAVQGKTTTPEGELSMSDTSLCGKTAAPV<br>EPEAPAKPTIDELAQEVLTGKWGNGSERKQRLEAAGHDYAAVQRRVNEILS<br>GNAPGEPTTPPTSEELTAAEIDALARAVIRGDYGNGVTRRAKLGSKYAAVQ<br>KRVNEILRG |
| CLC2-EAD + CPL44-CBD, SEQ ID NO: 261 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGYFPWNEFIAAVQGKTTTPEGELSMSDTSATVPTPTPST<br>PPVAGKTVWQLADEVLAGHHGSGDDRKISLGIQYDAVQAEINRRYGVVVV<br>APAEKTVSQLADEVLAGHGNGEQRRASLGNRFDEVQNEINRRLGGGGVA<br>PQGLNIAQLADAVMRGEYGSGQDRINRLGANYDAVQQEVNRRLGGNASPV<br>ANINALADAVLRGEYGNGDERVRRLGANYAAVQAEINRRYA |
| CLC2-EAD + CPL45-CBD, SEQ ID NO: 262 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGYFPWNEFIAAVQGKTTTPEGELSMSDTSNKVSGVSTS<br>KPSKPKSKSIDQLADEVIKGLHGSGAQRKNSLGSQYDAVQKRVNEKLLGSQ<br>PKPKPATKSIDQLVKETLAGKHGNGEARKKSLGKNYKAVQDIINGKSSAPK<br>KTDSKPKTLKVGQKV |
| CLC2-EAD + CPL46-CBD, SEQ ID NO: 263 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGYFPWNEFIAAVQGKTTTPEGELSMSDTSAVAPAATPA<br>TPPPTKGKTVWQLADEVLAGHHGSGDARKASLGAQYDAVQAEVNRRLGAG<br>TAAPKVKTISQLADEVIAGKHGTGAARQKSLGNQYTAVQNEINRRLGGGGV<br>APQGVNISALADRVLRGEFGSGDARVKALGKNYAAVQAEVNRRLGGGKAA<br>SAPKRVVNISALADAVIRGEYGSGEDRKRRLGANYAAVQAEVNRRYS |
| CLC2-EAD + CPL49-CBD, SEQ ID NO: 264 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGYFPWNEFIAAVQGKTTTPEGELSMSDTSPWLGSSAST<br>PAAPPSGDLNALADAVLRGEYGNGDERKRRLGSNYAAVQAIVNQKLGAGS<br>APAPAPAAPAVDLNALADAVIRGEYGNGDDRRNRLGANYDAVQNLVNRKL<br>QGAPAAGPDLNALADAVIRGEYGNGDERKRRLGANYAAVQALVNRKLR |
| CLC2-EAD + CPL50-CBD, SEQ ID NO: 265 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGYFPWNEFIAAVQGKTTTPEGELSMSDTSQTEPSPAVT<br>PSASPSIDLEAEAAKVIRGDYGNGDERRARLGDNYRAVQNVVNRMLAQ |
| CLC2-EAD + CPL51-CBD, SEQ ID NO: 266 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGYFPWNEFIAAVQGKTTTPEGELSMSDTSAPAPAPTPA<br>PAPTPSGSIDDLAQRVINGEFGNGDARKAALGDKYDAVQARVNEMLGVGG<br>GSHAPSPTPATDIDDLARRVINGEFGNGDARKAALGSKYDAVQARVNEMLG<br>CGGGGGSTSVDIDTLAWKVINGDYGNGQARRDALGDLYDRVQARVNELL |

TABLE 8-continued

Chimeric CWHs.

| Description, SEQ ID NO | Amino Acid Sequence |
|---|---|
| CLC2-EAD + CPL52-CBD, SEQ ID NO: 267 | MTFIQAAHRGGTSNTPITRLVIHATCPDVGFPSASRAGRAVSTAEYFASTSRS ASAHYVCDISTTVQCLSEATIGYHAPPNAHSIGIEICADGGSRASFEKASHAY TREQWLSPQVWPAVERAAILARDICHRHHIPIRRLSVAQVRAGERGICGHNE VSEAFHQSDHDDPGPYFPWNEFIAAVQGKTTTPEGELSMSDTSAVGNAAAA ASTDVSAATIDAEARR VIHGDFGNGAQRKAALGSHYAAVQQRVNELLHV |
| CLC2-EAD + CPL53-CBD, SEQ ID NO: 268 | MTFIQAAHRGGTSNTPITRLVIHATCPDVGFPSASRAGRAVSTAEYFASTSRS ASAHYVCDISTTVQCLSEATIGYHAPPNAHSIGIEICADGGSRASFEKASHAY TREQWLSPQVWPAVERAAILARDICHRHHIPIRRLSVAQVRAGERGICGHNE VSEAFHQSDHDDPGPYFPWNEFIAAVQGKTTTPEGELSMSDTSATVPVTPSE LDATNSTSIEELAREVIRGTWGNGNERYQRLTAAGFDYDAVQARVNELVGI ASKPANKNIDRLAREVIRGDWGNGQERYNRLTAAGYDYHTVQARVNQLLA |
| CLC2-EAD + CPL54-CBD, SEQ ID NO: 269 | MTFIQAAHRGGTSNTPITRLVIHATCPDVGFPSASRAGRAVSTAEYFASTSRS ASAHYVCDISTTVQCLSEATIGYHAPPNAHSIGIEICADGGSRASFEKASHAY TREQWLSPQVWPAVERAAILARDICHRHHIPIRRLSVAQVRAGERGICGHNE VSEAFHQSDHDDPGPYFPWNEFIAAVQGKTTTPEGELSMSDTSGSTAPTAKP APAPEKKTVETLADEVIKGLWGNGEERKRRLTASGYSYDAVQKKVNERLSV KPKKSINTLAREVIHGDWGNGNERKNRLTKAGYNYDAVQKRVNELL |
| CLC2-EAD + CPL55-CBD, SEQ ID NO: 270 | MTFIQAAHRGGTSNTPITRLVIHATCPDVGFPSASRAGRAVSTAEYFASTSRS ASAHYVCDISTTVQCLSEATIGYHAPPNAHSIGIEICADGGSRASFEKASHAY TREQWLSPQVWPAVERAAILARDICHRHHIPIRRLSVAQVRAGERGICGHNE VSEAFHQSDHDDPGPYFPWNEFIAAVQGKTTTPEGELSMSDTSISKSTSTSDK PKTDGKSIDQLADEVIAGKHGYGDARKKALGSQYDAVQKRVNEKLGSKPK KSSKSIDTLVKETLAGKHGNGEARKKSLGSNYEAVMDVINGKASKPKKSVS QMATEVIQGKHGFGHENRRKSLGISKTEYEKVRKEVNKRL |
| CLC2-EAD + CPL56-CBD, SEQ ID NO: 271 | MTFIQAAHRGGTSNTPITRLVIHATCPDVGFPSASRAGRAVSTAEYFASTSRS ASAHYVCDISTTVQCLSEATIGYHAPPNAHSIGIEICADGGSRASFEKASHAY TREQWLSPQVWPAVERAAILARDICHRHHIPIRRLSVAQVRAGERGICGHNE VSEAFHQSDHDDPGPYFPWNEFIAAVQGKTTTPEGELSMSDTSTSNNSSNSK KKPSKNKSIDQLAQEVIAGKYGTGASRKKALGSQYDAVQKRVNEILLGDKP KSSGKSINQMATEVIQGKHGNGHANRRKSLGISQSEYEKVRSEVNRRL |
| CLC2-EAD + CPL59-CBD, SEQ ID NO: 272 | MTFIQAAHRGGTSNTPITRLVIHATCPDVGFPSASRAGRAVSTAEYFASTSRS ASAHYVCDISTTVQCLSEATIGYHAPPNAHSIGIEICADGGSRASFEKASHAY TREQWLSPQVWPAVERAAILARDICHRHHIPIRRLSVAQVRAGERGICGHNE VSEAFHQSDHDDPGPYFPWNEFIAAVQGKTTTPEGELSMSDTSDANGNSVY PVESAPSKSVDTLAREVIAGNWGNGQDRVNRLTSAGYNYNSVQNRVNEILS GVSNKPSGKSIDTLAREVIRGDWGNGQDRKNRLERAGYDYDAVQKRVNEL L |
| CLC2-EAD + CPL60-CBD, SEQ ID NO: 273 | MTFIQAAHRGGTSNTPITRLVIHATCPDVGFPSASRAGRAVSTAEYFASTSRS ASAHYVCDISTTVQCLSEATIGYHAPPNAHSIGIEICADGGSRASFEKASHAY TREQWLSPQVWPAVERAAILARDICHRHHIPIRRLSVAQVRAGERGICGHNE VSEAFHQSDHDDPGPYFPWNEFIAAVQGKTTTPEGELSMSDTSDANGRSVYP VASTPSKSIDALAREVIAGNWGNGQYRVNRLRSAGYDYDAVQNRVNEILSG KSSSQSGGKSIDTLAREVIRGDWGNGQDRKNSLERAGYDYNAVQRRVNELL |
| CLC2-EAD + CPL61-CBD, SEQ ID NO: 274 | MTFIQAAHRGGTSNTPITRLVIHATCPDVGFPSASRAGRAVSTAEYFASTSRS ASAHYVCDISTTVQCLSEATIGYHAPPNAHSIGIEICADGGSRASFEKASHAY TREQWLSPQVWPAVERAAILARDICHRHHIPIRRLSVAQVRAGERGICGHNE VSEAFHQSDHDDPGPYFPWNEFIAAVQGKTTTPEGELSMSDTSEIKNVIANV ETPQITDSIEDLANEVIAGKYGNGEERKQLGSSYDEVQRRVNEILLGKDSST NTNEELAKEVIEGKWGNNPERKQRLLEAGYDYEAIQKIVNQRLK |
| CLC2-EAD + CPL62-CBD, SEQ ID NO: 275 | MTFIQAAHRGGTSNTPITRLVIHATCPDVGFPSASRAGRAVSTAEYFASTSRS ASAHYVCDISTTVQCLSEATIGYHAPPNAHSIGIEICADGGSRASFEKASHAY TREQWLSPQVWPAVERAAILARDICHRHHIPIRRLSVAQVRAGERGICGHNE VSEAFHQSDHDDPGPYFPWNEFIAAVQGKTTTPEGELSMSDTSKRLGLNGFE KTDGEKADIDKIAREVIRGEWGNGEERKERLKKAGYSYEEVQNRVNELLSE DKKSIDEIANEVIRGEWGNGEERKKRLRDAGYDYDAVQKRVNEKIG |
| CLC2-EAD + CPL63-CBD, SEQ ID NO: 276 | MTFIQAAHRGGTSNTPITRLVIHATCPDVGFPSASRAGRAVSTAEYFASTSRS ASAHYVCDISTTVQCLSEATIGYHAPPNAHSIGIEICADGGSRASFEKASHAY TREQWLSPQVWPAVERAAILARDICHRHHIPIRRLSVAQVRAGERGICGHNE VSEAFHQSDHDDPGPYFPWNEFIAAVQGKTTTPEGELSMSDTSKGNVVYPK AQPAPTKKSVDEIAREVIRGDWGNSDRTKRLSAAGYDANAVQNRVNEILG GSSTPKKSIDEVAHEVIRGEWGNGADRKNRLIAAGYNYDAVQKRVNEIL |
| CLC2-EAD + CPL64-CBD, SEQ ID NO: 277 | MTFIQAAHRGGTSNTPITRLVIHATCPDVGFPSASRAGRAVSTAEYFASTSRS ASAHYVCDISTTVQCLSEATIGYHAPPNAHSIGIEICADGGSRASFEKASHAY TREQWLSPQVWPAVERAAILARDICHRHHIPIRRLSVAQVRAGERGICGHNE VSEAFHQSDHDDPGPYFPWNEFIAAVQGKTTTPEGELSMSDTSVKPTPAPAP |

TABLE 8-continued

Chimeric CWHs.

| Description, SEQ ID NO | Amino Acid Sequence |
|---|---|
| | KPEPAKKSVDEIAREVIAGKWGAGEERKKLLTSAGYDYNAVQNKVNEILYD<br>PKPQPPKKSIDQIAREVIRGDWGAGEERRKRLTAAGYDYDAVQKRVNEILY<br>G |
| CLC2-EAD +<br>CPL65-CBD,<br>SEQ ID NO:<br>278 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGPYFPWNEFIAAVQGKTTTPEGELSMSDTSYIIENGLNG<br>YPKKPEKTLDELARDVIRGDWGNGEERYERLTEAGYDYDAVQKRVNEILYP<br>PLKPLDEVAREVIRGDWGNGEERYRRLTEAGYDYYQVQRKVNEILYN |
| CLC2-EAD +<br>CPL66-CBD,<br>SEQ ID NO:<br>279 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGPYFPWNEFIAAVQGKTTTPEGELSMSDTSSSDTAPGGG<br>STPSVSGTIDELARRVIAGEFGSGDTRKNALGDKYGAVQARVNEILNGTASA<br>PAKKSVSEIAKEVLAGAWGNGDARKQKLEAAGYNYSEVQAKVNSLASGSS<br>SSVDIDALARRVIAGEFGSGDARKKALGSNYDAVQKRVNEMLGGSSSSVNY<br>AAIAKEVINGKWGNGAARKKKLEAAGYNYNKVQKEVNKLL |
| CLC2-EAD +<br>CPL68-CBD,<br>SEQ ID NO:<br>280 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGPYFPWNEFIAAVQGKTTTPEGELSMSDTSLGTGSAAST<br>QPNAATGSIDDLAKRTIAGEFGNGDQRRAALGANYDAVQARVNEILGGGSS<br>SQPAVFDVDAAARDVIAGKYGNGDQRRTALGSHYDEVQARVNQMLGAAA<br>STSVNIDAEARKVIRGDYGNGGERRNALVAKFGANVANQIQTRVNDLLR |
| CLC2-EAD +<br>CPL69-CBD,<br>SEQ ID NO:<br>281 | MTFIQAAHRGGTSNTPITRLVIHATCPDVGFPSASRAGRAVSTAEYFASTSRS<br>ASAHYVCDISTTVQCLSEATIGYHAPPNAHSIGIEICADGGSRASFEKASHAY<br>TREQWLSPQVWPAVERAAILARDICHRHHIPIRRLSVAQVRAGERGICGHNE<br>VSEAFHQSDHDDPGPYFPWNEFIAAVQGKTTTPEGELSMSDTSVYDEQGVLI<br>YPKTNNKSIDELAREVINGLWGNGSDRKNKLISASYDYDAVQNRVNEILDG<br>GKATPSKSIDTLAKEVIRGDWGNGADRKKRLTAAGYNYDAVQKRVNQILG |
| CLC1-EAD +<br>CLB1-CW7-1-<br>CBD, SEQ ID<br>NO: 2942 | MTFIQARHHGGNSNTPITRLVIHATCPDVGYPSASKAGRAVSTAEYFASTSRS<br>ASAHYVCDVSATVQCLSEETIGYHAPPNSHSIGIEICADGGSRASFEKASHAY<br>TREQWLSPQVWPAVERAAILARGICHRHHIPVRKLTTAQVKSGMSGICGHD<br>NVSDAFHQSDHDDPGPYFPWNEFIAAIQGKNTNKGELSMSDVTSPNIDALAD<br>AVIRGEYGNGEERRRRLGANYAAVQKRVNEKLTG |
| CLC1-EAD +<br>CLB1-CW7-2-<br>CBD, SEQ ID<br>NO: 2943 | MTFIQARHHGGNSNTPITRLVIHATCPDVGYPSASKAGRAVSTAEYFASTSRS<br>ASAHYVCDVSATVQCLSEETIGYHAPPNSHSIGIEICADGGSRASFEKASHAY<br>TREQWLSPQVWPAVERAAILARGICHRHHIPVRKLTTAQVKSGMSGICGHD<br>NVSDAFHQSDHDDPGPYFPWNEFIAAIQGKNTNKGELSMSDVTSPNIDALAD<br>AVIRGDYGNGEERRRRLGNLYDQVQARVNQKLGY |

In some embodiments, a chimeric CWH of the disclosure comprises the amino acid sequence of SEQ ID NO: 106. In some embodiments, a chimeric CWH of the disclosure consists of the amino acid sequence of SEQ ID NO: 106. In some embodiments, a chimeric CWH of the disclosure has at least 40, 45, 50, 55, 60, 65, 70, 75, 80, 85, 90, or 95% identity with the amino acid sequence of SEQ ID NO: 106. In some embodiments, a chimeric CWH of the disclosure has at least 80, 81, 82, 83, 84, 85, 86, 87, 88, 89, 90, 91, 92, 93, 94, 95, 96, 97, 98, or 99% identity with the amino acid sequence of SEQ ID NO: 106. In some embodiments, the sequence of the chimeric CWH differs by 1, 2, 3, 4, 5, 6, 7, 8, 9, 10, 11, 12, 13, 14, or 15 amino acids from the amino acid sequence of SEQ ID NO: 106.

Linkers

In some embodiments, a chimeric protein herein comprises more than one domain, and the domains are joined by a linker. In some embodiments, the linker is a flexible linker. In some embodiments, the linker is an amino acid sequence between 1-100 amino acids in length, including all values and subranges therebetween. In some embodiments, the linker comprises one or more glycines and/or serines. Persons having ordinary skill in the art will be familiar with other linkers that can be used in the chimeric proteins of the present disclosure.

Protein Tags

In some embodiments, a recombinant protein of the disclosure comprises a protein tag. A protein tag is typically a short sequence of amino acids, or a protein domain, that is fused to a recombinant protein in order to facilitate purification and/or visualization. In some embodiments, a protein tag improves protein solubility. In some embodiments, the tag is a His tag, a GST tag, an MBP tag, a Strep tag, a FLAG tag, a GFP tag, an HA tag, a V5 tag, an Avi tag, a CBP tag, a ZZ tag, a SUMO tag, an Fc tag, a Thioredoxin tag, a Protein kinase A (PKA) tag, a Myc tag, or an S tag, or any combination thereof. In some embodiments, the tag is a His tag and comprises 6 histidine residues.

Nucleic Acids, Vectors, and Host Cells of the Disclosure

The present disclosure also provides nucleic acids encoding the recombinant proteins, e.g., CWHs, of the disclosure. The present disclosure also provides vectors and host cells for expression of the recombinant proteins of the disclosure. In some embodiments, the vector is a plasmid, a cosmid, a bacteriophage, or a virus comprising a nucleic acid of the disclosure. In some embodiments, the host cell comprises a nucleic acid of the disclosure or a vector of the disclosure. In some embodiments, the host cell is a bacterial cell, a yeast cell, an insect cell, a mammalian cell, or a plant cell.

Formulations of the Disclosure

The present disclosure provides compositions comprising the recombinant proteins disclosed herein. The present disclosure provides compositions comprising the EADs, enzymes, truncated enzymes, CBDs, chimeric CWHs, nucleic acids, vectors, and host cells disclosed herein. In some embodiments, these compositions are formulated for delivery to a subject for the treatment of a condition associated with *Cutibacterium acnes*.

Topical, Parenteral, and Enteral Formulations

In some embodiments, compositions of the disclosure are formulated for topical, parenteral, or enteral administration.

In some embodiments, a composition herein is formulated for topical administration. Formulations for topical administration include lotions, hydrogels, creams, ointments, gels, drops, transdermal patches, colloidal patches, powders, suppositories, sprays, liquids, semi-solids, monophasic compositions, multiphasic compositions (e.g., oil-in-water, water-in-oil), foams, microsponges, liposomes, nanoemulsions, aerosol foams, polymers, fullerenes, and powders. In some embodiments, carriers, bases, thickeners, penetration enhancers, buffers, diluents, emulsifiers, humectants, dispersing aids, binders, and/or excipients are added to the formulation. In some embodiments, the composition is formulated as a hydrogel. In some embodiments, the composition is formulated as a lotion. In some embodiments, the composition is formulated as a cream. In some embodiments, the composition is formulated as a freeze dried powder, e.g., which can be reconstituted with liquid prior to use. In some embodiments, the composition is a colloidal patch. In some embodiments, the composition is formulated as a colloidal patch. In some embodiments, the composition is formulated as a microneedle patch.

In some embodiments, the compositions of the disclosure are formulated for parenteral administration. As used herein, "parenteral administration" of a composition includes any route of administration characterized by physical breaching of a tissue of a subject and administration of the composition through the breach in the tissue, thus generally resulting in the direct administration into the blood stream, into muscle, or into an internal organ. Parenteral administration thus includes, but is not limited to, administration of a composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intratumoral, intrasynovial injection or infusions; and kidney dialytic infusion techniques.

In some embodiments, a composition herein is prepared for oral administration. The terms "oral", "enteral", "enterally", "orally", "non-parenteral", "non-parenterally", and the like, refer to administration of a compound or composition to an individual by a route or mode along the alimentary canal. Examples of "oral" routes of administration of a composition include, without limitation, swallowing liquid or solid forms of a composition from the mouth, administration of a composition through a nasojejunal or gastrostomy tube, intraduodenal administration of a composition, and rectal administration, e.g., using suppositories for the lower intestinal tract of the alimentary canal. The compositions of the present disclosure may be formulated into any of many possible dosage forms such as, but not limited to, tablets, capsules, liquid syrups, soft gels, suppositories, aerosols, and enemas. The compositions of the present disclosure may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Formulation Ingredients

In some embodiments, the composition comprises an emulsifier. In some embodiments, the composition comprises a mixture of emulsifiers. In some embodiments, the composition comprises about 0.5% to about 5% w/v of an emulsifier or a mixture of emulsifiers.

Examples of emulsifiers suitable for use in some embodiments of the disclosure include xanthan gum, polysorbate 80, oleoyl polyoxyl-6 glycerides, polyoxyl 35 hydrogenated castor oil, sucrose distearate, saponin, sodium alginate, guar gum, tocopherol polyethylene glycol 1000 succinate, lauroyl polyoxyl-32 glycerides, sorbitan monooleate, glyceryl stearate, cetearyl alcohol, sodium stearoyl lactylate, salts thereof, derivatives thereof, and mixtures thereof. In some embodiments, the emulsifier is xanthan gum.

In some embodiments, emulsifier components are selected from poly-glycolized glycerides and polyoxyethylene glycerides of medium to long chain mono-, di-, and triglycerides, such as: almond oil PEG-6 esters, almond oil PEG-60 esters, apricot kernel oil PEG-6 esters (Labrafil® M1944CS), caprylic/capric triglycerides PEG-4 esters (Labrafac® Hydro WL 1219), caprylic/capric triglycerides PEG-4 complex (Labrafac® Hydrophile), caprylic/capric glycerides PEG-6 esters (Softigen® 767), caprylic/capric glycerides PEG-8 esters (Labrasol®), castor oil PEG-50 esters, hydrogenated castor oil PEG-5 esters, hydrogenated castor oil PEG-7 esters, 9 hydrogenated castor oil PEG-9 esters, corn oil PEG-6 esters (Labrafil® M 2125 CS), corn oil PEG-8 esters (Labrafil® WL 2609 BS), corn glycerides PEG-60 esters, olive oil PEG-6 esters (Labrafil® M1980 CS), hydrogenated palm/palm kernel oil PEG-6 esters (Labrafil® M 2130 BS), hydrogenated palm/palm kernel oil PEG-6 esters with palm kernel oil, PEG-6, palm oil (Labrafil® M 2130 CS), palm kernel oil PEG-40 esters, peanut oil PEG-6 esters (Labrafil® M 1969 CS), glycerol esters of saturated C8-C18 fatty acids (Gelucire® 33/01), glyceryl esters of saturated C12-C18 fatty acids (Gelucire® 39/01 and 43/01), glyceryl laurate/PEG-32 laurate (Gelucire® 44/14), glyceryl laurate glyceryl/PEG 20 laurate, glyceryl laurate glyceryl/PEG 32 laurate, glyceryl, laurate glyceryl/PEG 40 laurate, glyceryl oleate/PEG-20 glyceryl, glyceryl oleate/PEG-30 oleate, glyceryl palmitostearate/PEG-32 palmitostearate (Gelucire® 50/13), glyceryl stearate/PEG stearate, glyceryl stearate/PEG-32 stearate (Gelucire® 53/10), saturated polyglycolized glycerides (Gelucire® 37/02 and Gelucire® 50/02), triisostearin PEG-6 esters (i.e. Labrafil® Isostearique), triolein PEG-6 esters, trioleate PEG-25 esters, polyoxyl 35 castor oil (Cremophor® EL or Kolliphor® EL), polyoxyl 40 hydrogenated castor oil (Cremophor® RH 40 or Kolliphor® RH40), polyoxyl 60 hydrogenated castor oil (Cremophor® RH60), lecithin, phospholipids and mixtures thereof.

In some embodiments, the emulsifier is polyglycolized derivatives and polyoxyethylene esters or ethers derivatives of medium to long chain fatty acids, commercially named Brij and Myrj variety surfactants, and propylene glycol esters of medium to long chain fatty acids, which can be used including caprylate/caprate diglycerides, glyceryl monooleate, glyceryl ricinoleate, glyceryl laurate, glyceryl dilaurate, glyceryl dioleate, glyceryl mono/dioleate, glyceryl caprylate/caprate, medium chain (C8/C10) mono- and diglycerides (Capmul® MCM, Capmul® MCM (L)), mono- and diacetylated monoglycerides, polyglyceryl oleate, polyglyceryl-2 dioleate, polyglyceryl-10 trioleate, polyglyceryl-10 laurate, polyglyceryl-10 oleate, and polyglyceryl-10 mono dioleate, propylene glycol caprylate/caprate (Labrafac® PC), propylene glycol dicaprylate/dicaprate (Miglyol® 840), propylene glycol monolaurate, propylene glycol ricinoleate, propylene glycol monooleate, propylene glycol dicaprylate/dicaprate, propylene glycol dioctanoate, and mixtures thereof.

In some embodiments, the composition comprises a humectant. In some embodiments, the composition is a topical formulation and comprises a humectant, which can be referred to as a soothing, smoothing, moisturizing, or protective agent. Humectants of the present disclosure function to stabilize the moisture content of the tissue to which it is applied in the presence of fluctuating humidity.

In some embodiments, the humectant is selected from: polyglycols (as hereinafter defined), propylene glycol, sorbitol, lactic acid, sodium lactate, glycerol, glycerine, ethoxylated castor oil, calamine, dodecylsulphate, sodium lauryl sulphate (SLS); a polyoxyethylene ester of polysorbitan, such as monooleate, monolaurate, monopalmitate, monostearate esters; esters of sorbitan, the polyoxyethylenes ethers, sodium dioctylsulphosuccinate (DOSS), lecithin, sodium docusate, hexylene glycol, butylene glycol, aloe vera gel, aloe vera powder, hyaluronic acid, alpha hydroxy acids such as lactic acid, egg yolk, egg white, glyceryl triacetate, honey, molasses, polymeric polyols such as polydextrose, quillaia, sodium hexametaphosphate e452i; sugar alcohols (sugar polyols) such as glycerol, sorbitol, xylitol, maltitol; urea, and castor oil.

In some embodiments, the composition comprises a humectant selected from the list consisting of: aloe vera, betaine, butylene glycol, caprylyl glycol, dimethicone, fructose, glucomannan, glucose, glycerin, glyceryl glucoside, honey, hyaluronic acid, lactic acid, panthenol, polyethylene glycol, propylene glycol, propanediol, sodium hyaluronate, sodium lactate, sodium pyrrolidone carboxylic acid, sorbitol, and urea. In some embodiments, the composition comprises 0.1-50% w/v humectant, including all values and subranges therebetween. In some embodiments, the composition comprises 0.5-10% w/v humectant.

In some embodiments, the composition comprises hyaluronic acid. In some embodiments, the composition is a hyaluronic-based hydrogel for topical application. In some embodiments, the composition comprises 0.1-10% w/v hyaluronic acid. In some embodiments, the composition comprises 0.5-5.0% w/v hyaluronic acid. In some embodiments, the composition comprises 1-2% w/v hyaluronic acid. In some embodiments, the composition comprises a hydrogel. In some embodiments, the hydrogel comprises a cellulose polymer. In some embodiments the hydrogel comprises hydroxypropyl methylcellulose.

In some embodiments, the composition comprises a cellulose polymer. In some embodiments, the cellulose polymer is hydroxyethyl cellulose, methylcellulose, hydroxy methylcellulose, carboxymethyl cellulose, microcrystalline cellulose, ethyl cellulose, sodium carboxymethyl cellulose, hydroxypropyl cellulose, or cellulose acetate. In some embodiments, the composition comprises 0.1-20% w/v cellulose polymer, including all values and subranges therebetween. In some embodiments, the composition comprises 0.5-10% w/v of a cellulose polymer. In some embodiments, the composition comprises 1-5% w/v of a cellulose polymer. In some embodiments, the composition comprises hydroxypropyl methylcellulose (HPMC). In some embodiments, the composition comprises 0.5-10% w/v of HPMC. In some embodiments, the composition comprises 1-5% w/v HPMC.

In some embodiments, the composition comprises a thickening agent, a gelling agent, and/or a polymer. In some embodiments, the composition comprises an acrylate. In some embodiments, the composition comprises a carbomer.

In some embodiments, the composition comprises a salt. In some embodiments, the composition comprises a salt selected from the list consisting of: calcium chloride, Dead Sea salt, Epsom salt, Himalayan pink salt, magnesium chloride, sea salt, and sodium chloride. In some embodiments, the composition comprises 10-500 mM of a salt, including all values and subranges therebetween. In some embodiments, the composition comprises 50-250 mM of a salt.

In some embodiments, the composition comprises a buffer. In some embodiments, the buffer is 4-(2-hydroxyethyl)-1-piperazineethanesulfonic acid, acetic acid, ammonium acetate, boric acid, citric acid, glycine, phosphoric acid, potassium hydroxide, potassium phosphate, sodium acetate, sodium bicarbonate, sodium borate, sodium carbonate, sodium citrate, sodium dihydrogen phosphate, sodium hydrogen phosphate, sodium hydroxide, sodium phosphate, sodium tetraborate, tris(hydroxymethyl)aminomethane, or trisodium phosphate. In some embodiments, the composition comprises 1-250 mM of a buffer, including all values and subranges therebetween. In some embodiments, the composition comprises 5-50 mM of a buffer.

In some embodiments, the composition comprises a surfactant. In some embodiments, the composition comprises a surfactant selected from the list consisting of: ceteareth-20, cocamidopropyl betaine, coco-glucoside, decyl glucoside, decyl polyglucose, disodium laureth sulfosuccinate, glycereth-26, lauryl glucoside, lauryl polyglucose, sodium cocoyl glutamate, sodium cocoyl isethionate, sodium laureth sulfate, and sodium lauryl sulfate. In some embodiments, the composition comprises 0.1-20% w/v of a surfactant, including all values and subranges therebetween. In some embodiments, the composition comprises 1-10% w/v of a surfactant.

In some embodiments, the composition comprises an oil. In some embodiments, the composition comprises an oil selected from the list consisting of: argan oil, avocado oil, baobab oil, camellia oil, carrot seed oil, coconut oil, evening primrose oil, grapeseed oil, hemp seed oil, jojoba oil, macadamia nut oil, marula oil, mineral oil, olive oil, pomegranate seed oil, raspberry seed oil, rosehip seed oil, squalane oil, sunflower seed oil, sweet almond oil, and tamanu oil. In some embodiments, the composition comprises 0.1-20% w/v of an oil, including all values and subranges therebetween.

In some embodiments, the composition comprises an alcohol. In some embodiments, the composition comprises an alcohol selected from the list consisting of: cetyl alcohol, ethyl alcohol, isopropyl alcohol, and stearyl alcohol. In some embodiments, the composition comprises 0.1-20% w/v of an alcohol, including all values and subranges therebetween. In some embodiments, the composition comprises 1-10% w/v of an alcohol.

In some embodiments, the composition comprises a free amino acid. In some embodiments, the composition comprises alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine. In some embodiments, the composition comprises an amino acid selected from the list consisting of: alanine, arginine, cysteine, glutamine, glycine, histidine, lysine, methionine, proline, serine, and threonine. In some embodiments, the composition comprises 10-250 mM of an amino acid, including all values and subranges therebetween. In some embodiments, the composition comprises 25-150 mM of an amino acid.

In some embodiments, the composition comprises glycerol. In some embodiments, the composition comprises 0.5-50% w/v glycerol, including all values and subranges therebetween. In some embodiments, the composition comprises 1-30% w/v glycerol. In some embodiments, the composition comprises 1-5% w/v glycerol.

In some embodiments, the composition comprises petrolatum. In some embodiments, the composition comprises 0.1-20% w/v petrolatum, including all values and subranges therebetween.

The compositions of the present disclosure can comprise an additional agent or agents, whether active or passive. Examples of such an agent include a sweetening agent, a flavoring agent, a coloring agent, a filling agent, a binding agent, a lubricating agent, an excipient, a preservative, an emollient, a hydrating agent, a smoothing agent, or a manufacturing agent. Additional excipients or additives can be added to the composition. For example, if desired, any generally accepted soluble or insoluble inert filler (diluent) material can be included in the final product (e.g., a solid dosage form). Such inert filler can comprise a monosaccharide, a disaccharide, a polyhydric alcohol, inorganic phosphates, sulfates or carbonates, and combinations thereof. Examples of suitable inert fillers include sucrose, dextrose, lactose, xylitol, fructose, sorbitol, calcium phosphate, calcium sulfate, calcium carbonate, microcrystalline cellulose, and combinations thereof. An effective amount of any generally accepted lubricant, such as calcium or magnesium soaps, can be added.

Depending on the dosage form, optional additives and modifiers further comprise one or more of acids, bases, acidity regulators, alcohol, anticaking agents, antifoaming agents, antioxidants, bulking agents, coagulation agents, colour retention agents, emulsifiers, flavor enhancers, flour treatment agents, gelling agents, glazing agents, humectants, leavening agents, tracer gases, preservatives, stabilizers, sweeteners, tenderizers, and thickeners.

The compositions of the present disclosure may additionally contain other conventional adjunct components. Thus, for example, the compositions may contain additional, compatible, active materials such as, for example, antipruritics, astringents, local anesthetics or anti-inflammatory agents, or may contain additional materials useful in physically formulating various dosage forms of the compositions of the present disclosure, such as dyes, flavoring agents, preservatives, antioxidants, opacifiers, thickening agents and stabilizers. However, such materials, when added, should not unduly interfere with the biological activities of the components of the compositions of the present disclosure. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

In some embodiments, the composition comprises a skin protectant. In some embodiments, the composition comprises an FDA-approved skin protectant. In some embodiments, the composition comprises colloidal oatmeal. In some embodiments, the composition comprises a skin protectant selected from the list consisting of allantoin, aluminum hydroxide gel, calamine, cocoa butter, cod liver oil, colloidal oatmeal, dimethicone, glycerin, hard fat, kaolin, lanolin, mineral oil, petrolatum, sodium bicarbonate, topical starch, white petrolatum, zinc acetate, zinc carbonate, and zinc oxide. In some embodiments, the composition comprises any one of the following skin protectants in the following ranges: allantoin, 0.5 to 2%; aluminum hydroxide gel, 0.15 to 5%; calamine, 1 to 25%; cocoa butter, 50 to 100%; cod liver oil, 5 to 13.56%; colloidal oatmeal, 0.007% minimum, or 0.003% minimum in combination with mineral oil; dimethicone, 1 to 30%; glycerin, 20 to 45%; hard fat, 50 to 100%; kaolin, 4 to 20%; lanolin, 12.5 to 50%; mineral oil, 50 to 100%, or 30 to 35% in combination with colloidal oatmeal; petrolatum, 30 to 100%; sodium bicarbonate; topical starch, 10 to 98%; white petrolatum, 30 to 100%; zinc acetate, 0.1 to 2%; zinc carbonate, 0.2 to 2%; zinc oxide, 1 to 25%. See, e.g., Sec. 347.10 of CFR Title 21, Volume 5, "Skin protectant active ingredients," incorporated by reference herein in its entirety.

In some embodiments, the composition comprises an ingredient that is FDA-approved for the treatment of acne. In some embodiments, the composition comprises Aklief (trifarotene), Arazlo (tazarotene), Avita (tretinoin) Gel and Cream, Benzamycin (erythromycin 3%-benzoyl peroxide 5% topical gel), Cabtreo (clindamycin phosphate, adapalene, and benzoyl peroxide) topical gel, Estrostep Fe (Norethindrone Acetate and Ethinyl Estradiol, USP and Ferrous Fumarate), Retin-A Micro (tretinoin gel) 0.06% and 0.08%, Seysara (sarecycline), Tazorac (tazarotene) gel and cream 0.05% and 0.1% Veltin (clindamycin phosphate and tretinoin), or Winlevi (clascoterone). In some embodiments, the composition comprises trifarotene, tazarotene, tretinoin, erythromycin, benzoyl peroxide, clindamycin phosphate, adapalene, norethindrone acetate, ethinyl estradiol, ferrous fumarate, sarecycline, and/or clascoterone.

In some embodiments, other ingredients are also present in the composition, such as antibiotics; antiseptics; antifungals; corticosteroids; soothing agents; anti-aging agents; smoothing agents; moisturizing agents; and protective agents. In some embodiments, the composition comprises an antibiotic.

Characteristics of Compositions of the Disclosure

The present disclosure provides chimeric proteins, as well as compositions comprising these chimeric proteins. These compositions have beneficial characteristics for therapeutic use against target *Cutibacterium acnes*.

In addition to issues with selectivity, prior CWHs and endolysins known in the art have properties that are not well-suited for therapeutic indications, e.g., topical application. For example, the previously characterized CWHs suffer from weak activity, low thermostability, low solubility, and/or narrow or unsuitable pH range.

The present disclosure provides chimeric CWHs with beneficial characteristics, such as, but not limited to, high anti-*Cutibacterium acnes* activity, *Cutibacterium acnes* species specificity, thermostability, solubility, and broader or more suitable pH range.

Anti-*Cutibacterium acnes* Activity

In some embodiments, compositions of the present disclosure are active against *Cutibacterium acnes* species. In some embodiments, a composition of the disclosure has activity against *Cutibacterium acnes* and the degree of that activity is determined based on its Minimum Inhibitory Concentration (MIC) against that target species. In some embodiments, the MIC is less than 100, 90, 80, 70, 60, 50, 40, 30, 20, or 10 µg/mL. In some embodiments, the MIC is less than 20, 19, 18, 17, 16, 15, 14, 13, 12, 11, 10, 9, 8, 7, 6, 5, 4, 3, 2, or 1 µg/mL. In some embodiments, the MIC is less than 5.0, 4.5, 4.0, 3.5, 3, 0, 2.5, 2.0, 1.5, 1.0, or 0.5 µg/mL. In some embodiments, the MIC is less than 1.0, 0.9, 0.8, 0.7, 0.6, 0.5, 0.4, 0.3, 0.2, or 0.1 µg/mL.

In some embodiments, a composition of the disclosure has activity against *Cutibacterium acnes* at a concentration of less than 50 µg/mL. In some embodiments, a composition of the disclosure has activity against *Cutibacterium acnes* at a concentration of less than 40, 30, 20, or 10 µg/mL. In some embodiments, a composition of the disclosure has activity against *Cutibacterium acnes* at a concentration of 50 µg/mL. In some embodiments, a composition of the disclosure has activity against *Cutibacterium acnes* at a concentration of 24 µg/mL. In some embodiments, a composition of the disclosure has activity against *Cutibacterium acnes* at a concentration of 12 µg/mL. In some embodiments, a composition of the disclosure has activity against *Cutibacterium acnes* at a concentration of 6 µg/mL.

In some embodiments, a composition of the disclosure is active against one or more different phylotypes of *Cutibacterium acnes*. In some embodiments, a composition of the disclosure is active against phylotype IA1. In some embodiments, a composition of the disclosure is active against phylotype IA2. In some embodiments, a composition of the disclosure is active against phylotype IA1, IA2, IB, II, and/or III. In some embodiments, a composition of the disclosure is active against phylotypes IA1, IA2, IB, and II.

Selectivity

The present inventors discovered that illustrative novel chimeras disclosed herein exhibited remarkable selective activity for *Cutibacterium acnes* over other bacterial species. As known in the art, the only CWH previously known in the art to exhibit lytic activity against *C. acnes* (CaLys1) also exhibits similar lytic activity towards other strains of bacteria, which is highly undesirable for a topical skin microbiome application. By contrast, illustrative chimeric CWHs of the present disclosure are able to distinguish between *C. acnes* and commensal skin bacteria.

In some embodiments, a recombinant protein of the disclosure shows specificity for *Cutibacterium acnes* over other species. In some embodiments, a recombinant protein of the disclosure shows specificity for *Cutibacterium acnes* over commensal bacterial species. In some embodiments, a recombinant protein of the disclosure shows specificity for *Cutibacterium acnes* over *Corynebacterium xerosis*, *Corynebacterium striatum*, and/or *Staphylococcus epidermidis*.

In some embodiments, a recombinant protein of the disclosure has at least 2, 3, 4, 5, 6, 7, 8, 9, or 10-fold selectivity. In some embodiments, a recombinant protein of the disclosure has at least 5, 10, 15, 20, 25, 30, 35, 40, 45, 50, 55, 60, 65, 70, 75, 80, 85, 90, 95, or 100-fold selectivity. In some embodiments, a recombinant protein of the disclosure has virtually no activity (or no detectable activity) against one species, while having measurable activity against *C. acnes*.

In some embodiments, a composition of the disclosure has broad range anti-*Cutibacterium acnes* activity. In some embodiments, the composition has high activity against multiple strains of *Cutibacterium acnes*. In some embodiments, the composition has high activity against a group of related *Cutibacterium acnes* strains. In some embodiments, the composition has high activity against a diverse group of *Cutibacterium acnes* strains. In some embodiments, the composition is suitable for use as a broad-range therapeutic.

Thermostability

The inventors of the present disclosure also surprisingly discovered that some of the novel chimeric CWHs of the disclosure exhibited desirable high thermostability.

In some embodiments, a composition of the disclosure exhibits thermostability at temperatures up to 37, 38, 39, 40, 41, 42, 43, 44, 45, 46, 47, 48, 49, 50, 51, 52, 53, 54, 55, 56, 57, 58, 59, or 60° C., including all values and ranges therebetween. In some embodiments, a composition of the disclosure exhibits thermostability at temperatures of at least 37, 38, 39, 40, 41, 42, 43, 44, 45, 46, 47, 48, 49, 50, 51, 52, 53, 54, 55, 56, 57, 58, 59, or 60° C., including all values and ranges therebetween.

As used herein, thermostability at a given temperature refers to the ability to maintain activity levels at that temperature, or after the protein is exposed to that temperature. In some embodiments, thermostability at a given temperature is measured after exposure to that temperature for a period of time. In some embodiments, thermostability is determined based on experiments testing activity at a temperature or after exposure to a given temperature for a period of time (e.g., showing measurable target bacterial density reductions at that temperature or after exposure to that temperature). Thus, in some embodiments, an EAD, CBD, or chimeric protein is considered thermostable at a temperature if it still exhibits measurable activity at that temperature or after exposure to that temperature. In some embodiments, an EAD, CBD, or recombinant chimeric protein is considered thermostable at a critical temperature, if it still exhibits measurable activity at its intended use temperature after being exposed to that critical temperature (e.g., activity tested after the protein is exposed to the critical temperature for 30 mins). In some embodiments, thermostability after exposure to a given temperature is determined based on assays conducted at room temperature. In some embodiments, thermostability is determined after exposure to a given temperature based on an assay that measures activity. In some embodiments, the assay is a turbidity reduction assay.

In the context of comparing two proteins (e.g., two EADs, two CBDs, or two chimeric CWHs), one protein may be considered more thermostable at a given temperature than the other if it exhibits higher absolute activity at that temperature or after exposure to that temperature (e.g., if it results in greater microbial density reductions in the measured time). In other embodiments, one protein may be considered more thermostable than the other at a given temperature if it exhibits higher relative activity at that temperature or after exposure to that temperature (e.g., if the protein exhibits a lesser reduction in activity after exposure to a given temperature compared to the relative reduction of activity of a second protein after exposure to that same temperature).

In some embodiments, thermostability at a given temperature is determined based on ability to maintain activity after exposure to that temperature for 10, 20, 30, 40, 50, or 60 minutes, including all values and ranges therebetween. In some embodiments, thermostability at a given temperature is determined after exposure to that temperature for 1, 2, 3, 4, 5, 6, 7, 8, 9, 10, 11, 12, 13, 14, 15, 16, 17, 18, 19, 20, 21, 22, 23, or 24 hours, including all values and ranges therebetween. In some embodiments, thermostability at a given temperature is determined after exposure to that temperature for 1, 2, 3, 4, 5, 6, or 7 days, including all values and ranges therebetween. In some embodiments, thermostability at a given temperature is determined after exposure to that temperature for 1, 2, 3, or 4 weeks, including all values and ranges therebetween. In some embodiments, thermostability at a given temperature is determined after exposure to that temperature for 1, 2, 3, 4, 5, or 6 months, including all values and ranges therebetween.

In some embodiments, thermostability is measured based on testing activity after maintaining a composition at a given temperature for a period of time, e.g., weeks or months. In some embodiments, thermostability is determined based on activity retained after 2 months at a given temperature.

In some embodiments, a composition herein is thermostable at 45° C. for at least four weeks. In some embodiments, a composition herein is thermostable at 45° C. for at least two months. In some embodiments, a composition herein is thermostable at 50° C. for at least two months.

In some embodiments, a composition herein is considered thermostable or shelf stable if it retains at least 10, 20, 30, 40, 50, 60, 70, 80, or 90% of its original activity, including all values and ranges therebetween, at room temperature after exposure to a temperature of 45° C. for four weeks.

pH Range

In some embodiments, a composition herein is stable at a range of pH values. A composition, e.g., a chimeric protein, is considered stable at a given pH level if it exhibits activity at that pH level. In some embodiments, pH stability at different pH values is determined based on activity assays conducted at different pH values. E.g., in some embodiments, pH stability is determined by incubating a composition of the disclosure (e.g., a chimeric protein) with target bacterial cells at different pH values (e.g., in a turbidity reduction assay). The results of the assay provide activity levels for the composition at different pH values, including a maximum activity level. In some embodiments, a composition is stable at a pH level if it has the same activity at that pH as its maximum activity level. In some embodiments, a composition is stable at a pH level if it exhibits at least 50, 60, 70, 80, 90, 95, 96, 97, 98, or 99% of its maximum activity at that pH. In some embodiments, a composition is stable at a pH level if it exhibits about 50, 60, 70, 80, 90, 95, 96, 97, 98, or 99% of its maximum activity at that pH.

In some embodiments, pH stability is determined based on an activity assay. In some embodiments, the assay is a turbidity reduction assay.

In some embodiments, a composition herein is stable at a pH of 3, 4, 5, 6, 7, 8, 9, or 10, or within any ranges therebetween. In some embodiments, a composition herein is stable in the pH range of 6-8. In some embodiments, a composition herein is stable in the pH range of 5-8. In some embodiments, a composition herein is stable at pH values most relevant for topical skin applications. E.g., in some embodiments, a composition herein is stable at a pH of 4, 5, or 6.

Synergy

In some embodiments, the present disclosure provides a combination composition comprising at least two compositions, e.g., chimeric proteins, of the disclosure. In some embodiments, at least two compositions of the disclosure are administered together. In some embodiments, two compositions of the disclosure are administered one after the other or simultaneously. In some embodiments, a combination composition of the disclosure exhibits synergistic results compared to the constituent compositions individually.

As used herein, the term "synergistic" as it refers to a composition of the disclosure, refers to a composition that exhibits an effect (y) that is in excess of the predicted effect of the composition as calculated by a reference model. In some embodiments, "synergistic" refers to an effect that is greater than a simple additive effect. In some embodiments, a synergistic combination is one for which the MIC of the combination is lower than the MIC for its constituent components. In some embodiments, a synergistic combination is one for which the MIC of the combination is lower than the MIC for its constituent components, as calculated by percent composition. In some embodiments, a composition is said to have synergistic effects if it exhibits more than the additive properties of its individual ingredients.

Methods of Treating *Cutibacterium acnes* Conditions

The present disclosure provides methods of treating conditions associated with *Cutibacterium acnes* comprising administering a composition of the disclosure.

A composition as disclosed herein may be used to treat subjects affected by a condition associated with a *Cutibacterium acnes* species as defined herein. In some embodiments, the subject is an animal. In some embodiments, the animal is a mammal. In some embodiments, the subject is a human.

Conditions

In some embodiments, a composition of the disclosure is used in the treatment of a condition associated with *Cutibacterium acnes*. In some embodiments, the condition is Acne vulgaris (acne).

In some embodiments, the condition is associated with the skin. In some embodiments, the condition is a skin infection. In some embodiments, the condition is impetigo, cellulitis, folliculitis, atopic dermatitis, acute radiation dermatitis, acne, or an abscess.

In some embodiments, the condition is a wound infection, pneumonia, food poisoning, toxic shock syndrome, a bloodstream infection, pneumonia, a urinary tract infection, a bone or joint infection (e.g., osteomyelitis, septic arthritis), endocarditis, meningitis, septicemia, an ear infection (e.g., otitis externa), an eye infection (e.g., conjunctivitis, keratitis), a sinus infection, gastroenteritis, mastitis, peritonitis, a prosthetic joint infection, a sternal wound infection, a catheter-related infection, or tonsillitis. In some embodiments, the condition is an infection of the skin. In some embodiments, the condition is an infection of the soft tissue. In some embodiments, the condition is an opportunistic infection. In some embodiments, the condition is a wound infection. In some embodiments, the condition is a chronic wound. In some embodiments, the condition is Acne Vulgaris, skin infection, cellulitis, orthopedic infection, endophthalmitis, prosthetic valve endocarditis, otitis media, or osteomyelitis. In some embodiments, the condition is an inflammatory lesion. In some embodiments, the condition is a comedone (pimple), papule, pustule, nodule, or cyst. In some embodiments, the condition is skin redness, swelling, pain, tenderness, or abnormal texture. In some embodiments, the condition is a psychosocial condition associated with Acne Vulgaris.

In some embodiments, the condition is the presence of *Cutibacterium acnes* species (especially over-abundance of phylotype $IA_1$) on the skin.

Dosages

In some embodiments, a composition of the disclosure comprises 0.1-100 µg/mL of a recombinant protein, e.g., a chimeric protein, disclosed herein. In some embodiments, the composition comprises 0.5-50 µg/mL of a recombinant protein of the disclosure. In some embodiments, the composition comprises 1-25 µg/mL of a recombinant protein of the disclosure. In some embodiments, the composition comprises 2-15 µg/mL of a recombinant protein of the disclosure.

In some embodiments, a composition of the disclosure comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 µg/mL of a protein of the disclosure.

Administration

For the purposes of administration, the present compositions may be formulated in a variety of forms. The term "dosage form" denotes any form of the formulation that contains an amount of a chimeric protein of the disclosure sufficient to achieve at least a partial therapeutic effect with a single or repeat administration. In some embodiments, the dosage form is a topical dosage form. In some embodiments, the dosage form is a lotion, an oil, a gel, a salve, or a body balm. In some embodiments, the dosage form is a lotion.

Compositions can be formulated in forms including but not limited to liquid, gel, semi-solid, and solid. Compositions disclosed herein can further be processed into forms including but not limited to solids, liquids, suspensions, gels, lotions, balms, and other forms discussed in this disclosure.

In some embodiments, an effective amount of a composition is administered to a subject. The term "effective amount" or "therapeutically effective amount" refers to that amount of a composition described herein that is sufficient to effect the intended application including but not limited to a decrease in a *Cutibacterium acnes* population. The therapeutically effective amount may vary depending upon the subject and condition being treated, e.g., the weight and age of the subject, the severity of the disease condition, the manner of administration and the like, which can readily be determined by one of ordinary skill in the art. The term also applies to a dose that will induce a particular response in a target location, e.g., a reduction in inflammation, pain, acne, fever, etc. The specific dose will vary depending on the particular formulation of the composition, the dosing regimen to be followed, whether it is administered in combination with other compounds, timing of administration, the tissue to which it is administered, route of administration and the physical delivery system in which it is carried.

In some embodiments, a composition as disclosed herein is said to be active, functional or therapeutically active or able to treat, prevent and/or delay a condition associated with *Cutibacterium acnes* when it reduces or ameliorates one or more symptoms associated with that condition. In some embodiments, a composition is considered therapeutically active when it decreases a symptom by at least 5, 10, 15, 20, 25, 30, 35, 40, 45, 50, 55, 60, 65, 70, 75, 80, 85, 90, 95, 96, 97, 98, 99, or 100% after treatment compared to the severity of that symptom before treatment. In some embodiments, the symptom is pain, fever, swelling, redness, dry skin, lesion number, lesion size, rash, warmness, drainage, discharge, cough, shortness of breath, rapid heart rate, low or high blood pressure, chills, nausea, vomiting, diarrhea, stomach cramps, chest pain, or organ failure.

In some embodiments, a composition herein is therapeutically active when it decreases the amount of a target *Cutibacterium acnes* species present in a subject or in an in vitro system and preferably means that 99%, 90%, 80%, 70%, 60%, 50%, 40%, 30%, 20%, 10%, 5% or less of the initial amount of a *Cutibacterium acnes* species, is still detectable after treatment. In some embodiments, no *Cutibacterium acnes* species is detectable after treatment. Herein, the expression "amount of *Cutibacterium acnes* species" refers to living *Cutibacterium acnes* species. In some embodiments, *Cutibacterium acnes* species are detected using sequencing techniques, such as 16S sequencing or shotgun sequencing, to quantify the amount of different *Cutibacterium acnes* species present in a sample, as well as evaluating species present in the overall microbiome in question. Living *Cutibacterium acnes* species may be detected using standard techniques known by the artisan such as microbiological bacterial culture techniques and/or real-time quantitative reverse transcription polymerase chain reaction to assay for bacterial mRNA. In some embodiments, said decrease is assessed in a tissue or in a cell of an individual or a patient by comparison to the amount present in said individual or patient before treatment with a composition disclosed herein. In some embodiments, the comparison is made with a tissue or cell of said individual or patient which has not yet been treated with the composition as disclosed herein in case the treatment is local.

A composition as disclosed herein may be administered to a subject in need thereof or to a cell, tissue or organ or said patient for at least one day, one week, one month, six months, one year or more.

Accordingly, there is provided a composition as disclosed herein, for use by a subject in need thereof. In some embodiments, the composition is use as a medicament in the prevention, delay or treatment of a condition in a subject, wherein the condition is associated with *Cutibacterium acnes*.

Further provided is the composition as disclosed herein for systemic or local administration to the subject.

In some embodiments, local administration is employed locally at the site of a condition or infection, or in association with surgery, or at the site of an implant. The medical use disclosed herein may be formulated as a product as disclosed herein for use as a medicament for treatment of the stated conditions but can equally be formulated as a method of treatment of the stated conditions using a product as disclosed herein, a product as disclosed herein for use in the preparation of a medicament to treat the stated conditions and use of a product as disclosed herein for the treatment of the stated conditions. Such medical uses are all envisaged by the present disclosure. The subject in need of treatment, delay and/or prevention of the listed conditions may be any animal subject, preferably a mammal, more preferably cattle, domestic animals like a dog or a cat, or a human subject.

Further provided is the in vitro use of a composition as disclosed herein or a nucleic acid construct as disclosed herein, or an expression construct as disclosed herein, or a host cell as disclosed herein, as an antimicrobial or as a disinfectant.

Further provided is the use of a composition as disclosed herein or a nucleic acid construct as disclosed herein, or an expression construct as disclosed herein, or a host cell as disclosed herein, or a composition as disclosed herein, for binding and/or detecting *Cutibacterium acnes*, in an ex vivo diagnostic application.

EXAMPLES

Summary Table for Examples of the Disclosure

| # | Description |
|---|---|
| | I. Examples 1-4: Novel Cutibacterium Endolysins |
| 1 | Identification of novel family of endolysins containing amidase domains in *Cutibacterium* sp. |
| 2 | CLC1 protein displays high solubility and significant anti-*C. acnes* lytic activity. |
| 3 | CLC1-truncation exhibits improved solubility and lytic activity compared to full length protein. |
| 4 | Removal of C-terminal regions of other CLC1-family proteins and CaLys1 also improves solubility and activity. |
| | II. Examples 5-7: Novel *C. acnes* Cell Wall Binding Domains |
| 5 | Identification of novel CLBD1-CLBD4 as putative cell wall hydrolases from *Cutibacterium* sp. and *Propionimicrobium* sp. containing CW_7 cell wall binding domains. |
| 6 | Identification of large family of CBDs with broad taxonomical diversity comprising CW_7 repeats. |
| 7 | CLB1-CBD and CLB2-CBD can target chimeric cell wall hydrolases against C. acnes. |
| | III. Examples 8-21: Novel CLC1-family EAD and CW_7 CBD chimeras |
| 8 | Chimeras comprising CLC1-3 EADs in combination with CLB1-4 CBDs exhibit anti-*C. acnes* activity. |
| 9 | Chimeric proteins comprising CLC1-family EADs and CW_7 CBDs display lytic activity across a broad range of pH values. |
| 10 | Chimeric proteins comprising CLC1-family EADs and CW_7 CBDs display strong selectivity for C. acnes. |
| 11 | Chimeric proteins comprising CLC1-family EADs and CW_7 CBDs display significant thermostability. |
| 12 | Quantitative killing assay demonstrates significant *C. acnes* lytic activity by the CLC1-EAD + CLB1-CBD chimera. |
| 13 | Chimeric CWHs comprising the broader CLC1 family of EADs in combination with CLB2 CBD exhibit lytic activity against *C. acnes*. |
| 14 | Chimeric CWHs comprising CLC1-family EADs and CLB2 CBD exhibit significant thermostability. |
| 15 | CLC16 EAD + CLB2 CBD chimera exhibits strong selectivity for *C. acnes* over commensal skin bacteria. |
| 16 | CLC1-EAD + CLB2-CBD and CLC16-EAD + CLB2-CBD chimeric enzymes are active against a broad panel of Cutibacterium acnes strains and phylotypes. |
| 17 | The CBD from CLB2 increases the enzymatic activity of the CaLys1 EAD. |
| 18 | Diverse CW_7 repeats are able to facilitate binding and lysis of C. acnes in chimeric CWHs in whole cell lysate screen. |
| 19 | Actinobacteria, viral, and Firmicute CW_7 CBDs facilitate binding and lysis of *C. acnes* in chimeric CWHs in turbidity reduction assays. |
| 20 | Single CW_7 repeat sufficient for increasing anti-*C. acnes* activity in chimeric combination with CLC1-family EAD. |
| 21 | Topical hydrogel formulations of chimeric proteins retained strong lytic activity against *C. acnes*. |

I. Examples 1-4: Novel *Cutibacterium* Endolysins

Example 1: Identification of Novel CLC1-Family of Endolysins Containing Amidase Domains in *Cutibacterium* sp Previous attempts to identify endolysins that target *C. acnes* have focused exclusively on searching the genomes of *C. acnes* phages or *C. acnes* strains containing prophages. However, this approach had only identified a single well-conserved endolysin, as exemplified by the protein sequence NCBI accession ID: YP_006907103.1, referred to as CaLys1 in this application (SEQ ID NO: 72).

Bioinformatic analysis was conducted in broader *Cutibacterium* species in order to identify novel endolysins that target *C. acnes*. Without wishing to be bound by any particular theory, it is hypothesized that putative endolysins and cell wall hydrolases found within the genomes of broader *Cutibacterium* sp. and phages that infect broader *Cutibacterium* sp. may also have activity against *C. acnes*.

Figure 1B:
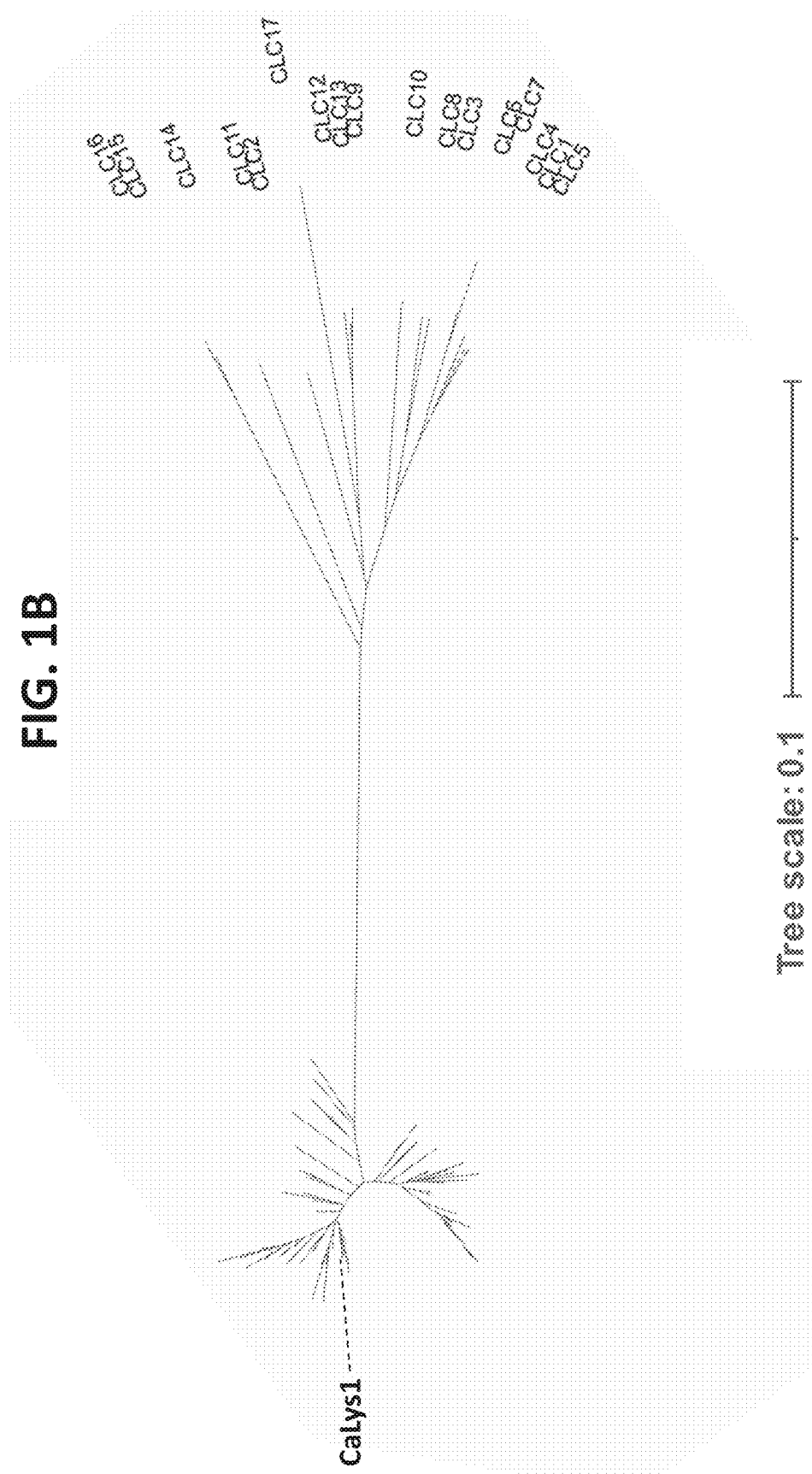
FIG. 1B shows a phylogenetic tree comparing the amidase domains of CLC1-CLC19 with the amidase domains of endolysins found in the genomes of *C. acnes* strains/phages including CaLys1. The amidase domains of the CLC1 family of proteins form a distinct grouping separate from the amidase domains found in the CaLys1 family of endolysins. The CLC18 amidase domain is identical to the CLC1 amidase domain, and the CLC19 amidase domain is identical to CLC13 amidase domain, such that these domains are not shown separately in FIG. 1B.
Figure 27:
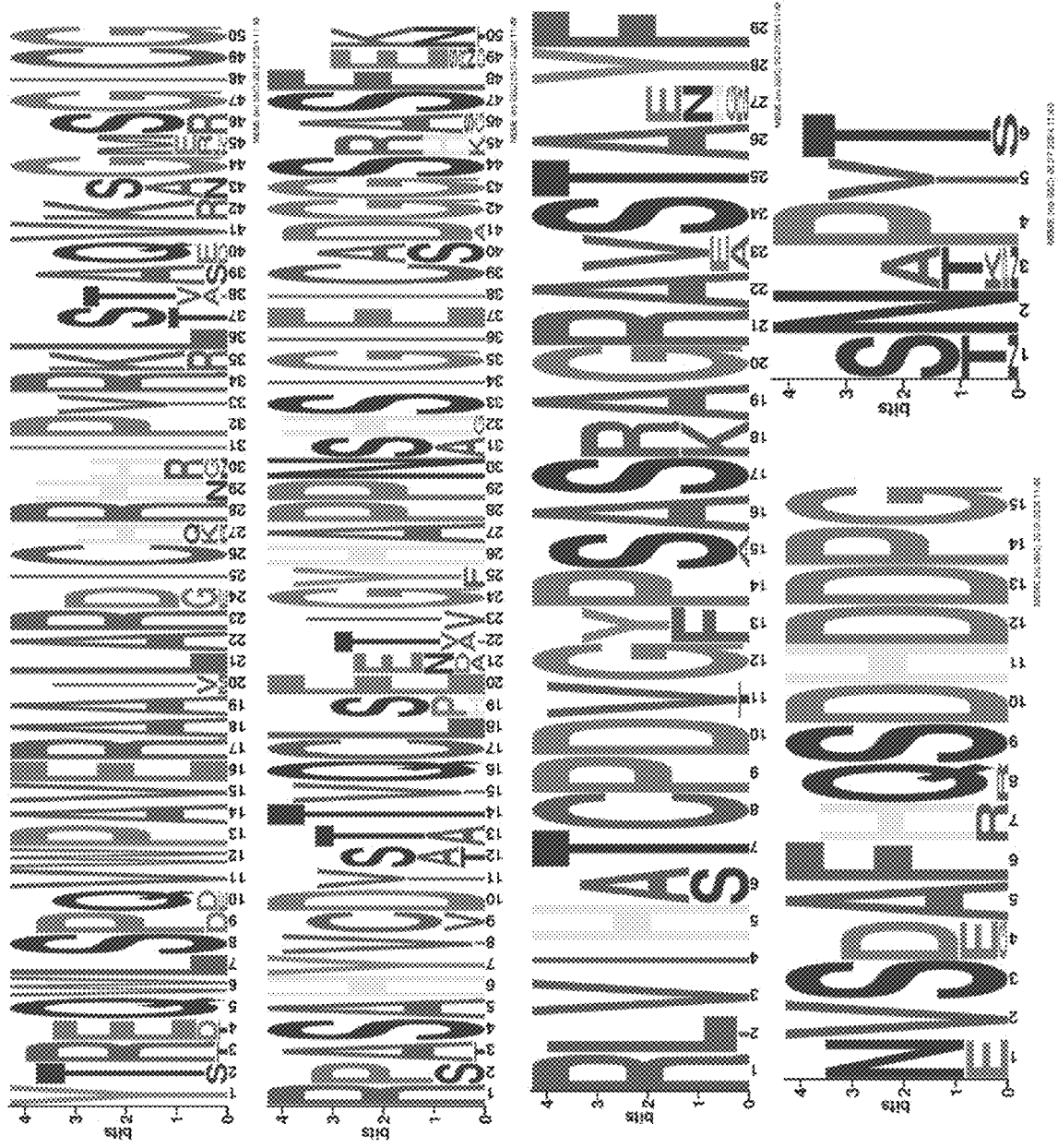
FIG. 27 shows a motif analysis of the CLC1-family EADs.

These genomes were bioinformatically analyzed for proteins that contain an N-acetylmuramoyl-L-alanine amidase domain (Pfam: Amidase_2) which is commonly found in endolysins across a broad range of bacteria, including the CaLys1 family. This search identified a novel family of amidases found in a number of *Cutibacterium* sp. including *C. avidum, C. granulosum*, and *C. porci*, including 19 proteins we have designated CLC1-CLC19 (all of which are referred to as the "CLC1 family" of amidases in this application). Amino acid sequences for full length CLC1-CLC19 are contained in SEQ ID NO: 1-19, respectively. These amidases show similarity to the CaLys1 endolysin family (~70% amino acid identity), but form a distinct phylogenetic grouping separate from the CaLys1 family found in *C. acnes* phages/prophages (FIG. 1A). Table 9 lists the GenBank ID numbers of the non-CLC1 family branches of the phylogenetic tree depicted in FIG. 1A. Phylogenetic comparison of just the amidase EADs of these proteins (SEQ ID NO: 20-36) also confirmed that the amidase EADs of the CLC1 family are distinct from the amidase EADs of the CaLys1 family (FIG. 1B). Table 10 lists the GenBank ID numbers, and amino acid region of the EADs, of the non-CLC family branches of the phylogenetic tree depicted in FIG. 1B. Using multiple sequence alignment tools (Clustal Omega and EMBOSS Cons, see Madeira et al., *Nucleic Acids Research* 2024 July; 52(W1): W521-W525), it was also determined that the CLC1-family EADs shared a significant core of conserved residues (SEQ ID NO: 2939). FIG. 27 provides the results of a further motif analysis identifying conserved motifs among the CLC1-family EADs.

TABLE 9

Non-CLC1-family branches of phylogenetic tree in FIG. 1A.

| Branch #* | GenBank ID No | Branch # | GenBank ID No | Branch # | GenBank ID No |
|---|---|---|---|---|---|
| 1 | WIW76974.1 | 28 | YP 009160118.2 | 55 | YP 009160253.2 |
| 2 | YP 008531700.1 | 29 | YP 009147244.1 | 56 | DAS49433.1 |
| 3 | AGI12425.1 | 30 | QHB37111.1 | 57 | ATN91960.1 |
| 4 | YP 009148336.1 | 31 | YP 009149934.1 | 58 | REB26552.1 |
| 5 | YP 008531655.1 | 32 | YP 008531564.1 | 59 | YP 008531926.1 |
| 6 | YP 009160074.1 | 33 | QPB11563.1 | 60 | YP 006907017.1 |
| 7 | YP 009146913.1 | 34 | YP 009214894.1 | 61 | YP 009152681.1 |
| 8 | YP 008531836.1 | 35 | DAW17174.1 | 62 | YP 009148291.1 |
| 9 | YP 009288342.1 | 36 | AUV62559.1 | 63 | WJJ53926.1 |
| 10 | YP 008531610.1 | 37 | YP 001285596.1 | 64 | QHB36558.1 |
| 11 | DAT38689.1 | 38 | DAQ10842.1 | 65 | DAP54624.1 |
| 12 | YP 009152381.1 | 39 | AUV62178.1 | 66 | DAQ38945.1 |
| 13 | YP 009152726.1 | 40 | YP 006906466.1 | 67 | YP 009191365.1 |
| 14 | CaLys1 | 41 | AUX13513.1 | 68 | ACG76347.1 |
| 15 | YP 006906916.1 | 42 | QHB37534.1 | 69 | ACG76345.1 |
| 16 | YP 009153269.1 | 43 | ATN90299.1 | 70 | YP 009159847.1 |
| 17 | YP 009145789.1 | 44 | YP 006906607.1 | 71 | YP 009277894.2 |
| 18 | YP 004414725.1 | 45 | EAD6310143.1 | 72 | YP 008531745.1 |
| 19 | DAO96639.1 | 46 | YP 008531791.1 | 73 | QPB11813.1 |
| 20 | YP 006906560.1 | 47 | YP 006906421.1 | 74 | ATN89071.1 |
| 21 | YP 009160208.2 | 48 | QFP94545.1 | 75 | DAR77727.1 |
| 22 | YP 009160163.1 | 49 | DAO94404.1 | 76 | YP 006906513.1 |
| 23 | YP 009152610.1 | 50 | QHB36809.1 | 77 | PZR03097.1 |
| 24 | YP 009277998.1 | 51 | YP 009145834.1 | 78 | AUV62306.1 |
| 25 | USN17903.1 | 52 | YP 009160298.1 | 79 | YP 009159893.1 |
| 26 | UZV39505.1 | 53 | YP 009152426.1 | 80 | YP 009151449.1 |
| 27 | YP 006906792.1 | 54 | YP 009603689.1 | 81 | YP 009160027.1 |

* Branch # is listed in clockwise order enumerated from the branch immediately clockwise from CLC1.

TABLE 10

Non-CLC1-family branches of phylogenetic tree in FIG. 1B.

| Branch #* | GenBank ID No. | EAD AA region | Branch # | GenBank ID No. | EAD AA region |
|---|---|---|---|---|---|
| 1 | YP_008531745.1 | 14-174 | 56 | YP_008531926.1 | 13-173 |
| 2 | DAT38689.1 | 13-173 | 57 | YP_009159893.1 | 13-173 |
| 3 | QFP94545.1 | 13-173 | 58 | DAR27346.1 | 13-173 |
| 4 | YP_008531882.1 | 13-173 | 59 | ATN90299.1 | 13-173 |
| 5 | DAX59447.1 | 14-174 | 60 | YP_009151220.1 | 14-174 |
| 6 | YP_009152610.1 | 13-173 | 61 | QPB11563.1 | 13-173 |
| 7 | YP_009151449.1 | 13-173 | 62 | QPB11659.1 | 13-173 |
| 8 | AUV62306.1 | 13-173 | 63 | DAQ38945.1 | 13-173 |
| 9 | PZR03097.1 | 13-173 | 64 | ATN90343.1 | 13-173 |
| 10 | YP_009277894.2 | 13-173 | 65 | AUV62178.1 | 14-174 |
| 11 | YP_009152681.1 | 13-173 | 66 | ATN90914.1 | 13-173 |
| 12 | YP_008531700.1 | 14-174 | 67 | CaLys1 | 13-173 |
| 13 | QPB11813.1 | 13-173 | 68 | YP_006906607.1 | 13-173 |
| 14 | YP_006906046.1 | 25-185 | 69 | DAJ24593.1 | 14-174 |
| 15 | YP_009603689.1 | 13-173 | 70 | USN17903.1 | 14-174 |
| 16 | YP_006906513.1 | 13-173 | 71 | EAD6310143.1 | 13-173 |
| 17 | DAR77727.1 | 13-173 | 72 | QHB37534.1 | 13-173 |
| 18 | ATN89071.1 | 13-173 | 73 | YP_006906421.1 | 13-173 |
| 19 | QHB36809.1 | 13-173 | 74 | YP_008531791.1 | 13-173 |
| 20 | YP_009151398.1 | 25-185 | 75 | AGI12651.1 | 14-174 |
| 21 | YP_009151538.1 | 14-174 | 76 | YP_009153269.1 | 14-174 |
| 22 | DAS49433.1 | 13-173 | 77 | QHB36558.1 | 13-173 |
| 23 | ATN91960.1 | 13-173 | 78 | AUX13513.1 | 13-173 |
| 24 | YP_009292055.1 | 13-173 | 79 | YP_009145789.1 | 18-178 |
| 25 | YP_006907017.1 | 13-173 | 80 | YP_001285596.1 | 14-174 |
| 26 | REB26552.1 | 13-173 | 81 | AUV62559.1 | 14-174 |
| 27 | YP_009160253.2 | 13-173 | 82 | ACG76345.1 | 13-173 |

TABLE 10-continued

Non-CLC1-family branches of phylogenetic tree in FIG. 1B.

| Branch # * | GenBank ID No. | EAD AA region | Branch # | GenBank ID No. | EAD AA region |
|---|---|---|---|---|---|
| 28 | YP_008531745.1 | 14-174 | 83 | ACG76347.1 | 13-173 |
| 29 | DAT38689.1 | 13-173 | 84 | DAQ10842.1 | 14-174 |
| 30 | QFP94545.1 | 13-173 | 85 | YP_009191365.1 | 13-173 |
| 31 | YP_008531882.1 | 13-173 | 86 | ASJ79920.1 | 14-174 |
| 32 | DAX59447.1 | 14-174 | 87 | DAW17174.1 | 14-174 |
| 33 | YP_009152610.1 | 13-173 | 88 | YP_009148291.1 | 13-173 |
| 34 | YP_009151449.1 | 13-173 | 89 | YP_009160027.1 | 13-173 |
| 35 | AUV62306.1 | 13-173 | 90 | YP_009150263.1 | 13-173 |
| 36 | PZR03097.1 | 13-173 | 91 | AII29464.1 | 14-174 |
| 37 | YP_009277894.2 | 13-173 | 92 | YP_008531564.1 | 14-174 |
| 38 | YP_009152681.1 | 13-173 | 93 | DAP54624.1 | 14-174 |
| 39 | YP_008531700.1 | 14-174 | 94 | YP_009149934.1 | 14-174 |
| 40 | QPB11813.1 | 13-173 | 95 | QHB37111.1 | 14-174 |
| 41 | YP_006906046.1 | 25-185 | 96 | YP_004414725.1 | 14-174 |
| 42 | YP_009603689.1 | 13-173 | 97 | YP_006906560.1 | 13-173 |
| 43 | YP_006906513.1 | 13-173 | 98 | YP_009160118.2 | 13-173 |
| 44 | DAR77727.1 | 13-173 | 99 | YP_009152726.1 | 14-174 |
| 45 | ATN89071.1 | 13-173 | 100 | YP_009152381.1 | 14-174 |
| 46 | QHB36809.1 | 13-173 | 101 | YP_008531610.1 | 25-185 |
| 47 | YP_009151398.1 | 25-185 | 102 | YP_009160208.2 | 13-173 |
| 48 | YP_009151538.1 | 14-174 | 103 | YP_009160074.1 | 13-173 |
| 49 | DAS49433.1 | 13-173 | 104 | YP_009160298.1 | 13-173 |
| 50 | ATN91960.1 | 13-173 | 105 | DAO94404.1 | 13-173 |
| 51 | YP_009292055.1 | 13-173 | 106 | WIW76974.1 | 14-174 |
| 52 | YP_006907017.1 | 13-173 | 107 | YP_009152426.1 | 18-178 |
| 53 | REB26552.1 | 13-173 | 108 | YP_009148336.1 | 18-178 |
| 54 | YP_009160253.2 | 13-173 | 109 | YP_008531655.1 | 13-173 |
| 55 | YP_009159847.1 | 13-173 | | | |

* Branch # is listed in clockwise order enumerated from the branch immediately clockwise from CLC5.

Figure 2:
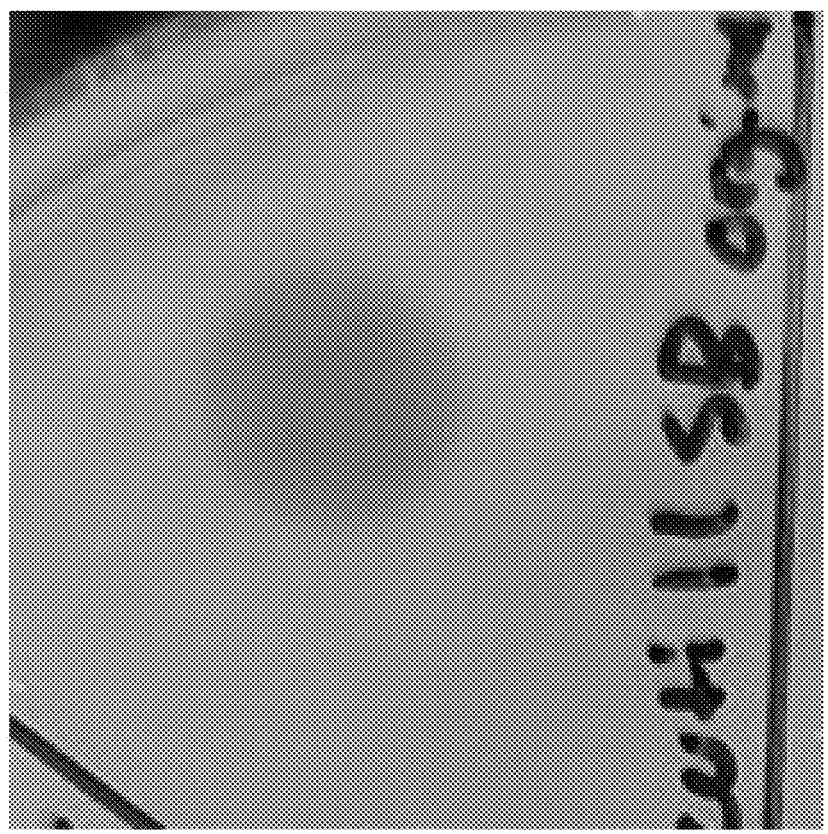
FIG. 2 is an image showing that the cell lysate from BL21 cells expressing CLC1 generated a zone clearing on plates embedded with *C. acnes*.

Example 2: CLC1 Protein Displays High Solubility and Significant Anti-*C. acnes* Lytic Activity To test if the CLC1 family of putative endolysins has lytic activity against *C. acnes*, CLC1 was cloned into an inducible expression plasmid and the protein was expressed in BL21 *E. coli* cells. A 6×His tag was added to the protein during these cloning steps. Cell lysate was then tested for activity in a clearing assay. Briefly, *C. acnes* cells were embedded in soft agar to create an opaque plate. Candidate enzymes (either purified or from *E. coli* lysate) can be spotted on these plates which results in a clearing/halo if the enzyme has anti-*C. acnes* activity. When lysate from BL21 *E. coli* cells expressing CLC1 was spotted in this halo assay, a clearing/halo was observed, indicating anti-*C. acnes* activity (FIG. 2).

Importantly, the observed anti-*C. acnes* activity with CLC1 did not require any extra steps to resolubilize the protein. In contrast, lysate from BL21 cells expressing CaLys1 did not result in any clearing in this halo assay, consistent with previous reports that CaLys1 protein is predominantly insoluble (and thus inactive) when expressed in *E. coli* without further manipulation.

Figure 3:
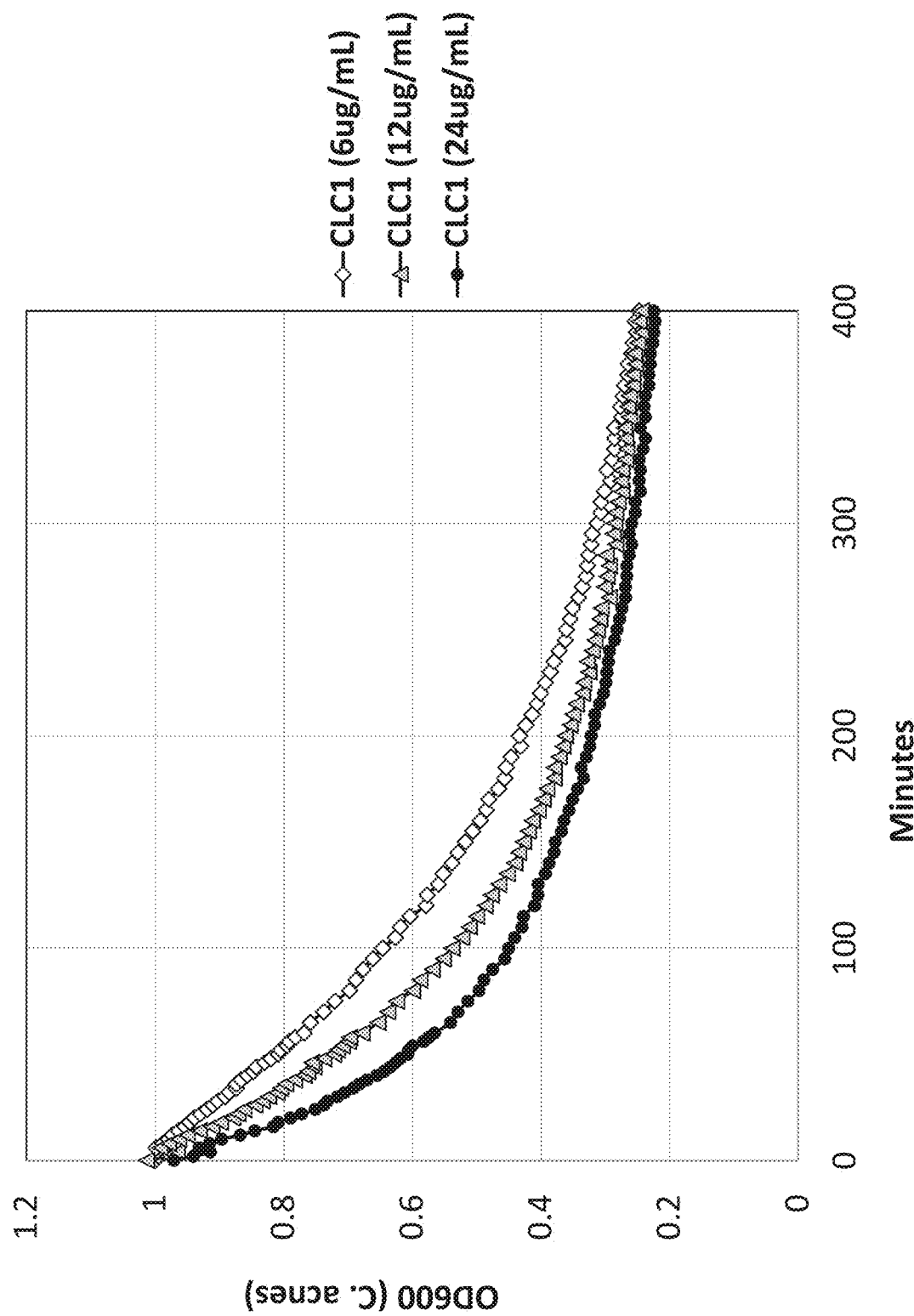
FIG. 3 is a chart showing the results of a turbidity reduction assay demonstrating that purified CLC1 displays lytic activity against *C. acnes*.

To further characterize the activity of CLC1, CLC1 was purified from cell lysate using the 6×His tag and then tested in a turbidity reduction assay. In this assay, *C. acnes* cells were resuspended at an $OD_{600}$ of ~1.0 and then treated with purified enzyme. If the enzyme has *C. acnes* lytic activity, the $OD_{600}$ decreases over time. The results confirmed that CLC1 had anti-*C. acnes* activity (FIG. 3). Notably, CLC1 had activity at a concentration range (6 µg/mL-24 µg/mL) which is lower than that reported for CaLys1 (100 µg/mL). Further, CLC1 protein remained soluble after purification using the 6×His tag. Thus, CLC1 represents a novel endolysin that is soluble expressed from *E. coli* and has lytic activity against *C. acnes*.

Example 3: CLC1-Truncation Exhibits Improved Solubility and Lytic Activity Compared to Full Length Protein Bioinformatically-predicted protein domains in the CLC1-family of enzymes were identified using SMART and CD-Search. Using these tools, the inventors discovered that the vast majority of CLC1-family members have an N-terminal amidase domain (the EAD) followed by a C-terminal region of approximately 100 amino acids with no predicted protein domains. The exception is CLC15, which is longer and is predicted to have repeat domains of unknown function.

Figure 4:
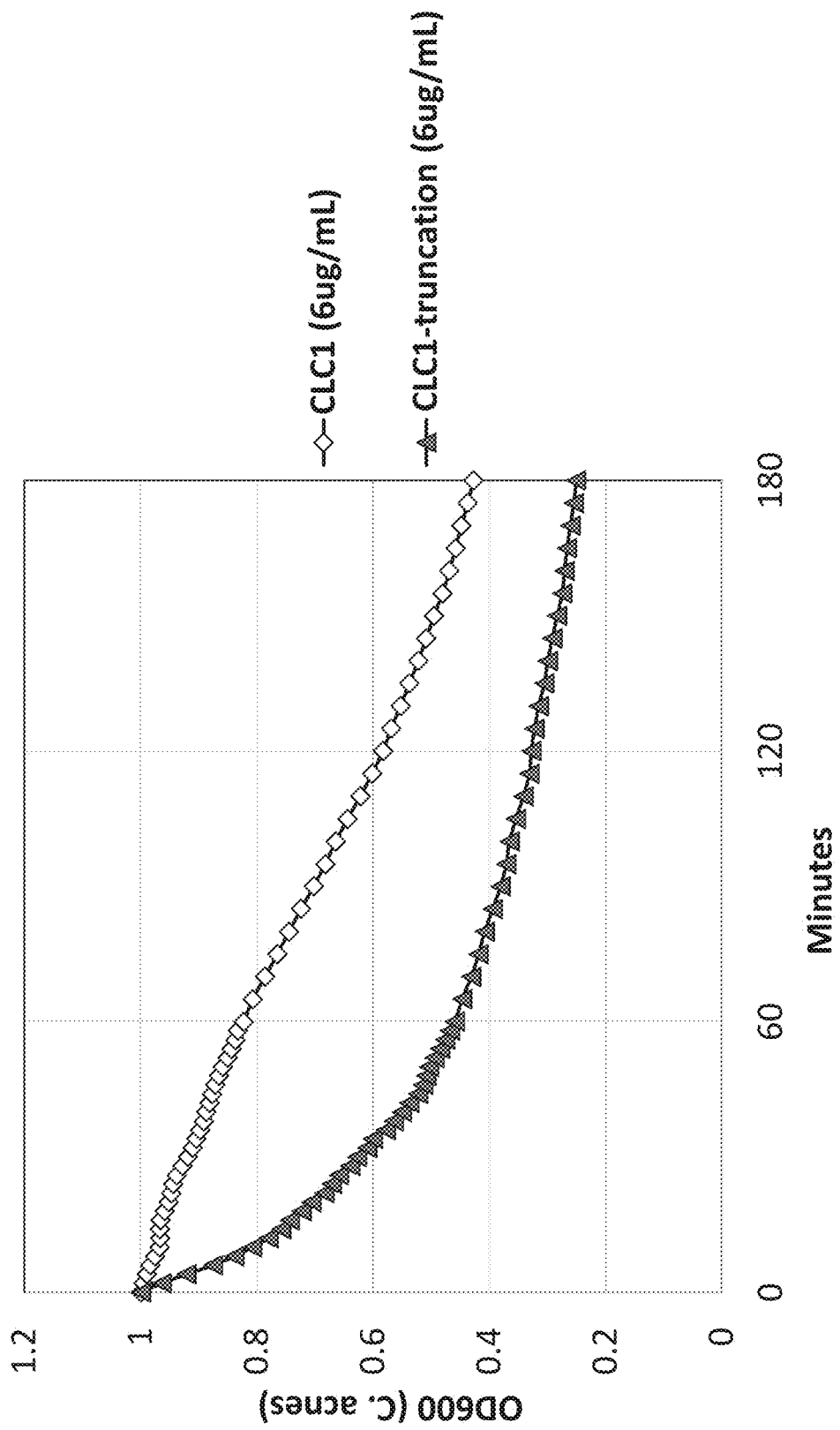
FIG. 4 shows the results of a turbidity reduction assay demonstrating that CLC1-truncation exhibits higher anti-*C. acnes* lytic activity than full-length native CLC1.

Despite the lack of any predicted protein domains, this C-terminal region is conserved across the CLC1-family members and in CaLys1, suggesting that it may have some biological function. To assess the effect of this C-terminal domain on CLC1 activity, the inventors generated a truncated form of CLC1 lacking the C-terminal 85 amino acids ("CLC1-truncation"). The protein was expressed in BL21 *E. coli*, purified, and tested in turbidity reduction assays. Surprisingly, the inventors found that CLC1-truncation had increased solubility as compared to full-length CLC1, as evidenced by significantly higher yields of soluble protein after *E. coli* expression. In addition, the CLC1-truncation was surprisingly found to be significantly more active than full-length CLC1 in a turbidity reduction assay measuring lytic activity against *C. acnes* (FIG. 4). These data indicate that removal of the C-terminal portion of the CLC1 protein has positive effects on both solubility and activity, resulting in a more stable protein with much stronger lytic activity against *C. acnes*.

Figure 5C:
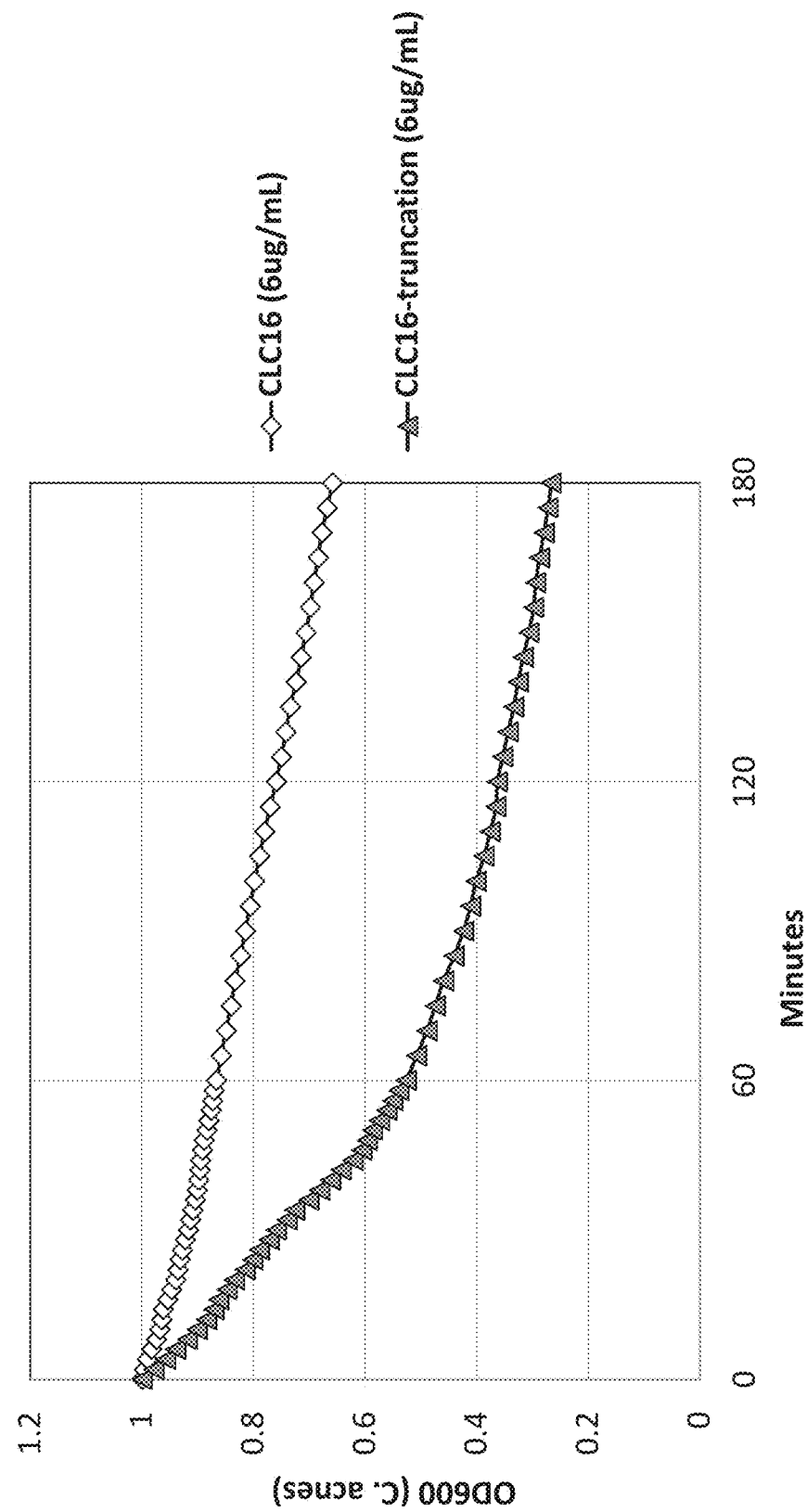
Figure 5D:
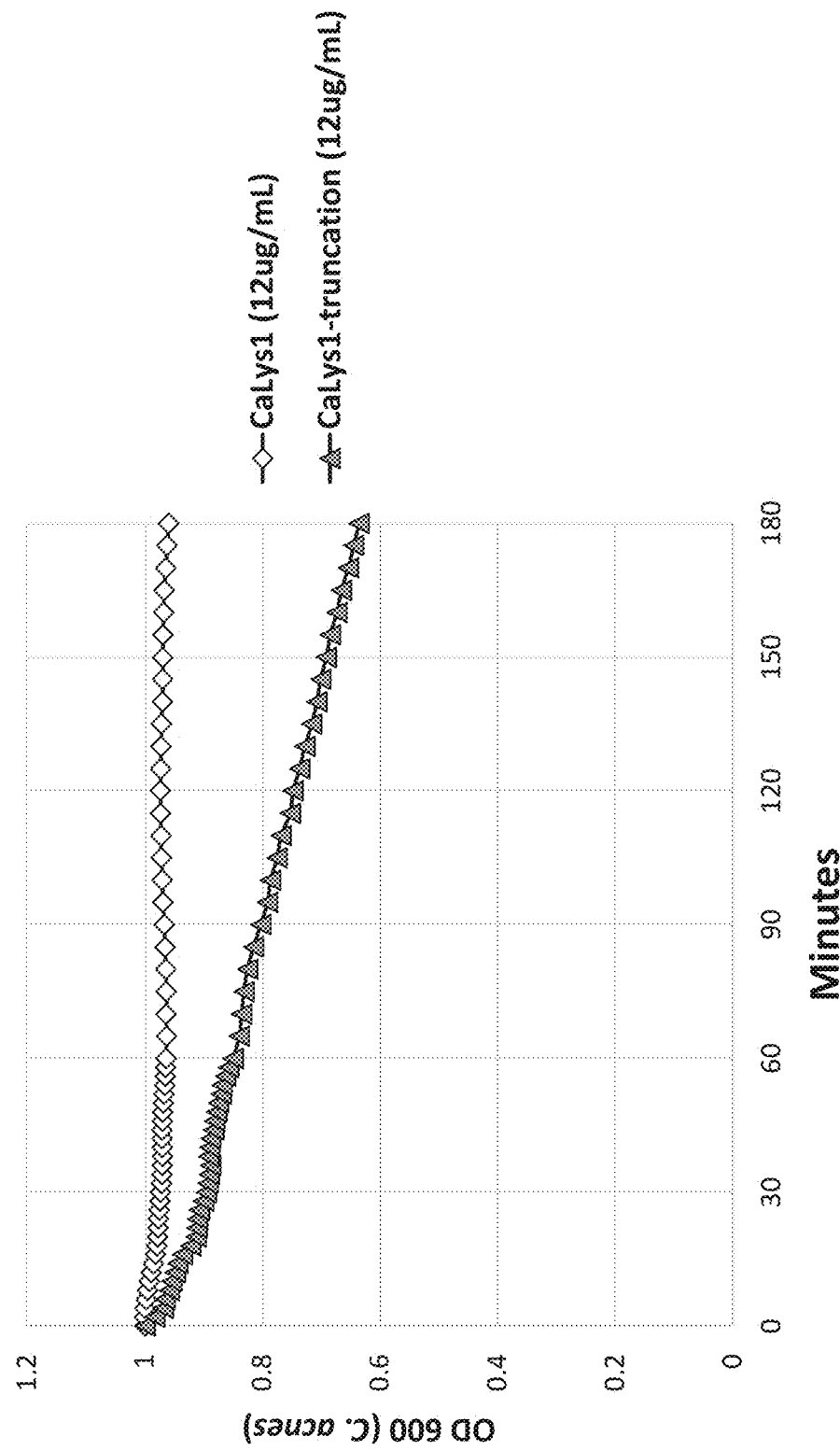

Example 4: Removal of C-Terminal Regions of Other CLC1-Family Proteins and CaLys1 Also Improves Solubility and Activity Full-length CLC2 and CLC3 showed relatively weaker *C. acnes* lytic activity when purified, with poorer soluble protein yields, compared to other CLC proteins. The inventors removed about 85 amino acids from the C-terminal ends of both proteins to generate a CLC2-truncation and a CLC3-truncation, respectively. Full-length CLC2, full-length CLC3, CLC2-truncation, and CLC3-truncation were purified and tested for *C. acnes* lytic activity in a turbidity reduction assay. The truncated proteins demonstrated both higher soluble proteins yields as well as significantly stronger *C. acnes* lytic activity in the turbidity reduction assays (FIG. 5A-5B). C-terminal truncations were also generated for CLC16 and CaLys1 and tested in a turbidity reduction assay against their full-length counterparts. In both cases, the truncation exhibited improved solubility and lytic activity compared to their full-length counterparts (FIG. 5C-5D). These data demonstrate that the removal of the C-terminal region of the CLC1-family of proteins, and of CaLys1, has positive effects on solubility and activity in turbidity reduction assays. The improved solubility and activity of CaLys1-truncation is particularly surprising in view of the known issues with solubility and activity for full-length CaLys1. Table 5 provides the sequences of the CLC1-family truncations, as well as the CaLys1 truncation, all of which are expected to exhibit improved solubility and lytic activity compared to their full-length counterparts, as was observed for CLC1, CLC2, CLC3, CLC16, and CaLys1.

II. Examples 5-7: Novel *C. acnes* Cell Wall Binding Domains

Figure 6:
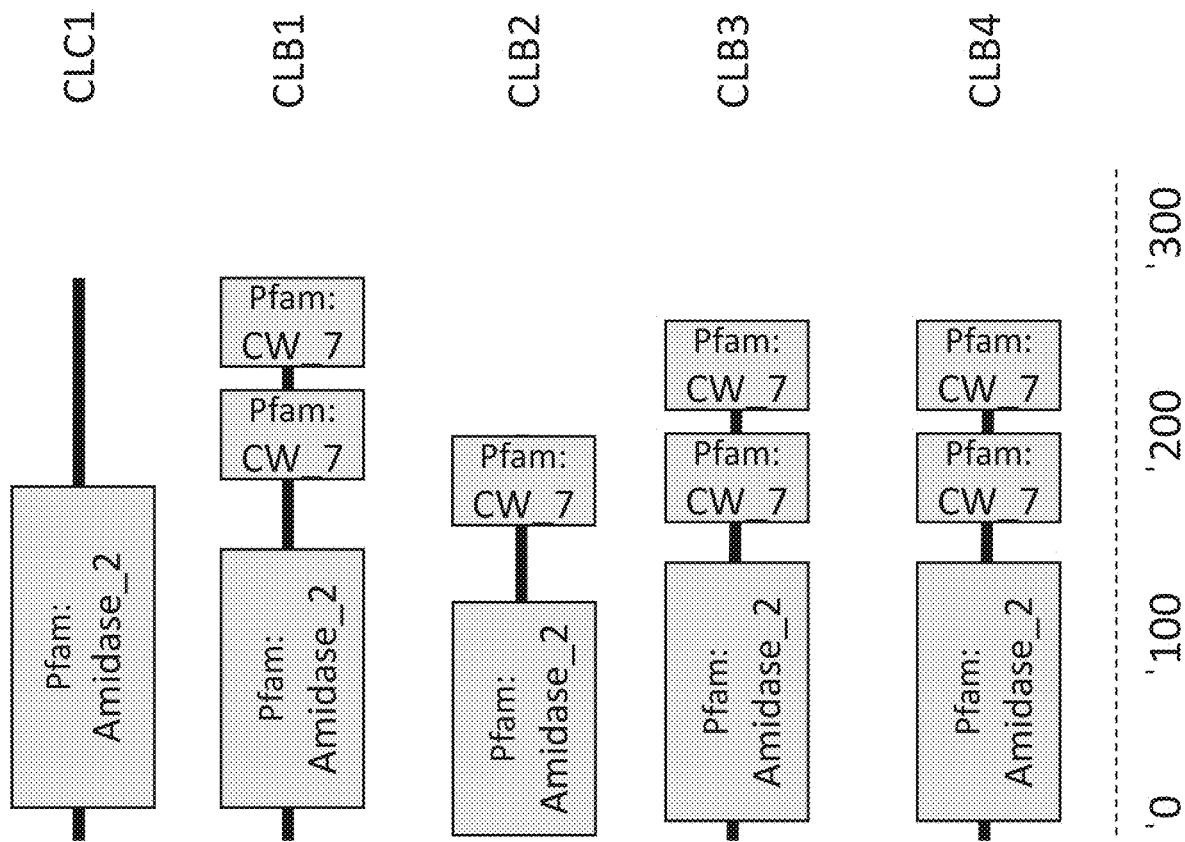
FIG. 6 shows schematics of domain organization of the indicated proteins. CLB1, CLB2, CLB3, and CLB4 containing putative cell wall binding domains composed of 1 or 2 CW_7 domains. In contrast, the C-terminal end of CLC1 does not encode a computationally predicted protein domain.

Example 5: Identification of CLB1-CLB4 as Putative Cell Wall Hydrolases from *Cutibacterium* sp. and *Propionimicrobium* Sp. Containing CW_7 Cell Wall Binding Domains Many endolysins, particularly endolysins that target gram-positive bacteria, contain both an enzymatically active domain (EAD) as well as a cell wall binding domain (CBD). The cell wall binding domain is responsible for recognizing and binding epitopes in the peptidoglycan of target bacteria, thus bringing the EAD to its target substrate. In this way, the CBD can increase specificity and/or activity. No known CBDs have been shown to recognize and bind *C. acnes*. To find a CBD that could recognize *C. acnes*, the genomes of *Cutibacterium* sp. and broader Propionibacteriaceae family bacteria were subjected to bioinformatics analysis for putative cell wall hydrolases that contain possible cell wall binding domains. Four uncharacterized putative proteins (CLB1-CLB4) were identified from *C. avidum* (CLB1), *C. acnes* (CLB2), and *Propionimicrobium lymphophilum* (CLB3 and CLB4). All four proteins contain an N-terminal amidase domain. CLB1, CLB3, and CLB4 have predicted C-terminal cell wall binding domains containing two CW_7 domain repeats, while CLB2 has a predicted C-terminal cell wall binding domain containing a single CW_7 repeat (FIG. 6).

Figure 7A:
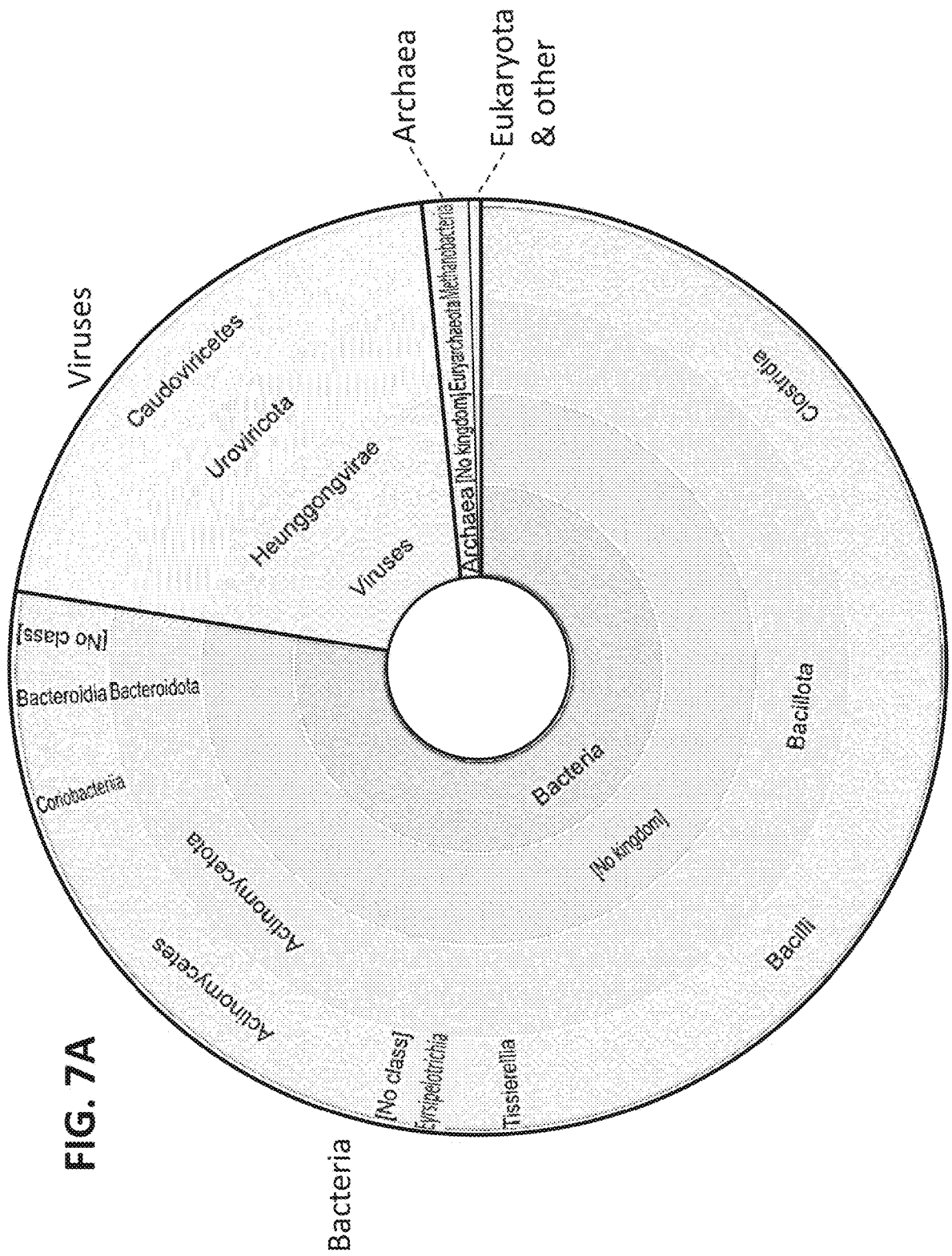
FIG. 7A shows the taxonomic distribution of proteins containing CW_7 repeat domains that were identified in a protein database search performed herein.
Figure 7B:
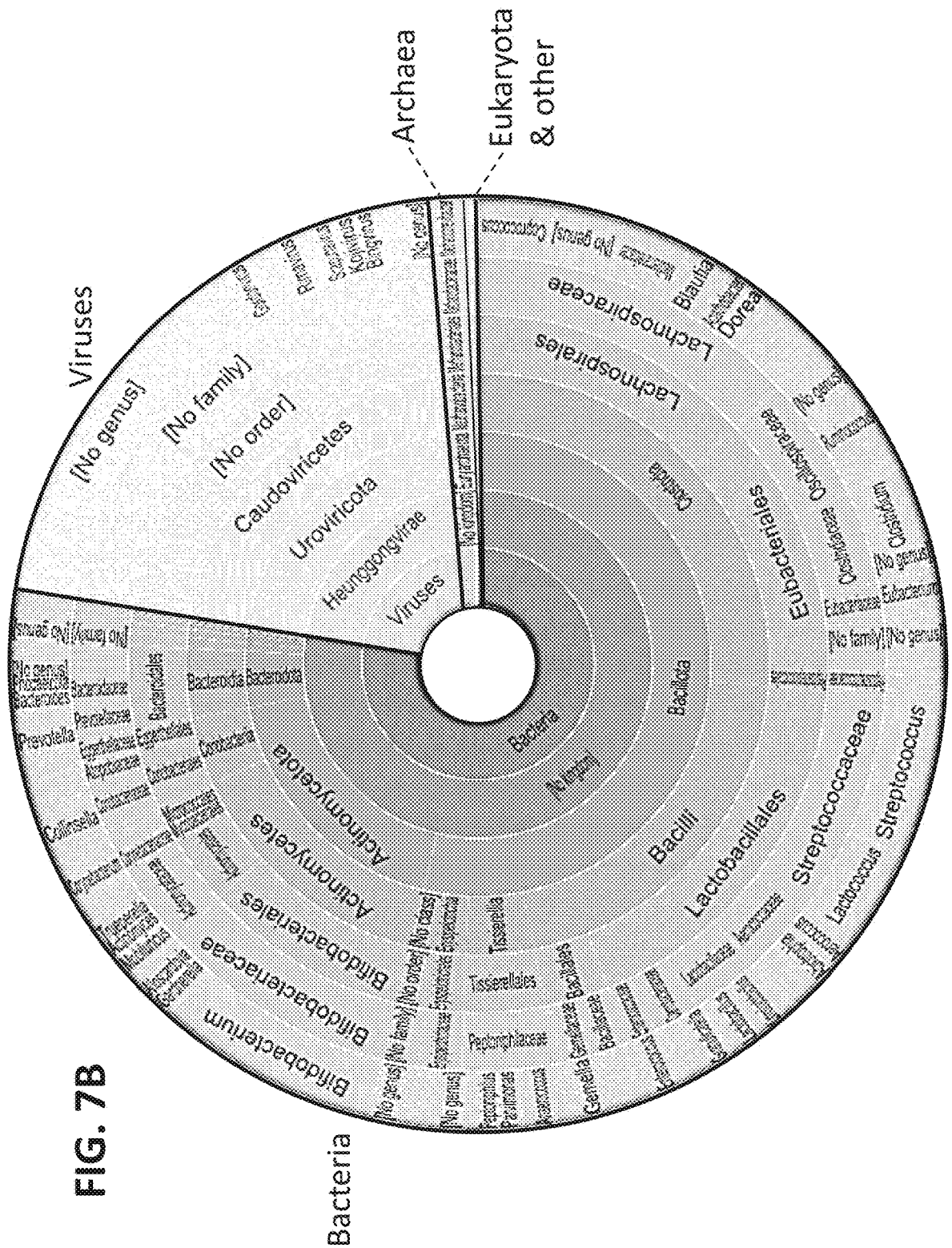
FIG. 7B shows the detailed taxonomic distribution of proteins containing CW_7 repeat domains that were identified in a protein database search performed herein.

Example 6: Identification of Large Family of CBDs with Broad Taxonomical Diversity Comprising CW_7 Repeats The CLB1-4 CBDs contain 1 or 2 CW_7 repeats. CW_7 repeats are fairly small (37-40 aa) and are believed to bind peptidoglycan chains. See Bustamante et al., *Sci Rep* 2017 Nov. 28; 7(1):16494. In order to characterize the taxonomical diversity of CW_7 repeats, the Uniprot database was searched for proteins containing CW_7 domains using the Interpro domain entry IPR013168. Uniprot contains ~1,333 proteins annotated to have 1 or more CW_7 repeats that are found in a broad range of bacterial species, primarily within the Actinobacteria and Firmicutes bacterial phyla as well as associated bacteriophage viruses with a smaller representation in Bacteriodota (FIG. 7A-7B). A BLASTP search was also performed in the non-redundant protein database using the CLB2-CBD CW_7 repeat sequence as a query. Using this search, 2,656 protein sequences were identified with an E-value <0.05. The CW_7 repeat sequences in these proteins range from 43.59% to 100% amino acid identity to the CLB2-CBD CW_7 query and, again, come from a broad diversity of bacterial species and associated viruses. For each protein, the GenBank Accession Number, SEQ ID NO, and percent identity of the top CW_7 match are listed in Table 7. Sequences for the CW_7 CBD comprising proteins identified in this search are provided in SEQ ID NO: 282-2938.

Example 7: CLB1-CBD and CLB2-CBD can Target Chimeric Cell Wall Hydrolases Against *C. acnes*

Figure 8B:
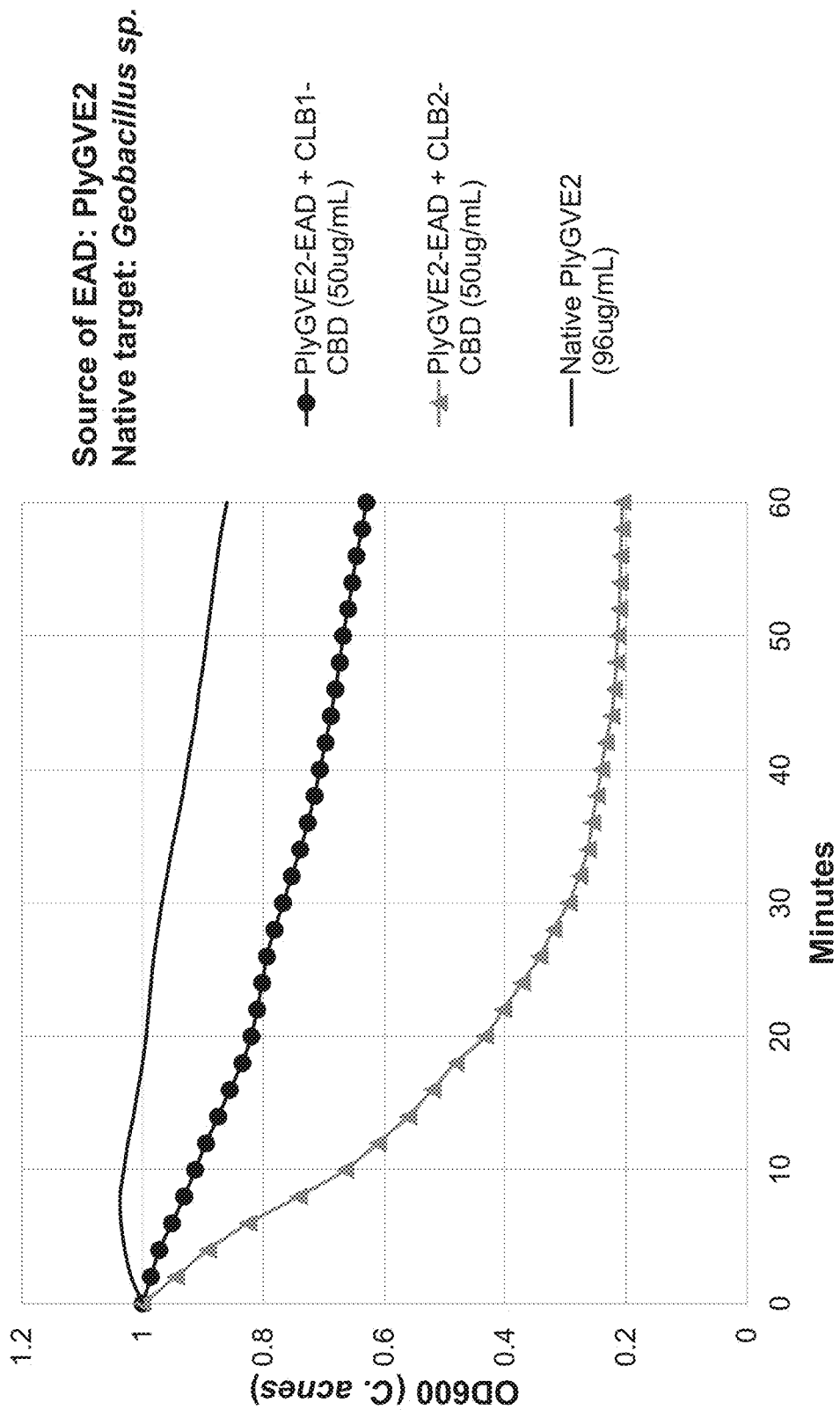

To prove that the newly identified CBDs bind to *C. acnes*, the inventors explored the possibility of using the CLB1 and CLB2 CBDs to create chimeric proteins with activity against *C. acnes*. To test this idea, two endolysins that natively target other genera of bacteria and not *C. acnes* were selected: CD27L, which typically targets *Clostridium difficle* (Mayer et al., J Bacteriol. 2008 October; 190(20):6734-40); and PlyGVE2, which comes from a thermophilic phage shown to infect *Geobacillus* sp. (Jin et al., Microbiology (Reading). 2013 August; 159(Pt 8):1597-1605). The EADs from these two endolysins were fused to either CLB1-CBD or CLB2-CBD. The resultant chimeric proteins were expressed, purified and their activity was tested against *C. acnes* in a turbidity reduction assay. The native CD27L and PlyGVE2 proteins were also expressed, purified, and tested. While the native CD27L and PlyGVE2 did not exhibit any lytic activity against *C. acnes*, the four chimeric CWHs were able to lyse *C. acnes*, a bacterium which is well outside the native target genera of the two source endolysins, demonstrating that CLB1-CBD and CLB2-CBD can be used to create chimeric cell wall hydrolases that target *C. acnes* by fusing EADs to these CBDs (FIG. 8A-8B).

III. Examples 8-19: Novel CLC1-Family EAD and CW_7 CBD Chimeras

Example 8: Chimeras Comprising CLC1-3 EADs in Combination with CLB1-4 CBDs Exhibit Anti-*C. acnes* Activity The CLC1 family of amidases is composed of an N-terminal amidase with conserved sequences at the C-terminal end. However, while conserved, there is no predicted protein domain encoded by this sequence and thus no clear CBD (FIG. 4). Thus, without wishing to be bound by any particular theory, it was hypothesized by the inventors that the activity of the CLC1 family of amidases could be modified by fusing the EADs of the CLC1 family to CBDs that can recognize and bind *C. acnes*.

A set of 8 chimeric proteins composed of combinations of the EADs from CLC1, CLC2, and CLC3 and the CBDs from CLB1, CLB2, CLB3, and CLB4 were generated to test if the CBDs of CLB1-CLB4 could target *C. acnes*. The design of these proteins is provided in Table 11 below.

TABLE 11

Design of Chimeric Proteins

| CHIMERIC PROTEINS CREATED | | Enzymatic Domains (EADs) | | |
|---|---|---|---|---|
| | | CLC1-EAD | CLC2-EAD | CLC3-EAD |
| Cell Wall Binding Domains (CBDs) | CLB1-CBD | CLC1-EAD + CLB1-CBD | CLC2-EAD + CLB1-CBD | CLC3-EAD + CLB1-CBD |
| | CLB2-CBD | CLC1-EAD + CLB2-CBD | CLC2-EAD + CLB2-CBD | CLC3-EAD + CLB2-CBD |
| | CLB3-CBD | CLC1-EAD + CLB3-CBD | | |
| | CLB4-CBD | CLC1-EAD + CLB4-CBD | | |

Figure 9A:
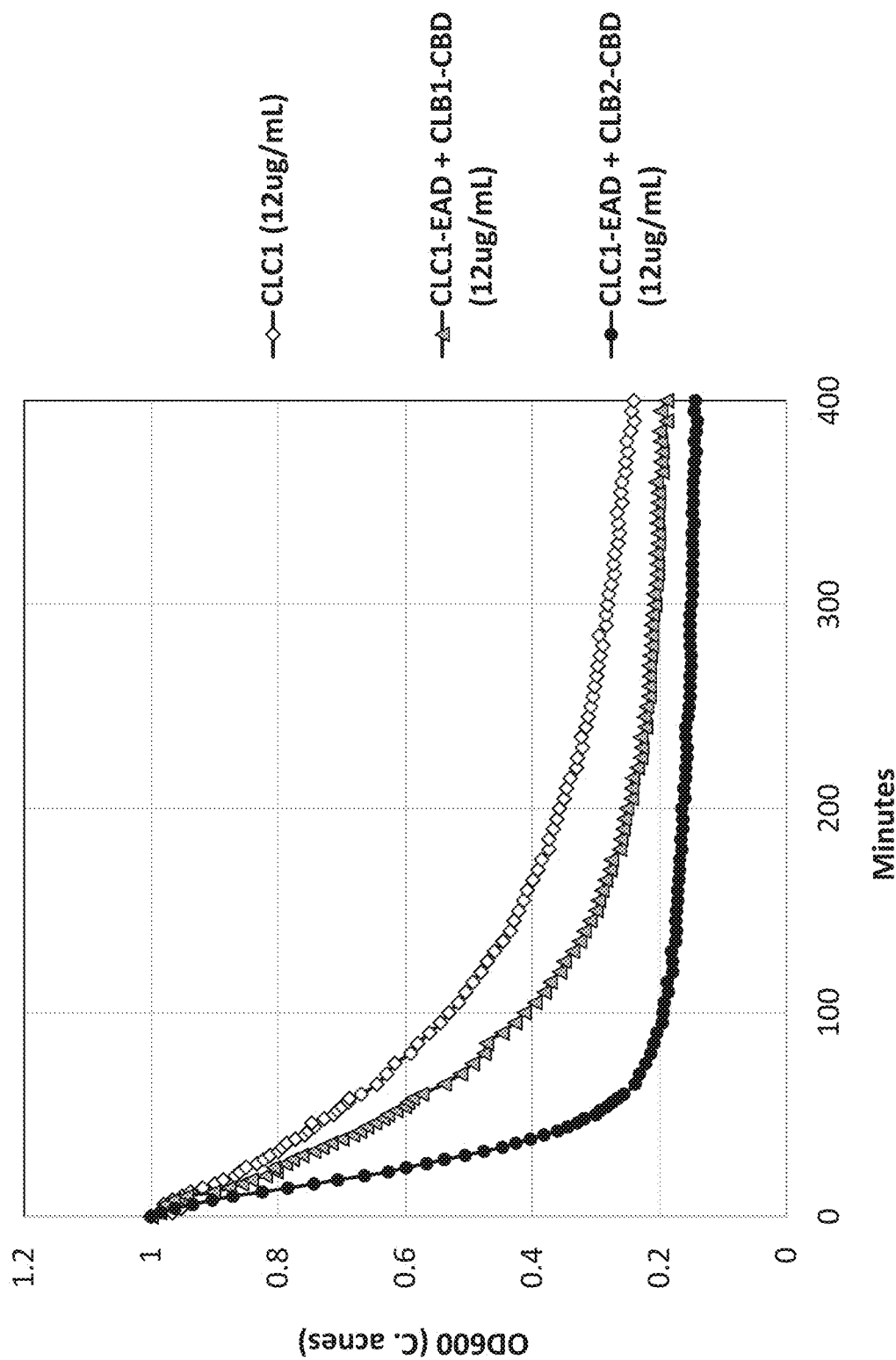
FIG. 9A is a chart of turbidity reduction assay results showing that chimeric proteins linking the CLC1 EAD with the CLB1 CBD and the CLB2 CBD displayed significantly increased *C. acnes* lytic activity compared to the native CLC1 protein.
Figure 9B:
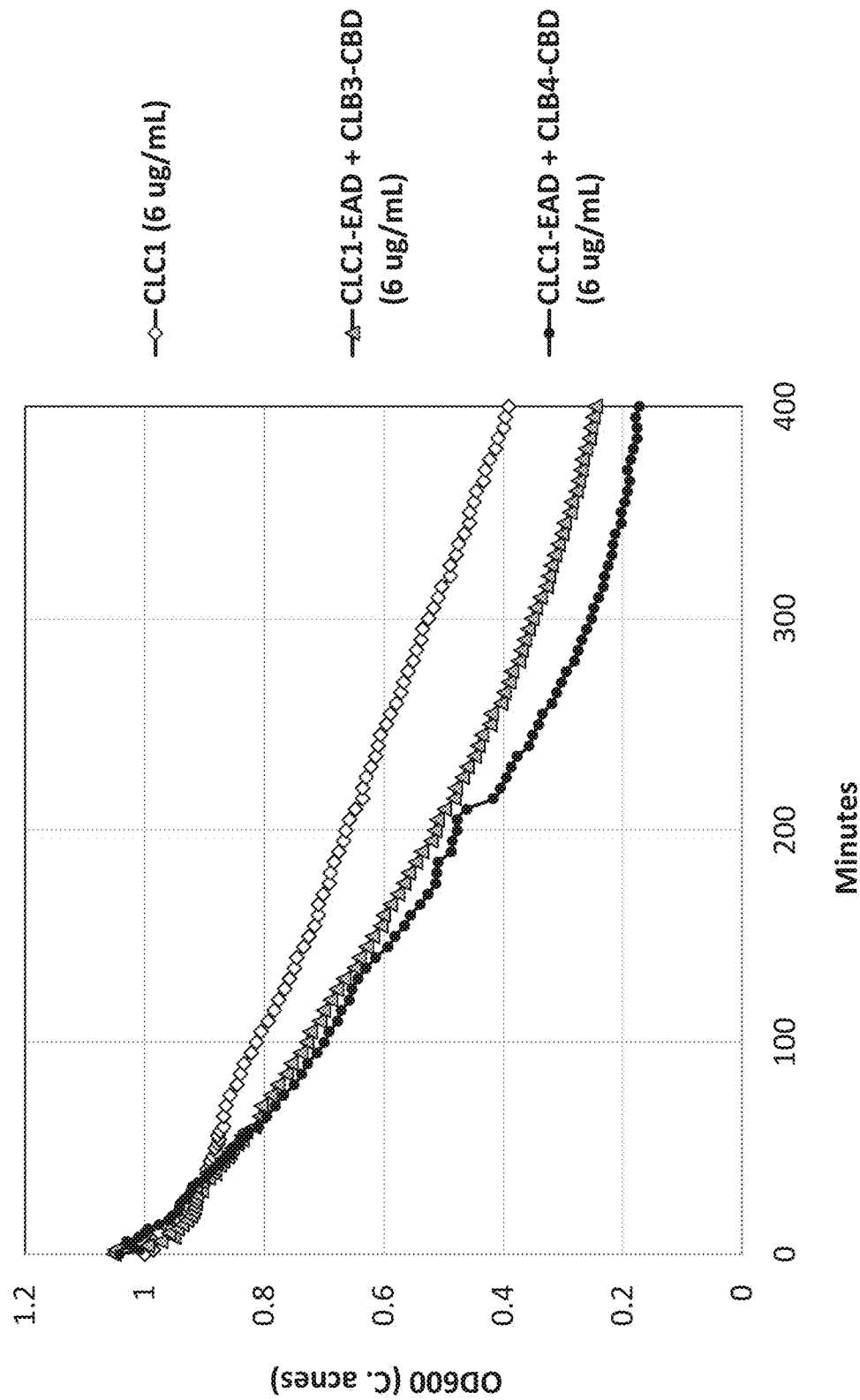
FIG. 9B is a chart of turbidity reduction assay results showing that chimeric proteins linking the CLC1 EAD with the CLB3 CBD and the CLB4 CBD displayed significantly increased *C. acnes* lytic activity compared to the native CLC1 protein.
Figure 9C:
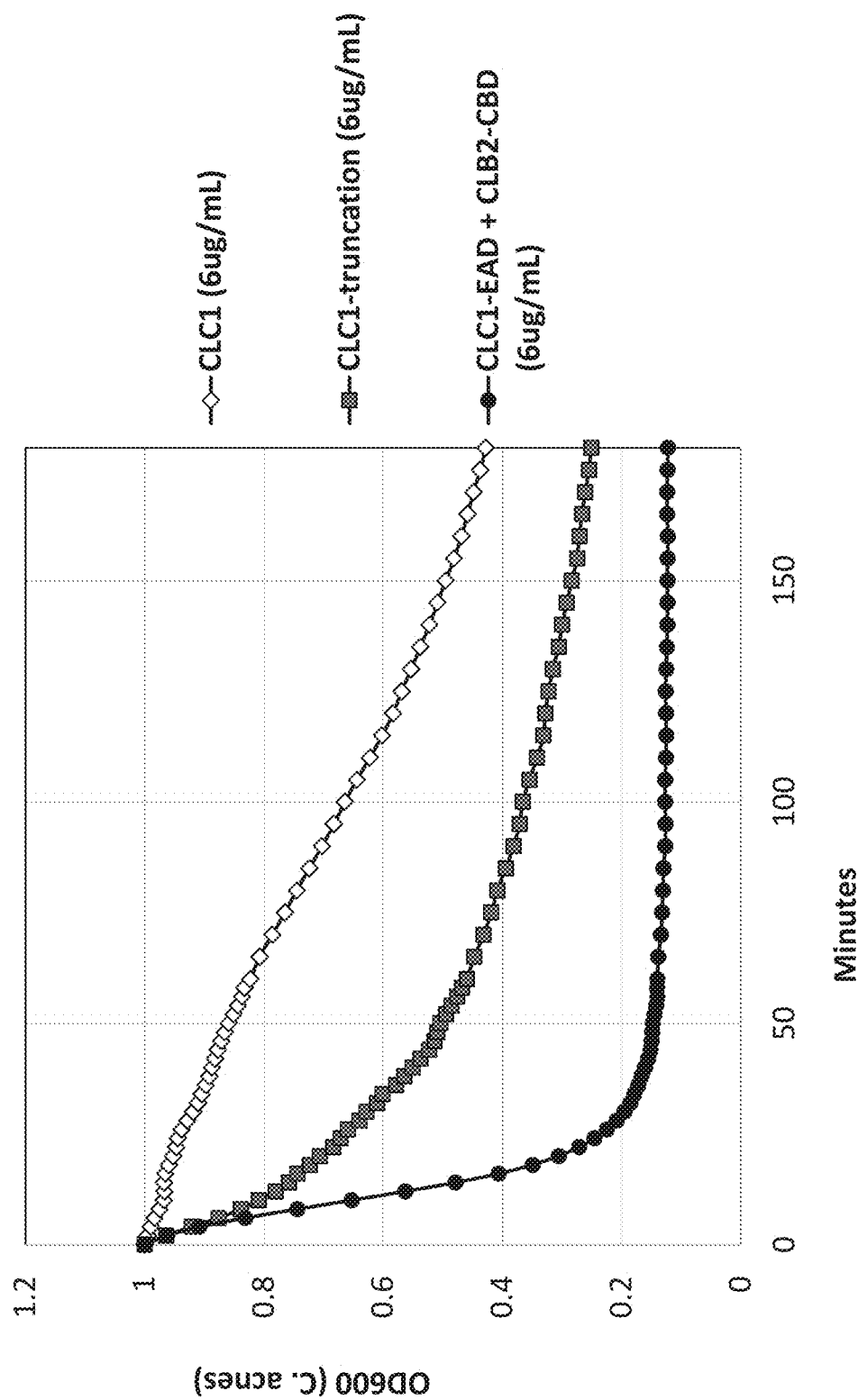
FIG. 9C is a chart of turbidity reduction assay results showing that the CLC1 EAD+CLB2 CBD chimera displayed significantly increased *C. acnes* lytic activity compared to the native CLC1 protein and the CLC1-truncation.

These 8 chimeric proteins were expressed, purified and tested in a turbidity reduction assay. As shown in FIG. 9A and FIG. 9B, native CLC1 protein was compared with chimeric proteins where the CLC1 EAD was linked to the different candidate CBDs (CLC1-EAD+CLB1-CBD, CLC1-EAD+CLB2-CBD, CLC1-EAD+CLB3-CBD, and CLC1-EAD+CLB4-CBD). The results show that all four chimeric proteins demonstrated higher *C. acnes* lytic activity in a turbidity reduction assay compared to the native, full-length CLC1 protein. These data indicate that chimeric cell wall hydrolases comprising the EAD of CLC1 in combination with the CBDs of CLB1-CLB4 can bind and recognize *C. acnes* and exhibit increased activity against *C. acnes* compared to native CLC1. In a further turbidity reduction assay, it was also demonstrated that the CLC1-EAD+CLB2-CBD chimera outperformed both full length CLC1 and the higher activity CLC1-truncation in terms of anti-*C. acnes* lytic activity (FIG. 9C).

Figure 10A:
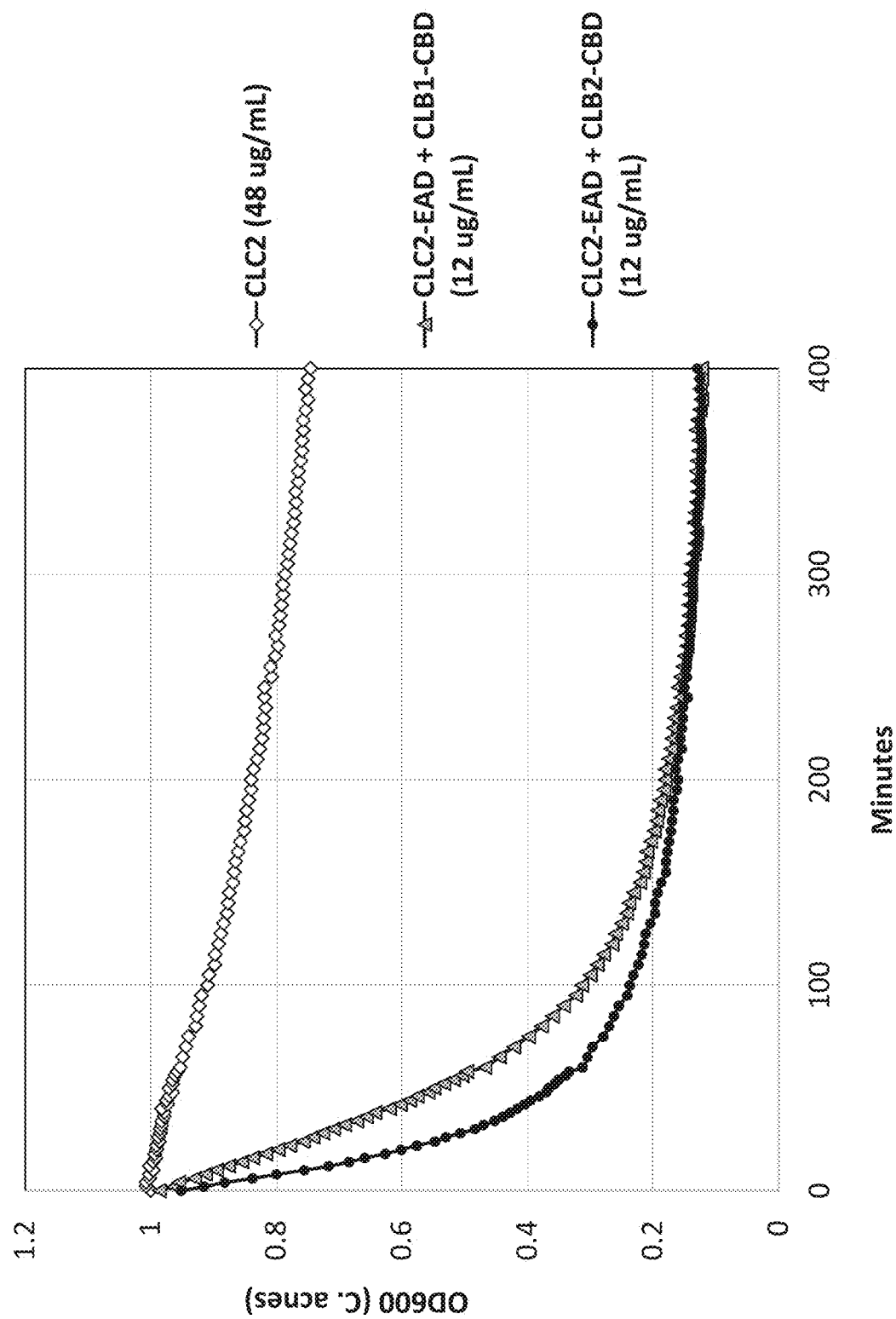
FIG. 10A is a chart of turbidity reduction assay results showing that chimeric proteins linking the CLC2 EAD with the CLB1 CBD and the CLB2 CBD displayed significantly increased *C. acnes* lytic activity compared to the native CLC2 protein.
Figure 10B:
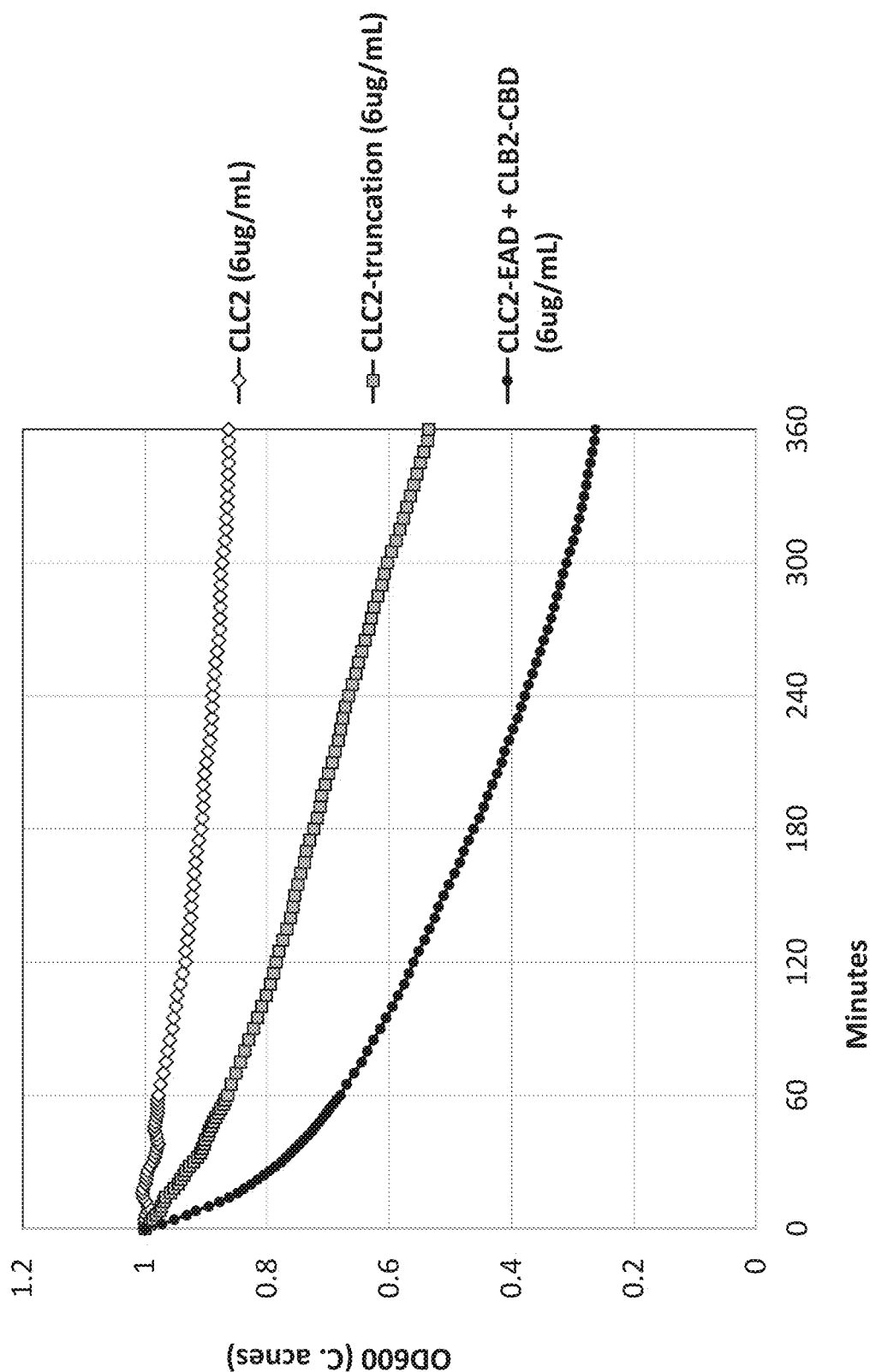
FIG. 10B is a chart of turbidity reduction assay results showing that the CLC2 EAD+CLB2 CBD chimera displayed significantly increased *C. acnes* lytic activity compared to the native CLC2 protein and the CLC2-truncation.
Figure 11A:
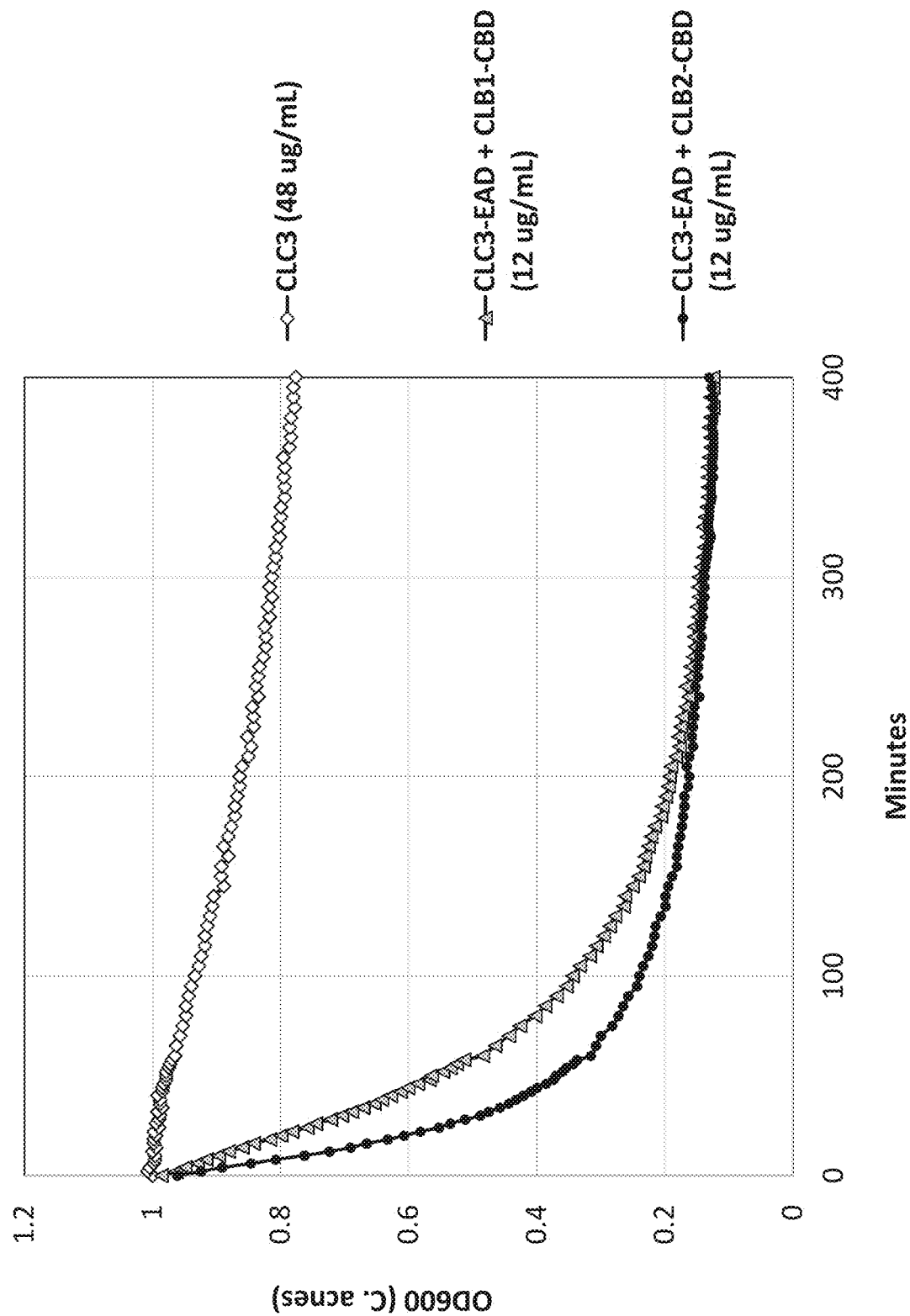
FIG. 11A is a chart of turbidity reduction assay results showing that chimeric proteins linking the CLC3 EAD with the CLB1 CBD and the CLB2 CBD displayed significantly increased *C. acnes* lytic activity compared to the native CLC3 protein.
Figure 11B:
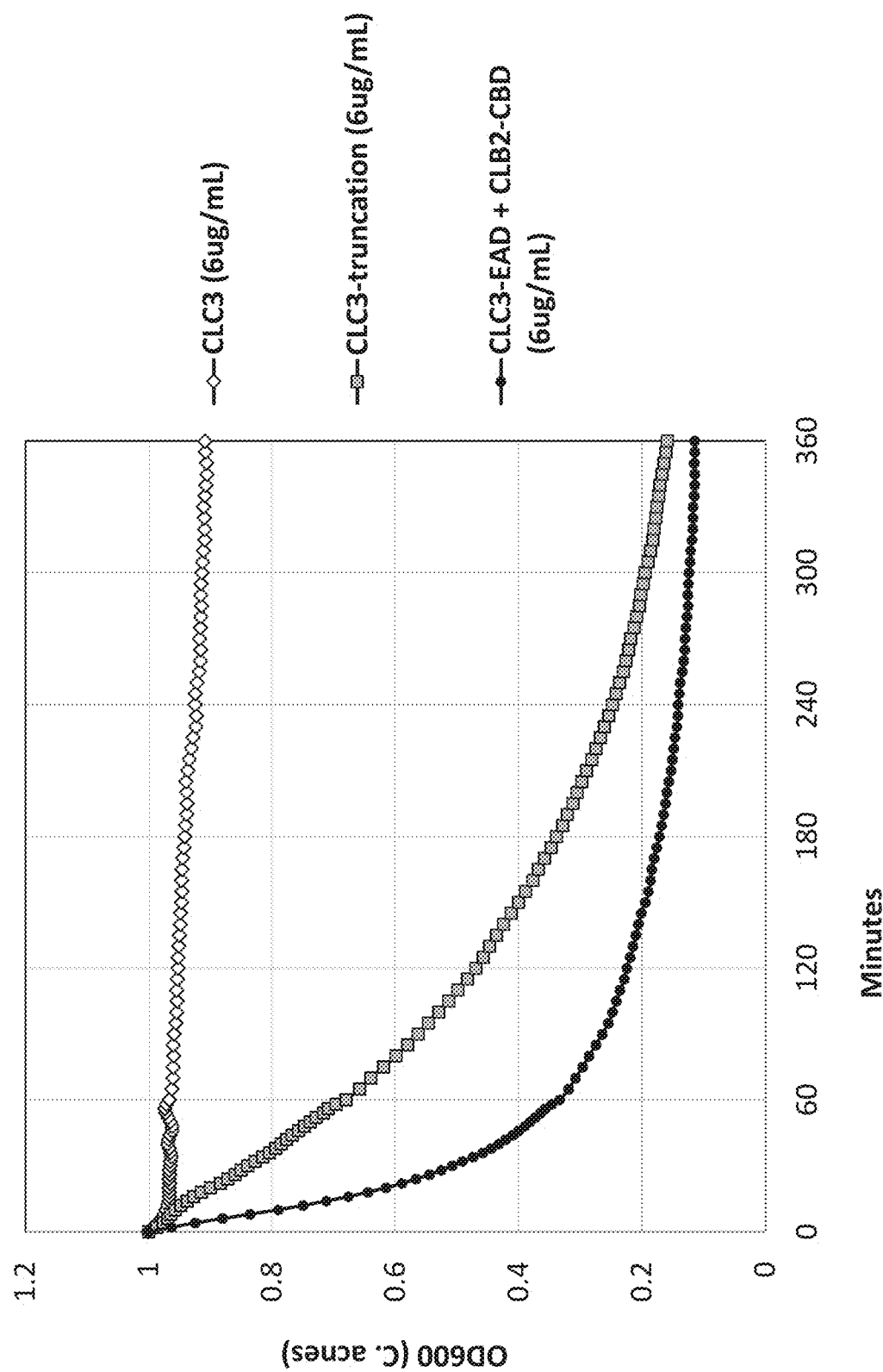
FIG. 11B is a chart of turbidity reduction assay results showing that the CLC3 EAD+CLB2 CBD chimera displayed significantly increased *C. acnes* lytic activity compared to the native CLC3 protein and the CLC3-truncation.

FIG. 10A and FIG. 11A show the results of lytic assays comparing the CLC2 and CLC3 native proteins with the CLC2-EAD chimeras (CLC2-EAD+CLB1-CBD and CLC2-EAD+CLB2-CBD) and CLC3-EAD chimeras (CLC3-EAD+CLB1-CBD and CLC3-EAD+CLB2-CBD). Full-length CLC2 and CLC3 both displayed relatively low *C. acnes* lytic activity. Linking either the CLB1 CBD or the CLB2 CBD to the CLC2 or CLC3 EAD resulted in a dramatic increase in lytic activity compared to native CLC2 or CLC3, similar to the results observed for CLC1. In a further turbidity reduction assay, it was also demonstrated that the CLC2-EAD+CLB2-CBD chimera outperformed both full length CLC2 and the higher activity CLC2-truncation (FIG. 10B). The CLC3-EAD+CLB2-CBD chimera similarly exhibited improved lytic activity compared to both full length CLC3 and the higher activity CLC3-truncation (FIG. 11B).

Example 9: Chimeric Proteins Comprising CLC1-Family EADs and CW_7 CBDs Display Lytic Activity Across a Broad Range of pH Values The enzymatic properties of two CLC1 EAD chimeric proteins (CLC1-EAD+CLB1-CBD and CLC1-EAD+CLB2-CBD) and two CLC3 EAD chimeric proteins (CLC3-EAD+CLB1-CBD and CLC3-EAD+CLB2-CBD) were further characterized at different pH levels.

Figure 12:
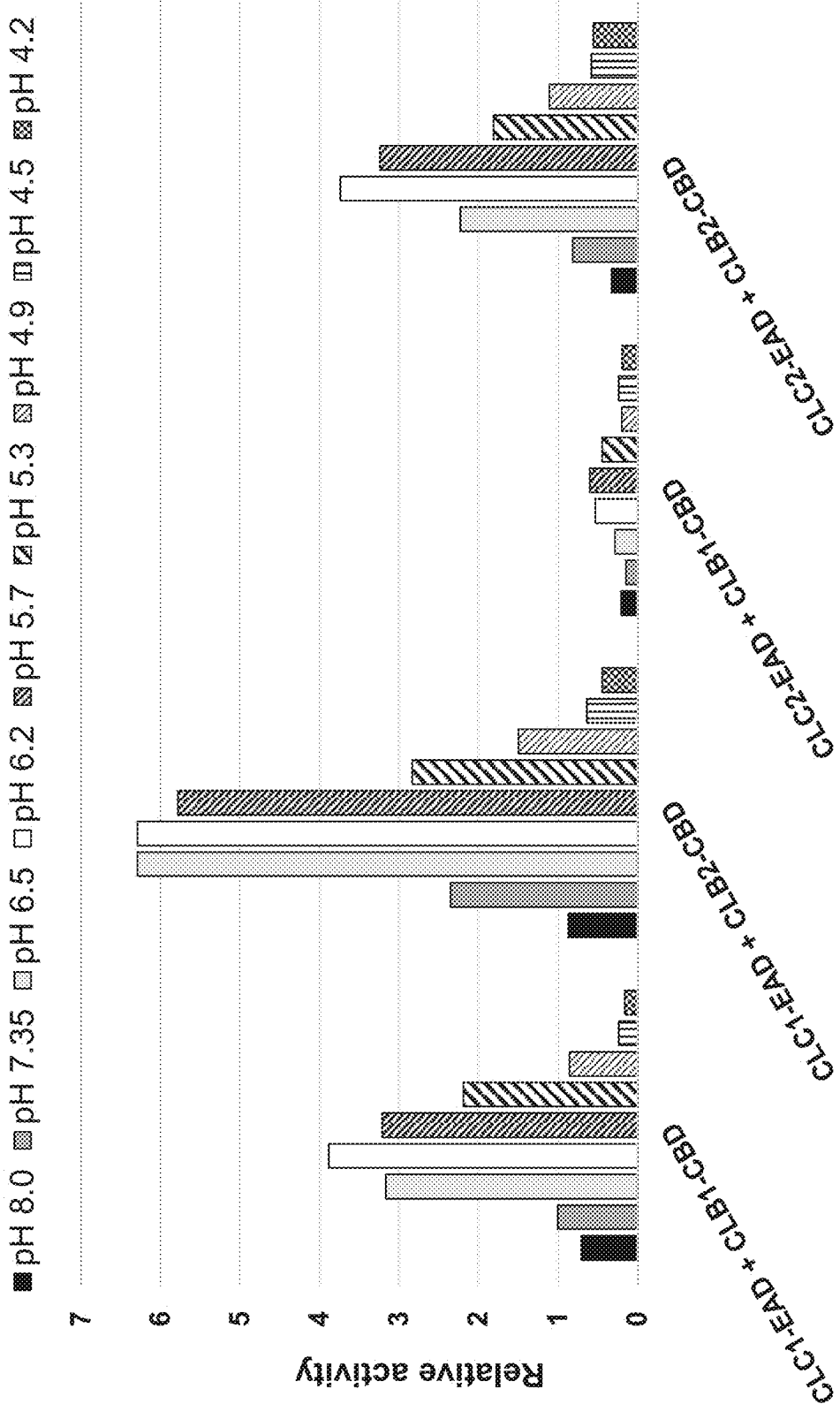
FIG. 12 is a chart showing that the indicated four chimeric proteins are active across a broad range of pH with peak activity at pH~6.
Figure 13A:
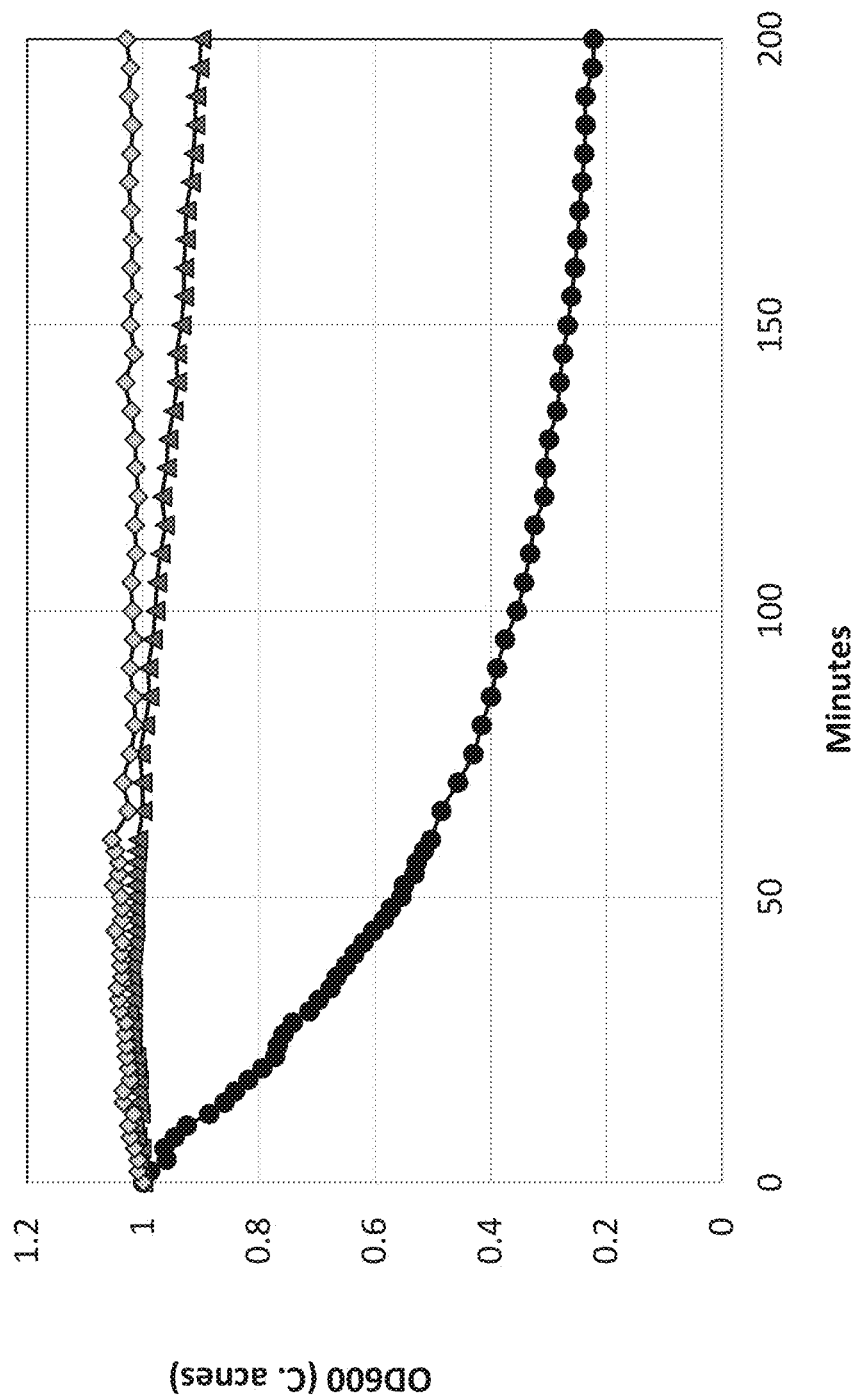
Figure 13B:
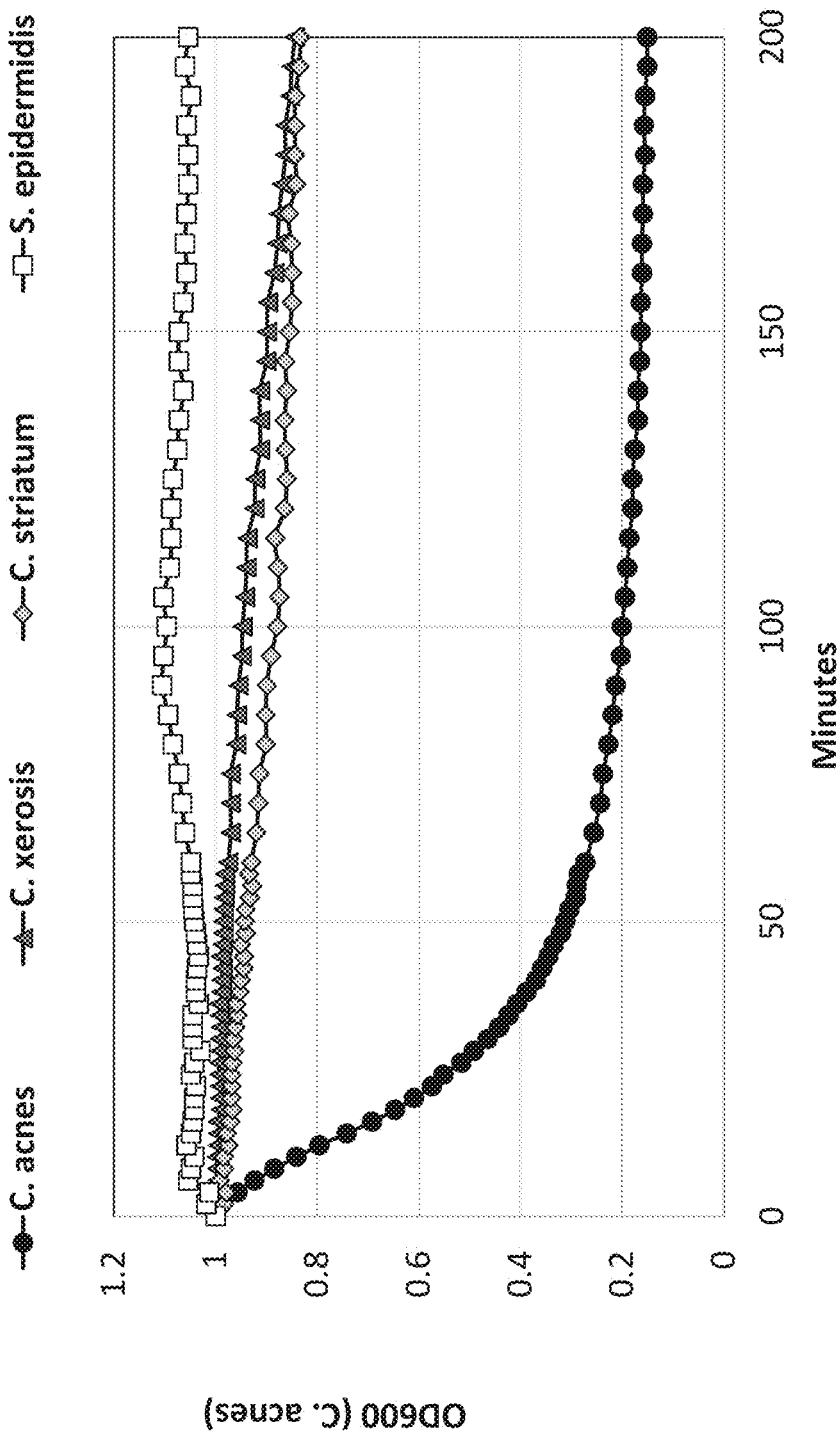
Figure 14C:
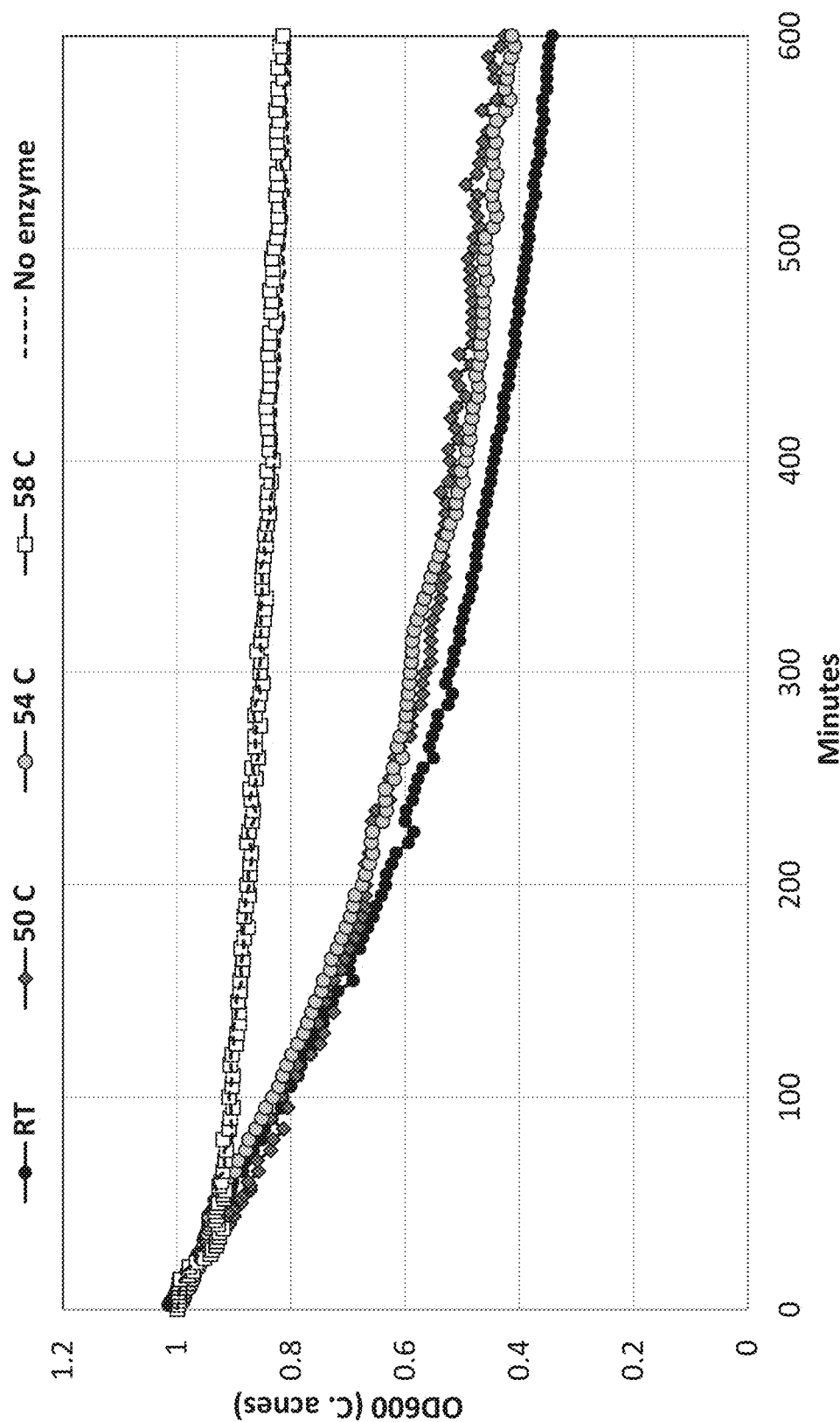

The activity of enzymes can be affected by pH. For commercial applications, it is important that an enzyme is functional at the relevant pH for that application. For example, in the case of a topical skin application, the normal pH of healthy skin is slightly acidic (~pH 5-6). In addition, many topical skin products are formulated to be slightly acidic. Thus, an enzyme that is to be used in these types of applications ideally should be functional at pH 5-6. The well-conserved *C. acnes* endolysin CaLys1, however, has been reported to have peak activity at pH 7 (see WO 2021/175606). Four chimeras of the present application were tested in the turbidity reduction assay at a range of pH 4.2-pH 8.0: CLC1-EAD+CLB1-CBD, CLC1-EAD+CLB2-CBD, CLC2-EAD+CLB1-CBD, and CLC2-EAD+CLB2-CBD. Surprisingly, all four enzymes demonstrated peak lytic activity at pH~6.0 (FIG. 12). Activity was increased approximately 3-fold at pH~6 compared to pH~7.3. Furthermore, the enzymes were active across a very broad range of pH, including the highest pH (8.0) as well as at the lowest pH (4.2) that were tested in this study.

Example 10: Chimeric Proteins Comprising CLC1-Family EADs and CW_7 CBDs Display Strong Selectivity for *C. acnes*

Four chimeric enzymes were tested for genus selectivity: CLC1-EAD+CLB1-CBD, CLC1-EAD+CLB2-CBD, CLC3-EAD+CLB1-CBD, and CLC3-EAD+CLB2-CBD. In particular, these four chimeras were tested for activity on commensal skin bacteria from other genera including *Corynebacterium xerosis*, *Corynebacterium striatum*, and *Staphylococcus epidermidis* using a turbidity reduction assay. In all four cases, strong lytic activity was observed against *C. acnes*, but none of the other commensal skin bacteria tested, demonstrating that these chimeric proteins have the ability to lyse target bacteria relevant for *acnes vulgaris* without damaging important commensal skin bacteria (FIG. 13A-13D).

Example 11: Chimeric Proteins Comprising CLC1-Family EADs and CW_7 CBDs Display Significant Thermostability Thermostability is an important factor in commercial applications. The thermostability of these chimeric enzymes was tested by incubating aliquots of proteins for 30 min at a range of temperatures and then measuring the remaining lytic activity in the aliquot in the turbidity reduction assay at room temperature (FIG. 14A-14D). The results showed that the CLC1-EAD+CLB1-CBD chimera retained activity until incubation at 50° C. The CLC1-EAD+CLB2-CBD chimera demonstrated higher thermostability, retaining some activity until incubation at 54° C. The two CLC3 EAD chimeric enzymes displayed even higher thermostability, with the CLC3-EAD+CLB1-CBD chimera retaining activity until incubation at 58° C. and the CLC3-EAD+CLB2-CBD chimera retaining some activity even at the highest temperature tested (58° C.).

Figure 15:
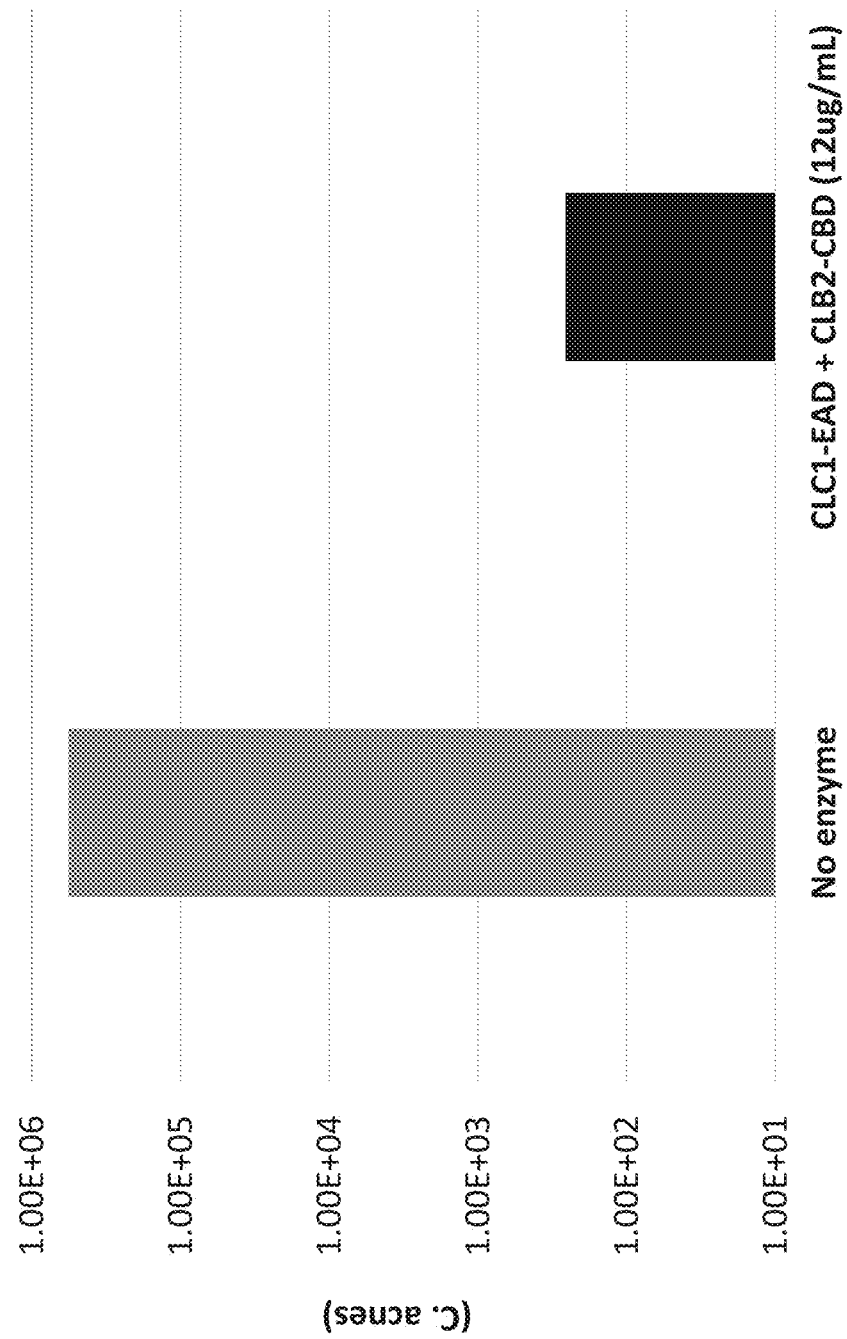
FIG. 15 is a chart showing the CFU of *C. acnes* cells under indicated conditions in a quantitative killing assay. Six-hour incubation with CLC1-EAD+CLB1-CBD resulted in >3 orders of magnitude decrease in viable *C. acnes* cells.

Example 12: Quantitative Killing Assay Demonstrates Significant *C. acnes* Lytic Activity by the CLC1-EAD+CLB1-CBD Chimera The turbidity reduction assay measures lysis of *C. acnes* through an observed decrease in optical density. A more direct method to measure antibacterial activity is to use a quantitative killing assay. In this assay, antibacterial activity is measured via the decrease in viable cells after incubation with an enzyme. Specifically, ~1×10⁶ *C. acnes* cells were incubated with and without the enzyme being tested for 2-6 hours, at which point serial dilutions of the mix are plated on BHI agar plates and CFU are quantified. The CLC1-EAD+CLB1-CBD chimera was tested in this assay. The result shows that the number of viable C. acnes cells were reduced by 3 orders of magnitude after a 6-hour incubation (FIG. 15).

Example 13: Chimeric CWHs Comprising the Broader CLC1 Family of EADs in Combination with CLB2 CBD Exhibit Lytic Activity Against C. acnes To test the activity level of the broader CLC1-family of amidase proteins and their ability to function as components of chimeric cell wall hydrolases, chimeric enzymes were constructed by linking the CLC4-CLC17 EADs to the CLB2 CBD. The CLC18 EAD and the CLC19 EAD have identical amino acid sequences to the CLC13 EAD and were thus not separately included.

Figure 16A:
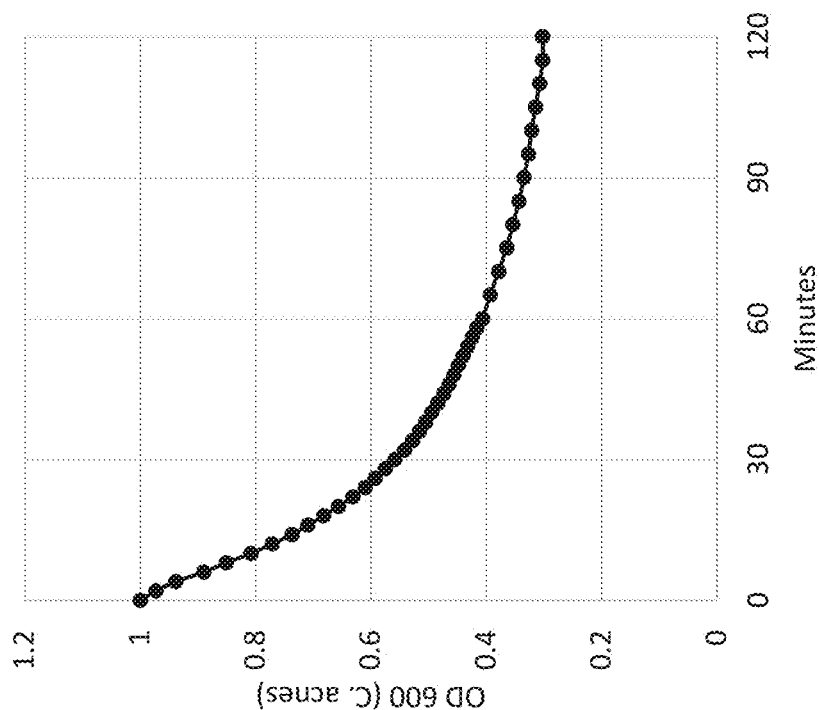
FIG. 16A-16F show the results of turbidity reduction assays against *C. acnes* for six chimeric proteins of the disclosure: CLC4-EAD+CLB2-CBD (FIG. 16A); CLC5-EAD+CLB2-CBD (FIG. 16B); CLC8-EAD+CLB2-CBD (FIG. 16C); CLC10-EAD+CLB2-CBD (FIG. 16D); CLC14-EAD+CLB2-CBD (FIG. 16E); and CLC16-EAD+CLB2-CBD (FIG. 16F).
Figure 16B:
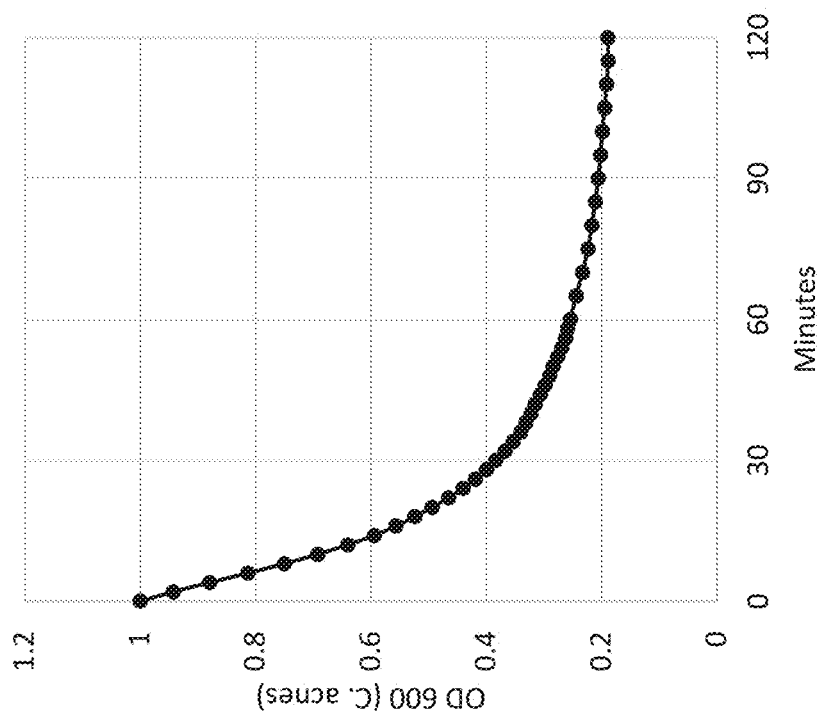
Figure 16D:
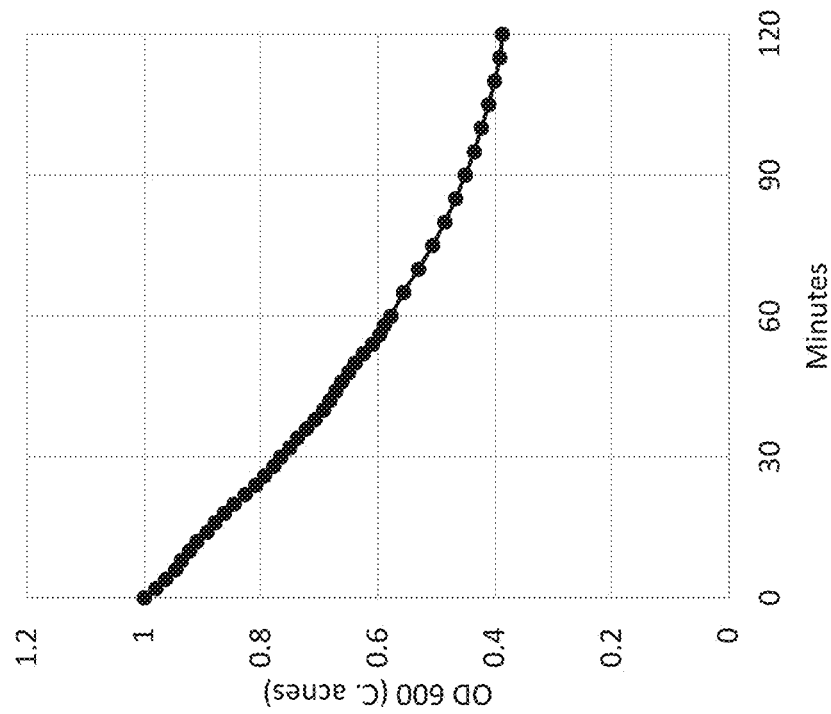
Figure 16C:
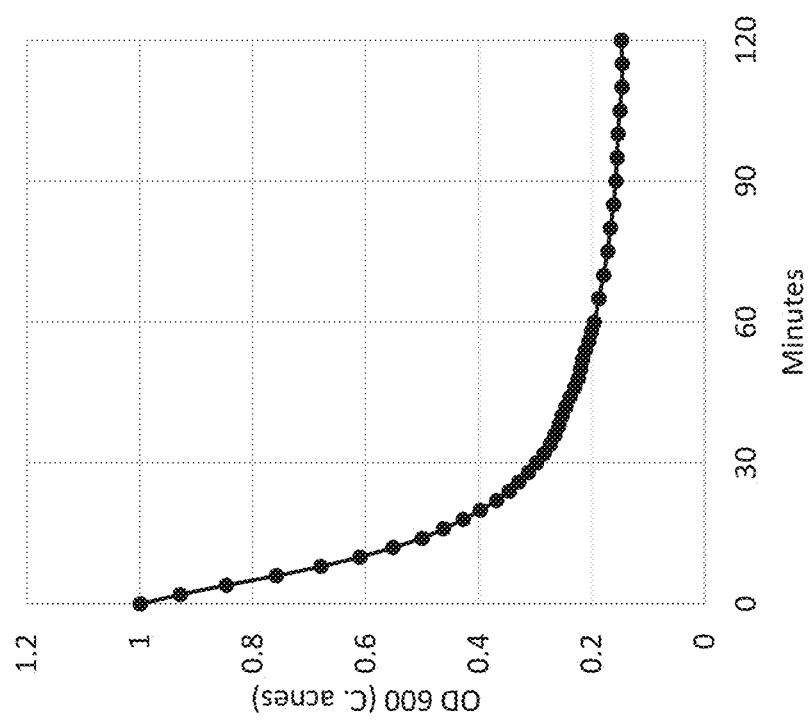
Figure 16E:
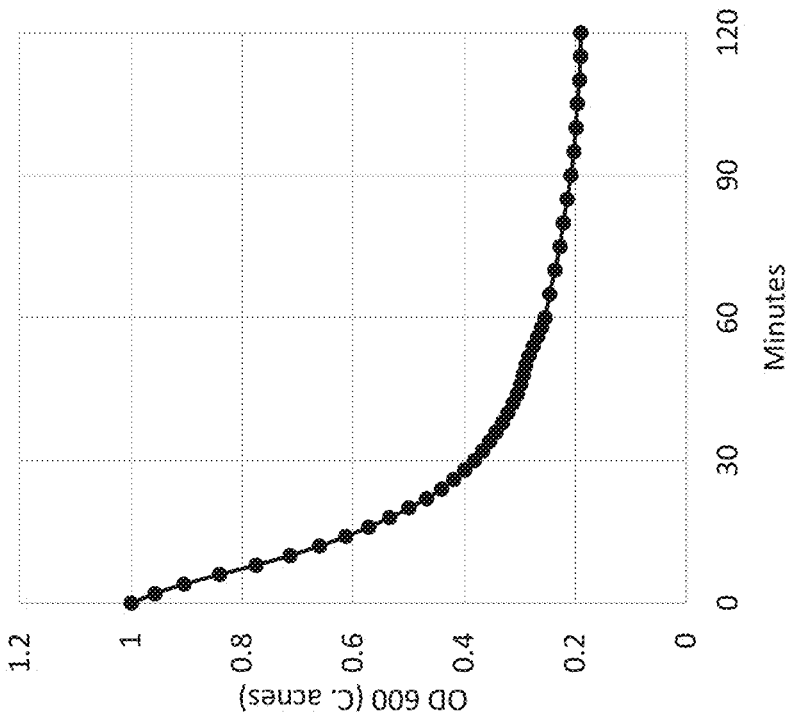
Figure 16F:
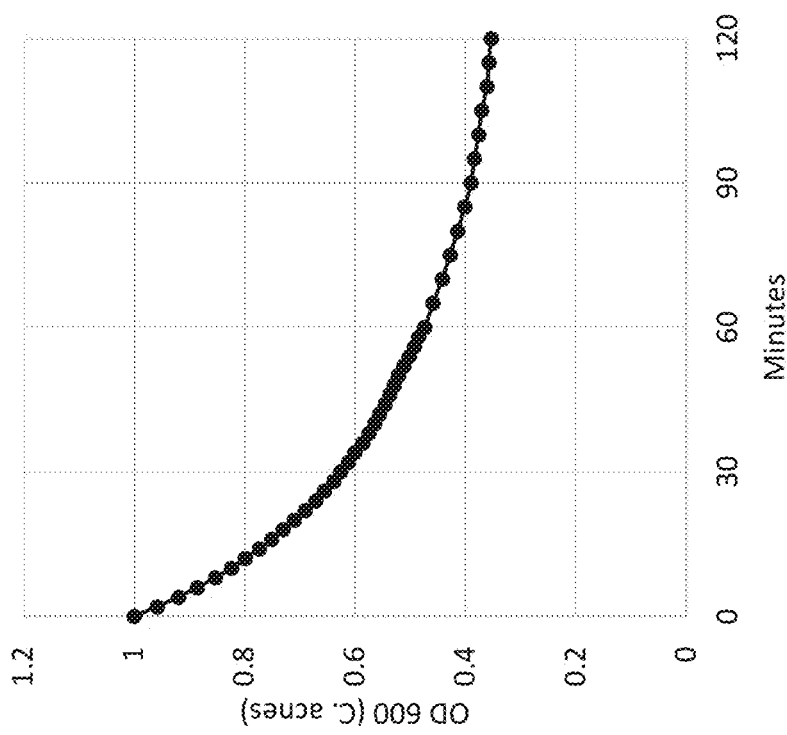
Figure 16G:
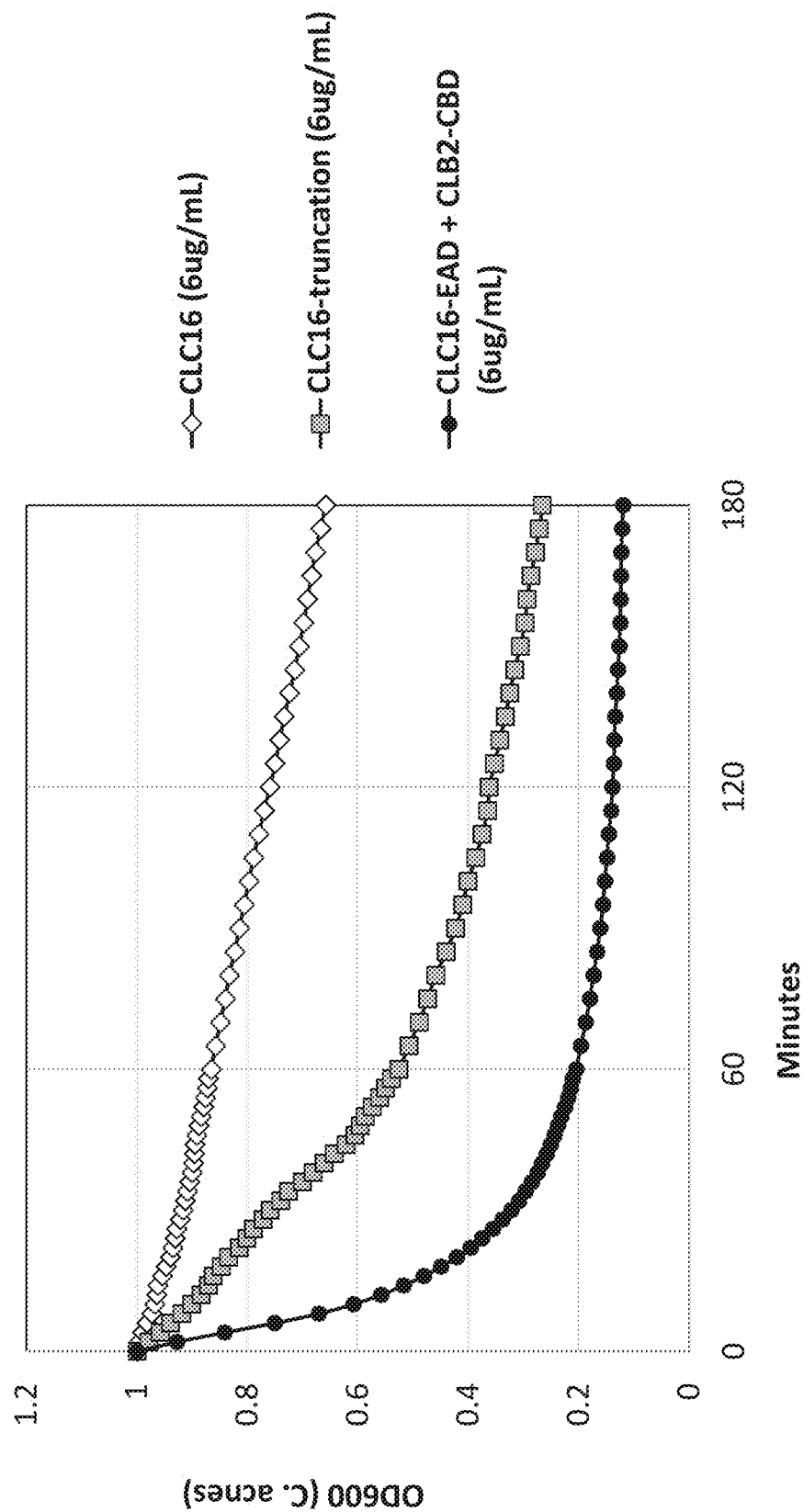
FIG. 16G shows turbidity reduction assay results for the CLC16-EAD+CLB2-CBD chimera in comparison with full length CLC16 and CLC16-truncation.

Expression vectors containing the cloned CLC1-family EAD+CLB2 CBD chimeric CWHs were transformed into BL21 E. coli cells. Protein expression was induced, and cell lysate was isolated for each chimeric enzyme. These cell lysates were tested for lytic activity against C. acnes using a clearing/halo assay. In this assay, six of the tested lysates generated a significant clearing indicative of C. acnes lytic activity. These lysates comprised chimeric CWHs comprising the CLB2 CBD in combination with the EAD from CLC4, CLC5, CLC8, CLC10, CLC14, or CLC16. To confirm these results, these chimeric proteins were purified and tested in a turbidity reduction assay (FIG. 16A-16F). Proteins were tested at 12 µg/mL. All six chimeric proteins showed strong lytic activity against C. acnes, confirming the results from the clearing assay. In a further turbidity reduction assay, it was also demonstrated that the CLC16-EAD+CLB2-CBD chimera outperformed both full-length CLC16 and the higher activity CLC16-truncation in terms of anti-C. acnes lytic activity (FIG. 16G).

These active CLC1-family EADs range from 77%-96% amino acid identity with each other (FIG. 17) and demonstrate the utility of the broader CLC1-family of proteins as sources of highly active EADs that can target C. acnes.

Example 14: Chimeric CWHs Comprising CLC1-Family EADs and CLB2 CBD Exhibit Significant Thermostability The thermostability of chimeric proteins comprising CLC1-family EADs was characterized. The thermostability of the proteins was measured by incubating aliquots of purified chimeric protein for 30 minutes at the indicated temperatures. The lytic activity of the incubated enzyme was then measured using a turbidity reduction assay against C. acnes and calculated relative to activity after room temperature incubation.

Figure 18A:
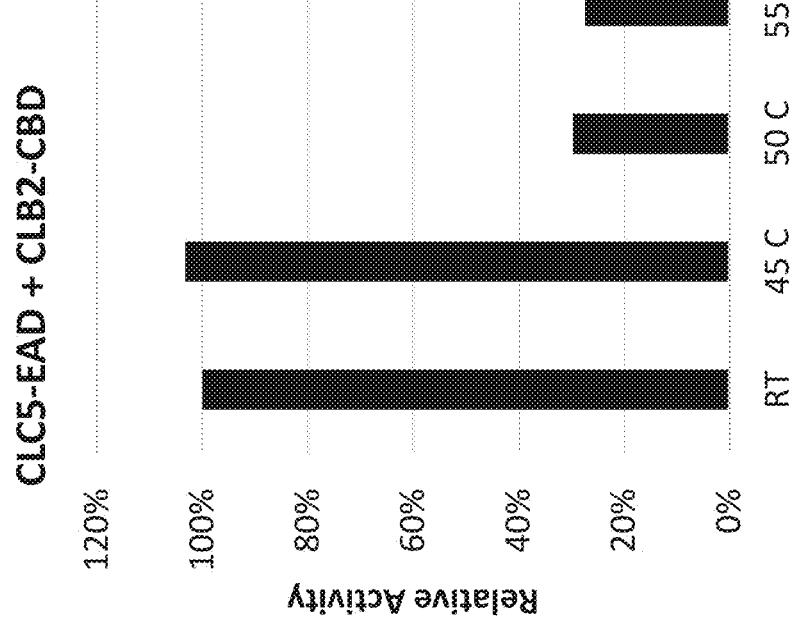
FIG. 18A-18F show the results of thermostability assays for six chimeric proteins of the disclosure: CLC4-EAD+CLB2-CBD (FIG. 18A); CLC5-EAD+CLB2-CBD (FIG. 18B); CLC8-EAD+CLB2-CBD (FIG. 18C); CLC10-EAD+CLB2-CBD (FIG. 18D); CLC14-EAD+CLB2-CBD (FIG. 18E); and CLC16-EAD+CLB2-CBD (FIG. 18F).
Figure 18B:
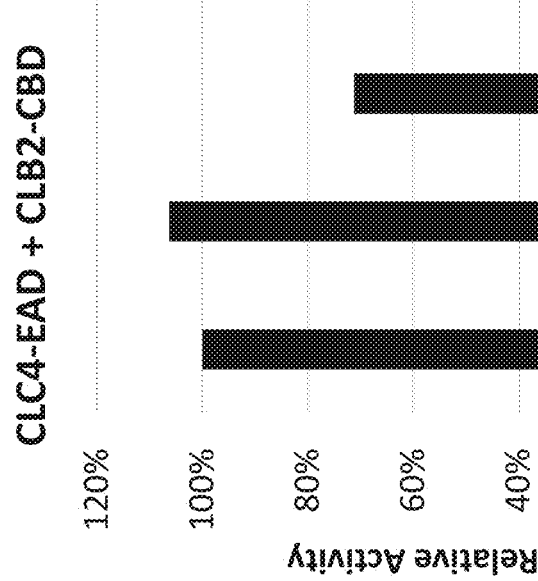
Figure 18C:
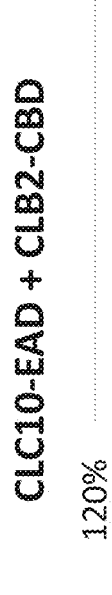
Figure 18D:
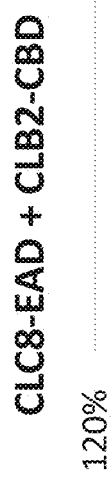
Figure 18E:
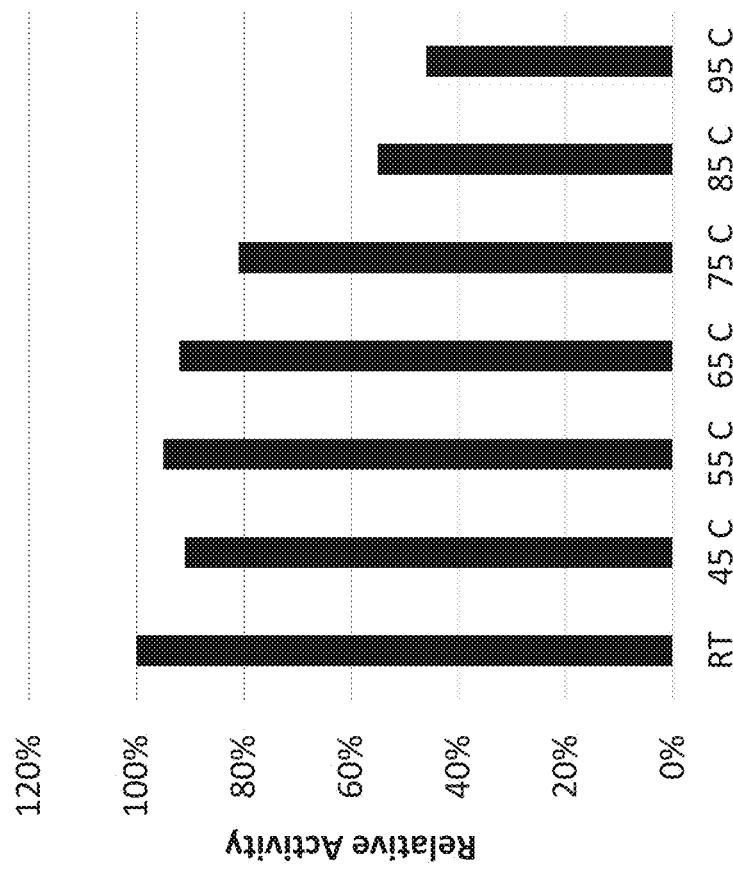
Figure 18F:
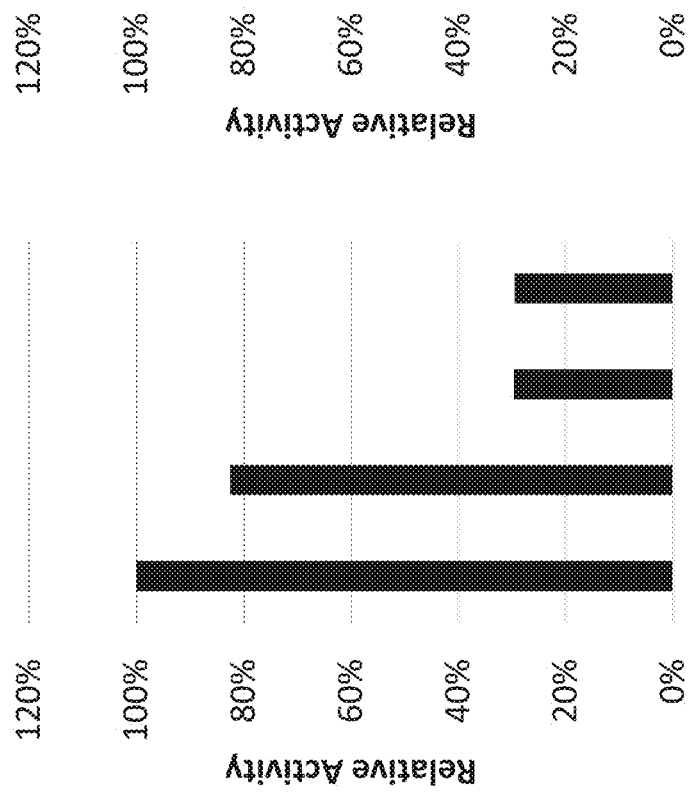

Results are shown in FIG. 18A-18F. All six proteins retained significant activity after exposure to 45° C. Chimeric CWHs comprising the EAD from CLC4, CLC5, CLC8, CLC10, and CLC14 demonstrated loss of activity after 30-minute incubation between 50° C.-55° C., similar to the CLC1-EAD, CLC2-EAD, and CLC3-EAD chimeric proteins. Surprisingly, the CLC16-EAD+CLB2-CBD chimeric protein showed extraordinary thermostability, retaining greater than 80% activity after a 30 minute incubation at 75° C., and retaining greater than 40% activity even after 30 minutes incubation at 95° C. (FIG. 18F).

Figure 19:
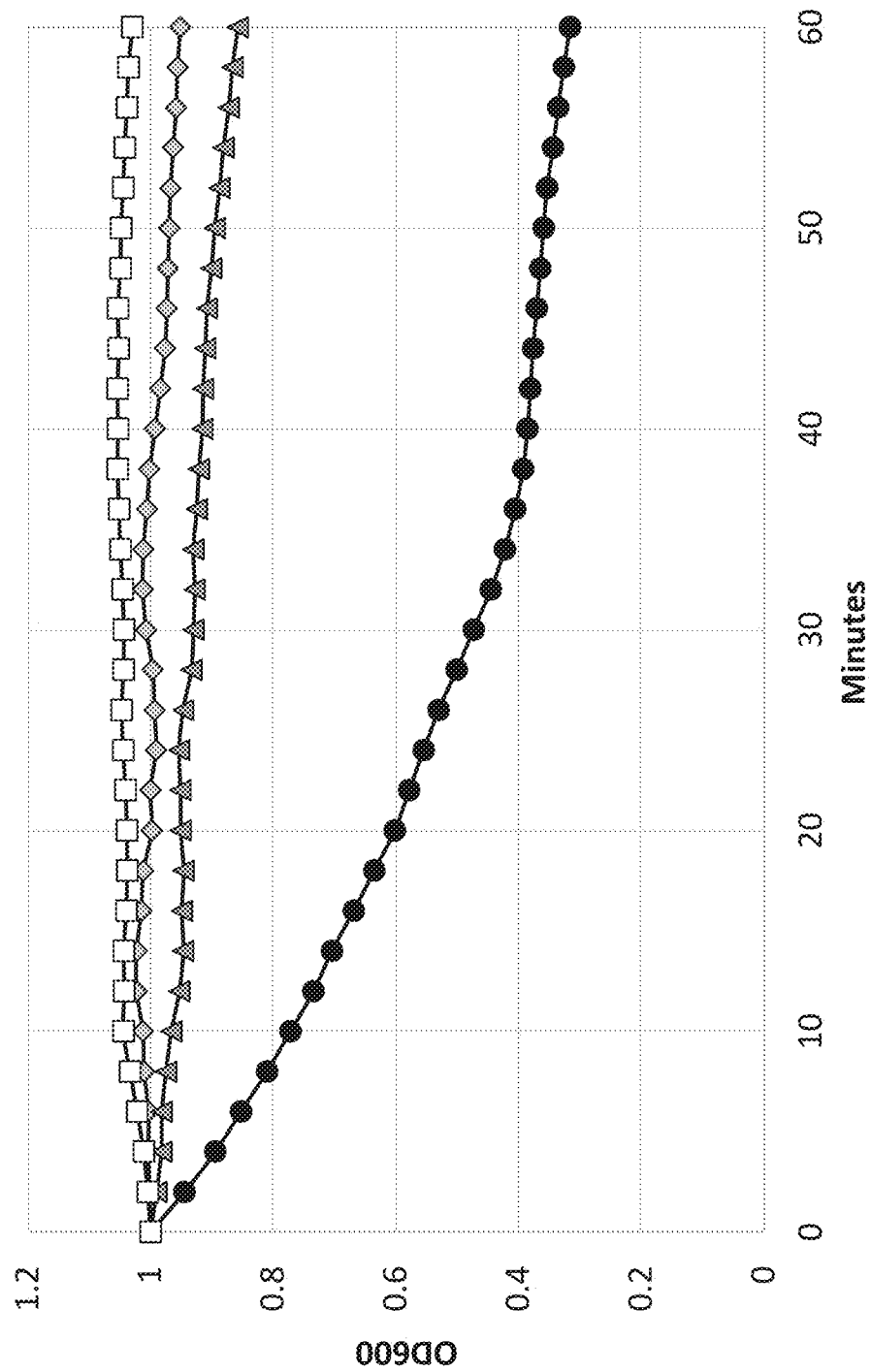
FIG. 19 shows the results of turbidity reduction assays against *C. acnes* and three other commensal strains of bacteria for the CLC16-EAD+CLB2-CBD chimeric protein.
Figure 20B:
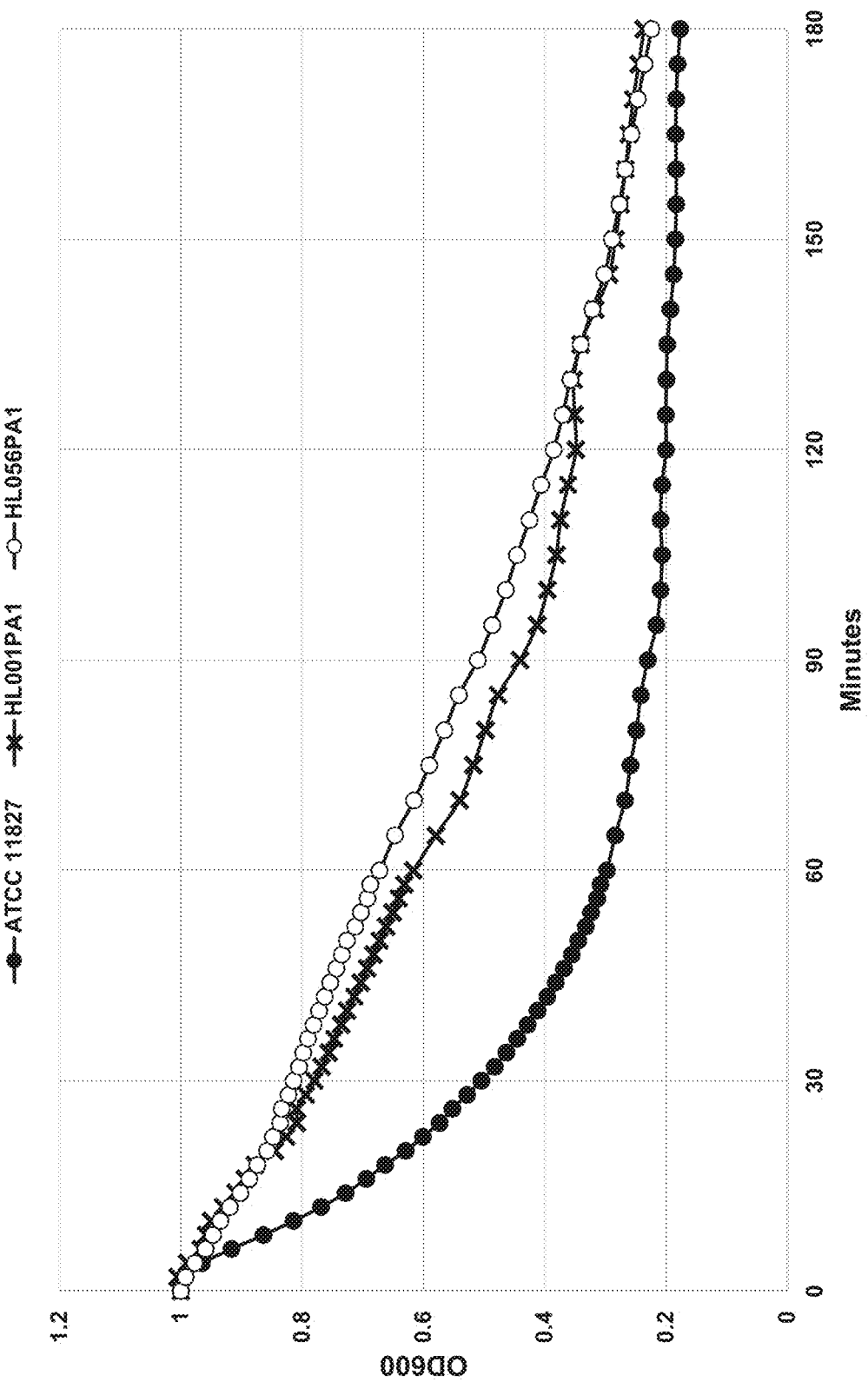
Figure 20C:
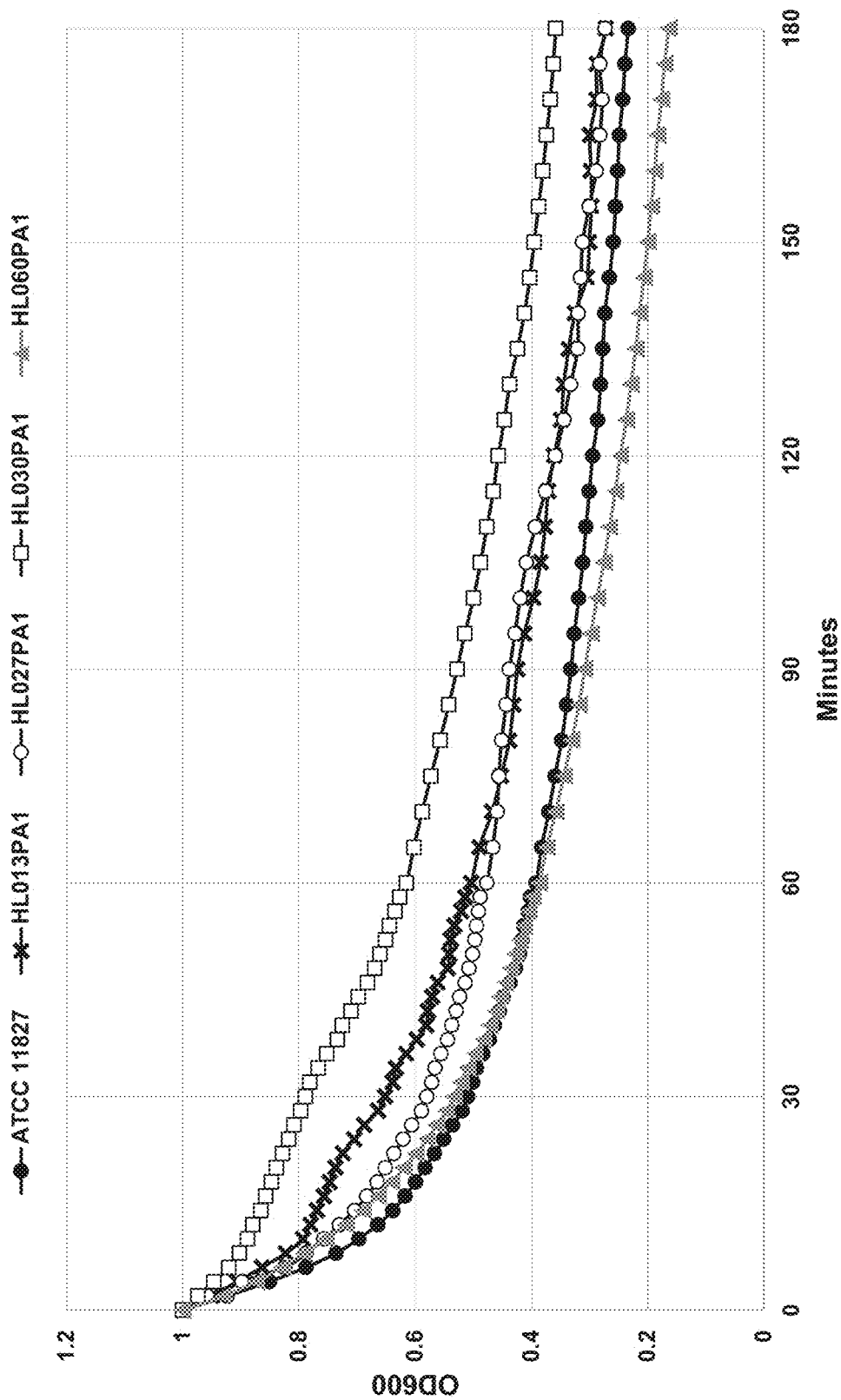
Figure 20D:
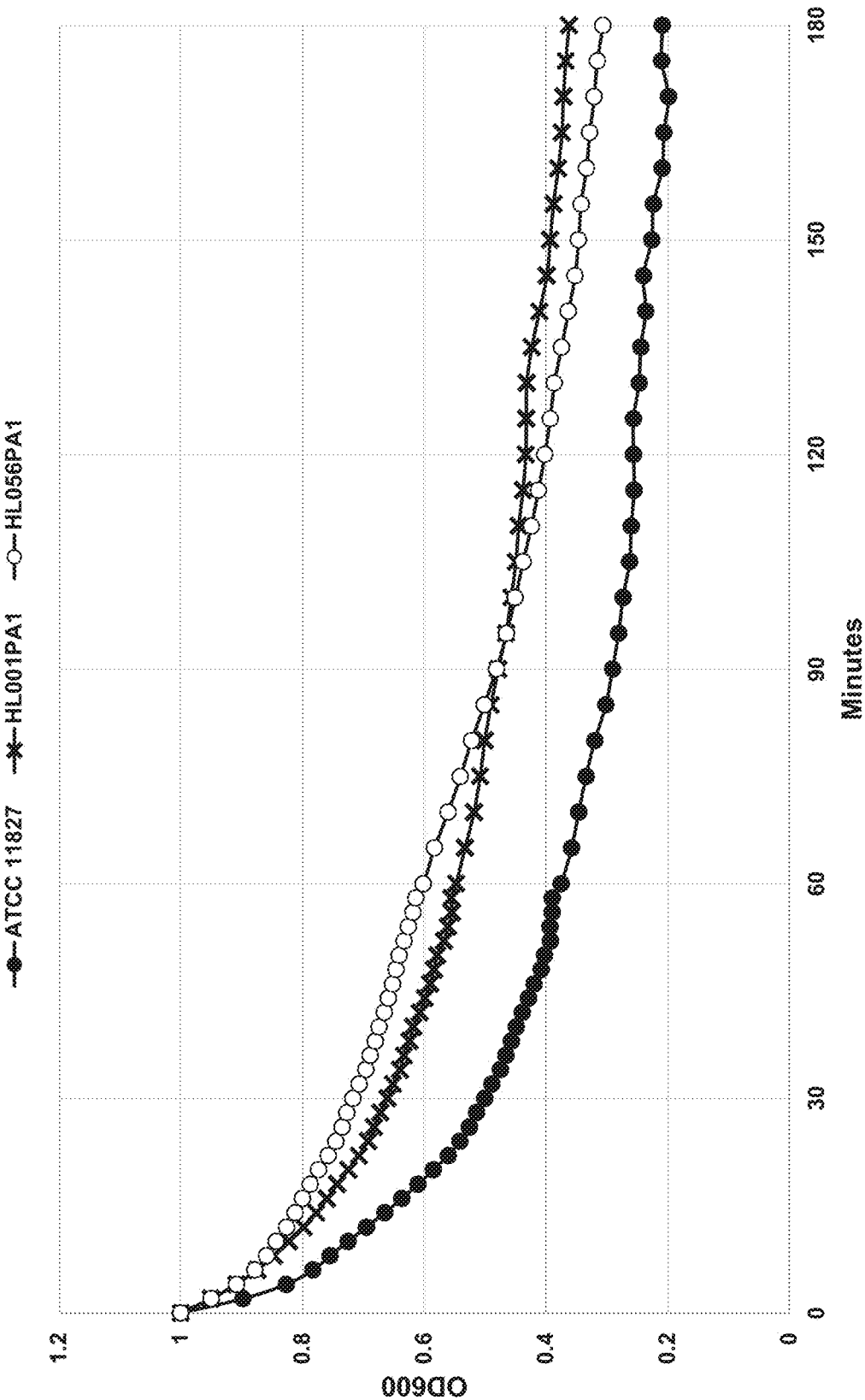

Example 15: CLC16 EAD+CLB2 CBD Chimera Exhibits Strong Selectivity for C. acnes Over Commensal Skin Bacteria The CLC16-EAD+CLB2-CBD chimeric CWH was tested for lytic activity against C. acnes and three commensal skin bacteria—C. xerosis, C. striatum, and S. epidermidis—in a turbidity reduction assay. The CLC16-EAD+CLB2-CBD chimeric CWH showed strong, selective activity for C. acnes over the three other bacteria (FIG. 19).

Example 16: CLC1-EAD+CLB2-CBD and CLC16-EAD+CLB2-CBD Chimeric Enzymes are Active Against a Broad Panel of *Cutibacterium acnes* Strains and Phylotypes C. acnes strains can be categorized into five major phylotypes (IA1, IA2, IB, II and III) based on phylogenetic analysis, such as the use of a multilocus sequence typing (MLST) scheme. See, e.g., McDowell et al., Plos One 2012; 7(7): e41480. Phylotypes IA1 and IA2 are most often associated with acne lesions.

To assess the activity of the CLC1-EAD+CLB2-CBD and CLC16-EAD+CLB2-CBD chimeric enzymes against different strains of C. acnes, these enzymes were tested in turbidity reduction assays against a panel of C. acnes strains from a variety of phylotypes (Table 12).

TABLE 12

| C. acnes strains and phylotypes. | |
|---|---|
| Strain | Phylotype |
| ATCC 11827 | IA1 |
| HL001PA1 (HM-488) | II |
| HL013PA1 (HM-497) | IA2 |
| HL027PA1 (HM-502) | IA2 |
| HL030PA1 (HM-504) | IB |
| HL056PA1 (HM-524) | IA1 |
| HL060PA1 (HM-527) | II |

Results are shown in FIG. 20A-20D. Both the CLC1-EAD+CLB2-CBD and CLC16-EAD+CLB2-CBD chimeric enzymes exhibited strong lytic activity against every tested C. acnes strain, indicating that these chimeric enzymes are active against a broad set of C. acnes strains and phylotypes.

Example 17: The CBD from CLB2 Increases the Enzymatic Activity of the CaLys1 EAD The well-conserved CaLys1 endolysin that is commonly found in C. acnes phage genomes has been characterized as having weak lytic activity, often requiring concentrations of greater than 100 mg/mL to see activity. This activity has also been observed to be largely non-specific, e.g., demonstrating similar levels of activity against S. aureus as against C. acnes. See Varotsou C et al., Int J Mol Sci 2023 May 10; 24(10):8523. In order to test whether the CLB2-CBD could improve the activity and specificity of the CaLys1-EAD, a CaLys1-EAD+CLB2-CBD chimeric CWH was generated. The CaLys1-EAD+CLB2-CBD chimeric CWH was expressed and purified, as well as the native CaLys1 protein. The lytic activity of the chimera was compared to the native protein in turbidity reduction assays against C. acnes, C. striatum, and S. aureus. These assays utilized a concentration of 12 µg/mL of each protein.

Figure 21B:
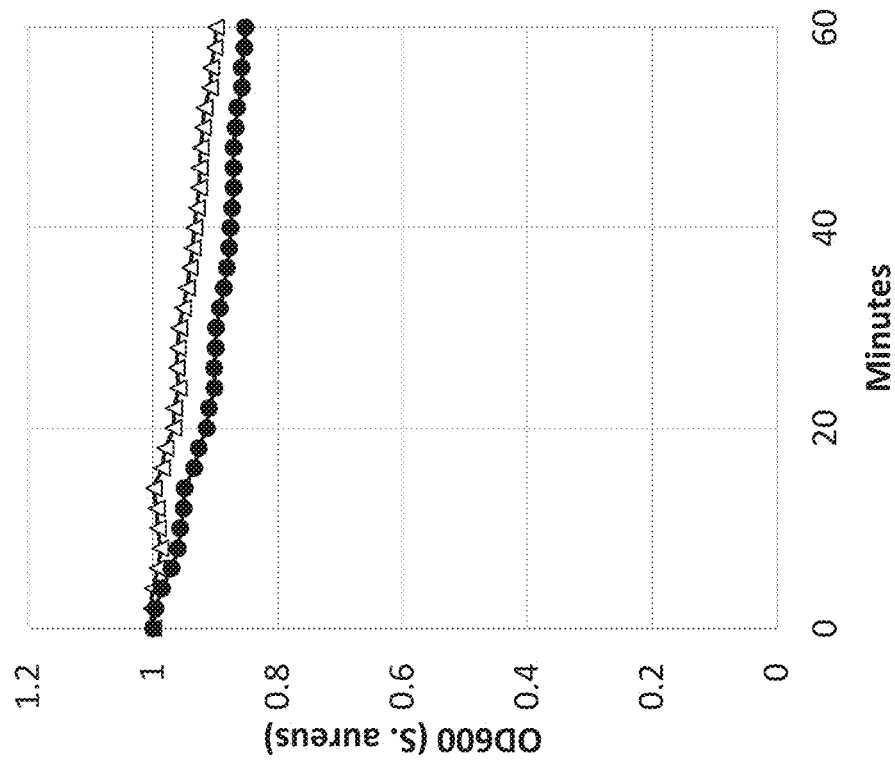
Figure 21C:
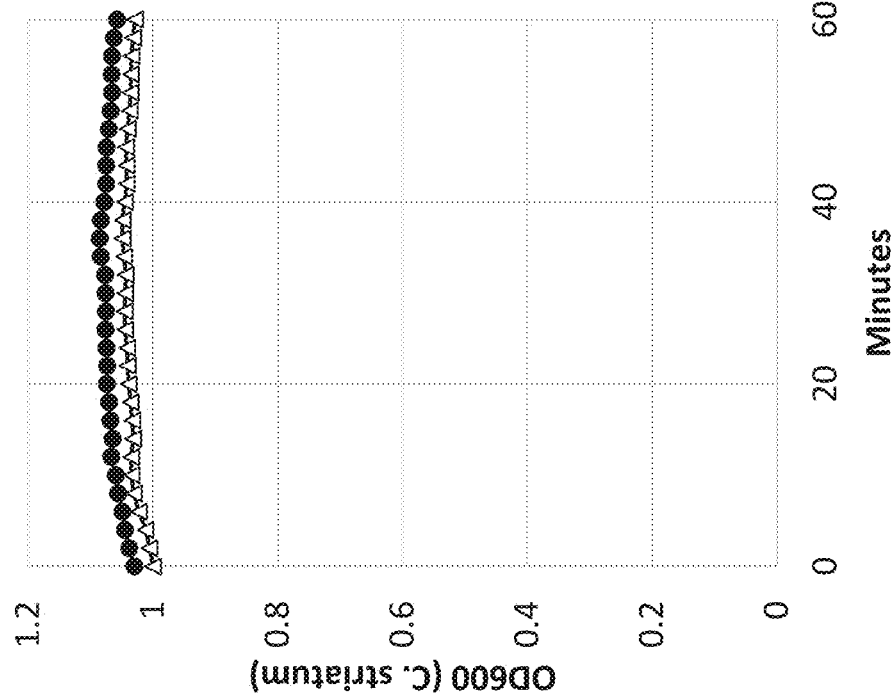
Figure 22:
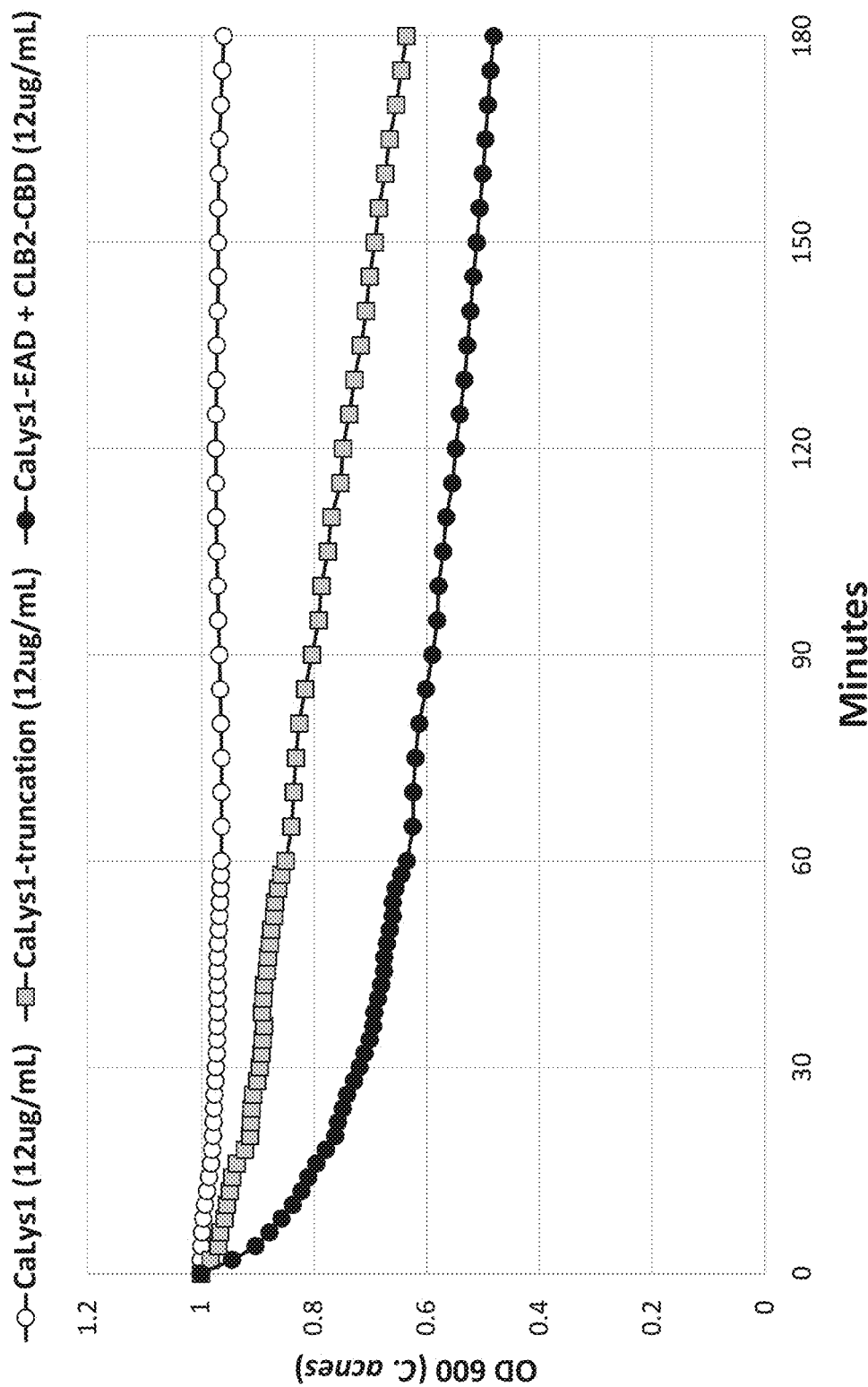
FIG. 22 shows the results of a turbidity reduction assay against *C. acnes* for full length CaLys1, the CaLys1-truncation, and the CaLys1-EAD+CLB2-CBD chimeric protein.

Results are shown in FIG. 21A-21C. At this low concentration, CaLys1 had no detectable lytic activity against any of the three bacteria. In contrast, the CaLys1-EAD+CLB2-CBD chimeric CWH showed strong lytic activity against *C. acnes* and no detectable lytic activity against *C. striatum* and *S. aureus*. These data demonstrate that a CBD derived from the CLB1-CLB4 proteins was able to increase the *C. acnes*-specific lytic activity of the canonical CaLys1 EAD in a chimeric CWH. While CaLys1 is reported to have equivalent lytic activity against *C. acnes* and other bacteria such as *S. aureus*, a chimeric CWH comprising the CLB2-CBD in combination with the CaLys1-EAD exhibited increased *C. acnes*-specific lytic activity without increasing *C. striatum* or *S. aureus* lytic activity. In a further turbidity reduction assay, it was also demonstrated that the CaLys1-EAD+CLB2-CBD chimera exhibited increased anti-*C. acnes* lytic activity compared to both full-length CaLys1 and the higher activity CaLys1-truncation (FIG. 22).

Figure 23B:
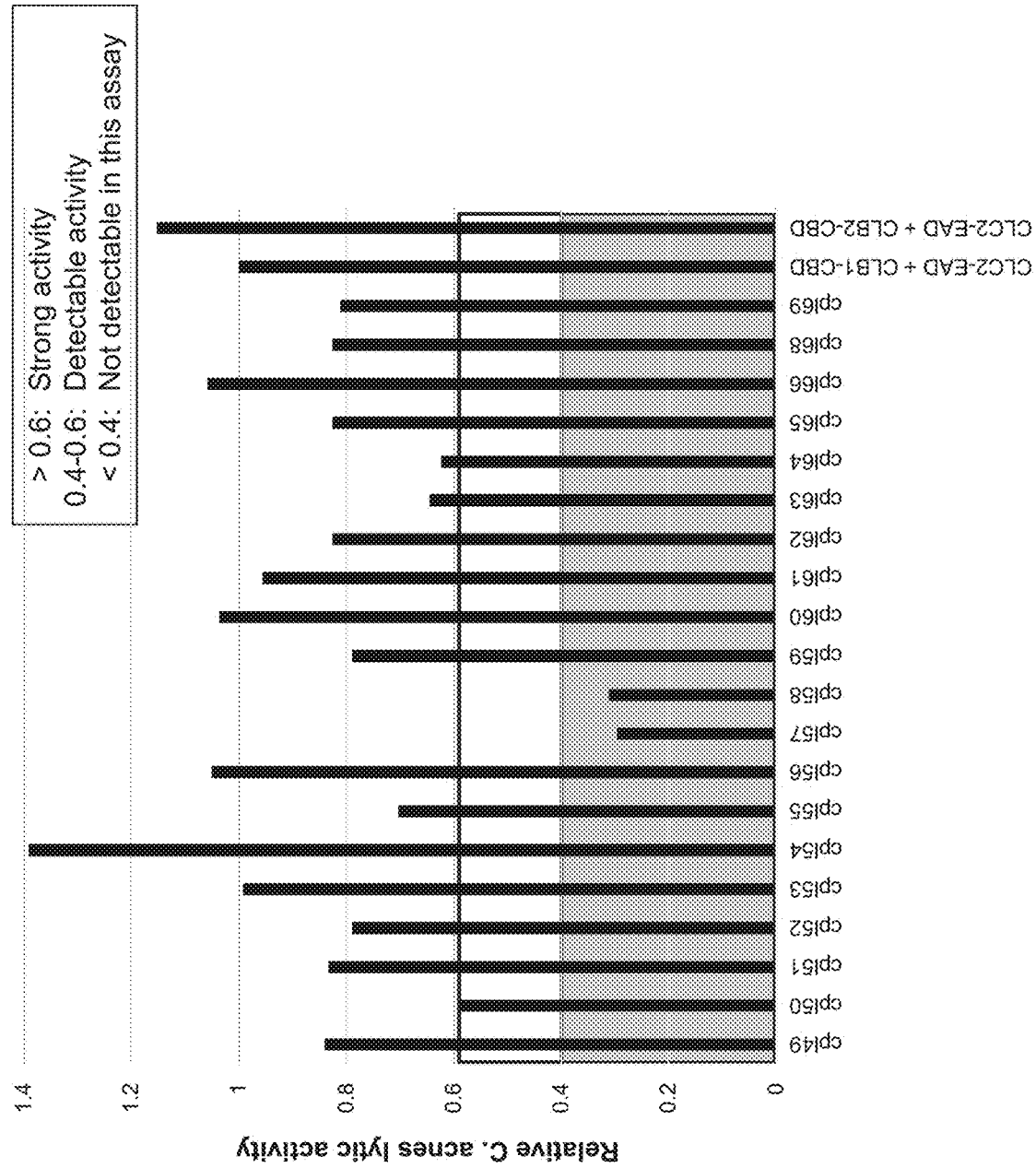
FIG. 23B shows the result of whole cell lysate screening of additional diverse CW_7 CBD comprising chimeras in a turbidity reduction assay.

Example 18: Diverse CW_7 Repeats are Able to Facilitate Binding and Lysis of *C. acnes* in Chimeric CWHs in Whole Cell Lysate Screen To test the ability of diverse CW_7-containing CBDs to target *C. acnes* in chimeric CWHs, sixty-seven CBDs were selected from the broad range of bacterial species and viruses identified in Example 6. These CBDs contained one to four CW_7 repeats, ranging from 58.5%-89% amino acid identity to the CLB2-CBD CW_7 sequence. EADs associated with these CBDs included both amidases and glycohydrolases. Chimeric proteins were generated that comprised the CLC2-EAD in combination with each of these CW_7-comprising CBDs. These proteins were expressed in BL21 *E. coli* cells. Whole cell culture lysates were tested for *C. acnes* lytic activity in a turbidity reduction assay. Activity was measured relative to the activity of the CLC2-EAD+CLB2-CBD chimeric CWH. Results are shown in FIG. 23A-23B. Of the sixty-seven CBDs tested, nine were categorized as having no detectable activity in this assay (relative activity <0.4), possibly due to solubility or assay format; nine had "detectable activity" (relative activity between 0.4 and 0.6); and 49 were categorized as having "strong activity" (relative activity >0.6).

The CBDs found to have "strong" or "detectable" activity were comprised of CW_7 repeats that ranged anywhere from 58.5%-89% AA ID to the CLB2-CBD CW_7 and come from a broad range of bacterial species (Table 13). Chimeras comprising a wide variety of these CBDs exhibited activity similar to the activity observed for the highly active CLC2-EAD+CLB2-CBD chimera. These data indicate that, surprisingly, the *C. acnes*-specific lytic activity of EADs can be improved by combining EADs with a wide variety of CW_7 repeat-containing CBDs, irrespective of taxonomic source or amino acid identity to the CLB2-CBD.

Figure 23C:
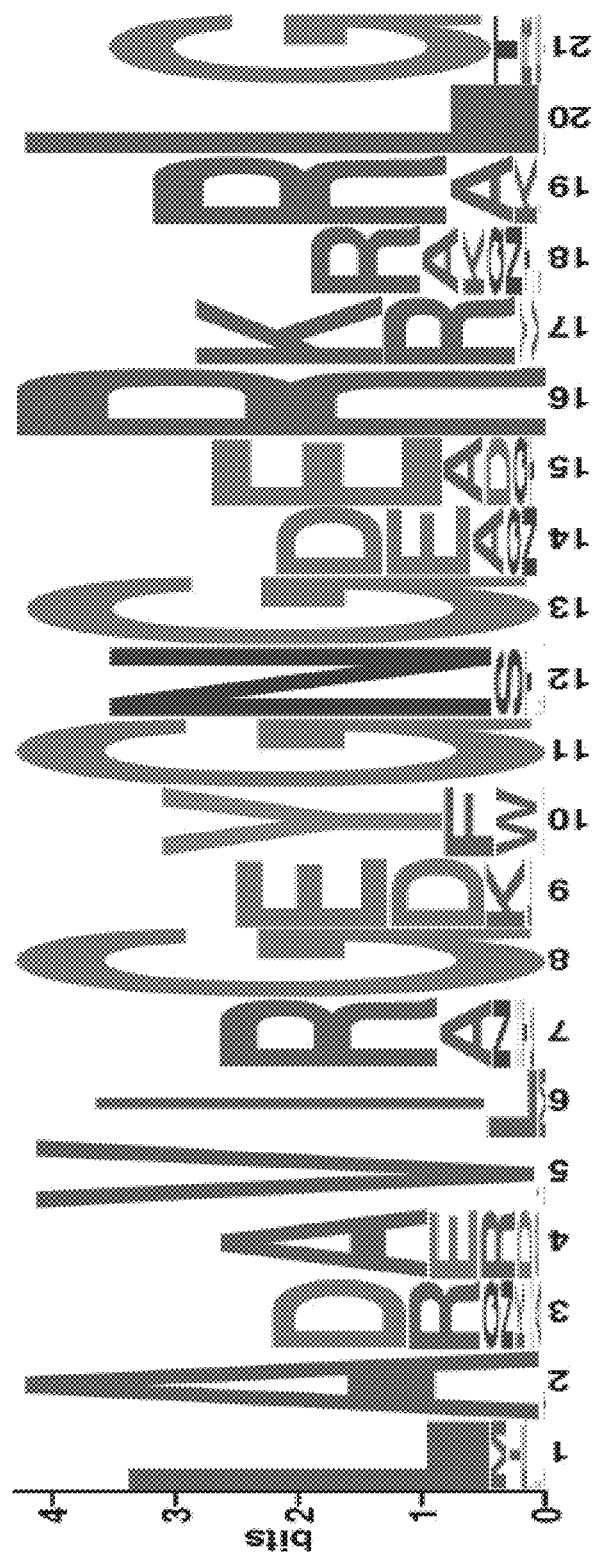
FIG. 23C visually depicts a sequence motif shared by CW_7 repeats exhibiting anti-*C. acnes* activity in chimeric combination with CLC2-EAD.

The CW_7 repeat sequences from the CBDs with strong or detectable activity were compiled and bioinformatically analyzed using MEME (see Bailey et al., "The MEME Suite," *Nucleic Acids Research*, 2015; 43(W1): W39-W49), a bioinformatic tool that discovers novel, ungapped sequence motifs in nucleotide and protein sequences. MEME identified two similar amino acid motifs characteristic of the analyzed CBDS. The 21-amino-acid motif contains 12 highly conserved residues, while the 19-amino-acid motif contains 10 highly conserved residues, that exemplify CW_7 repeats found in CBDs that can be utilized in chimeric cell wall hydrolases to increase activity against *C. acnes*. FIG. 23C visually represents the relative frequency of amino acids at each position of this conserved stretch of the CW_7 repeat sequences characterized in this example. The identified motif sequences are as follows:

```
CW_7-21-motif:
                                           (SEQ ID NO: 2940)
L A X X V I/L X G X X G N/S G X X R K/R X X L G;
and CW_7-19-motif:
                                           (SEQ ID NO: 2941)
A X X V I/L X G X X G N/S G X X R K/R X X L.
```

TABLE 13

CW_7 repeat sequences, source protein, taxonomy and sequence identity to the CLB2-CBD CW_7 repeat.

| Label | Activity Level* | GenBank Acc. # | Phylum | Taxonomy | AA ID %** | Protein SEQ ID | CBD SEQ ID | Chimera SEQ ID |
|---|---|---|---|---|---|---|---|---|
| CPL01 | Strong | HAT1491020.1 | Actinobacteria | *Corynebacterium striatum* | 89.47 | 108 | 166 | 224 |
| CPL02 | Strong | KDS92380.1 | Actinobacteria | *Dermabacter_hominis*_1368 | 89.47 | 109 | 167 | 225 |
| CPL03 | Strong | WP_253254962.1 | Actinobacteria | *Corynebacterium_striatum* | 89.47 | 110 | 168 | 226 |
| CPL04 | Strong | WP_197551992.1 | Actinobacteria | *Trueperella pecoris* | 89.47 | 111 | 169 | 227 |
| CPL05 | Strong | MCI6532281.1 | Actinobacteria | *Bifidobacterium animalis* | 89.47 | 112 | 170 | 228 |
| CPL06 | Strong | WP_291499654.1 | Actinobacteria | *Actinomyces* sp. | 89.47 | 113 | 171 | 229 |
| CPL07 | Strong | WP_134316353.1 | Actinobacteria | *Corynebacterium silvaticum* | 86.84 | 114 | 172 | 230 |
| CPL08 | Strong | MDU7484863.1 | Actinobacteria | *Cutibacterium avidum* | 86.84 | 115 | 173 | 231 |
| CPL09 | Strong | WP_049619209.1 | Actinobacteria | *Actinobaculum suis* | 86.84 | 116 | 174 | 232 |
| CPL10 | Strong | MDD7505539.1 | Actinobacteria | *Actinomycetaceae* bacterium | 84.21 | 117 | 175 | 233 |
| CPL11 | Strong | CRH60380.1 | Chlamydiota | *Chlamydia trachomatis* | 86.84 | 118 | 176 | 234 |
| CPL12 | Strong | MDO5722416.1 | Actinobacteria | *Actinomycetaceae* bacterium | 89.47 | 119 | 177 | 235 |
| CPL13 | Strong | OFQ56130.1 | Actinobacteria | *Corynebacterium* sp. HMSC074H12 | 84.21 | 120 | 178 | 236 |
| CPL14 | Strong | MBS6276004.1 | Actinobacteria | *Actinomycetaceae* bacterium | 81.58 | 121 | 179 | 237 |
| CPL15 | Strong | WP_288336691.1 | Actinobacteria | uncultured *Varibaculum* sp. | 81.58 | 122 | 180 | 238 |
| CPL16 | Strong | WP_165315851.1 | Actinobacteria | *Schaalia* sp. ZJ405 | 81.58 | 123 | 181 | 239 |
| CPL18 | Detectable | WP_323456950.1 | Actinobacteria | *Cutibacterium granulosum* | 81.58 | 124 | 182 | 240 |
| CPL20 | Strong | WP_235810848.1 | Actinobacteria | *Tractidigestivibacter scatoligenes* | 78.95 | 125 | 183 | 24 |
| CPL21 | Strong | WP_236842337.1 | Actinobacteria | *Boudabousia tangfeifanii* | 78.95 | 126 | 184 | 242 |
| CPL22 | Detectable | DAQ44887.1 | Virus | *Caudoviricetes* sp. | 78.95 | 127 | 185 | 243 |
| CPL23 | Detectable | WP_274959455.1 | Actinobacteria | *Thermophilibacter provencensis* | 78.95 | 128 | 186 | 244 |

TABLE 13-continued

CW_7 repeat sequences, source protein, taxonomy and sequence identity to the CLB2-CBD CW_7 repeat.

| Label | Activity Level* | GenBank Acc. # | Phylum | Taxonomy | AA ID %** | Protein SEQ ID | CBD SEQ ID | Chimera SEQ ID |
|---|---|---|---|---|---|---|---|---|
| CPL24 | Strong | WP_277035292.1 | Actinobacteria | Propionimicrobium lymphophilum | 76.32 | 129 | 187 | 245 |
| CPL25 | Strong | WP_330029979.1 | Actinobacteria | Parolsenella sp. | 81.58 | 130 | 188 | 246 |
| CPL26 | Detectable | WP_087201200.1 | Actinobacteria | Collinsella sp. An271 | 81.58 | 131 | 189 | 247 |
| CPL28 | Detectable | MEE8722860.1 | Actinobacteria | Eggerthellaceae bacterium | 76.32 | 132 | 190 | 248 |
| CPL29 | Strong | WP_003841933.1 | Actinobacteria | Bifidobacterium dentium | 78.95 | 133 | 191 | 249 |
| CPL30 | Detectable | RDB69432.1 | Actinobacteria | Eggerthella sinensis | 71.05 | 134 | 192 | 250 |
| CPL31 | Strong | WP_018340121.1 | Actinobacteria | Corynebacterium caspium | 76.32 | 135 | 193 | 251 |
| CPL32 | Strong | MBP3885850.1 | Actinobacteria | Olsenella sp. | 76.32 | 136 | 194 | 252 |
| CPL33 | Strong | WP_288766823.1 | Actinobacteria | uncultured Varibaculum sp. | 73.68 | 137 | 195 | 253 |
| CPL34 | Strong | WP_306718268.1 | Actinobacteria | Actinotignum urinale | 76.32 | 138 | 196 | 254 |
| CPL35 | Strong | MDY5585074.1 | Actinobacteria | Arcanobacterium sp. | 73.68 | 139 | 197 | 255 |
| CPL36 | Strong | DAO39398.1 | Virus | Caudoviricetes sp. | 76.32 | 140 | 198 | 256 |
| CPL38 | Strong | WP_316114142.1 | Actinobacteria | Bifidobacterium scardovii | 73.68 | 141 | 199 | 257 |
| CPL39 | Strong | CAG9066035.1 | Actinobacteria | Bifidobacterium pseudocatenulatum | 68.42 | 142 | 200 | 258 |
| CPL40 | Detectable | MBR4886392.1 | Bacteroidota | Muribaculaceae bacterium | 61.11 | 143 | 201 | 259 |
| CPL43 | Strong | DAH93651.1 | Virus | Caudoviricetes sp. | 73.68 | 144 | 202 | 260 |
| CPL44 | Detectable | YP_009603465.1 | Virus | Arthrobacter phage Gordon | 74.29 | 145 | 203 | 261 |
| CPL45 | Strong | WP_064468301.1 | Firmicute | Lederbergia galactosidilytica | 65.79 | 146 | 204 | 262 |
| CPL46 | Strong | QFP95395.1 | Virus | Arthrobacter phage Makai | 74.29 | 147 | 205 | 263 |
| CPL49 | Strong | HOU67165.1 | Firmicute | Paludibacteraceae bacterium | 76.32 | 148 | 206 | 264 |
| CPL50 | Detectable | HAP28934.1 | Bacteroidota | Porphyromonadaceae bacterium | 63.16 | 149 | 207 | 265 |
| CPL51 | Strong | MBQ0159319.1 | Bacteroidota | Candidatus Colimorpha merdihippi | 65.79 | 150 | 208 | 266 |
| CPL52 | Strong | MDE6928620.1 | Bacteroidota | Muribaculaceae bacterium | 60.53 | 151 | 209 | 267 |
| CPL53 | Strong | CRH88545.1 | Chlamydiota | Chlamydia trachomatis | 64.1 | 152 | 210 | 268 |
| CPL54 | Strong | WP_071705048.1 | Firmicute | Murdochiella vaginalis | 58.54 | 153 | 211 | 269 |
| CPL55 | Strong | WP_212927898.1 | Firmicute | Oceanobacillus sp. J11TS1 | 65.79 | 154 | 212 | 270 |
| CPL56 | Strong | WP_163583485.1 | Firmicute | Gracilibacillus saliphilus | 63.16 | 155 | 213 | 271 |
| CPL59 | Strong | WP_271528891.1 | Firmicute | Enterococcus faecalis | 60.98 | 156 | 214 | 272 |
| CPL60 | Strong | WP_269310727.1 | Firmicute | Peptostreptococcus equinus | 58.54 | 157 | 215 | 273 |
| CPL61 | Strong | MDO4391700.1 | Firmicute | Clostridium sp. | 65.79 | 158 | 216 | 274 |
| CPL62 | Strong | MCI5948801.1 | Firmicute | Oscillospiraceae bacterium | 63.41 | 159 | 217 | 275 |
| CPL63 | Strong | MBD8989282.1 | Firmicute | Clostridiales bacterium | 63.41 | 160 | 218 | 276 |
| CPL64 | Strong | WP_028505417.1 | Firmicute | Ruminococcus sp. FC2018 | 60.98 | 161 | 219 | 277 |
| CPL65 | Strong | MDE6733460.1 | Firmicute | Oscillospiraceae bacterium | 60.98 | 162 | 220 | 278 |
| CPL66 | Strong | WP_288704103.1 | Firmicute | uncultured Catenibacterium sp. | 68.42 | 163 | 221 | 279 |
| CPL68 | Strong | WP_105302716.1 | Firmicute | Anaerolactibacter massiliensis | 65.79 | 164 | 222 | 280 |
| CPL69 | Strong | WP_163104227.1 | Firmicute | Amedibacterium intestinale | 60.98 | 165 | 223 | 281 |

*Activity level for CBD in initial screen in combination with CLC2-EAD.
**Amino acid percent sequence identity of top CW_7 match within the CBD to CLB2-CBD CW_7 repeat sequence.

Figure 24A:
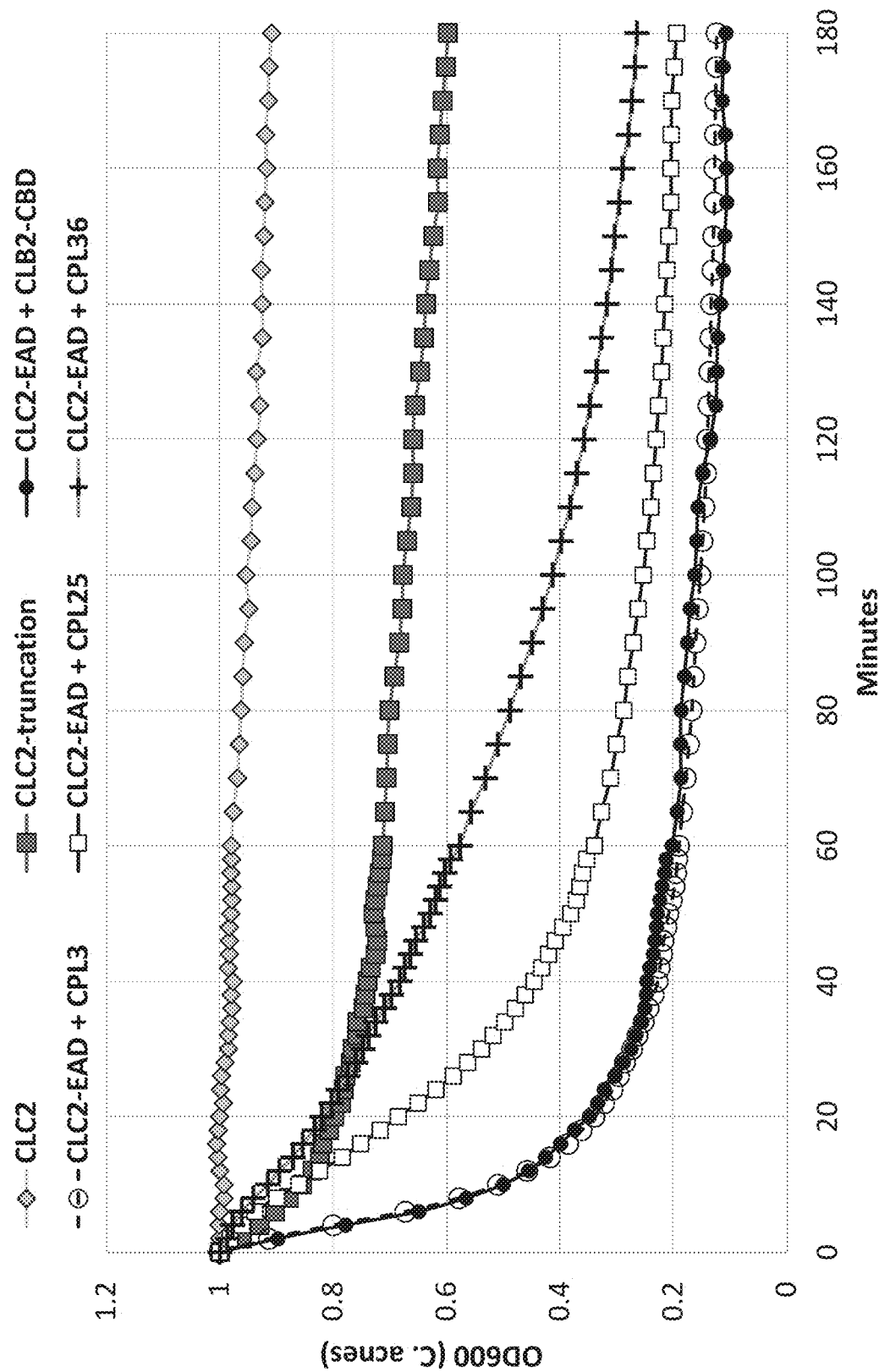
FIG. 24A-24B show the results of turbidity reduction assays for chimeric proteins comprising CPL3, CPL25, and CPL36 CBDs (FIG. 24A) and for chimeric proteins comprising CPL46, CPL54, and CPL66 CBDs (FIG. 24B). For comparison, also shown are the results for full length CLC2, the CLC2-truncation, and the CLC2-EAD+CLB2-CBD chimeric protein.
Figure 24B:
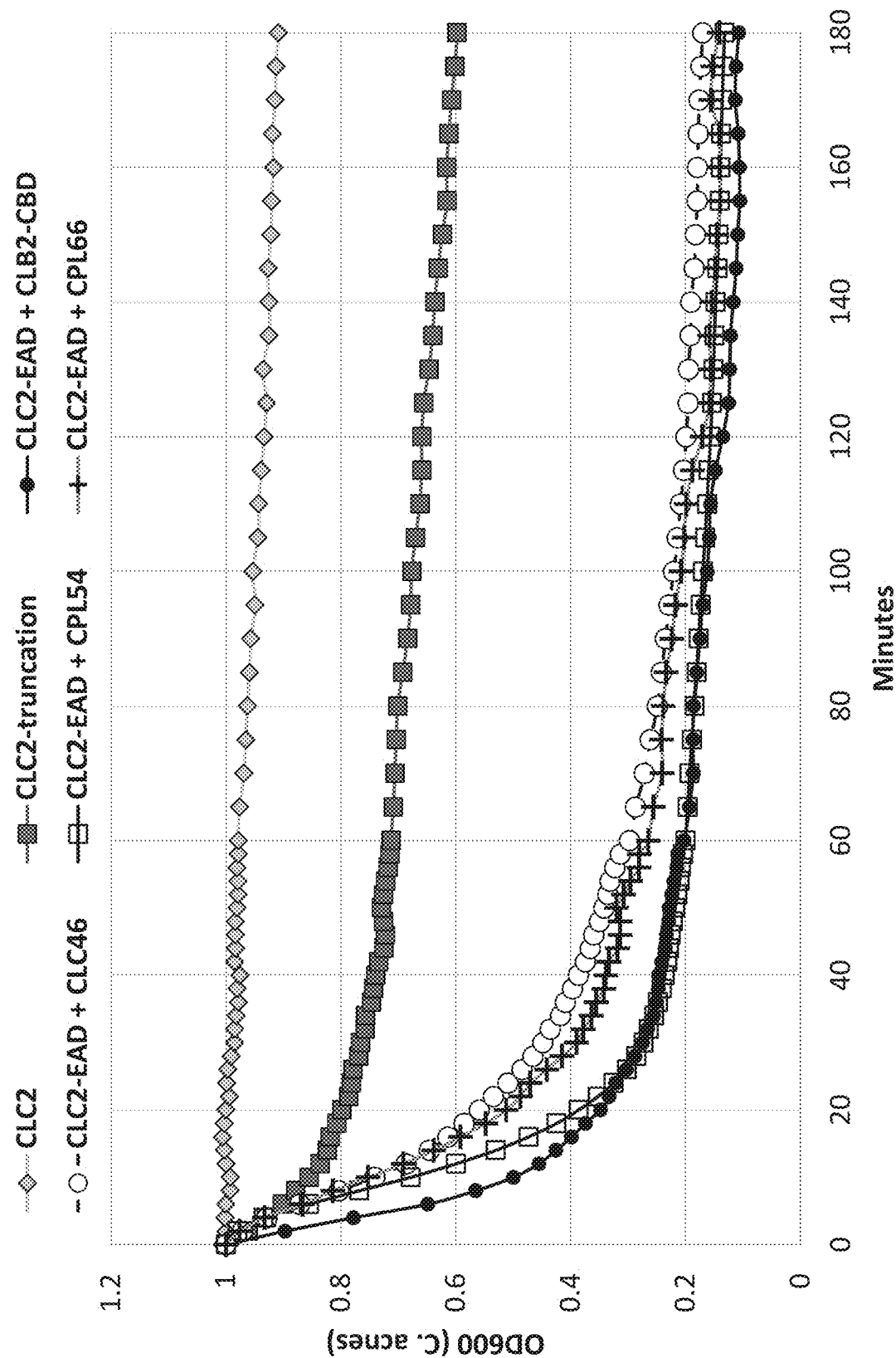

Example 19: Actinobacteria, Viral, and Firmicute CW_7 CBDs Facilitate Binding and Lysis of C. acnes in Chimeric CWHs in Turbidity Reduction Assays From the diverse CW_7-containing CBDs identified in Example 6 and explored in Example 18, six CBDs were selected for protein purification and activity testing, with an emphasis on selecting from a broad diversity of taxonomies and similarity ranges to the CLB2-CBD CW_7 sequence. As such, two candidates were selected from each of Actinobacteria diversity, viral diversity, and Firmicute (also known as "bacillota") diversity. These six CBDs contain two to four CW_7 repeats, with a top CW_7 sequence match ranging from 63%-89% amino acid identity to the CLB2-CBD CW_7 sequence, as listed in Table 14. Chimeric proteins were generated that comprised the CLC2-EAD in combination with each of these CW_7-comprising CBDs. These proteins were expressed in BL21 E. coli cells, purified using the C-terminal 6xHis tag, and assayed for C. acnes lytic activity in a turbidity reduction assay. As controls, the results were compared to full length CLC2 protein, CLC2-truncation, and the CLC2-EAD+CLB2-CBD chimeric protein. As shown in FIG. 24A-24B, all six diverse CW_7 chimeric proteins produced C. acnes lytic activity that was stronger than full length CLC2, as well as the more active CLC2-truncation, indicating that these CW_7 repeat-containing CBDs enhanced the C. acnes lytic activity of the CLC1-family EAD. These data indicate that CW_7 repeat-containing CBDs from diverse organisms can facilitate binding and lysis of C. acnes.

TABLE 14

CW_7 repeat sequences, source protein, taxonomy
and sequence identity to the CLB2-CBD CW_7 repeat.

| Identifier | Accession # | Taxonomic Assignment | CBD SEQ ID NO | AA ID %* |
|---|---|---|---|---|
| CPL03 | WP_253254962.1 | Corynebacterium striatum/Actinobacteria | 168 | 89.474 |
| CPL25 | WP_330029979.1 | Parolsenella sp./Actinobacteria | 188 | 81.579 |
| CPL36 | DAO39398.1 | Caudoviricetes sp./Virus | 198 | 76.316 |
| CPL46 | QFP95395.1 | Arthrobacter_phage_Makai/Virus | 205 | 74.286 |
| CPL54 | WP_071705048.1 | Murdochiella vaginalis/Firmicute | 211 | 63.415 |
| CPL66 | WP_288704103.1 | Catenibacterium sp./Firmicute | 221 | 68.421 |

*Amino acid percent sequence identity of top CW_7 match within the CBD to CLB2-CBD CW_7 repeat sequence.

Example 20: Single CW_7 Repeat Sufficient for Increasing Anti-C. acnes Activity in Chimeric Combination with CLC1-Family EAD The CLB1-CBD contains two CW_7 repeats, CLB1-CW7-1 (SEQ ID NO: 45) and CLB1-CW7-2 (SEQ ID NO: 46), which are 82% identical at the amino acid level. To test whether either single CW_7 repeat is sufficient to improve the activity of the native CLC1 protein, two chimeric proteins were constructed, linking the CLC1-EAD to an individual CW_7 repeat of CLB1: CLC1-EAD+CLB1-CW7-1-CBD (SEQ ID NO: 2942) and CLC1-EAD+CLB1-CW7-2-CBD (SEQ ID NO: 2943). Sequences of these chimeric proteins are shown in Table 15.

TABLE 15

Single CW_7 repeat comprising chimeric enzymes.

| Description | Sequence |
|---|---|
| CLC1-EAD + CLB1-CW7-1-CBD | MTFIQARHHGGNSNTPITRLVIHATCPDVG YPSASKAGRAVSTAEYFASTSRSASAHYVC DVSATVQCLSEETIGYHAPPNSHSIGIEIC ADGGSRASFEKASHAYTREQWLSPQVWPAV ERAAILARGICHRHHIPVRKLTTAQVKSGM SGICGHDNVSDAFHQSDHDDPGPYFPWNEF IAAIQGKNTNKGELSMSDVTSPNIDALADA VIRGEYGNGEERRRRLGANYAAVQKRVNEK LTG (SEQ ID NO: 2942) |
| CLC1-EAD + CLB1-CW7-2-CBD | MTFIQARHHGGNSNTPITRLVIHATCPDVG YPSASKAGRAVSTAEYFASTSRSASAHYVC DVSATVQCLSEETIGYHAPPNSHSIGIEIC ADGGSRASFEKASHAYTREQWLSPQVWPAV ERAAILARGICHRHHIPVRKLTTAQVKSGM SGICGHDNVSDAFHQSDHDDPGPYFPWNEF IAAIQGKNTNKGELSMSDVTSPNIDALADA VIRGDYGNGEERRRRLGNLYDQVQARVNQK LGY (SEQ ID NO: 2943) |

Figure 25:
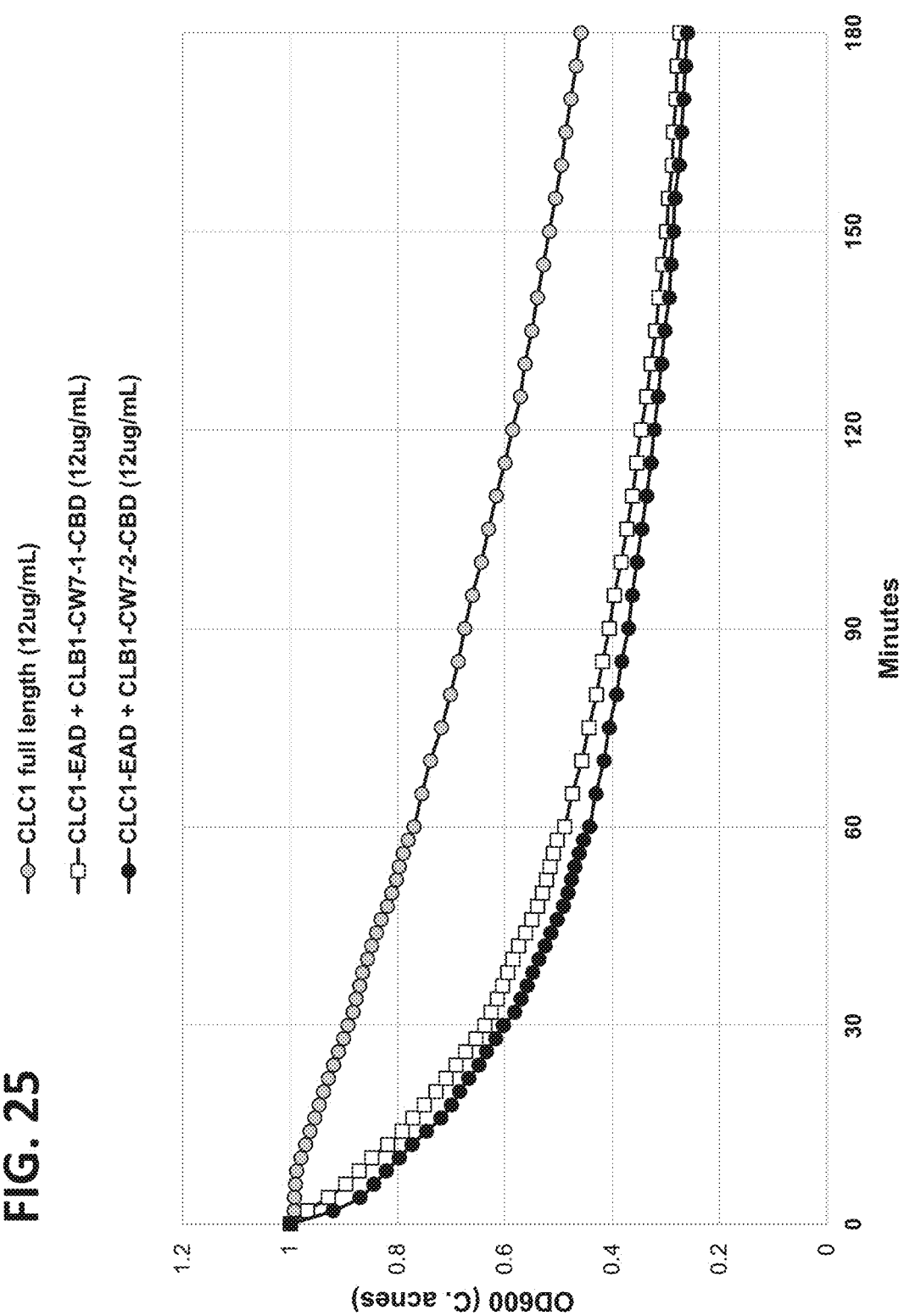
FIG. 25 shows the results of turbidity reduction assays against *C. acnes* for a CLC1-EAD+CLB1-CW7-1 chimera and a CLC1-EAD+CLB1-CW7-2 chimera in comparison to full length CLC1.

These chimeric proteins were expressed and purified, and then tested in turbidity reduction assays against C. acnes. Results are shown in FIG. 25, with the activity of the native full length CLC1 enzyme shown for comparison. In both cases, the chimeric proteins containing a single CW_7 repeat from CLB1-CBD exhibited significantly improved activity compared to the native CLC1 protein, demonstrating that a single CW_7 repeat from a CBD containing multiple CW_7 repeats is sufficient to improve activity of a CLC1-family enzyme.

Figure 26:
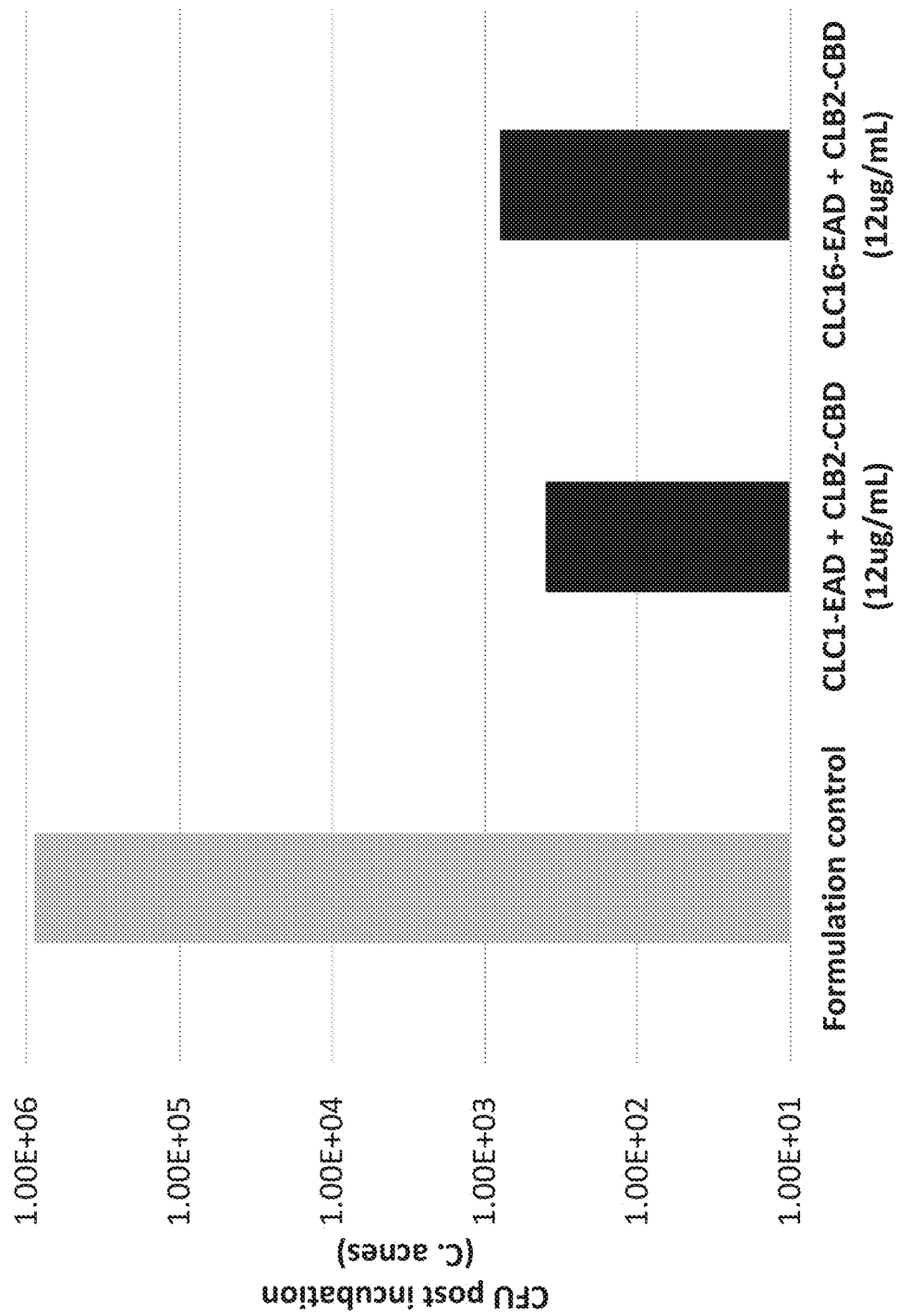
FIG. 26 shows the results of quantitative killing assays against *C. acnes* for HPMC-based hydrogel formulations of CLC1-EAD+CLB2-CBD and CLC16-EAD+CLB2-CBD chimeras, compared to untreated control.

Example 21: Topical Hydrogel Formulations of Chimeric Proteins Retained Strong Lytic Activity Against C. acnes The CLC1-EAD+CLB2-CBD (SEQ ID NO: 53) and CLC16-EAD+CLB2-CBD (SEQ ID NO: 106) chimeric enzymes were formulated in a hydroxypropyl methylcellulose (HPMC)-based hydrogel at a concentration of 12 µg/mL. HPMC is a commonly used ingredient in skin care formulations. These formulations were incubated at room temperature for 7 days and then an aliquot was used in quantitative killing assays of C. acnes. In brief, about $1 \times 10^6$ cells of C. acnes were added to either a hydrogel formulation control (no added enzyme) or hydrogels containing enzyme. The amount of viable C. acnes remaining after 6 hours of incubation were measured via serial dilutions onto BHI plates incubated at 37° C. under anaerobic conditions for 4-5 days. Results are shown in FIG. 26. Formulations containing either enzyme showed a 3-4 order of magnitude reduction in viable C. acnes cells relative to the formulation control, demonstrating that these chimeric enzymes were stable and retained enzymatic activity in topical formulations.

Materials and Methods

Key Materials and Methods used in the Examples are described below:

Phylogenetic Analysis of CLC1 Family Proteins and their Amidase Domains

A multiple sequence alignment of CLC1-CLC19 compared to members of the well-conserved CaLys1 endolysin family found in C. acnes and C. acnes phages was generated using MUSCLE (world wide web at ebi.ac.uk/Tools/msa/muscle/) and visualized as an unrooted tree using standard parameters using the Interactive Tree of Life online tool (world wide web at academic.oup.com/nar/article/49/W1/W293/6246398). Similarly, to analyze specifically the amidase domains, the amino acid sequences encoding the amidase domains in these 100 proteins were delineated using SMART or CDD and a multiple sequence alignment and phylogenetic tree were generated as described above.

Bacterial Strains and Culture Conditions

Cutibacterium acnes (ATCC11827) used in this study was grown at 37° C. with shaking in Brain Heart Infusion (BHI) Broth containing Oxyrase® for Broth to remove dissolved oxygen or on BHI plates containing 2% (w/v) agar placed at 37° C. in a GasPak EZ pouch to generate an anaerobic environment (Becton Dickinson). Corynebacterium xerosis (ATCC 373) and Corynebacterium striatum (ATCC BAA-1293) were grown in BHI Broth at 37° C. Staphylococcus epidermidis (NRLL B4268) was grown in tryptic soy broth (TSB; Difco, Frankling Lakes, NJ) at 37° C. with shaking.

*Escherichia coli* DH10B (Invitrogen, Carlsbad, CA) was used for cloning and storage. *E. coli* BL21 (DE3) (EMD Biosciences, San Diego, CA) was used for protein expression. All *E. coli* strains were grown at 37° C. with shaking in 2×YT medium (16 g/L tryptone, 10 g/L yeast extract, 5 g/L NaCl) or on plates containing LB (10 g/L tryptone, 10 g/L NaCl, 5 g/L yeast extract) supplemented with 2% (w/v) agar. 50 µg/ml kanamycin was used for proper selection of *E. coli* clones.

Construction of Full-Length, Truncated, and Chimeric Cell Wall Hydrolases

Full-length cell wall hydrolases were synthesized with NdeI/HindIII sites and ligated into the NdeI/HindIII sites of pET24a (+). Truncated versions of cell wall hydrolases were amplified from full length wild-type genes with NdeI/HindIII sites and ligated into the NdeI/HindIII sites of pET24a (+). For chimeric enzymes, individual enzymatic domains including up to 50 amino acids upstream and downstream were synthesized with NdeI/SpeI sites. Individual cell wall binding domains including up to 25 amino acids upstream and downstream were synthesized with SpeI/HindIII sites. The chimeric lysins were constructed by ligating both an enzymatic domain and a cell wall binding domain into the NdeI/HindIII sites of pET24a (+).

The expression vectors containing the chimeric cell wall hydrolases were chemically transformed into BL21 *E. coli* for downstream protein expression and purification.

Protein Production and Purification

BL21 cells containing the appropriate expression plasmid were grown in 2×YT media overnight at 37° C. with shaking. The next morning, cells were back diluted 1:1000 in flasks containing 50 mLs of ZYM-5052 autoinduction media (Fisher scientific cat no. NC1093977) and incubated with shaking for 2-3 hrs at 37° C. Flasks were then transferred to 22° C. and incubated with shaking overnight. Cultures were spun down, supernatant was poured off, and pellets were stored at −80° C. for at least 30 minutes. Each frozen pellet was resuspended in 5 mL of lysis buffer (NPI-10 (100 uM Tris pH 8, 300 mM NaCl, 10 mM imidazole) with the addition of 5 mg lysozyme and 100 units of DNAseI) and incubated at 30° C. with gentle shaking for 30 mins. Cells were then spun down until a clear lysate was obtained and a solid pellet formed. The clear lysate was transferred to a column containing Nickel-NTA Agarose Resin (Gold Bio) suspended in NPI-10. Columns were inverted several times to completely resuspend the resin and incubated at 4° C. for a minimum of one hour to allow for protein binding. Once the resin was completely settled, the lysate was allowed to run off the column and the columns were washed with two column volumes of NPI-20 (100 uM Tris pH 8, 300 mM NaCl, 20 mM imidazole). Proteins were then eluted by adding 3 mLs of NPI-250 (100 uM Tris pH 8, 300 mM NaCl, 250 mM imidazole) and fractions were collected. Proteins were quantified and purity checked via Bradford assay and SDS-PAGE gel and Coomassie staining. Proteins were then concentrated and buffer exchanged into protein storage buffer (50 mM Tris pH6.8, 300 mM NaCl) using Amicon Ultra-15 Filter Units. For long term storage, proteins were stored at −80° C. with 30% glycerol.

Clearing Assays

Candidate cell wall hydrolases were tested for lytic activity against *C. acnes* via a clearing assay. *C. acnes* was grown for 4 days on BHI agar plates at 37° C. under anaerobic conditions. Cells were then harvested from the plates and washed 2× in 25 mM HEPES buffer pH 7.3. The washed cells were resuspended in 25 mM HEPES buffer pH 7.3 at 10 ODs/mL. Next, 1 mL of cells was mixed with 20 mL of 0.5% agar and poured into a petri plate. After the agar set, 15 µL of purified protein from the candidate cell wall hydrolases were spotted onto the agar. The plates were incubated at room temperature and checked for clearing around the spots after 24 hours.

Turbidity Reduction Assays

Purified candidate cell wall hydrolases were tested for lytic activity against *C. acnes* via a turbidity reduction assay. *C. acnes* was grown for 4 days on BHI agar plates at 37° C. under anaerobic conditions. Cells were then harvested from the plates and washed 2× in 25 mM HEPES pH 7.3. The OD of the cells was adjusted to an $OD_{600}$~1.0 and mixed with 2-fold dilutions of purified protein (e.g. 12 µg/mL to 0.75 µg/mL) to a final volume of 200 µl of 25 mM HEPES pH 7.3 in a flat bottom microtiter plate. The $OD_{600}$ of each well was then measured every two minutes for 1 hour and then every 5 minutes using a microplate reader. Specific activity was calculated as previously described (Briers et al., J Biochem Biophys Methods. 2007 Apr. 10; 70(3):531-3). To test thermostability of proteins, an aliquot of the protein was incubated for 30 minutes at temperatures ranging from 37° C. to 58° C. Proteins were then immediately tested in turbidity reductions assays as described above. To test the pH range of proteins, turbidity reduction assays were performed using 25 mM Tris HCl pH 8.0, 25 mM HEPES pH 7.3, 25 mM Citrate buffer pH 6.5, 25 mM Citrate buffer pH 6.2, 25 mM Citrate buffer pH 5.7, 25 mM Citrate buffer pH 5.3, 25 mM Citrate buffer pH 4.9, 25 mM Citrate buffer pH 4.5, and 25 mM Citrate buffer pH 4.2.

Quantitative Killing Experiments

The antimicrobial activity of candidate cell wall hydrolases were measured via quantitative killing assays. *C. acnes* was grown for 4 days on BHI agar plates at 37° C. under anaerobic conditions. Cells were then harvested from the plates and washed 2× in 25 mM HEPES pH 7.3. Approximately $1 \times 10^6$ cells per reaction were then mixed with the desired amount of protein in a final volume of 200 µL of 25 mM HEPES pH 7.3 and incubated at room temperature. At the appropriate time points (e.g., 0 time point and the 6 hour time point), 20 µl of the reaction was removed and serial dilutions were plated on BHI agar plates and grown for 4-5 days at 37° C. under anaerobic conditions. CFUs were then counted to calculate the number of viable cells.

REFERENCES

The following references are incorporated herein by reference in their entireties for all purposes.

1. Bickers, D. R. et al. The burden of skin diseases: 2004. *Journal of the American Academy of Dermatology* 55, 490-500 (2006).
2. Gallitano, S. M. & Berson, D. S. How Acne Bumps Cause the Blues: The Influence of Acne Vulgaris on Self-Esteem. *Int J Womens Dermatol* 4, 12-17 (2018).
3. Mias, C., Mengeaud, V., Bessou-Touya, S. & Duplan, H. Recent advances in understanding inflammatory acne: Deciphering the relationship between *Cutibacterium acnes* and Th17 inflammatory pathway. *Acad Dermatol Venereol* 37, 3-11 (2023).
4. Fitz-Gibbon, S. et al. *Propionibacterium acnes* strain populations in the human skin microbiome associated with acne. *J Invest Dermatol* 133, 2152-2160 (2013).
5. Lomholt, H. B., Scholz, C. F. P., Bruggemann, H., Tettelin, H. & Kilian, M. A comparative study of *Cutibacterium (Propionibacterium) acnes* clones from acne patients and healthy controls. *Anaerobe* 47, 57-63 (2017).

6. Zhang, N., Yuan, R., Xin, K. Z., Lu, Z. & Ma, Y. Antimicrobial Susceptibility, Biotypes and Phylotypes of Clinical *Cutibacterium* (Formerly *Propionibacterium*) *acnes* Strains Isolated from Acne Patients: An Observational Study. *Dermatol Ther (Heidelb)* 9, 735-746 (2019).
7. Bruggemann, H., Salar-Vidal, L., Gollnick, H. P. M. & Lood, R. A Janus-Faced Bacterium: Host-Beneficial and -Detrimental Roles of *Cutibacterium acnes. Front Microbiol* 12, 673845 (2021).
8. Zaenglein, A. L. et al. Guidelines of care for the management of acne vulgaris. *Journal of the American Academy of Dermatology* 74, 945-973.e33 (2016).
9. Chien, A. L. et al. Association of Systemic Antibiotic Treatment of Acne With Skin Microbiota Characteristics. *JAMA Dermatol* 155, 425-434 (2019).
10. Patangia, D. V., Anthony Ryan, C., Dempsey, E., Paul Ross, R. & Stanton, C. Impact of antibiotics on the human microbiome and consequences for host health. *Microbiologyopen* 11, e1260 (2022).
11. Antimicrobial Resistance Collaborators. Global burden of bacterial antimicrobial resistance in 2019: a systematic analysis. *Lancet* 399, 629-655 (2022).
12. Dams, D. & Briers, Y. Enzybiotics: Enzyme-Based Antibacterials as Therapeutics. *Adv Exp Med Biol* 1148, 233-253 (2019).
13. Gerstmans, H., Criel, B. & Briers, Y. Synthetic biology of modular endolysins. *Biotechnology Advances* 36, 624-640 (2018).
14. Natarelli, N., Gahoonia, N. & Sivamani, R. K. Bacteriophages and the Microbiome in Dermatology: The Role of the Phageome and a Potential Therapeutic Strategy. *Int J Mol Sci* 24, 2695 (2023).

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

NUMBERED EMBODIMENTS OF THE INVENTION

Notwithstanding the appended claims, the disclosure sets forth the following numbered embodiments:

I. Novel Truncated Proteins

1. An enzymatically active, C-terminally truncated recombinant CLC1-family protein.
2. The recombinant protein of embodiment 1, wherein the recombinant protein is truncated in comparison to the corresponding full-length, native CLC1-family protein sequence.
3. The recombinant protein of embodiment 1 or 2, wherein the recombinant protein exhibits increased lytic activity and/or solubility compared to the corresponding full-length, native CLC1-family protein sequence.
4. The recombinant protein of any one of embodiments 1-3, wherein the truncation is a truncation of the conserved C-terminal region of the full-length, native CLC1-family protein sequence.
5. The recombinant protein of any one of embodiments 1-4, wherein the truncation is a truncation of the entire C-terminal region of the CLC1-family protein that follows the enzymatically active domain of the full-length, native CLC1-family protein sequence.
6. The recombinant protein of any one of embodiments 1-5, wherein the truncation is a truncation of residue number 195-205 and all subsequent residues from the full-length, native CLC1-family protein amino acid sequence.
7. The recombinant protein of any one of embodiments 1-6, wherein the truncation is a truncation of about 5, 10, 15, 20, 25, 30, 35, 40, 45, 50, 55, 60, 65, 70, 75, 80, 85, 90, 95, 100, 105, 110, 115, 120, 125, or 130 amino acids from the C-terminus of the full-length, native CLC1-family protein.
8. The recombinant protein of any one of embodiments 1-7, wherein the CLC1-family protein is CLC1 (SEQ ID NO: 1).
9. The recombinant protein of any one of embodiments 1-7, wherein the CLC1-family protein is CLC2 (SEQ ID NO: 2).
10. The recombinant protein of any one of embodiments 1-7, wherein the CLC1-family protein is CLC3 (SEQ ID NO: 3).
11. The recombinant protein of any one of embodiments 1-7, wherein the CLC1-family protein is CLC4 (SEQ ID NO: 4).
12. The recombinant protein of any one of embodiments 1-7, wherein the CLC1-family protein is CLC5 (SEQ ID NO: 5).
13. The recombinant protein of any one of embodiments 1-7, wherein the CLC1-family protein is CLC6 (SEQ ID NO: 6).
14. The recombinant protein of any one of embodiments 1-7, wherein the CLC1-family protein is CLC7 (SEQ ID NO: 7).
15. The recombinant protein of any one of embodiments 1-7, wherein the CLC1-family protein is CLC8 (SEQ ID NO: 8).
16. The recombinant protein of any one of embodiments 1-7, wherein the CLC1-family protein is CLC9 (SEQ ID NO: 9).
17. The recombinant protein of any one of embodiments 1-7, wherein the CLC1-family protein is CLC10 (SEQ ID NO: 10).
18. The recombinant protein of any one of embodiments 1-7, wherein the CLC1-family protein is CLC11 (SEQ ID NO: 11).
19. The recombinant protein of any one of embodiments 1-7, wherein the CLC1-family protein is CLC12 (SEQ ID NO: 12).
20. The recombinant protein of any one of embodiments 1-7, wherein the CLC1-family protein is CLC13 (SEQ ID NO: 13).
21. The recombinant protein of any one of embodiments 1-7, wherein the CLC1-family protein is CLC14 (SEQ ID NO: 14).
22. The recombinant protein of any one of embodiments 1-7, wherein the CLC1-family protein is CLC15 (SEQ ID NO: 15).
23. The recombinant protein of any one of embodiments 1-7, wherein the CLC1-family protein is CLC16 (SEQ ID NO: 16).

24. The recombinant protein of any one of embodiments 1-7, wherein the CLC1-family protein is CLC17 (SEQ ID NO: 17).

25. The recombinant protein of any one of embodiments 1-7, wherein the CLC1-family protein is CLC18 (SEQ ID NO: 18).

26. The recombinant protein of any one of embodiments 1-7, wherein the CLC1-family protein is CLC19 (SEQ ID NO: 19).

27. The recombinant protein of any one of embodiments 1-7, wherein the CLC1-family protein is CLC1, CLC2, CLC3, CLC4, CLC5, CLC6, CLC7, CLC8, CLC9, CLC10, CLC11, CLC12, CLC13, CLC14, CLC16, CLC18, or CLC19, and wherein the C-terminal truncation is a truncation of about 70-90 amino acids compared to the full-length, native CLC1-family protein sequence.

28. The recombinant protein of any one of embodiments 1-7, wherein the CLC1-family protein is CLC1, CLC2, CLC3, CLC4, CLC5, CLC6, CLC7, CLC8, CLC9, CLC10, CLC11, CLC12, CLC13, CLC14, CLC16, CLC18, or CLC19, and wherein the C-terminal truncation is a truncation of about 80, 81, or 82 amino acids compared to the full-length, native CLC1-family protein sequence.

29. The recombinant protein of any one of embodiments 1-7, wherein the CLC1-family protein is CLC15, and wherein the C-terminal truncation is a truncation of about 115-135 amino acids compared to the full-length, native CLC1-family protein sequence.

30. The recombinant protein of any one of embodiments 1-7, wherein the CLC1-family protein is CLC15, and wherein the C-terminal truncation is a truncation of about 123 amino acids compared to the full-length, native CLC1-family protein sequence.

31. The recombinant protein of any one of embodiments 1-7, wherein the CLC1-family protein is CLC17, and wherein the C-terminal truncation is a truncation of about 55-75 amino acids compared to the full-length, native CLC1-family protein sequence.

32. The recombinant protein of any one of embodiments 1-7, wherein the CLC1-family protein is CLC17, and wherein the C-terminal truncation is a truncation of about 66 amino acids compared to the full-length, native CLC1-family protein sequence.

33. The recombinant protein of any one of embodiments 1-32, wherein the recombinant protein comprises an amino acid sequence having at least 40, 45, 50, 55, 60, 65, 70, 75, 80, 85, 90, 95, 96, 97, 98, or 99% sequence identity to an amino acid sequence selected from the group consisting of SEQ ID NO: 75-93.

34. The recombinant protein of any one of embodiments 1-33, wherein the recombinant protein comprises an amino acid sequence selected from the group consisting of SEQ ID NO: 75-93.

35. The recombinant protein of any one of embodiments 1-34, wherein the recombinant protein comprises an amino acid sequence having at least 40, 45, 50, 55, 60, 65, 70, 75, 80, 85, 90, 95, 96, 97, 98, or 99% sequence identity to an amino acid sequence selected from the group consisting of SEQ ID NO: 20-36.

36. The recombinant protein of any one of embodiments 1-35, wherein the recombinant protein comprises an amino acid sequence selected from the group consisting of SEQ ID NO: 20-36.

37. An enzymatically active, C-terminally truncated recombinant CLC16 protein.

38. The recombinant protein of embodiment 37, wherein the C-terminal truncation is a truncation of about 5, 10, 15, 20, 25, 30, 35, 40, 45, 50, 55, 60, 65, 70, 75, 80, 85, 90, 95, 100, 105, or 110 amino acids compared to the full-length, native CLC16 protein sequence (SEQ ID NO: 16).

39. The recombinant protein of embodiment 37 or 38, wherein the C-terminal truncation is a truncation of about 81 amino acids compared to the full-length, native CLC16 protein sequence (SEQ ID NO: 16).

40. The recombinant protein of any one of embodiments 37-39, wherein the truncation is a truncation from residue number 195-210 to residue number 282 of the full-length, native CLC16 protein amino acid sequence (SEQ ID NO: 16).

41. The recombinant protein of any one of embodiments 37-40, wherein the recombinant protein comprises the amino acid sequence of SEQ ID NO: 90.

42. The recombinant protein of any one of embodiments 37-41, wherein the recombinant protein comprises the amino acid sequence of SEQ ID NO: 35.

43. The recombinant protein of any one of embodiments 37-42, wherein the recombinant protein exhibits increased lytic activity and/or solubility compared to full-length, native CLC16.

44. An enzymatically active, C-terminally truncated recombinant CLC2 protein.

45. The recombinant protein of embodiment 44, wherein the C-terminal truncation is a truncation of about 5, 10, 15, 20, 25, 30, 35, 40, 45, 50, 55, 60, 65, 70, 75, 80, 85, 90, 95, 100, 105, or 110 amino acids compared to the full-length, native CLC2 protein sequence (SEQ ID NO: 2).

46. The recombinant protein of embodiment 44 or 45, wherein the C-terminal truncation is a truncation of about 82 amino acids compared to the full-length, native CLC2 protein sequence (SEQ ID NO: 2).

47. The recombinant protein of any one of embodiments 44-46, wherein the truncation is a truncation from residue number 195-210 to residue number 282 of the full-length, native CLC2 protein amino acid sequence (SEQ ID NO: 2).

48. The recombinant protein of any one of embodiments 44-47, wherein the recombinant protein comprises the amino acid sequence of SEQ ID NO: 76.

49. The recombinant protein of any one of embodiments 44-48, wherein the recombinant protein comprises the amino acid sequence of SEQ ID NO: 21.

50. The recombinant protein of any one of embodiments 44-49, wherein the recombinant protein exhibits increased lytic activity and/or solubility compared to full-length, native CLC2.

51. A recombinant protein comprising a sequence having at least 40, 45, 50, 55, 60, 65, 70, 75, 80, 85, 90, 95, 96, 97, 98, or 99% sequence identity to an amino acid sequence selected from the group consisting of SEQ ID NO: 75-93.

52. A recombinant protein comprising a sequence having at least 40, 45, 50, 55, 60, 65, 70, 75, 80, 85, 90, 95, 96, 97, 98, or 99% sequence identity to an amino acid sequence selected from the group consisting of SEQ ID NO: 20-36.

53. The recombinant protein of any one of embodiments 1-52, wherein the recombinant protein exhibits increased anti-*Cutibacterium acnes* lytic activity compared to a corresponding full-length native CLC1-family protein.

54. The recombinant protein of any one of embodiments 1-53, wherein the recombinant protein has improved solubility compared to a corresponding full-length native CLC1-family protein.
55. An enzymatically active, C-terminally truncated recombinant CaLys1-family protein.
56. The recombinant protein of embodiment 55, wherein the recombinant protein is truncated in comparison to the corresponding full-length, native CaLys1-family protein sequence.
57. The recombinant protein of embodiment 55 or 56, wherein the truncation is a truncation of the conserved C-terminal region of the full-length, native CaLys1-family protein sequence.
58. The recombinant protein of any one of embodiments 55-57, wherein the truncation is a truncation of the entire C-terminal region of the CaLys1-family protein that follows the enzymatically active domain of the full-length, native CaLys1-family protein sequence.
59. The recombinant protein of any one of embodiments 55-58, wherein the truncation is a truncation of residue number 195-205 and all subsequent residues from the full-length, native CaLys1-family protein amino acid sequence.
60. The recombinant protein of any one of embodiments 55-59, wherein the truncation is a truncation of about 5, 10, 15, 20, 25, 30, 35, 40, 45, 50, 55, 60, 65, 70, 75, 80, 85, 90, 95, 100, 105, 110, 115, 120, 125, or 130 amino acids from the C-terminus of the full-length, native CaLys1-family protein.
61. The recombinant protein of any one of embodiments 55-60, wherein the CaLys1-family protein is CaLys1 (SEQ ID NO: 72).
62. The recombinant protein of any one of embodiments 55-61, wherein the CaLys1-family protein is CaLys1, and wherein the C-terminal truncation is a truncation of about 70-90 amino acids compared to full-length, native CaLys1 sequence.
63. The recombinant protein of any one of embodiments 55-62, wherein the CaLys1-family protein is CaLys1, and wherein the C-terminal truncation is a truncation of about 83 amino acids compared to the full-length, native CaLys1 sequence.
64. The recombinant protein of any one of embodiments 55-63, wherein the recombinant protein comprises an amino acid sequence having at least 40, 45, 50, 55, 60, 65, 70, 75, 80, 85, 90, 95, 96, 97, 98, or 99% sequence identity to SEQ ID NO: 74.
65. The recombinant protein of any one of embodiments 55-64, wherein the recombinant protein comprises the amino acid sequence of SEQ ID NO: 74.
66. The recombinant protein of any one of embodiments 55-65, wherein the recombinant protein comprises an amino acid sequence having at least 40, 45, 50, 55, 60, 65, 70, 75, 80, 85, 90, 95, 96, 97, 98, or 99% sequence identity to SEQ ID NO: 73.
67. The recombinant protein of any one of embodiments 55-66, wherein the recombinant protein comprises the amino acid sequence of SEQ ID NO: 73.
68. A recombinant protein comprising an amino acid sequence having at least 40, 45, 50, 55, 60, 65, 70, 75, 80, 85, 90, 95, 96, 97, 98, or 99% sequence identity to SEQ ID NO: 74.
69. A recombinant protein comprising the amino acid sequence of SEQ ID NO: 74.
70. A recombinant protein comprising an amino acid sequence having at least 40, 45, 50, 55, 60, 65, 70, 75, 80, 85, 90, 95, 96, 97, 98, or 99% sequence identity to SEQ ID NO: 73.
71. A recombinant protein comprising the amino acid sequence of SEQ ID NO: 73.
72. The recombinant protein of any one of embodiments 1-71, wherein the recombinant protein is enzymatically active against *Cutibacterium acnes*.
73. The recombinant protein of any one of embodiments 55-72, wherein the recombinant protein has higher anti-*Cutibacterium acnes* lytic activity compared to the corresponding native, full-length CaLys1-family protein sequence.
74. The recombinant protein of any one of embodiments 1-73, wherein the recombinant protein has higher anti-*Cutibacterium acnes* lytic activity than full-length, native CaLys1.
75. The recombinant protein of any one of embodiments 55-74, wherein the recombinant protein has improved solubility compared to the corresponding native, full-length CaLys1-family protein sequence.
76. The recombinant protein of any one of embodiments 1-75, wherein the recombinant protein has improved solubility compared to native, full-length CaLys1.

II. Novel EAD Embodiments

1. A recombinant protein comprising a CLC1-family enzymatically active domain (EAD).
2. The recombinant protein of embodiment 1, wherein the EAD is derived from CLC1, CLC2, CLC3, CLC4, CLC5, CLC6, CLC7, CLC8, CLC9, CLC10, CLC11, CLC12, CLC13, CLC14, CLC15, CLC16, CLC17, CLC18, or CLC19.
3. The recombinant protein of embodiment 1 or 2, wherein the EAD is derived from SEQ ID NO: 1-19.
4. The recombinant protein of any one of embodiments 1-3, wherein the EAD comprises an amino acid sequence having at least 40, 45, 50, 55, 60, 65, 70, 75, 80, 85, 90, 95, 96, 97, 98, or 99% sequence identity to an amino acid sequence selected from the group consisting of SEQ ID NO: 20-36.
5. A recombinant protein comprising an enzymatically active domain (EAD) having at least 40, 45, 50, 55, 60, 65, 70, 75, 80, 85, 90, 95, 96, 97, 98, or 99% sequence identity to an amino acid sequence selected from the group consisting of SEQ ID NO: 20-36.
6. The recombinant protein of any one of embodiments 1-5, wherein the EAD comprises an amino acid sequence selected from the group consisting of SEQ ID NO: 20-36.
7. The recombinant protein of any one of embodiments 1-6, wherein the EAD comprises an amino acid sequence having at least 40, 45, 50, 55, 60, 65, 70, 75, 80, 85, 90, 95, 96, 97, 98, or 99% sequence identity to SEQ ID NO: 35.
8. The recombinant protein of any one of embodiments 1-6, wherein the EAD comprises the amino acid sequence of SEQ ID NO: 35.
9. The recombinant protein of any one of embodiments 1-6, wherein the EAD comprises an amino acid sequence having at least 40, 45, 50, 55, 60, 65, 70, 75, 80, 85, 90, 95, 96, 97, 98, or 99% sequence identity to SEQ ID NO: 21.

10. The recombinant protein of any one of embodiments 1-6, wherein the EAD comprises the amino acid sequence of SEQ ID NO: 21.
11. The recombinant protein of any one of embodiments 1-10, wherein the recombinant protein exhibits lytic activity against *Cutibacterium acnes*.
12. The recombinant protein of any one of embodiments 1-11, wherein the recombinant protein exhibits lytic activity against *Cutibacterium acnes* of a phylotype selected from the list consisting of: IA1, IA2, IB, II, and III.
13. The recombinant protein of any one of embodiments 1-12, wherein the recombinant protein exhibits lytic activity against phylotypes IA1, IA2, IB, and II of *Cutibacterium acnes*.
14. The recombinant protein of any one of embodiments 1-13, wherein the recombinant protein exhibits improved solubility and/or anti-*Cutibacterium acnes* activity compared to native CaLys1 (SEQ ID NO: 72).
14.1 The recombinant protein of any one of embodiments 1-14, wherein the recombinant protein comprises the CLC1-family EAD motif (SEQ ID NO: 2939).
15. The recombinant protein of any one of embodiments 1-14.1, wherein the recombinant protein comprises a heterologous cell wall binding domain (CBD).
16. The recombinant protein of embodiment 15, wherein the CBD comprises a CW_7 repeat with at least 40, 45, 50, 55, 60, 65, 70, 75, 80, 85, 90, 95, 96, 97, 98, or 99% sequence identity to SEQ ID NO: 47.
17. The recombinant protein of embodiment 15 or 16, wherein the CBD comprises a CW_7 repeat having the amino acid sequence of SEQ ID NO: 47.
18. The recombinant protein of any one of embodiments 15-17, wherein the CBD comprises a CW_7 repeat with at least 40, 45, 50, 55, 60, 65, 70, 75, 80, 85, 90, 95, 96, 97, 98, or 99% sequence identity to an amino acid sequence selected from the group consisting of SEQ ID NO: 45-51.
19. The recombinant protein of any one of embodiments 15-18, wherein the CBD comprises a CW_7 repeat having an amino acid sequence selected from the group consisting of SEQ ID NO: 45-51.
20. The recombinant protein of any one of embodiments 15-19, wherein the CBD comprises a CW_7 repeat with at least 40, 45, 50, 55, 60, 65, 70, 75, 80, 85, 90, 95, 96, 97, 98, or 99% sequence identity to a CW_7 repeat comprised by an amino acid sequence selected from the group consisting of SEQ ID NO: 166-223.
21. The recombinant protein of any one of embodiments 15-20, wherein the CBD comprises a CW_7 repeat comprised by an amino acid sequence selected from the group consisting of SEQ ID NO: 166-223.
22. The recombinant protein of any one of embodiments 15-21, wherein the CBD comprises a CW_7 repeat with at least 40, 45, 50, 55, 60, 65, 70, 75, 80, 85, 90, 95, 96, 97, 98, or 99% sequence identity to a CW_7 repeat comprised by an amino acid sequence selected from the group consisting of SEQ ID NO: 168, 188, 198, 205, 211, and 221.
23. The recombinant protein of any one of embodiments 15-22, wherein the CBD comprises a CW_7 repeat comprised by an amino acid sequence selected from the group consisting of SEQ ID NO: 168, 188, 198, 205, 211, and 221.
24. The recombinant protein of any one of embodiments 15-23, wherein the CBD comprises a CW_7 repeat with at least 40, 45, 50, 55, 60, 65, 70, 75, 80, 85, 90, 95, 96, 97, 98, or 99% sequence identity to a CW_7 repeat comprised by an amino acid sequence selected from the group consisting of SEQ ID NO: 282-2938.
25. The recombinant protein of any one of embodiments 15-24, wherein the CBD comprises a CW_7 repeat comprised by an amino acid sequence selected from the group consisting of SEQ ID NO: 282-2938.
26. The recombinant protein of any one of embodiments 15-25, wherein the CBD comprises a CW_7 repeat with at least 40, 45, 50, 55, 60, 65, 70, 75, 80, 85, 90, 95, 96, 97, 98, or 99% sequence identity to a CW_7 comprised by a protein listed in Table 7.
27. The recombinant protein of any one of embodiments 15-26, wherein the CBD comprises a CW_7 repeat comprised by a protein listed in Table 7.
28. The recombinant protein of any one of embodiments 15-27, wherein the CBD comprises an amino acid sequence having at least 40, 45, 50, 55, 60, 65, 70, 75, 80, 85, 90, 95, 96, 97, 98, or 99% sequence identity to an amino acid sequence selected from the group consisting of SEQ ID NO: 41-44.
29. The recombinant protein of any one of embodiments 15-27, wherein the CBD comprises an amino acid sequence selected from the group consisting of SEQ ID NO: 41-44.
30. The recombinant protein of any one of embodiments 15-27, wherein the CBD comprises an amino acid sequence having at least 40, 45, 50, 55, 60, 65, 70, 75, 80, 85, 90, 95, 96, 97, 98, or 99% sequence identity to SEQ ID NO: 42.
31. The recombinant protein of any one of embodiments 15-27, wherein the CBD comprises the amino acid sequence of SEQ ID NO: 42.
32. The recombinant protein of any one of embodiments 15-27, wherein the CBD comprises an amino acid sequence having at least 40, 45, 50, 55, 60, 65, 70, 75, 80, 85, 90, 95, 96, 97, 98, or 99% sequence identity to an amino acid sequence selected from the group consisting of SEQ ID NO: 166-223.
33. The recombinant protein of any one of embodiments 15-27, wherein the CBD comprises an amino acid sequence selected from the group consisting of SEQ ID NO: 166-223.
34. The recombinant protein of any one of embodiments 15-27, wherein the CBD comprises an amino acid sequence having at least 40, 45, 50, 55, 60, 65, 70, 75, 80, 85, 90, 95, 96, 97, 98, or 99% sequence identity to a CW_7 repeat comprised by an amino acid sequence selected from the group consisting of SEQ ID NO: 168, 188, 198, 205, 211, and 221.
35. The recombinant protein of any one of embodiments 15-27, wherein the CBD comprises an amino acid sequence selected from the group consisting of SEQ ID NO: 168, 188, 198, 205, 211, and 221.
36. The recombinant protein of any one of embodiments 15-27, wherein the recombinant protein comprises a CBD having at least 40, 45, 50, 55, 60, 65, 70, 75, 80, 85, 90, 95, 96, 97, 98, or 99% sequence identity to a CBD comprised by an amino acid sequence selected from the group consisting of SEQ ID NO: 282-2938.
37. The recombinant protein of any one of embodiments 15-27, wherein the recombinant protein comprises a CBD comprised by an amino acid sequence selected from the group consisting of SEQ ID NO: 282-2938.
38. The recombinant protein of any one of embodiments 15-27, wherein the recombinant protein comprises a CBD with at least 40, 45, 50, 55, 60, 65, 70, 75, 80, 85, 90, 95, 96, 97, 98, or 99% sequence identity to a CBD comprised by a protein listed in Table 7.

39. The recombinant protein of any one of embodiments 15-27, wherein the recombinant protein comprises a CBD comprised by a protein listed in Table 7.

40. The recombinant protein of any one of embodiments 15-39, wherein the CBD comprises 1, 2, 3, 4, 5, 6, 7, 8, 9, or 10 CW_7 repeats.

41. The recombinant protein of any one of embodiments 1-40, wherein the recombinant protein is a chimeric cell wall hydrolase (CWH).

42. The recombinant protein of any one of embodiments 1-41, wherein the recombinant protein binds to *Cutibacterium acnes*.

43. The recombinant protein of any one of embodiments 1-42, wherein the recombinant protein has lytic activity against *Cutibacterium acnes*.

44. The recombinant protein of any one of embodiments 1-43, wherein the recombinant protein comprises a cell wall binding domain (CBD), and wherein the CBD is located at the C-terminal end of the EAD.

45. The recombinant protein of any one of embodiments 1-44, wherein the recombinant protein displays a higher lytic activity against *C. acnes* than native CaLys1 (SEQ ID NO: 72).

46. The recombinant protein of any one of embodiments 1-45, wherein the recombinant protein displays a higher lytic activity against *C. acnes* than the native protein from which the EAD is derived.

47. The recombinant protein of any one of embodiments 1-46, wherein the recombinant protein displays minimal or no lytic activity against *Corynebacterium xerosis, Corynebacterium striatum*, and/or *Staphylococcus epidermidis*.

48. The recombinant protein of any one of embodiments 1-47, wherein the recombinant protein has lytic activity against *Cutibacterium acnes*, and wherein the lytic activity is measured using a turbidity reduction assay.

49. The recombinant protein of any one of embodiments 1-48, wherein the recombinant protein has lytic activity against *Cutibacterium acnes* across a pH range of 4.2-8.0.

50. The recombinant protein of any one of embodiments 1-49, wherein the recombinant protein has peak *C. acnes* lytic activity at a pH that is less than 7.

51. The recombinant protein of any one of embodiments 1-50, wherein the recombinant protein has peak *C. acnes* lytic activity at a pH of 5.5-6.5, 5.8-6.2, 5.9-6.1, or about 6.0.

52. The recombinant protein of any one of embodiments 1-51, wherein the recombinant protein retains at least 50% of its activity at 25° C. after being exposed to a temperature of up to 45° C., 50° C., 55° C., or 58° C. for 30 minutes.

53. The recombinant protein of any one of embodiments 1-52, wherein the recombinant protein comprises the CLC16 EAD (SEQ ID NO: 35) and retains at least 50% of its activity at 25° C. after being exposed to a temperature of up to 75° C. for 30 minutes.

54. The recombinant protein of any one of embodiments 1-53, wherein the recombinant protein comprises the CLC16 EAD (SEQ ID NO: 35) and retains at least 40% of its activity at 25° C. after being exposed to a temperature of up to 90° C. for 30 minutes.

55. The recombinant protein of any one of embodiments 1-54, wherein the solubility of the recombinant protein is at least 2-fold, at least 5-fold, at least 10-fold, or at least 100-fold higher than the solubility of CaLys1 (SEQ ID NO: 72).

III. Novel CBD Embodiments

1. A recombinant protein comprising a CW_7 cell wall binding domain (CBD).
2. The recombinant protein of embodiment 1, wherein the CBD comprises a CW_7 repeat with at least 40, 45, 50, 55, 60, 65, 70, 75, 80, 85, 90, 95, 96, 97, 98, or 99% sequence identity to SEQ ID NO: 47.
3. The recombinant protein of embodiment 1 or 2, wherein the CBD comprises a CW_7 repeat having the amino acid sequence of SEQ ID NO: 47.
4. The recombinant protein of any one of embodiments 1-3, wherein the CBD comprises a CW_7 repeat with at least 40, 45, 50, 55, 60, 65, 70, 75, 80, 85, 90, 95, 96, 97, 98, or 99% sequence identity to an amino acid sequence selected from the group consisting of SEQ ID NO: 45-51.
5. The recombinant protein of any one of embodiments 1-4, wherein the CBD comprises a CW_7 repeat having an amino acid sequence selected from the group consisting of SEQ ID NO: 45-51.
6. The recombinant protein of any one of embodiments 1-5, wherein the CBD comprises a CW_7 repeat with at least 40, 45, 50, 55, 60, 65, 70, 75, 80, 85, 90, 95, 96, 97, 98, or 99% sequence identity to a CW_7 repeat comprised by an amino acid sequence selected from the group consisting of SEQ ID NO: 166-223.
7. The recombinant protein of any one of embodiments 1-6, wherein the CBD comprises a CW_7 repeat comprised by an amino acid sequence selected from the group consisting of SEQ ID NO: 166-223.
8. The recombinant protein of any one of embodiments 1-7, wherein the CBD comprises a CW_7 repeat with at least 40, 45, 50, 55, 60, 65, 70, 75, 80, 85, 90, 95, 96, 97, 98, or 99% sequence identity to a CW_7 repeat comprised by an amino acid sequence selected from the group consisting of SEQ ID NO: 168, 188, 198, 205, 211, and 221.
9. The recombinant protein of any one of embodiments 1-8, wherein the CBD comprises a CW_7 repeat comprised by an amino acid sequence selected from the group consisting of SEQ ID NO: 168, 188, 198, 205, 211, and 221.
10. The recombinant protein of any one of embodiments 1-9, wherein the CBD comprises a CW_7 repeat with at least 40, 45, 50, 55, 60, 65, 70, 75, 80, 85, 90, 95, 96, 97, 98, or 99% sequence identity to a CW_7 repeat comprised by an amino acid sequence selected from the group consisting of SEQ ID NO: 282-2938.
11. The recombinant protein of any one of embodiments 1-10, wherein the CBD comprises a CW_7 repeat comprised by an amino acid sequence selected from the group consisting of SEQ ID NO: 282-2938.
12. The recombinant protein of any one of embodiments 1-11, wherein the CBD comprises a CW_7 repeat with at least 40, 45, 50, 55, 60, 65, 70, 75, 80, 85, 90, 95, 96, 97, 98, or 99% sequence identity to a CW_7 comprised by a protein listed in Table 7.
13. The recombinant protein of any one of embodiments 1-12, wherein the CBD comprises a CW_7 repeat comprised by a protein listed in Table 7.
14. The recombinant protein of any one of embodiments 1-13, wherein the CBD comprises an amino acid sequence having at least 40, 45, 50, 55, 60, 65, 70, 75, 80, 85, 90, 95, 96, 97, 98, or 99% sequence identity to an amino acid sequence selected from the group consisting of SEQ ID NO: 41-44.
15. The recombinant protein of any one of embodiments 1-13, wherein the CBD comprises an amino acid sequence selected from the group consisting of SEQ ID NO: 41-44.
16. The recombinant protein of any one of embodiments 1-13, wherein the CBD comprises an amino acid sequence having at least 40, 45, 50, 55, 60, 65, 70, 75, 80, 85, 90, 95, 96, 97, 98, or 99% sequence identity to SEQ ID NO: 42.
17. The recombinant protein of any one of embodiments 1-13, wherein the CBD comprises the amino acid sequence of SEQ ID NO: 42.
18. The recombinant protein of any one of embodiments 1-13, wherein the CBD comprises an amino acid sequence having at least 40, 45, 50, 55, 60, 65, 70, 75, 80, 85, 90, 95, 96, 97, 98, or 99% sequence identity to an amino acid sequence selected from the group consisting of SEQ ID NO: 166-223.
19. The recombinant protein of any one of embodiments 1-13, wherein the CBD comprises an amino acid sequence selected from the group consisting of SEQ ID NO: 166-223.
20. The recombinant protein of any one of embodiments 1-13, wherein the CBD comprises an amino acid sequence having at least 40, 45, 50, 55, 60, 65, 70, 75, 80, 85, 90, 95, 96, 97, 98, or 99% sequence identity to a CW_7 repeat comprised by an amino acid sequence selected from the group consisting of SEQ ID NO: 168, 188, 198, 205, 211, and 221.
21. The recombinant protein of any one of embodiments 1-13, wherein the CBD comprises an amino acid sequence selected from the group consisting of SEQ ID NO: 168, 188, 198, 205, 211, and 221.
22. The recombinant protein of any one of embodiments 1-13, wherein the recombinant protein comprises a CBD having at least 40, 45, 50, 55, 60, 65, 70, 75, 80, 85, 90, 95, 96, 97, 98, or 99% sequence identity to a CBD comprised by an amino acid sequence selected from the group consisting of SEQ ID NO: 282-2938.
23. The recombinant protein of any one of embodiments 1-13, wherein the recombinant protein comprises a CBD comprised by an amino acid sequence selected from the group consisting of SEQ ID NO: 282-2938.
24. The recombinant protein of any one of embodiments 1-13, wherein the recombinant protein comprises a CBD with at least 40, 45, 50, 55, 60, 65, 70, 75, 80, 85, 90, 95, 96, 97, 98, or 99% sequence identity to a CBD comprised by a protein listed in Table 7.
25. The recombinant protein of any one of embodiments 1-13, wherein the recombinant protein comprises a CBD comprised by a protein listed in Table 7.
26. The recombinant protein of any one of embodiments 1-25, wherein the CBD comprises 1, 2, 3, 4, 5, 6, 7, 8, 9, or 10 CW_7 repeats.
27. The recombinant protein of any one of embodiments 1-26, wherein the recombinant protein is an enzyme.
28. The recombinant protein of any one of embodiments 1-27, wherein the recombinant protein is a chimeric protein.
29. The recombinant protein of any one of embodiments 1-28, wherein the recombinant protein is a chimeric cell wall hydrolase (CWH).
29.1 The recombinant protein of any one of embodiments 1-29, wherein the recombinant protein comprises the CW_7-21 motif (SEQ ID NO: 2940).
29.2 The recombinant protein of any one of embodiments 1-29.1, wherein the recombinant protein comprises the CW_7-19 motif (SEQ ID NO: 2941).
30. The recombinant protein of any one of embodiments 1-29.2, wherein the recombinant protein comprises an enzymatically active domain (EAD).
31. The recombinant protein of embodiment 30, wherein the EAD is heterologous to the CBD.
32. The recombinant protein of embodiment 30 or 31, wherein the EAD has at least 40, 45, 50, 55, 60, 65, 70, 75, 80, 85, 90, 95, 96, 97, 98, or 99% sequence identity to a CaLys1-family EAD.
33. The recombinant protein of any one of embodiments 30-32, wherein the EAD comprises a CaLys1-family EAD.
34. The recombinant protein of any one of embodiments 30-33, wherein the EAD has at least 40, 45, 50, 55, 60, 65, 70, 75, 80, 85, 90, 95, 96, 97, 98, or 99% sequence identity to SEQ ID NO: 73.
35. The recombinant protein of any one of embodiments 30-34, wherein the EAD comprises the amino acid sequence of SEQ ID NO: 73.
36. The recombinant protein of any one of embodiments 30-31, wherein the EAD has at least 40, 45, 50, 55, 60, 65, 70, 75, 80, 85, 90, 95, 96, 97, 98, or 99% sequence identity to a CLC1-family EAD.
37. The recombinant protein of any one of embodiments 30-31 and 36, wherein the EAD comprises a CLC1-family EAD.
38. The recombinant protein of any one of embodiments 30-31 and 36-37, wherein the EAD has at least 40, 45, 50, 55, 60, 65, 70, 75, 80, 85, 90, 95, 96, 97, 98, or 99% sequence identity to an amino acid sequence selected from the list consisting of SEQ ID NO: 20-36.
39. The recombinant protein of any one of embodiments 30-31 and 36-38, wherein the EAD comprises an amino acid sequence selected from the list consisting of SEQ ID NO: 20-36.
40. The recombinant protein of any one of embodiments 30-31 and 36-39, wherein the EAD has at least 40, 45, 50, 55, 60, 65, 70, 75, 80, 85, 90, 95, 96, 97, 98, or 99% sequence identity to SEQ ID NO: 21.
41. The recombinant protein of any one of embodiments 30-31 and 36-40, wherein the EAD comprises the amino acid sequence of SEQ ID NO: 21.
42. The recombinant protein of any one of embodiments 30-31 and 36-39, wherein the EAD has at least 40, 45, 50, 55, 60, 65, 70, 75, 80, 85, 90, 95, 96, 97, 98, or 99% sequence identity to SEQ ID NO: 35.
43. The recombinant protein of any one of embodiments 30-31 and 36-39, wherein the EAD comprises the amino acid sequence of SEQ ID NO: 35.
44. The recombinant protein of any one of embodiments 1-43, wherein the recombinant protein binds to *Cutibacterium acnes*.
45. The recombinant protein of any one of embodiments 1-44, wherein the recombinant protein has lytic activity against *Cutibacterium acnes*.
46. The recombinant protein of any one of embodiments 1-45, wherein the recombinant protein comprises an enzymatically active domain (EAD), and wherein the CBD is located at the C-terminal end of the EAD.
47. The recombinant protein of any one of embodiments 1-46, wherein the recombinant protein displays a higher lytic activity against *C. acnes* than the native protein from which the CW_7 and/or CBD is derived.
48. The recombinant protein of any one of embodiments 1-47, wherein the recombinant protein displays minimal or no lytic activity against *Corynebacterium xerosis, Corynebacterium striatum*, and/or *Staphylococcus epidermidis*.
49. The recombinant protein of any one of embodiments 1-48, wherein the recombinant protein has lytic activity against *Cutibacterium acnes*, and wherein the lytic activity is measured using a turbidity reduction assay.
50. The recombinant protein of any one of embodiments 1-49, wherein the recombinant protein has lytic activity against *Cutibacterium acnes* across a pH range of 4.2-8.0.
51. The recombinant protein of any one of embodiments 1-50, wherein the recombinant protein has peak *C. acnes* lytic activity at a pH that is less than 7.
52. The recombinant protein of any one of embodiments 1-51, wherein the recombinant protein has peak *C. acnes* lytic activity at a pH of 5.5-6.5, 5.8-6.2, 5.9-6.1, or about 6.0.
53. The recombinant protein of any one of embodiments 1-52, wherein the recombinant protein retains at least 50% of its activity at 25° C. after being exposed to a temperature of up to 45° C., 50° C., 55° C., or 58° C. for 30 minutes.
54. The recombinant protein of any one of embodiments 1-53, wherein the solubility of the recombinant protein is at least 2-fold, at least 5-fold, at least 10-fold, or at least 100-fold higher than the solubility of native CaLys1 (SEQ ID NO: 72).

IV. Novel Chimeric Cell Wall Hydrolase Embodiments

1. A chimeric cell wall hydrolase (CWH) comprising:
a) a CW_7 cell wall binding domain (CBD), and
b) a CLC1-family enzymatically active domain (EAD).
2. The chimeric CWH of embodiment 1, wherein the EAD is derived from CLC1, CLC2, CLC3, CLC4, CLC5, CLC6, CLC7, CLC8, CLC9, CLC10, CLC11, CLC12, CLC13, CLC14, CLC15, CLC16, CLC17, CLC18, or CLC19.
3. The chimeric CWH of embodiment 1 or embodiment 2, wherein the EAD is derived from SEQ ID NO: 1-19.
4. The chimeric CWH of any one of embodiments 1-3, wherein the EAD comprises an amino acid sequence having at least 40, 45, 50, 55, 60, 65, 70, 75, 80, 85, 90, 95, 96, 97, 98, or 99% sequence identity to an amino acid sequence selected from the group consisting of SEQ ID NO: 20-36.
5. The chimeric CWH of any one of embodiments 1-4, wherein the EAD comprises an amino acid sequence selected from the group consisting of SEQ ID NO: 20-36.
6. The chimeric CWH of any one of embodiments 1-5, wherein the EAD comprises an amino acid sequence having at least 40, 45, 50, 55, 60, 65, 70, 75, 80, 85, 90, 95, 96, 97, 98, or 99% sequence identity to SEQ ID NO: 35.
7. The chimeric CWH of any one of embodiments 1-5, wherein the EAD comprises the amino acid sequence of SEQ ID NO: 35.
8. The chimeric CWH of any one of embodiments 1-5, wherein the EAD comprises an amino acid sequence having at least 40, 45, 50, 55, 60, 65, 70, 75, 80, 85, 90, 95, 96, 97, 98, or 99% sequence identity to SEQ ID NO: 21.
9. The chimeric CWH of any one of embodiments 1-5, wherein the EAD comprises the amino acid sequence of SEQ ID NO: 21.
10. A chimeric cell wall hydrolase (CWH) comprising:
a) a CW_7 cell wall binding domain (CBD), and
b) the enzymatically active domain (EAD) from CLC16 (SEQ ID NO: 35).
11. A chimeric cell wall hydrolase (CWH) comprising:
a) a CW_7 cell wall binding domain (CBD), and
b) the enzymatically active domain (EAD) from CLC2 (SEQ ID NO: 21).
12. A chimeric cell wall hydrolase (CWH) comprising:
a) a CW_7 cell wall binding domain (CBD), and
b) a CaLys1-family enzymatically active domain (EAD).
13. The chimeric CWH of embodiment 12, wherein the EAD has at least 40, 45, 50, 55, 60, 65, 70, 75, 80, 85, 90, 95, 96, 97, 98, or 99% sequence identity to SEQ ID NO: 73.
14. The chimeric CWH of embodiment 12 or 13, wherein the EAD comprises the amino acid sequence of SEQ ID NO: 73.
14.1 A chimeric cell wall hydrolase (CWH) comprising:
a) a CW_7 cell wall binding domain (CBD), and
b) the PlyGVE2 enzymatically active domain (EAD) (SEQ ID NO: 64) or the CD27L EAD (SEQ ID NO: 63).
15. A chimeric cell wall hydrolase (CWH) comprising:
a) a CW_7 cell wall binding domain (CBD), and
b) the enzymatically active domain (EAD) from CaLys1 (SEQ ID NO: 73).
16. The chimeric CWH of any one of embodiments 1-15, wherein the CBD comprises a CW_7 repeat with at least 40, 45, 50, 55, 60, 65, 70, 75, 80, 85, 90, 95, 96, 97, 98, or 99% sequence identity to SEQ ID NO: 47.
17. The chimeric CWH of any one of embodiments 1-16, wherein the CBD comprises a CW_7 repeat having the amino acid sequence of SEQ ID NO: 47.
18. The chimeric CWH of any one of embodiments 1-17, wherein the CBD comprises a CW_7 repeat with at least 40, 45, 50, 55, 60, 65, 70, 75, 80, 85, 90, 95, 96, 97, 98, or 99% sequence identity to an amino acid sequence selected from the group consisting of SEQ ID NO: 45-51.
19. The chimeric CWH of any one of embodiments 1-18, wherein the CBD comprises a CW_7 repeat having an amino acid sequence selected from the group consisting of SEQ ID NO: 45-51.
20. The chimeric CWH of any one of embodiments 1-19, wherein the CBD comprises a CW_7 repeat with at least 40, 45, 50, 55, 60, 65, 70, 75, 80, 85, 90, 95, 96, 97, 98, or 99% sequence identity to a CW_7 repeat comprised by an amino acid sequence selected from the group consisting of SEQ ID NO: 166-223.
21. The chimeric CWH of any one of embodiments 1-20, wherein the CBD comprises a CW_7 repeat comprised by an amino acid sequence selected from the group consisting of SEQ ID NO: 166-223.
22. The chimeric CWH of any one of embodiments 1-21, wherein the CBD comprises a CW_7 repeat with at least 40, 45, 50, 55, 60, 65, 70, 75, 80, 85, 90, 95, 96, 97, 98, or 99% sequence identity to a CW_7 repeat comprised by an amino acid sequence selected from the group consisting of SEQ ID NO: 168, 188, 198, 205, 211, and 221.

23. The chimeric CWH of any one of embodiments 1-22, wherein the CBD comprises a CW_7 repeat comprised by an amino acid sequence selected from the group consisting of SEQ ID NO: 168, 188, 198, 205, 211, and 221.

24. The chimeric CWH of any one of embodiments 1-23, wherein the CBD comprises a CW_7 repeat with at least 40, 45, 50, 55, 60, 65, 70, 75, 80, 85, 90, 95, 96, 97, 98, or 99% sequence identity to a CW_7 repeat comprised by an amino acid sequence selected from the group consisting of SEQ ID NO: 282-2938.

25. The chimeric CWH of any one of embodiments 1-24, wherein the CBD comprises a CW_7 repeat comprised by an amino acid sequence selected from the group consisting of SEQ ID NO: 282-2938.

26. The chimeric CWH of any one of embodiments 1-25, wherein the CBD comprises a CW_7 repeat with at least 40, 45, 50, 55, 60, 65, 70, 75, 80, 85, 90, 95, 96, 97, 98, or 99% sequence identity to a CW_7 comprised by a protein listed in Table 7.

27. The chimeric CWH of any one of embodiments 1-26, wherein the CBD comprises a CW_7 repeat comprised by a protein listed in Table 7.

28. The chimeric CWH of any one of embodiments 1-27, wherein the CBD comprises an amino acid sequence having at least 40, 45, 50, 55, 60, 65, 70, 75, 80, 85, 90, 95, 96, 97, 98, or 99% sequence identity to an amino acid sequence selected from the group consisting of SEQ ID NO: 41-44.

29. The chimeric CWH of any one of embodiments 1-27, wherein the CBD comprises an amino acid sequence selected from the group consisting of SEQ ID NO: 41-44.

30. The chimeric CWH of any one of embodiments 1-27, wherein the CBD comprises an amino acid sequence having at least 40, 45, 50, 55, 60, 65, 70, 75, 80, 85, 90, 95, 96, 97, 98, or 99% sequence identity to SEQ ID NO: 42.

31. The chimeric CWH of any one of embodiments 1-27, wherein the CBD comprises the amino acid sequence of SEQ ID NO: 42.

32. The chimeric CWH of any one of embodiments 1-27, wherein the CBD comprises an amino acid sequence having at least 40, 45, 50, 55, 60, 65, 70, 75, 80, 85, 90, 95, 96, 97, 98, or 99% sequence identity to an amino acid sequence selected from the group consisting of SEQ ID NO: 166-223.

33. The chimeric CWH of any one of embodiments 1-27, wherein the CBD comprises an amino acid sequence selected from the group consisting of SEQ ID NO: 166-223.

34. The chimeric CWH of any one of embodiments 1-27, wherein the CBD comprises an amino acid sequence having at least 40, 45, 50, 55, 60, 65, 70, 75, 80, 85, 90, 95, 96, 97, 98, or 99% sequence identity to a CW_7 repeat comprised by an amino acid sequence selected from the group consisting of SEQ ID NO: 168, 188, 198, 205, 211, and 221.

35. The chimeric CWH of any one of embodiments 1-27, wherein the CBD comprises an amino acid sequence selected from the group consisting of SEQ ID NO: 168, 188, 198, 205, 211, and 221.

36. The chimeric CWH of any one of embodiments 1-27, wherein the recombinant protein comprises a CBD having at least 40, 45, 50, 55, 60, 65, 70, 75, 80, 85, 90, 95, 96, 97, 98, or 99% sequence identity to a CBD comprised by an amino acid sequence selected from the group consisting of SEQ ID NO: 282-2938.

37. The chimeric CWH of any one of embodiments 1-27, wherein the recombinant protein comprises a CBD comprised by an amino acid sequence selected from the group consisting of SEQ ID NO: 282-2938.

38. The chimeric CWH of any one of embodiments 1-27, wherein the recombinant protein comprises a CBD with at least 40, 45, 50, 55, 60, 65, 70, 75, 80, 85, 90, 95, 96, 97, 98, or 99% sequence identity to a CBD comprised by a protein listed in Table 7.

39. The chimeric CWH of any one of embodiments 1-27, wherein the recombinant protein comprises a CBD comprised by a protein listed in Table 7.

40. The chimeric CWH of any one of embodiments 1-39, wherein the CBD comprises 1, 2, 3, 4, 5, 6, 7, 8, 9, or 10 CW_7 repeats.

41. A chimeric cell wall hydrolase (CWH) comprising:
    a) the cell wall binding domain (CBD) from CLB2 (SEQ ID NO: 42), and
    b) the enzymatically active domain (EAD) from CLC16 (SEQ ID NO: 35).

42. A chimeric cell wall hydrolase (CWH) comprising an amino acid sequence having at least 70, 75, 80, 85, 90, 95, 96, 97, 98, or 99% sequence identity with SEQ ID NO: 106.

43. A chimeric cell wall hydrolase (CWH) comprising the amino acid sequence of SEQ ID NO: 106.

44. A chimeric cell wall hydrolase (CWH) comprising:
    a) the cell wall binding domain (CBD) from CLB2 (SEQ ID NO: 42), and
    b) the enzymatically active domain (EAD) from CLC2 (SEQ ID NO: 21).

45. A chimeric cell wall hydrolase (CWH) comprising an amino acid sequence having at least 70, 75, 80, 85, 90, 95, 96, 97, 98, or 99% sequence identity with SEQ ID NO: 57.

46. A chimeric cell wall hydrolase (CWH) comprising the amino acid sequence of SEQ ID NO: 57.

47. A chimeric cell wall hydrolase (CWH) comprising an amino acid sequence having at least 70, 75, 80, 85, 90, 95, 96, 97, 98, or 99% sequence identity with an amino acid sequence selected from the list consisting of SEQ ID NO: 52-59.

48. A chimeric cell wall hydrolase (CWH) comprising an amino acid sequence selected from the list consisting of SEQ ID NO: 52-59.

49. A chimeric cell wall hydrolase (CWH) comprising an amino acid sequence having at least 70, 75, 80, 85, 90, 95, 96, 97, 98, or 99% sequence identity with an amino acid sequence selected from the list consisting of SEQ ID NO: 53, 57, 59, and 94-107.

50. A chimeric cell wall hydrolase (CWH) comprising an amino acid sequence selected from the list consisting of SEQ ID NO: 52-59.

51. A chimeric cell wall hydrolase (CWH) comprising an amino acid sequence having at least 70, 75, 80, 85, 90, 95, 96, 97, 98, or 99% sequence identity with an amino acid sequence selected from the list consisting of SEQ ID NO: 224-281.

52. A chimeric cell wall hydrolase (CWH) comprising an amino acid sequence selected from the list consisting of SEQ ID NO: 224-281.

53. A chimeric cell wall hydrolase (CWH) comprising an amino acid sequence having at least 70, 75, 80, 85, 90, 95, 96, 97, 98, or 99% sequence identity with an amino acid sequence selected from the list consisting of SEQ ID NO: 66-69.

54. A chimeric cell wall hydrolase (CWH) comprising an amino acid sequence selected from the list consisting of SEQ ID NO: 66-69.

55. The chimeric CWH of any one of embodiments 1-54, wherein the chimeric CWH binds to *Cutibacterium acnes*.

56. The chimeric CWH of any one of embodiments 1-55, wherein the chimeric CWH exhibits lytic activity against *Cutibacterium acnes*.

57. The chimeric CWH of any one of embodiments 1-56, wherein the chimeric CWH exhibits lytic activity against *Cutibacterium acnes* of a phylotype selected from the list consisting of: IA1, IA2, IB, II, and III.

58. The chimeric CWH of any one of embodiments 1-57, wherein the chimeric CWH exhibits lytic activity against phylotypes IA1 and IA2 of *Cutibacterium acnes*.

59. The chimeric CWH of any one of embodiments 1-58 wherein the chimeric CWH exhibits lytic activity against phylotypes IA1, IA2, IB, and II of *Cutibacterium acnes*.

60. The chimeric CWH of any one of embodiments 1-59, wherein the chimeric CWH exhibits improved anti-*Cutibacterium acnes* activity compared to native CaLys1 (SEQ ID NO: 72).

61. The chimeric CWH of any one of embodiments 1-60, wherein the CBD is located at the C-terminal end of the EAD.

62. The chimeric CWH of any one of embodiments 1-61, wherein the chimeric CWH displays a higher lytic activity against *C. acnes* than the native protein from which the CBD is derived.

63. The chimeric CWH of any one of embodiments 1-62, wherein the chimeric CWH displays a higher lytic activity against *C. acnes* than the native protein from which the EAD is derived.

64. The chimeric CWH of any one of embodiments 1-63, wherein the chimeric CWH displays minimal or no lytic activity against *Corynebacterium xerosis*, *Corynebacterium striatum*, and/or *Staphylococcus epidermidis*.

65. The chimeric CWH of any one of embodiments 1-64, wherein the chimeric CWH has lytic activity against *Cutibacterium acnes*, and wherein the lytic activity is measured using a turbidity reduction assay.

66. The chimeric CWH of any one of embodiments 1-65, wherein the chimeric CWH has lytic activity against *Cutibacterium acnes* across a pH range of 4.2-8.0.

67. The chimeric CWH of any one of embodiments 1-66, wherein the chimeric CWH has peak *C. acnes* lytic activity at a pH that is less than 7.

68. The chimeric CWH of any one of embodiments 1-67, wherein the chimeric CWH has peak *C. acnes* lytic activity at a pH of 5.5-6.5, 5.8-6.2, 5.9-6.1, or about 6.0.

69. The chimeric CWH of any one of embodiments 1-68, wherein the chimeric CWH retains at least 50% of its activity at 25° C. after being exposed to a temperature of up to 45° C., 50° C., 55° C., or 58° C. for 30 minutes.

70. The chimeric CWH of any one of embodiments 1-69, wherein the chimeric CWH comprises the CLC16 EAD (SEQ ID NO: 35), or an EAD having an amino acid sequence having at least 70, 75, 80, 85, 90, 95, 96, 97, 98, or 99% sequence identity thereto, and wherein the chimeric CWH retains at least 50% of its activity at 25° C. after being exposed to a temperature of up to 75° C. for 30 minutes.

71. The chimeric CWH of any one of embodiments 1-70, wherein the chimeric CWH comprises the CLC16 EAD (SEQ ID NO: 35), or an EAD having an amino acid sequence having at least 70, 75, 80, 85, 90, 95, 96, 97, 98, or 99% sequence identity thereto, and wherein the chimeric CWH retains at least 40% of its activity at 25° C. after being exposed to a temperature of up to 90° C. for 30 minutes.

72. The chimeric CWH of any one of embodiments 1-71, wherein the chimeric CWH exhibits improved solubility compared to native CaLys1 (SEQ ID NO: 72).

73. The chimeric CWH of any one of embodiments 1-72, wherein the solubility of the chimeric CWH is at least 2-fold, at least 5-fold, at least 10-fold, or at least 100-fold higher than the solubility of native CaLys1 (SEQ ID NO: 72).

V. Novel Formulation & Method Embodiments

1. A formulation comprising a recombinant protein or a chimeric CWH of any of the foregoing embodiments.
2. A formulation comprising a chimeric cell wall hydrolase (CWH) comprising:
   a) a cell wall binding domain (CBD) having at least 40, 45, 50, 55, 60, 65, 70, 75, 80, 85, 90, 95, 96, 97, 98, or 99% sequence identity to the CBD from CLB2 (SEQ ID NO: 42), and
   b) an enzymatically active domain (EAD) having at least 40, 45, 50, 55, 60, 65, 70, 75, 80, 85, 90, 95, 96, 97, 98, or 99% sequence identity to the EAD from CLC16 (SEQ ID NO: 35).
3. A formulation comprising a chimeric cell wall hydrolase (CWH) comprising:
   a) the cell wall binding domain (CBD) from CLB2 (SEQ ID NO: 42), and
   b) the enzymatically active domain (EAD) from CLC16 (SEQ ID NO: 35).
4. A formulation comprising a chimeric CWH comprising an amino acid sequence having at least 80, 81, 82, 83, 84, 85, 86, 87, 88, 89, 90, 91, 92, 93, 94, 95, 96, 97, 98, or 99% identity with SEQ ID NO: 106.
5. A formulation comprising a chimeric CWH comprising the amino acid sequence of SEQ ID NO: 106.
6. The formulation of any one of embodiments 1-5, wherein the formulation is a topical formulation.
7. The formulation of any one of embodiments 1-6, wherein the formulation is a hydrogel, lotion, cream, gel-cream, colloidal patch, or microneedle patch.
8. The formulation of any one of embodiments 1-7, wherein the formulation is a hydrogel.
9. The formulation of any one of embodiments 1-8, wherein the formulation comprises a humectant.
10. The formulation of any one of embodiments 1-9, wherein the formulation comprises a humectant, and wherein the humectant is selected from the list consisting of: aloe vera, betaine, butylene glycol, caprylyl glycol, dimethicone, fructose, glucomannan, glucose, glycerin, glyceryl glucoside, honey, hyaluronic acid, lactic acid, panthenol, polyethylene glycol, propylene glycol, propanediol, sodium hyaluronate, sodium lactate, sodium pyrrolidone carboxylic acid, sorbitol, and urea.

11. The formulation of any one of embodiments 1-10, wherein the formulation comprises 0.1-50% w/v humectant.
12. The formulation of any one of embodiments 1-11, wherein the formulation comprises 0.5-10% w/v humectant.
13. The formulation of any one of embodiments 1-12, wherein the formulation comprises a cellulose polymer.
14. The formulation of any one of embodiments 1-13, wherein the formulation comprises a cellulose polymer, and wherein the cellulose polymer is selected from the list consisting of: hydroxyethyl cellulose, methylcellulose, hydroxy methylcellulose, carboxymethyl cellulose, microcrystalline cellulose, ethyl cellulose, sodium carboxymethyl cellulose, hydroxypropyl cellulose, and cellulose acetate.
15. The formulation of any one of embodiments 1-14, wherein the formulation comprises 0.5-10% w/v of a cellulose polymer.
16. The formulation of any one of embodiments 1-15, wherein the formulation comprises 1-5% w/v of a cellulose polymer.
17. The formulation of any one of embodiments 1-16, wherein the formulation comprises a salt.
18. The formulation of any one of embodiments 1-17, wherein the formulation comprises a salt, and wherein the salt is selected from the list consisting of calcium chloride, Dead Sea salt, Epsom salt, Himalayan pink salt, magnesium chloride, sea salt, and sodium chloride.
19. The formulation of any one of embodiments 1-18, wherein the formulation comprises 10-500 mM of a salt.
20. The formulation of any one of embodiments 1-19, wherein the formulation comprises 50-250 mM of a salt.
21. The formulation of any one of embodiments 1-20, wherein the formulation comprises a buffer.
22. The formulation of any one of embodiments 1-21, wherein the formulation comprises a buffer, and wherein the buffer is selected from the list consisting of: 4-(2-hydroxyethyl)-1-piperazineethanesulfonic acid, acetic acid, ammonium acetate, boric acid, citric acid, glycine, phosphoric acid, potassium hydroxide, potassium phosphate, sodium acetate, sodium bicarbonate, sodium borate, sodium carbonate, sodium citrate, sodium dihydrogen phosphate, sodium hydrogen phosphate, sodium hydroxide, sodium phosphate, sodium tetraborate, tris(hydroxymethyl)aminomethane, and trisodium phosphate.
23. The formulation of any one of embodiments 1-22, wherein the formulation comprises 5-50 mM of a buffer.
24. The formulation of any one of embodiments 1-23, wherein the formulation comprises a surfactant.
25. The formulation of any one of embodiments 1-24, wherein the formulation comprises a surfactant, and wherein the surfactant is selected from the list consisting of: ceteareth-20, cocamidopropyl betaine, cocoglucoside, decyl glucoside, decyl polyglucose, disodium laureth sulfosuccinate, glycereth-26, lauryl glucoside, lauryl polyglucose, sodium cocoyl glutamate, sodium cocoyl isethionate, sodium laureth sulfate, and sodium lauryl sulfate.
26. The formulation of any one of embodiments 1-25, wherein the formulation comprises 0.1-20% w/v of a surfactant.
27. The formulation of any one of embodiments 1-26, wherein the formulation comprises 1-10% w/v of a surfactant.
28. The formulation of any one of embodiments 1-27, wherein the formulation comprises a free amino acid.
29. The formulation of any one of embodiments 1-28, wherein the formulation comprises a free amino acid, and wherein the free amino acid is selected from the list consisting of: alanine, arginine, cysteine, glutamine, glycine, histidine, lysine, methionine, proline, serine, and threonine.
30. The formulation of any one of embodiments 1-29, wherein the formulation comprises 10-250 mM of a free amino acid.
31. The formulation of any one of embodiments 1-30, wherein the formulation comprises an oil.
32. The formulation of any one of embodiments 1-31, wherein the formulation comprises an oil, and wherein the oil is selected from the list consisting of: argan oil, avocado oil, baobab oil, camellia oil, carrot seed oil, coconut oil, evening primrose oil, grapeseed oil, hemp seed oil, jojoba oil, macadamia nut oil, marula oil, mineral oil, olive oil, pomegranate seed oil, raspberry seed oil, rosehip seed oil, squalane oil, sunflower seed oil, sweet almond oil, and tamanu oil.
33. The formulation of any one of embodiments 1-32, wherein the formulation comprises 0.1-20% w/v of an oil.
34. The formulation of any one of embodiments 1-33, wherein the formulation comprises an alcohol.
35. The formulation of any one of embodiments 1-34, wherein the formulation comprises an alcohol, and wherein the alcohol is selected from the list consisting of: cetyl alcohol, ethyl alcohol, isopropyl alcohol, and stearyl alcohol.
36. The formulation of any one of embodiments 1-35, wherein the formulation comprises 0.1-20% w/v of an alcohol.
37. The formulation of any one of embodiments 1-36, wherein the formulation comprises 1-10% w/v of an alcohol.
38. The formulation of any one of embodiments 1-37, wherein the formulation comprises glycerol.
39. The formulation of any one of embodiments 1-38, wherein the formulation comprises 0.5-50% w/v glycerol, 1-30% w/v glycerol, or 1-5% w/v glycerol.
40. The formulation of any one of embodiments 1-39, wherein the formulation comprises petrolatum
41. The formulation of any one of embodiments 1-40, wherein the formulation comprises 0.1-20% w/v petrolatum.
42. The formulation of any one of embodiments 1-41, wherein the formulation is thermostable at 45° C. or 50° C. for at least four weeks or for at least two months.
43. The formulation of any one of embodiments 1-42, wherein the formulation is active within a pH range of 6-8, optionally within a pH range of 5-8.
44. A method of treating a condition associated with *Cutibacterium acnes* (*C. acnes*), the method comprising: administering a composition comprising a recombinant protein or chimeric CWH of any one of the foregoing embodiments.
45. A method of treating a condition associated with *Cutibacterium acnes* (*C. acnes*), the method comprising: administering a formulation according to any one of embodiments 1-43.

46. The method of embodiment 44 or embodiment 45, wherein the condition is Acne vulgaris (acne).

47. The method of any one of embodiments 44-46, wherein the condition is C. acnes infection.

48. A method of restoring the phylotype diversity of Cutibacterium acnes (C. acnes), the method comprising: administering a composition comprising a recombinant protein or chimeric CWH of any one of the foregoing embodiments.

49. A method of restoring the phylotype diversity of Cutibacterium acnes (C. acnes), the method comprising: administering a formulation according to any one of embodiments 1-43.

50. The method of any one of embodiments 44-49, wherein the condition is associated with an over-abundance of C. acnes phylotype IA1 and/or IA2.

51. The method of any one of embodiments 44-50, wherein the method decreases the relative abundances of C. acnes phylotype IA1 and/or IA2.

52. The method of any one of embodiments 44-51, wherein the composition or formulation is administered topically, enterally, or parenterally.

53. The method of any one of embodiments 44-52, wherein the composition or formulation is administered topically.

54. The method of any one of embodiments 44-53, wherein the method further comprises administering an antibiotic.

55. The method of any one of embodiments 44-54, wherein the method reduces the number and/or size of acne lesions.

56. The method of any one of embodiments 44-55, wherein the method reduces skin redness and/or pain.

57. The method of any one of embodiments 44-56, wherein the method reduces C. acnes abundance.

58. A method of identifying a novel CW_7 cell wall binding domain for use in binding, targeting and/or lysing Cutibacterium acnes, the method comprising the steps of:
   a) Searching a genetic database with a known CW_7 query sequence;
   b) Identifying sequences exceeding an amino acid sequence identity cutoff to the query sequence;
   c) Cloning the CW_7 sequence, or the CW_7-comprising CBD sequence, into a chimeric cell wall hydrolase in combination with an enzymatically active domain (EAD) to form a CW_7 chimera; and
   d) Assaying the CW_7 chimera for binding, targeting, and/or lytic activity against Cutibacterium acnes.

59. The method of embodiment 58, wherein the CW_7 query sequence is:
   a) a CW_7 sequence disclosed herein;
   b) a CW_7 sequence disclosed in Table 7; or
   c) a CW_7 sequence from CLB1-4.

60. The method of embodiment 58, wherein the CW_7 query sequence is the CW_7 sequence from CLB2.

61. The method of any one of embodiments 58-60, wherein the EAD is:
   a) An EAD disclosed herein;
   b) An EAD from Table 2; or
   c) An EAD from Table 4.

62. The method of any one of embodiments 58-61, wherein the cutoff is any number selected from the range of 30-99%.

63. The method of any one of embodiments 58-62, wherein the cutoff is 40%.

SEQUENCE LISTING

The patent contains a lengthy sequence listing. A copy of the sequence listing is available in electronic form from the USPTO web site (https://seqdata.uspto.gov/?pageRequest=docDetail&DocID=US12312617B2). An electronic copy of the sequence listing will also be available from the USPTO upon request and payment of the fee set forth in 37 CFR 1.19(b)(3).

The invention claimed is:

1. A chimeric cell wall hydrolase (CWH) comprising the fusion of:
   a) a CLC1-family enzymatically active domain (EAD), said EAD having at least 95% sequence identity to SEQ ID NO: 2939; and
   b) a heterologous cell well binding domain (CBD), wherein the chimeric CWH exhibits lytic activity against Cutibacterium acnes.

2. The chimeric CWH of claim 1, wherein the EAD comprises SEQ ID NO: 2939.

3. The chimeric CWH of claim 1, wherein the EAD has at least 90% sequence identity to SEQ ID NO: 35.

4. The chimeric CWH of claim 1, wherein the EAD comprises SEQ ID NO: 35.

5. The chimeric CWH of claim 1, wherein the EAD has at least 90% sequence identity to SEQ ID NO: 20.

6. The chimeric CWH of claim 1, wherein the EAD comprises SEQ ID NO: 20.

7. The chimeric CWH of claim 1, wherein the EAD has a C-terminal truncation compared to any one of SEQ ID NO: 1-19.

8. The chimeric CWH of claim 7, wherein the chimeric CWH exhibits the lytic activity across a pH range of pH 4.2-8.0.

9. The chimeric CWH of claim 7, wherein the chimeric CWH exhibits peak lytic activity at a pH of about pH 5.5-6.5.

10. The chimeric CWH of claim 7, wherein the chimeric CWH retains at least 50% of its activity at 25° C. after being exposed to a temperature of up to 50° C. for 30 minutes.

11. The chimeric CWH of claim 7, wherein the chimeric CWH retains at least 50% of its activity at 25° C. after being exposed to a temperature of up to 75° C. for 30 minutes.

12. The chimeric CWH of claim 1, wherein the chimeric CWH exhibits minimal or no lytic activity against Corynebacterium xerosis, Corynebacterium striatum, and/or Staphylococcus epidermidis.

13. The chimeric CWH of claim 1, wherein the heterologous CBD comprises a sequence selected from the group consisting of SEQ ID NO: 2941, SEQ ID NO: 2940, SEQ ID NO: 47, and SEQ ID NO: 42.

14. The chimeric CWH of claim 1, wherein the CBD has at least 90% sequence identity to SEQ ID NO: 42.

15. The chimeric CWH of claim 1, wherein the CBD comprises SEQ ID NO: 42.

16. A topical formulation comprising the chimeric CWH according to claim 1.

17. The formulation of claim 16, wherein the formulation is a hydrogel.

18. The formulation of claim 16, wherein the formulation comprises 5-20 μg/mL of the chimeric CWH.

19. The formulation of claim 16, wherein the formulation comprises 1-5% w/v of a cellulose polymer selected from the group consisting of: hydroxyethyl cellulose, methylcellulose, hydroxypropyl methyl cellulose, carboxymethyl cellulose, microcrystalline cellulose, ethyl cellulose, sodium carboxymethyl cellulose, hydroxypropyl cellulose, and cellulose acetate.

20. The topical formulation of claim 16, which is comprised in a microneedle patch or a colloidal patch.

21. The topical formulation of claim 16, comprising a humectant selected from the list consisting of: aloe vera, betaine, butylene glycol, caprylyl glycol, dimethicone, fructose, glucomannan, glucose, glycerin, glyceryl glucoside, honey, hyaluronic acid, lactic acid, panthenol, polyethylene glycol, propylene glycol, propanediol, sodium hyaluronate, sodium lactate, sodium pyrrolidone carboxylic acid, sorbitol, and urea.

22. The topical formulation of claim 16, comprising betaine.

23. A method of treating a skin condition associated with *Cutibacterium acnes*, the method comprising applying the chimeric CWH of claim 1 to the skin.

24. The method of claim 23, wherein the skin condition is Acne vulgaris (acne), *C. acnes* infection, or is associated with overabundance of *C. acnes*.

25. The method of claim 23, wherein the method reduces number of acne lesions, severity of acne lesions, size of acne lesions, skin redness and/or pain.

* * * * *